(12) United States Patent
Eastmond et al.

(10) Patent No.: US 12,281,317 B2
(45) Date of Patent: Apr. 22, 2025

(54) NON-HUMAN ORGANISM FOR PRODUCING TRIACYLGLYCEROL

(71) Applicant: ROTHAMSTED RESEARCH LTD, Harpenden (GB)

(72) Inventors: Peter Eastmond, Harpenden (GB); Henricus Egbertus Gerardus Van Erp, Harpenden (GB); Govindprasad Bhutada, Harpenden (GB)

(73) Assignee: ROTHAMSTED RESEARCH LTD, Harpenden (GB)

( * ) Notice: Subject to any disclaimer, the term of this patent is extended or adjusted under 35 U.S.C. 154(b) by 550 days.

(21) Appl. No.: 17/633,390

(22) PCT Filed: Aug. 6, 2020

(86) PCT No.: PCT/GB2020/051875
§ 371 (c)(1),
(2) Date: Feb. 7, 2022

(87) PCT Pub. No.: WO2021/023991
PCT Pub. Date: Feb. 11, 2021

(65) Prior Publication Data
US 2022/0282267 A1 Sep. 8, 2022

(30) Foreign Application Priority Data

Aug. 7, 2019 (GB) ..................................... 1911317

(51) Int. Cl.
| | | |
|---|---|---|
| C12N 1/20 | (2006.01) | |
| A23L 33/115 | (2016.01) | |
| C12N 15/82 | (2006.01) | |

(52) U.S. Cl.
CPC ........ *C12N 15/8247* (2013.01); *A23L 33/115* (2016.08)

(58) Field of Classification Search
CPC ...... C12N 15/8247; C12N 15/82; C12N 1/20; A23L 33/115
See application file for complete search history.

(56) References Cited

U.S. PATENT DOCUMENTS

| | | | |
|---|---|---|---|
| 5,563,058 A | 10/1996 | Davies | |
| 5,968,791 A | 10/1999 | Davies et al. | |
| 8,524,485 B2* | 9/2013 | Yadav ....................... | A61P 3/10 |
| | | | 435/254.2 |
| 9,096,834 B2* | 8/2015 | Seshadri ................... | C12N 9/16 |
| 10,005,713 B2 | 6/2018 | Petrie et al. | |
| 2006/0094092 A1 | 5/2006 | Damude et al. | |
| 2006/0206960 A1 | 9/2006 | Zou | |
| 2011/0239323 A1 | 9/2011 | Hutcheon | |
| 2018/0171312 A1 | 6/2018 | Davis | |

FOREIGN PATENT DOCUMENTS

| | | |
|---|---|---|
| AU | 2013255080 A1 | 12/2014 |
| AU | 2020325789 A1 | 2/2022 |
| CN | 1331744 A | 1/2002 |
| CN | 102170774 A | 8/2011 |
| CN | 104364386 A | 2/2015 |
| CN | 105767213 A | 7/2016 |
| CN | 106016798 A | 10/2016 |
| CN | 106916798 A | 7/2017 |
| CN | 107960101 A | 4/2018 |
| CN | 114736916 A | 7/2022 |
| CN | 115786149 A | 3/2023 |
| EP | 2182071 A1 | 5/2010 |
| EP | 2966157 A1 | 1/2016 |
| FR | 2785911 A1 | 5/2000 |
| KR | 20220056928 A | 5/2022 |
| WO | 1998054303 A1 | 12/1998 |
| WO | 2003025165 | 3/2003 |
| WO | 2009129582 A1 | 10/2009 |

(Continued)

OTHER PUBLICATIONS

Bhuiyan et al., "Determination and differentiation of triacylglycerol molecular species in Antarctic and non-Antarctic yeasts by atmospheric pressure-chemical ionization-mass spectrometry." Journal of microbiological methods 94.3 (2013): 249-256.
Bourgis et al. "A plastidial lysophosphatidic acid acyltransferase from oilseed rape." Plant physiology 120(3): 913-922 (1999).
Marudhupandi et al. "Heterotrophic cultivation of Nannochloropsis salina for enhancing biomass and lipid production." Biotechnology Reports (10): 8-16 (2016).
Misra et al. "Genome-wide identification and evolutionary analysis of algal LPAT genes involved in TAG biosynthesis using bioinformatic approaches." Molecular biology reports 41(12): 8319-8332 (2014).
Nobusawa et al. "Differently localized lysophosphatidic acid acyltransferases crucial for triacylglycerol biosynthesis in the oleaginous alga Nannochloropsis." The Plant Journal 90(3): 547-559 (2017).

(Continued)

*Primary Examiner* — Tekchand Saidha
(74) *Attorney, Agent, or Firm* — Nixon Peabody LLP; David S. Resnick; Nicole D. Kling

(57) ABSTRACT

Described herein are non-human organisms for producing triacylglycerol wherein the non-human organism is genetically modified to express a lysophosphatidic acid acyltransferase specific for C16:0-Coenzyme A (C16:0 LPAT) and wherein, once expressed, the C16:0 LPAT is localised in the endoplasmic reticulum. Also described are non-human organisms for producing triacylglycerol in which (a) a lysophosphatidic acid acyltransferase specific for C16:0-Coenzyme A (C16:0 LPAT) is localised in the endoplasmic reticulum; and (b) activity of native endoplasmic reticulum lysophosphatidic acid acyltransferase (ER LPAT) is suppressed or prevented. Further described are non-human organisms in which a chloroplast lysophosphatidic acid acyltransferase (LPAT) is expressed, wherein said chloroplast LPAT lacks a functional chloroplast targeting signal. The disclosure also relates to methods for extracting triacylglycerol from the organisms and the use thereof in infant formula.

23 Claims, 12 Drawing Sheets

Figure 3:
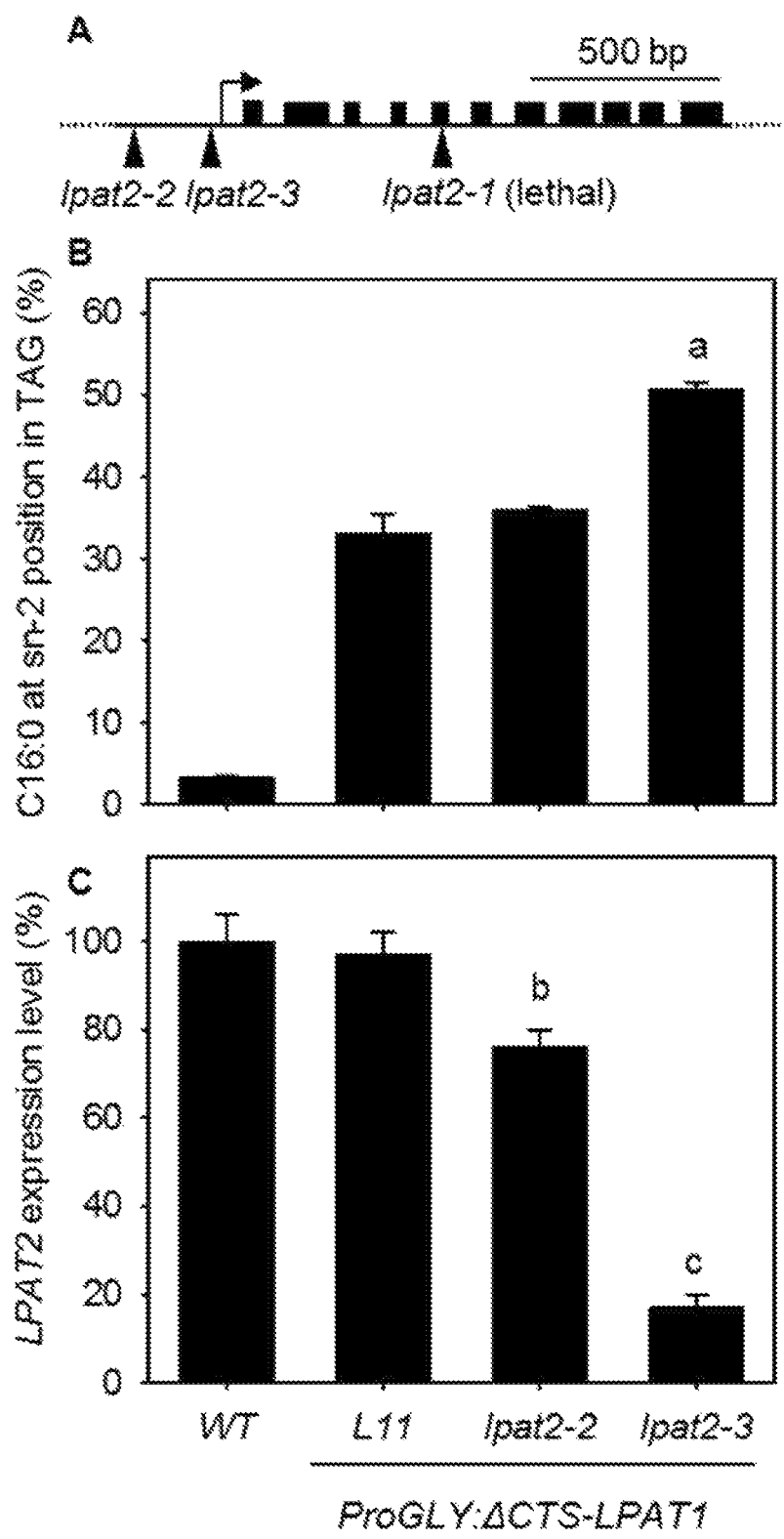

Specification includes a Sequence Listing.

(56) References Cited

FOREIGN PATENT DOCUMENTS

| WO | 2013158938 A1 | 10/2013 |
|---|---|---|
| WO | 2013163684 A1 | 11/2013 |
| WO | 2014100467 A1 | 6/2014 |
| WO | 2016014968 A1 | 1/2016 |
| WO | 2016101894 A1 | 6/2016 |
| WO | 2016164495 A1 | 10/2016 |
| WO | 2021023991 A1 | 2/2021 |

OTHER PUBLICATIONS

Simpson et al. "A novel pathway for triacylglycerol biosynthesis is responsible for the accumulation of massive quantities of glycerolipids in the surface wax of bayberry (*Myrica pensylvanica*) fruit." The Plant Cell 28(1): 248-264 (2016).

Van Erp et al. "Engineering the stereoisomeric structure of seed oil to mimic human milk fat." Proceedings of the National Academy of Sciences 116(42): 20947-20952 (2019).

Wang et al. "Establishment of an evaluation model for human milk fat substitutes." Journal of agricultural and food chemistry 58(1): 642-649 (2010).

Wang et al. "Dual expression of plastidial GPAT1 and LPAT1 regulates triacylglycerol production and the fatty acid profile in Phaeodactylum tricornutum." Biotechnology for biofuels 11(1): 1-14 (2018).

Wei et al. "Human milk fat substitutes: Past achievements and current trends." Progress in lipid research (74): 69-86 (2019).

Bhutada et al. "Production of human milk fat substitute by engineered strains of Yarrowia lipolytica" Metabolic Engineering Communications 14:e00192 (Jan. 6, 2022).

"Study on important nodes related to triglyceride synthesis and accumulation pathway in Phaeodactylum tricornutum" (2018).

Van Erp et al. "Production of the infant formula ingredient 1,3-olein-2-palmitin in *Arabidopsis thaliana* seeds" Metabolic Engineering 67:67-74 (2021).

Kim et al. "Plastid lysophosphatidyl acyltransferase is essential for embryo development in *Arabidopsis*." Plant physiology 134.3: 1206-1216 (2004).

Kim et al. "Endoplasmic reticulum acyltransferase with prokaryotic substrate preference contributes to triacylglycerol assembly in Chlamydomonas." Proceedings of the National Academy of Sciences 115.7: 1652-1657 (2018).

Robertson et al. "A two-helix motif positions the lysophosphatidic acid acyltransferase active site for catalysis within the membrane bilayer." Nature structural & molecular biology 24.8: 666-671 (2017).

Weier et al. "Characterisation of acyltransferases from *Synechocystis* sp. PCC6803." Biochemical and biophysical research communications 334.4: 1127-1134 (2005).

Yamaoka et al. "Identification of a Chlamydomonas plastidial 2-lysophosphatidic acid acyltransferase and its use to engineer microalgae with increased oil content." Plant biotechnology journal 14.11: 2158-2167 (2016).

Zhang et al. "Cloning, characterization, and expression analysis of a gene encoding a putative lysophosphatidic acid acyltransferase from seeds of Paeonia rockii." Applied Biochemistry and Biotechnology 182: 721-741 (2017).

* cited by examiner

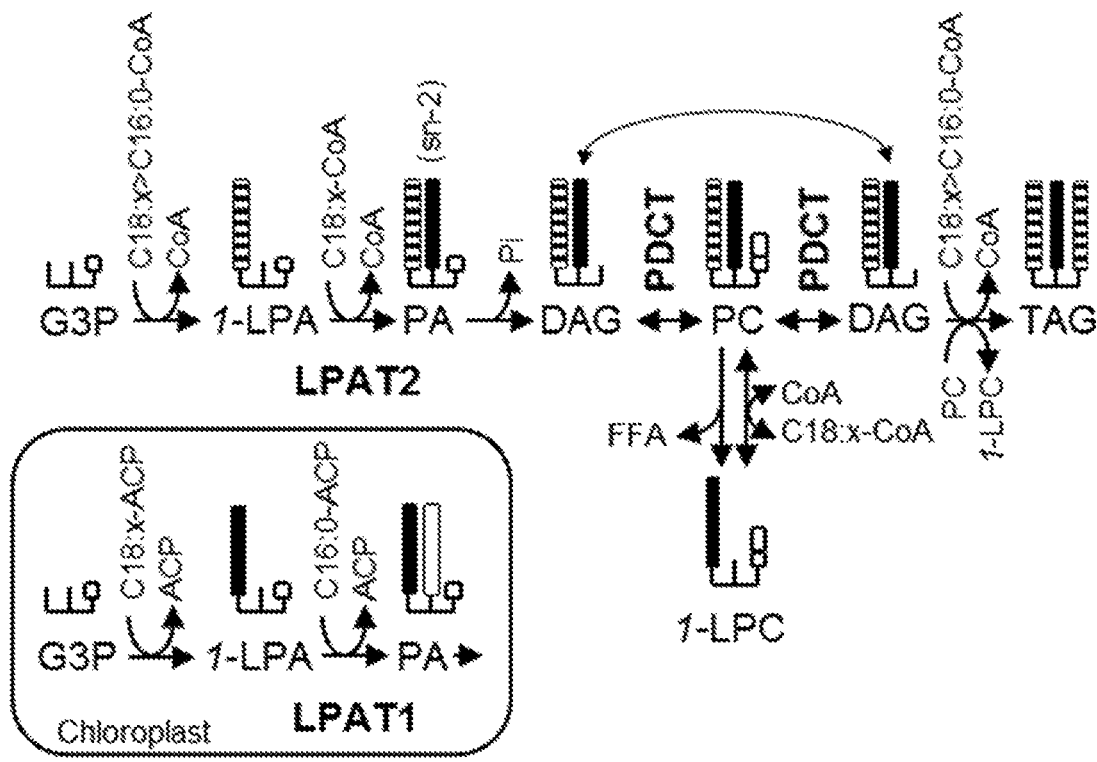

Fig 1A

```
>DNA sequence of ACTS-LPAT1
ATGTCGGATCTTTCAGGAGCTGCAACCCCTGAATCTACTTATCCAGAACCAGAGATTAAGTTGA
GCTCAAGACTCAGAGGGATATGCTTTTGTCTCGTTGCTGGCGTTTCCGCCATTGTTCTCATCGT
CCTGATGATCACTGGCCATCCTTTCGTCCTTCTATTTGATCGTTACAGGAGGAAGTTCCATCAC
TTCATTGCTAAGCTCTGGGCTTCCATAAGCATCTACCCGTTTTACAAAACCGACATCCAAGGTT
TGGAGAATCTGCCATCATCAGACACTCCTTGTGTGTACGTTTCGAACCACCAGAGTTTTCTGGA
TATATACACACTTCTCAGCCTTGGCCAAAGCTATAAGTTCATCAGCAAGACAGGGATATTCGTT
ATTCCTGTCATCGGTTGGGCTATGTCCATGATGGGGGTTGTTCCCTTGAAGAGGATGGACCCAA
GAAGCCAAGTGGATTGCTTAAAACGCTGCATGGAACTAGTGAAGAAGGGAGCTTCCGTCTTTTT
CTTCCCAGAGGGAACGAGGAGTAAGGATGGTCGGTTAGGTCCTTTCAAGAAGGGGCTTTTACG
ATAGCAGCTAAGACAGGAGTTCCAGTGGTGCCAATAACGCTGATGGGAACAGGGAAGATCATGC
CGACGGGTAGTGAAGGTATACTGAATCATGGGGATGTGAGAGTGATCATCCACAAGCCGATATA
TGGAAGCAAAGCTGATCTTCTTTGCGATGAGGCTAGAAACAAGATAGCTGAATCTATGAATCTC
TTGAGTTGA (SEQ ID NO:1)

>Amino acid sequence of ACTS-LPAT1
MSDLSGAATPESTYPEPEIKLSSRLRGICFCLVAGVSAIVLIVLMITGHPFVLLFDRYRRKFHH
FIAKLWASISIYPFYKTDIQGLENLPSSDTPCVYVSNHQSFLDIYTLLSLGQSYKFISKTGIFV
IPVIGWAMSMMGVVPLKRMDPRSQVDCLKRCMELVKKGASVFFFPEGTRSKDGRLGPFKKGAFT
IAAKTGVPVVPITLMGTGKIMPTGSEGILNHGDVRVIIHKPIYGSKADLLCDEARNKIAESMNL
LS (SEQ ID NO:2)
```

Fig 1B

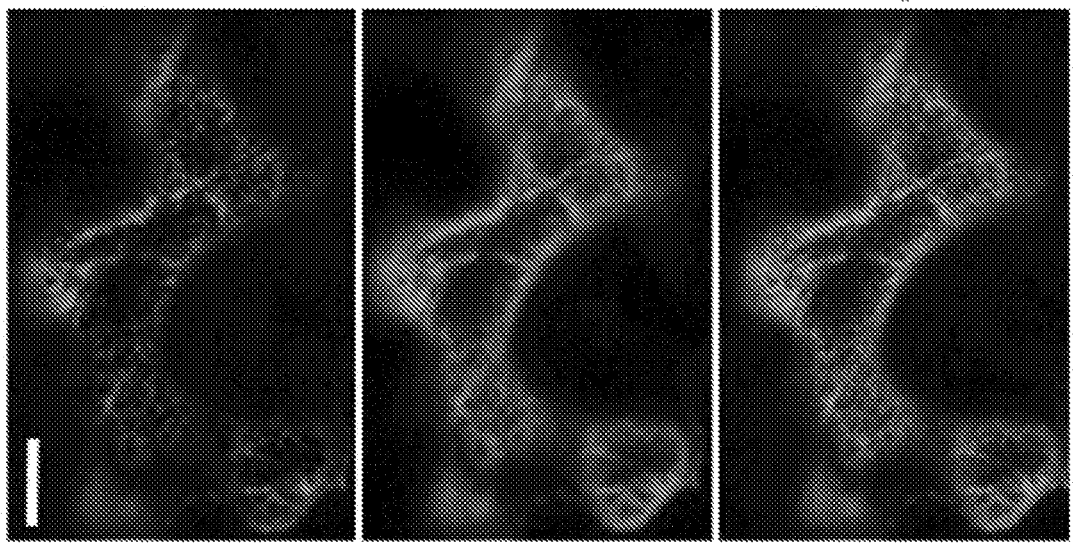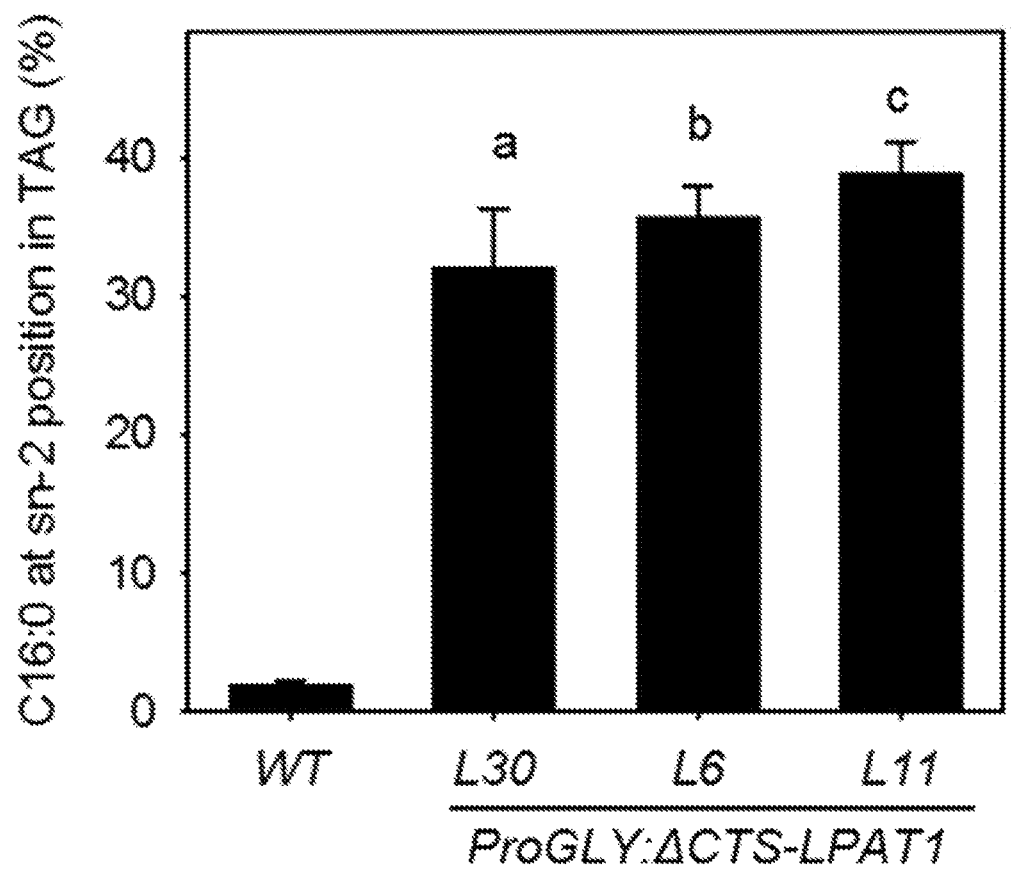
Fig 2

NON-HUMAN ORGANISM FOR PRODUCING TRIACYLGLYCEROL

CROSS-REFERENCE TO RELATED APPLICATIONS

This application is a 35 U.S.C. § 371 National Phase Entry Application of International Application No. PCT/GB2020/051875 filed Aug. 6, 2020, which designates the U.S. and claims benefit under 35 U.S.C. § 119 (a) of G.B. Provisional Application No. 1911317.4 filed Aug. 7, 2019, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 6, 2020, is named P16317S-PCT sequence listing.txt and is 139,428 bytes in size.

The present invention relates to non-human organisms, in particular to plants, fungi and yeast, for producing triacylglycerol.

Infant formula is a manufactured food designed to substitute for human breast milk. Around half the calories in human milk are provided by fat (triacylglycerol; TAG) and in infant formula this fat is mainly sourced from plants. Although blended vegetable fats can replicate the fatty acyl composition of human milk fat (HMF), which mainly comprises palmitate (C16:0) and oleate (C18:1), the arrangement of acyl groups esterified to the glycerol backbone (i.e. the stereoisomeric structure) is profoundly different. In vegetable fats, saturated long-chain fatty acyl groups such as C16:0 occupy the outer stereospecific numbering (sn) positions (sn-1/3) and are virtually excluded from the middle (sn-2 or β) position. Whereas in HMF more than 70% of the C16:0 is present at the sn-2 position, with unsaturated fatty acyl groups (mainly C18:1) occupying the outer sn-1/3 positions.

Multiple clinical trials on preterm and term infants have suggested that the unusual stereoisomeric structure of HMF is important for nutrient absorption in the neonatal gut. The proposed mechanism is as follows. During the intestinal phase of digestion lipases attack ingested fat at the sn-1/3 positions yielding 2-monoacylglycerols, which are easily absorbed. When unsaturated fatty acids are released from sn-1/3 positions they are also absorbed easily, but the release of long-chain saturated fatty acids such as C16:0 presents a problem. Their melting point is higher than body temperature and, at intestinal pH they are prone to form hydrated fatty acid soaps with minerals such as calcium and magnesium. The arrangement of C16:0 at the sn-1/3 positions of vegetable fats thus means that they are more poorly absorbed than HMF. There is evidence that the formation of C16:0 soaps also reduces calcium absorption, thus impairing early bone development, and accumulation of these soaps in the intestine also disrupts transit, causing infants discomfort.

To mimic the stereoisomeric structure of HMF several companies have developed HMF substitutes (HMFS). HMFS are made by enzyme-catalyzed acidolysis (or alcoholysis and esterification) using tripalmitin, unsaturated free fatty acids (mainly C18:1) together with an immobilized recombinant sn-1/3-regioselective lipase. The price of HMFS is substantially higher than that of conventional vegetable fat blends, primarily reflecting the added cost of enzyme-based catalysis, including generation of organic solvent waste. Different grades of HMFS are also available, providing a complete fat phase with between ~40 and ~70% of C16:0 at the sn-2 position. True HMF mimetics (with >70% of C16:0 at sn-2) are most expensive to produce because they require a two-step catalytic process and a pure tripalmitin feedstock derived from palm oil by special fractionation procedures and chemical randomisation. The tension between price and quality is one factor that has likely restricted the use of HMFS and despite mounting clinical evidence that this ingredient is beneficial, it is currently only found in around 10% of infant formula, particularly premium products formulated and marketed for ease-of-digestion. Even in these products, there remains a substantial gap in C16:0 enrichment at the sn-2 position versus HMF.

It is, therefore, an object of the present invention to seek to alleviate the above identified problems.

SUMMARY OF THE INVENTION

According to one aspect of the present invention, there is provided a non-human organism for producing triacylglycerol wherein the non-human organism is genetically modified to express a lysophosphatidic acid acyltransferase specific for C16:0-Coenzyme A (C16:0 LPAT) and wherein, once expressed, the C16:0 LPAT is localised in the endoplasmic reticulum.

Preferably, activity of native endoplasmic reticulum lysophosphatidic acid acyltransferase (ER LPAT) is suppressed or prevented in the organism.

According to another aspect of the present invention, there is provided a non-human organism for producing triacylglycerol in which:—
(a) a lysophosphatidic acid acyltransferase specific for C16:0-Coenzyme A (C16:0 LPAT) is localised in the endoplasmic reticulum; and
(b) activity of native endoplasmic reticulum lysophosphatidic acid acyltransferase (ER LPAT) is suppressed or prevented.

Preferably, the activity of diacylglycerol conversion to and from phosphatidylcholine is suppressed or prevented.

Preferably, the activity of one or more native endoplasmic reticulum lysophosphatidic acid acyltransferases (ER LPATs) is suppressed or prevented.

According to another aspect of the present invention, there is provided a non-human organism for producing triacylglycerol in which:—
(a) a lysophosphatidic acid acyltransferase specific for C16:0-Coenzyme A (C16:0 LPAT) is localised in the endoplasmic reticulum;
(b) activity of native endoplasmic reticulum lysophosphatidic acid acyltransferase (ER LPAT) is suppressed or prevented; and
(c) activity of diacylglycerol conversion to and from phosphatidylcholine is suppressed or prevented.

Remarkably, as discussed in further detail herein, by providing a lysophosphatidic acid acyltransferase specific for C16:0-Coenzyme A (CoA) which is localised in the endoplasmic reticulum, the enzyme operates within the cytosolic glycerolipid biosynthetic pathway to esterify C16:0 to the middle position during TAG biosynthesis. This, combined with suppression of native endoplasmic reticulum lysophosphatidic acid acyltransferase and optionally suppression of diacylglycerol conversion to and from phosphatidylcholine, means that a much greater amount of C16:0 is esterified to the middle position on the glycerol backbone than to the outer positions.

Preferably, the organism comprises an endoplasmic reticulum.

Preferably, the organism is a plant, fungi, yeast or algae.

Preferably, the organism is not a mammal.

Preferably, the organism is a plant. Preferably, the plant is an oilseed plant.

Preferably, the organism is a plant belonging to the order of Brassicales, Asterales, Fabales, Malpighiales, Malvales, Rosales, Lamiales, Solanales, Arecales or Poales. Most preferably, the plant belongs to the order Brassicales or Asterales, more preferably Brassicales.

Preferably, the organism is a plant belonging to the family of Brassicaceae, Asteraceae, Fabaceae, Linaceae, Malvaceae, Cannabaceae, Pedaliaceae, Oleaceae, Solanaceae, Arecaceae or Poaceae. Most preferably, the plant belongs to the family Brassicaceae or Asteraceae, more preferably Brassicaceae.

Preferably, the organism is a plant belonging to the genus of *Arabidopsis, Camelina, Brassica, Thlaspi, Lepidium, Helianthus, Glycine, Arachis, Linum, Nicotiana, Gossypium, Cannabis, Sesamum, Olea, Elaeis, Zea, Avena* or *Oryza*. Most preferably, the plant belongs to the genus *Arabidopsis, Camelina, Brassica* or *Helianthus*.

Preferably, the plant is selected from *Arabidopsis thaliana, Camelina sativa, Brassica napus, Brassica carinata, Brassica oleracea, Brassica rapa, Brassica juncea, Thlaspi arvense, Lepidium sativum, Helianthus annuus, Glycine max, Arachis hypogaea, Linum usitatissimum, Gossypium hirsutum, Cannabis sativa, Sesamum indicum, Olea europaea, Nicotiana benthamiana, Elaeis guineensis, Elaeis oleifera, Zea mays, Avena sativa* or *Oryza sativa*.

Preferably, the plant is selected from *Arabidopsis thaliana, Helianthus annuus, Glycine max, Camelina sativa* and *Brassica napus*.

Preferably, the plant is selected from *Arabidopsis thaliana, Camelina sativa* and *Brassica napus*.

Preferably, the plant is *Arabidopsis thaliana*.

Preferably, the organism is a plant from which triacylglycerol can be extracted, for example from the seeds, fruits or leaves of the plant.

Preferably, an oilseed plant is a plant from which triacylglycerol can be extracted from seeds or fruits.

Preferably, the organism is a yeast.

Preferably, the organism is a fermentative and/or respiratory yeast.

Preferably, the organism is a yeast of an oleaginous species.

Preferably, the organism is a yeast capable of accumulating at least about 20% triacylglycerol in cellular biomass.

Preferably, the organism is a fungus belonging to the order of Saccharomycetales, Saccharomycetes Tremellales, Ustilaginales, Sporidiobolales, Mucorales, Mortierellales or Eurotiales. Most preferably, the organism is from the order of Saccharomycetales.

Preferably, the organism is a fungus belonging to the family of Dipodascaceae, Saccharomycetaceae, Saccharomycopsidaceae, Tremellaceae, Ustilaginaceae, Sporidiobolaceae, Trichosporonaceae, Phaffomycetaceae, Trichomonascaceae, Mucoraceae, Mortierellaceae, Cunninghamellaceae or Trichocomaceae. Most preferably, the organism is from the family of Dipodascaceae.

Preferably, the organism is a fungus belonging to the genus of *Saccharomyces, Yarrowia, Cryptococcus, Candida, Rhodosporidium, Rhodotorula, Lipomyces, Trichosporon, Wickerhamomyces, Pichia, Endomycopsis, Zygoascus, Mucor, Mortierella, Cunninghamella* or *Aspergillus*. Most preferably, the organism is from the genus of *Yarrowia*.

Preferably, the organism is an obligate respiratory and crabtree-negative yeast.

Preferably, the organism is *Yarrowia lipolytica*.

Preferably, the organism is *Yarrowia lipolytica* and the C16:0 LPAT is CreLPAT.

Preferably, the organism is a gsy1Δ-CreLPAT strain of *Yarrowia lipolytica*.

Preferably, the organism is cultured in a media comprising a carbon source, wherein the carbon source comprises one or more sugars.

Preferably, the one or more sugars comprise one or more fermentable sugars.

Preferably, the one or more sugars is selected from one or more of xylose, lactose, cellulose, glucose, fructose, sucrose, or hydrolysed lignocellulosic materials.

Preferably, the organism is cultured in a media comprising a carbon source, wherein the carbon source comprises one or more fatty acids and/or fatty acid esters.

Preferably, the carbon source comprises C16:0.

Preferably, the carbon source comprises a mixture of fatty acids and/or fatty acid esters wherein at least about 30% w/w of the fatty acids and/or fatty acid esters comprises C16:0 and/or at least about 30% w/w of the fatty acids and/or fatty acid esters comprises C18:1.

Preferably, the organism is cultured in a media comprising a carbon source, wherein the carbon source comprises one or more vegetable oils.

Preferably, the organism is cultured in a media comprising a carbon source, wherein the carbon source comprises a mixture of (i) one or more sugars and (ii) one or more fatty acids and/or fatty acid esters.

Preferably, the organism is cultured in a media comprising a carbon source, wherein the carbon source comprises a mixture of (i) one or more sugars and (ii) one or more oils, preferably vegetable oils.

Preferably, the carbon source comprises glycerol.

Preferably, the organism is cultured in a media comprising a carbon source, wherein the carbon source is selected from glycerol, glucose and/or palm oil.

Preferably, the carbon source comprises palm oil.

Preferably, the carbon source comprises palm oil in combination with glucose and/or glycerol.

Preferably, the carbon source is present at a concentration of at least about 5 gL$^{-1}$, preferably at least about 10 gL$^{-1}$, preferably at least about 15 gL$^{-1}$, preferably at least about 20 gL$^{-1}$.

Preferably, the carbon source is present at a concentration of between about 5 gL$^{-1}$ and about 35 gL$^{-1}$, preferably between about 10 gL$^{-1}$ and about 30 gL$^{-1}$, preferably between about 15 gL$^{-1}$ and about 25 gL$^{-1}$, preferably at a concentration of about 20 gL$^{-1}$.

Preferably, the media comprises a first carbon source at a concentration of at least about 2.5 gL$^{-1}$ and a second carbon source at a concentration of at least about 2.5 gL$^{-1}$.

Preferably, the media comprises a first carbon source at a concentration of at least about 5 gL$^{-1}$, preferably at least about 10 gL$^{-1}$, and a second carbon source at a concentration of at least about 5 gL$^{-1}$, preferably at least about 10 gL$^{-1}$.

Preferably, the media comprises a first carbon source at a concentration of between about 2.5 gL$^{-1}$ and about 20 gL$^{-1}$, and a second carbon source at a concentration of between about 2.5 gL$^{-1}$ and about 20 gL$^{-1}$.

Preferably, the media comprises a first carbon source at a concentration of between about 5 gL$^{-1}$ and about 15 gL$^{-1}$, preferably about 10 gL$^{-1}$, and a second carbon source at a concentration of between about 5 gL$^{-1}$ and about 15 gL$^{-1}$, preferably about 10 gL$^{-1}$.

Preferably, the first carbon source comprises one or more sugars.

Preferably, the one or more sugars comprise one or more fermentable sugars.

Preferably, the one or more sugars is selected from one or more of xylose, lactose, cellulose, glucose, fructose, sucrose, or hydrolysed lignocellulosic materials.

Preferably, the first carbon source glycerol and/or one or more sugars.

Preferably, the second carbon source comprises one or more fatty acids and/or fatty acid esters.

Preferably, the second carbon source comprises C16:0.

Preferably, the second carbon source comprises a mixture of fatty acids and/or fatty acid esters wherein at least about 30% w/w of the fatty acids and/or fatty acid esters comprises C16:0 and/or at least about 30% w/w of the fatty acids and/or fatty acid esters comprises C18:1.

Preferably, the second carbon source comprises one or more vegetable oils.

Preferably, the second carbon source comprises palm oil.

Preferably, the media is a nitrogen limited media.

Preferably, the media comprises carbon and nitrogen, wherein the carbon to nitrogen ratio is greater than about 40.

Preferably, the organism is a yeast and the C16:0 LPAT is AGPAT1.

Preferably, the organism is *Saccharomyces cerevisiae* and the C16:0 LPAT is AGPAT1.

According to another aspect of the present invention, there is provided a non-human organism, wherein the organism is *Saccharomyces cerevisiae* genetically modified to express AGPAT1.

Preferably, the organism is a Prototheca algae.

Preferably, the C16:0 LPAT is selected from:—
(i) a chloroplast LPAT which lacks a functional chloroplast targeting sequence, preferably a plant chloroplast LPAT which lacks a functional chloroplast targeting sequence;
(ii) AGPAT1 (Human 1-acylglycerol-3-phosphate O-acyltransferase isoform 1);
(iii) CreLPAT;
(iv) *Nannochloropsis* sp. LPAT2;
(v) *Nannochloropsis* sp. LPAT3;
(vi) *Nannochloropsis* sp. LPAT4; and
(vii) *Synechocystis* sp. LPAT.

Preferably, the organism is treated or genetically modified to disrupt the chloroplast targeting sequence.

Preferably, the chloroplast LPAT is treated or genetically modified to disrupt the chloroplast targeting sequence.

Preferably, the chloroplast LPAT is a modified chloroplast LPAT which lacks at least a part of, preferably all of, a chloroplast targeting sequence, preferably a modified plant chloroplast LPAT which lacks at least a part of, preferably all of, a chloroplast targeting sequence.

Preferably, the chloroplast targeting sequence is an N-terminal chloroplast targeting sequence.

Preferably, the organism is modified or treated to disrupt the chloroplast LPAT chloroplast targeting sequence, for example by genetic modification, preferably by genetic modification of the chloroplast targeting sequence.

Preferably, said genetic modification comprises the addition or removal of nucleic acid and/or amino acid residues.

Preferably, the organism is genetically modified to express a lysophosphatidic acid acyltransferase specific for C16:0-CoA (C16:0 LPAT) localised in the endoplasmic reticulum.

Preferably, the organism is a plant and the C16:0 LPAT is expressed under the control of a seed-specific promoter, preferably the oleosin, napin or glycinin seed specific promoter, most preferably, the seed-specific soybean glycinin-1 promoter (ProGLY).

Preferably, the organism is treated or genetically modified to suppress or prevent activity of native ER LPAT.

Preferably, the organism is treated or genetically modified to suppress or prevent activity of one or more native ER LPATs.

Preferably, the ER LPAT is not specific for C16:0-CoA.

Preferably, the activity of native ER LPAT is suppressed or prevented using artificial micro-RNA.

Preferably, the activity of native ER LPAT is suppressed or prevented using RNAi and/or genome editing and/or mutation breeding.

Preferably, the artificial micro-RNA is under the control of a seed-specific promoter, preferably the oleosin, napin or glycinin seed specific promoter.

Preferably, the organism comprises a disruptive insertion in a non-coding region 5' of the ER LPAT translational start site. Preferably, the disruptive insertion is at about 139 bp 5' of the ER LPAT translational start site. Preferably, the disruptive insertion is 139 bp 5' of the ER LPAT translational start site. Preferably, the disruptive insertion is a T-DNA insertion.

Alternatively, the disruptive insertion is at about 302 bp 5', for example 302 bp 5', of the ER LPAT translational start site.

Preferably, conversion of diacylglycerol to phosphatidylcholine is suppressed or prevented in the organism.

Preferably, conversion of diacylglycerol to phosphatidylcholine is suppressed or prevented in the organism by suppressing or preventing the activity of choline phosphotransferase (CPT1) and/or ethanolamine phosphotransferase (EPT1).

Preferably, the organism is treated or genetically modified to disrupt CPT1 and/or EPT1.

Preferably, the activity of phosphatidylcholine:diacylglycerol cholinephosphotransferase (PDCT) is suppressed or prevented in the organism.

Preferably, the activity of one or more phosphatidylcholine:diacylglycerol cholinephosphotransferases (PDCTs) is suppressed or prevented in the organism.

Preferably, diacylglycerol conversion to and/or from phosphatidylcholine is reduced by suppressing or preventing the activity of phosphatidylcholine:diacylglycerol cholinephosphotransferase (PDCT) in the organism, for example by suppressing or preventing the activity of one or more phosphatidylcholine:diacylglycerol cholinephosphotransferases (PDCTs) in the organism.

Preferably, the organism is treated or genetically modified to increase total C16:0 content.

Preferably, the organism is a plant which is treated or genetically modified to increase total C16:0 content, preferably in the seeds, fruits or the leaves, most preferably in the seeds or fruits.

Preferably, the organism expresses a FATB thioesterase, preferably an *Arabidopsis thaliana* FATB thioesterase.

Preferably, the organism is genetically modified to expresses the/a FATB thioesterase.

Preferably, the organism is treated or genetically modified to disrupt plastidic beta-ketoacyl-ACP synthase II.

Preferably, the organism is treated or genetically modified to disrupt the KASII gene FAB1 (At1g74960).

Preferably, the organism is treated or genetically modified to disrupt the fatty acid elongase gene (FAE1).

Preferably, the organism is treated or genetically modified to disrupt the fatty acid desaturase 2 gene (FAD2).

Preferably, the organism expresses a FATB thioesterase, preferably an *Arabidopsis thaliana* FATB thioesterase and is treated or genetically modified to disrupt the fatty acid desaturase 2 gene (FAD2).

Preferably, the organism is treated or genetically modified to express the/a FATB thioesterase gene and is treated or genetically modified to disrupt the fatty acid desaturase 2 gene (FAD2).

Preferably, the organism, preferably a plant, is treated or genetically modified to disrupt the KASII gene FAB1, fatty acid elongase gene (FAE1) and fatty acid desaturase 2 gene (FAD2).

Preferably, (i) the organism, preferably a plant, is treated or genetically modified to disrupt the KASII gene FAB1, fatty acid elongase gene (FAE1), and fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

Preferably, (i) the organism, preferably a plant, is treated or genetically modified to disrupt the KASII gene FAB1, fatty acid elongase gene (FAE1), and fatty acid desaturase 2 gene (FAD2), (ii) conversion of diacylglycerol to phosphatidylcholine is suppressed or prevented in the organism, (iii) activity of native endoplasmic reticulum lysophosphatidic acid acyltransferase (ER LPAT) is suppressed or prevented in the organism, and (iv) the C16:0 LPAT is ACTS-LPAT1 or AGPAT1.

Preferably, (i) the organism, preferably a plant, expresses a FATB thioesterase, preferably an *Arabidopsis thaliana* FATB thioesterase and is treated or genetically modified to disrupt the fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

Preferably, (i) the organism, preferably a plant, expresses a FATB thioesterase, preferably an *Arabidopsis thaliana* FATB thioesterase and is treated or genetically modified to disrupt the fatty acid desaturase 2 gene (FAD2), (ii) conversion of diacylglycerol to phosphatidylcholine is suppressed or prevented in the organism, (iii) activity of native endoplasmic reticulum lysophosphatidic acid acyltransferase (ER LPAT) is suppressed or prevented in the organism, and (iv) the C16:0 LPAT is ACTS-LPAT1 or AGPAT1.

According to another aspect of the present invention, there is provided a non-human organism, preferably a plant, in which a C16:0 LPAT is expressed and wherein (i) the organism is treated or genetically modified to disrupt the KASII gene FAB1, fatty acid elongase gene (FAE1), and fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

According to another aspect of the present invention, there is provided a non-human organism, preferably a plant, in which a C16:0 LPAT is expressed and wherein (i) the organism expresses a FATB thioesterase, preferably an *Arabidopsis thaliana* FATB thioesterase and is treated or genetically modified to disrupt the fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

According to another aspect of the present invention, there is provided a non-human organism, preferably a plant, in which ACTS-LPAT1 is expressed and wherein (i) the organism is treated or genetically modified to disrupt the KASII gene FAB1, fatty acid elongase gene (FAE1), and fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

According to another aspect of the present invention, there is provided a non-human organism, preferably a plant, in which ACTS-LPAT1 is expressed and wherein (i) the organism expresses a FATB thioesterase, preferably an *Arabidopsis thaliana* FATB thioesterase and is treated or genetically modified to disrupt the fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

According to another aspect of the present invention, there is provided a non-human organism, preferably a plant, in which AGPAT1 is expressed and wherein (i) the organism is treated or genetically modified to disrupt the KASII gene FAB1, fatty acid elongase gene (FAE1), and fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

According to another aspect of the present invention, there is provided a non-human organism, preferably a plant, in which AGPAT1 is expressed and wherein (i) the organism expresses a FATB thioesterase, preferably an *Arabidopsis thaliana* FATB thioesterase and is treated or genetically modified to disrupt the fatty acid desaturase 2 gene (FAD2), (ii) conversion of diacylglycerol to phosphatidylcholine is suppressed or prevented in the organism, and (iii) activity of native endoplasmic reticulum lysophosphatidic acid acyltransferase (ER LPAT) is suppressed or prevented in the organism.

Preferably, conversion of diacylglycerol to phosphatidylcholine is suppressed or prevented in the organism by suppressing or preventing the activity of phosphatidylcholine:diacylglycerol cholinephosphotransferase (PDCT).

Preferably, conversion of diacylglycerol to phosphatidylcholine is suppressed or prevented in the organism by suppressing or preventing the activity of choline phosphotransferase (CPT1) and/or ethanolamine phosphotransferase (EPT1).

Preferably, the organism is treated or genetically modified to expresses the/a FATB thioesterase gene.

According to another aspect of the present invention, there is provided a non-human organism, preferably a plant, in which a chloroplast lysophosphatidic acid acyltransferase (LPAT) is expressed, wherein said chloroplast LPAT lacks a functional chloroplast targeting signal.

As detailed above, remarkably, when the N-terminal chloroplast targeting signal is prevented from functioning, it has been found that the chloroplast LPAT relocates to the endoplasmic reticulum where it esterifies C16:0 to the sn-2 position on the glycerol backbone.

Preferably, the organism is treated or genetically modified to disrupt the chloroplast targeting sequence.

Preferably, the chloroplast LPAT is treated or genetically modified to disrupt the chloroplast targeting sequence.

Preferably, the chloroplast LPAT is a modified chloroplast LPAT which lacks at least a part of, preferably all of, a chloroplast targeting sequence, preferably a modified plant chloroplast LPAT which lacks at least a part of, preferably all of, a chloroplast targeting sequence.

Preferably, the chloroplast targeting sequence is an N-terminal chloroplast targeting sequence.

Preferably, the organism is modified or treated to disrupt the chloroplast LPAT chloroplast targeting sequence, for example by genetic modification, preferably by genetic modification of the chloroplast targeting sequence.

Preferably, said genetic modification comprises the addition or removal of nucleic acid and/or amino acid residues.

Preferably, activity of native endoplasmic reticulum (ER) LPAT is suppressed or prevented in the organism.

Preferably, activity of one or more native endoplasmic reticulum (ER) LPATs is suppressed or prevented in the organism.

Preferably, the non-human organism is polyploid.

Within this specification, reference to "suppressed" means reduced but not prevented.

Preferably, suppressed means reduced by at least about 50%, preferably by at least about 60%, preferably by at least about 70%, preferably by at least about 80%, preferably by at least about 85%, preferably by at least about 90%, preferably by at least about 95%, preferably by at least about 98%.

Preferably, suppressed means reduced by about 83%.

Preferably, suppressed means reduced by between about 50% and about 98%, preferably between about 60% and about 95%, preferably between about 70% and about 90%, preferably between about 80% and about 90%.

Preferably, the C16:0 LPAT is codon optimised for expression in the organism.

Preferably, the C16:0 LPAT is codon optimised for expression in plants, fungi, yeast or algae. Most preferably, the lysophosphatidic acid acyltransferase is codon optimised for expression in plants or yeast.

Preferably, reference to a "modified chloroplast lysophosphatidic acid acyltransferase (LPAT)" means a protein encoded by a nucleotide sequence having at least about 80% sequence identity to SEQ ID NO:1 or SEQ ID NO:38, preferably SEQ ID NO:1, preferably at least about 85% sequence identity, preferably at least about 90% sequence identity, preferably at least about 95% sequence identity, preferably at least about 98% sequence identity, preferably at least about 99% sequence identity to SEQ ID NO:1 or SEQ ID NO:38, preferably to SEQ ID NO:1.

Preferably, reference to a "modified chloroplast lysophosphatidic acid acyltransferase (LPAT)" means a protein comprising an amino acid sequence having at least about 80% sequence identity to SEQ ID NO:2, preferably at least about 85% sequence identity, preferably at least about 90% sequence identity, preferably at least about 95% sequence identity, preferably at least about 98% sequence identity, preferably at least about 99% sequence identity to SEQ ID NO:2.

Preferably, reference to a "modified chloroplast lysophosphatidic acid acyltransferase (LPAT)" means a protein encoded by the nucleotide sequence of SEQ ID NO:1 or SEQ ID NO:38 and/or a protein comprising the amino acid sequence of SEQ ID NO:2.

Preferably, the modified chloroplast LPAT is expressed under the control of a seed-specific promoter.

Preferably, the modified chloroplast LPAT is expressed under the control of the seed-specific soybean glycinin-1 promoter (ProGLY).

Preferably, the modified chloroplast LPAT is a truncated chloroplast LPAT which lacks a functional chloroplast targeting signal.

Preferably, the organism comprises a disruptive insertion in a non-coding region 5' of the ER LPAT translational start site. Preferably, the disruptive insertion is at about 139 bp 5' of the ER LPAT translational start site. Preferably, the disruptive insertion is 139 bp 5' of the ER LPAT translational start site. Preferably, the disruptive insertion is a T-DNA insertion.

Preferably, the activity of phosphatidylcholine:diacylglycerol cholinephosphotransferase (PDCT) is suppressed or prevented in the organism.

Preferably, reference to "AGPAT1" means a protein comprising an amino acid sequence having at least about 80% sequence identity to SEQ ID NO:40, preferably, at least about 85% sequence identity, preferably at least about 90% sequence identity, preferably at least about 95% sequence identity, preferably at least about 98% sequence identity, preferably at least about 99% sequence identity to SEQ ID NO: 40.

Preferably, reference to "AGPAT1" means a protein encoded by a nucleotide sequence having at least about 80% sequence identity to SEQ ID NO:26, 37 or 39, preferably, at least about 85% sequence identity, preferably at least about 90% sequence identity, preferably at least about 95% sequence identity, preferably at least about 98% sequence identity, preferably at least about 99% sequence identity to SEQ ID NO:26, 37 or 39.

Preferably, reference to a "AGPAT1" means a protein encoded by the nucleotide sequence of SEQ ID NO:26, 37 or 39 and/or a protein comprising the amino acid sequence of SEQ ID NO:40.

Preferably, reference to "CreLPAT" means a protein comprising an amino acid sequence having at least about 80% sequence identity to SEQ ID NO:42, preferably, at least about 85% sequence identity, preferably at least about 90% sequence identity, preferably at least about 95% sequence identity, preferably at least about 98% sequence identity, preferably at least about 99% sequence identity to SEQ ID NO: 42.

Preferably, reference to "CreLPAT" means a protein encoded by a nucleotide sequence having at least about 80% sequence identity to SEQ ID NO:36 or SEQ ID NO:41, preferably, at least about 85% sequence identity, preferably at least about 90% sequence identity, preferably at least about 95% sequence identity, preferably at least about 98% sequence identity, preferably at least about 99% sequence identity to SEQ ID NO:36 or SEQ ID NO:41.

Preferably, reference to a "CreLPAT" means a protein encoded by the nucleotide sequence of SEQ ID NO:36 or SEQ ID NO:41 and/or a protein comprising the amino acid sequence of SEQ ID NO:42.

Preferably, reference to "*Nannochloropsis* sp. LPAT2" means a protein comprising an amino acid sequence having at least about 80% sequence identity to SEQ ID NO:44, preferably, at least about 85% sequence identity, preferably at least about 90% sequence identity, preferably at least about 95% sequence identity, preferably at least about 98% sequence identity, preferably at least about 99% sequence identity to SEQ ID NO: 44.

Preferably, reference to "*Nannochloropsis* sp. LPAT2" means a protein encoded by a nucleotide sequence having at least about 80% sequence identity to SEQ ID NO:43, preferably, at least about 85% sequence identity, preferably at least about 90% sequence identity, preferably at least about 95% sequence identity, preferably at least about 98% sequence identity, preferably at least about 99% sequence identity to SEQ ID NO:43.

Preferably, reference to a "*Nannochloropsis* sp. LPAT2" means a protein encoded by the nucleotide sequence of SEQ ID NO:43 and/or a protein comprising the amino acid sequence of SEQ ID NO:44.

Preferably, reference to "*Nannochloropsis* sp. LPAT3" means a protein comprising an amino acid sequence having at least about 80% sequence identity to SEQ ID NO:46, preferably, at least about 85% sequence identity, preferably at least about 90% sequence identity, preferably at least about 95% sequence identity, preferably at least about 98% sequence identity, preferably at least about 99% sequence identity to SEQ ID NO: 46.

Preferably, reference to "*Nannochloropsis* sp. LPAT3" means a protein encoded by a nucleotide sequence having at least about 80% sequence identity to SEQ ID NO:45, preferably, at least about 85% sequence identity, preferably at least about 90% sequence identity, preferably at least about 95% sequence identity, preferably at least about 98% sequence identity, preferably at least about 99% sequence identity to SEQ ID NO:45.

Preferably, reference to a "*Nannochloropsis* sp. LPAT3" means a protein encoded by the nucleotide sequence of SEQ ID NO:45 and/or a protein comprising the amino acid sequence of SEQ ID NO:46.

Preferably, reference to "*Nannochloropsis* sp. LPAT4" means a protein comprising an amino acid sequence having at least about 80% sequence identity to SEQ ID NO:48, preferably, at least about 85% sequence identity, preferably at least about 90% sequence identity, preferably at least about 95% sequence identity, preferably at least about 98% sequence identity, preferably at least about 99% sequence identity to SEQ ID NO: 48.

Preferably, reference to "*Nannochloropsis* sp. LPAT4" means a protein encoded by a nucleotide sequence having at least about 80% sequence identity to SEQ ID NO:47, preferably, at least about 85% sequence identity, preferably at least about 90% sequence identity, preferably at least about 95% sequence identity, preferably at least about 98% sequence identity, preferably at least about 99% sequence identity to SEQ ID NO:47.

Preferably, reference to a "*Nannochloropsis* sp. LPAT4" means a protein encoded by the nucleotide sequence of SEQ ID NO:47 and/or a protein comprising the amino acid sequence of SEQ ID NO:48.

Preferably, reference to a "*Synechocystis* sp. LPAT" means a protein comprising an amino acid sequence having at least about 80% sequence identity to SEQ ID NO:50, preferably, at least about 85% sequence identity, preferably at least about 90% sequence identity, preferably at least about 95% sequence identity, preferably at least about 98% sequence identity, preferably at least about 99% sequence identity to SEQ ID NO:50.

Preferably, reference to a "*Synechocystis* sp. LPAT" means a protein encoded by a nucleotide sequence having at least about 80% sequence identity to SEQ ID NO:49, preferably, at least about 85% sequence identity, preferably at least about 90% sequence identity, preferably at least about 95% sequence identity, preferably at least about 98% sequence identity, preferably at least about 99% sequence identity to SEQ ID NO:49.

Preferably, reference to a "*Synechocystis* sp. LPAT" means a protein encoded by the nucleotide sequence of SEQ ID NO:49 and/or a protein comprising the amino acid sequence of SEQ ID NO:50.

Preferably, reference to "native endoplasmic reticulum lysophosphatidic acid acyltransferase" means a protein comprising an amino acid sequence having at least about 80% sequence identity to SEQ ID NO:52, SEQ ID NO:54, SEQ ID NO:56, SEQ ID NO:58, SEQ ID NO:60 or SEQ ID NO:62, preferably, at least about 85% sequence identity, preferably at least about 90% sequence identity, preferably at least about 95% sequence identity, preferably at least about 98% sequence identity, preferably at least about 99% sequence identity to SEQ ID NO:52, SEQ ID NO:54, SEQ ID NO:56, SEQ ID NO:58, SEQ ID NO:60 or SEQ ID NO:62.

Preferably, reference to "native endoplasmic reticulum lysophosphatidic acid acyltransferase" means a protein encoded by a nucleotide sequence having at least about 80% sequence identity to SEQ ID NO:51, SEQ ID NO:53, SEQ ID NO:55, SEQ ID NO:57, SEQ ID NO:59 or SEQ ID NO:61, preferably, at least about 85% sequence identity, preferably at least about 90% sequence identity, preferably at least about 95% sequence identity, preferably at least about 98% sequence identity, preferably at least about 99% sequence identity to SEQ ID NO:51, SEQ ID NO:53, SEQ ID NO:55, SEQ ID NO:57, SEQ ID NO:59 or SEQ ID NO:61.

Preferably, reference to a "native endoplasmic reticulum lysophosphatidic acid acyltransferase" means a protein encoded by the nucleotide sequence of SEQ ID NO:51, SEQ ID NO:53, SEQ ID NO:55, SEQ ID NO:57, SEQ ID NO:59 or SEQ ID NO:61 and/or a protein comprising the amino acid sequence of SEQ ID NO:52, SEQ ID NO:54, SEQ ID NO:56, SEQ ID NO:58, SEQ ID NO:60 or SEQ ID NO:62.

Preferably, reference to "phosphatidylcholine:diacylglycerol cholinephosphotransferase" means a protein comprising an amino acid sequence having at least about 80% sequence identity to SEQ ID NO:64, SEQ ID NO:66, SEQ ID NO:68, SEQ ID NO:70 or SEQ ID NO:72, preferably, at least about 85% sequence identity, preferably at least about 90% sequence identity, preferably at least about 95% sequence identity, preferably at least about 98% sequence identity, preferably at least about 99% sequence identity to SEQ ID NO:64, SEQ ID NO:66, SEQ ID NO:68, SEQ ID NO:70 or SEQ ID NO:72.

Preferably, reference to "phosphatidylcholine:diacylglycerol cholinephosphotransferase" means a protein encoded by a nucleotide sequence having at least about 80% sequence identity to SEQ ID NO:63, SEQ ID NO:65, SEQ ID NO:67, SEQ ID NO:69 or SEQ ID NO:71, preferably, at least about 85% sequence identity, preferably at least about 90% sequence identity, preferably at least about 95% sequence identity, preferably at least about 98% sequence identity, preferably at least about 99% sequence identity to SEQ ID NO:63, SEQ ID NO:65, SEQ ID NO:67, SEQ ID NO:69 or SEQ ID NO:71.

Preferably, reference to a "phosphatidylcholine:diacylglycerol cholinephosphotransferase" means a protein encoded by the nucleotide sequence of SEQ ID NO:63, SEQ ID NO:65, SEQ ID NO:67, SEQ ID NO:69 or SEQ ID NO:71 and/or a protein comprising the amino acid sequence of SEQ ID NO:64, SEQ ID NO:66, SEQ ID NO:68, SEQ ID NO:70 or SEQ ID NO:72.

Preferably, reference to "*Arabidopsis thaliana* FATB thioesterase" means a protein comprising an amino acid sequence having at least about 80% sequence identity to SEQ ID NO:73, preferably, at least about 85% sequence identity, preferably at least about 90% sequence identity, preferably at least about 95% sequence identity, preferably at least about 98% sequence identity, preferably at least about 99% sequence identity to SEQ ID NO:73.

Preferably, reference to "*Arabidopsis thaliana* FATB thioesterase" means a protein encoded by a nucleotide sequence having at least about 80% sequence identity to SEQ ID NO:33, preferably, at least about 85% sequence identity, preferably at least about 90% sequence identity, preferably at least about 95% sequence identity, preferably at least about 98% sequence identity, preferably at least about 99% sequence identity to SEQ ID NO:33.

Preferably, reference to a "*Arabidopsis thaliana* FATB thioesterase" means a protein encoded by the nucleotide sequence of SEQ ID NO:33 and/or a protein comprising the amino acid sequence of SEQ ID NO:73.

Preferably, reference to "FAB1" means a protein comprising an amino acid sequence having at least about 80% sequence identity to SEQ ID NO:79, preferably, at least about 85% sequence identity, preferably at least about 90% sequence identity, preferably at least about 95% sequence identity, preferably at least about 98% sequence identity, preferably at least about 99% sequence identity to SEQ ID NO:79.

Preferably, reference to "FAB1" means a protein encoded by a nucleotide sequence having at least about 80% sequence identity to SEQ ID NO:78, preferably, at least about 85% sequence identity, preferably at least about 90% sequence identity, preferably at least about 95% sequence identity, preferably at least about 98% sequence identity, preferably at least about 99% sequence identity to SEQ ID NO:78.

Preferably, reference to "FAB1" means a protein encoded by the nucleotide sequence of SEQ ID NO:78 and/or a protein comprising the amino acid sequence of SEQ ID NO:79.

Preferably, reference to "FAD2" means a protein comprising an amino acid sequence having at least about 80% sequence identity to SEQ ID NO:81 or 85, preferably, at least about 85% sequence identity, preferably at least about 90% sequence identity, preferably at least about 95% sequence identity, preferably at least about 98% sequence identity, preferably at least about 99% sequence identity to SEQ ID NO:81 or 85.

Preferably, reference to "FAD2" means a protein encoded by a nucleotide sequence having at least about 80% sequence identity to SEQ ID NO:80 or 84, preferably, at least about 85% sequence identity, preferably at least about 90% sequence identity, preferably at least about 95% sequence identity, preferably at least about 98% sequence identity, preferably at least about 99% sequence identity to SEQ ID NO:80 or 84.

Preferably, reference to "FAD2" means a protein encoded by the nucleotide sequence of SEQ ID NO:80 or 84 and/or a protein comprising the amino acid sequence of SEQ ID NO:81 or 85.

Preferably, reference to "FAE1" means a protein comprising an amino acid sequence having at least about 80% sequence identity to SEQ ID NO:83 or 87, preferably, at least about 85% sequence identity, preferably at least about 90% sequence identity, preferably at least about 95% sequence identity, preferably at least about 98% sequence identity, preferably at least about 99% sequence identity to SEQ ID NO:83 or 87.

Preferably, reference to "FAE1" means a protein encoded by a nucleotide sequence having at least about 80% sequence identity to SEQ ID NO:82 or 86, preferably, at least about 85% sequence identity, preferably at least about 90% sequence identity, preferably at least about 95% sequence identity, preferably at least about 98% sequence identity, preferably at least about 99% sequence identity to SEQ ID NO:82 or 86.

Preferably, reference to a "FAE1" means a protein encoded by the nucleotide sequence of SEQ ID NO:83 or 87 and/or a protein comprising the amino acid sequence of SEQ ID NO:82 or 86.

Preferably, reference to "choline phosphotransferase (CPT1)" means a protein comprising an amino acid sequence having at least about 80% sequence identity to SEQ ID NO:89, preferably, at least about 85% sequence identity, preferably at least about 90% sequence identity, preferably at least about 95% sequence identity, preferably at least about 98% sequence identity, preferably at least about 99% sequence identity to SEQ ID NO:89.

Preferably, reference to "choline phosphotransferase (CPT1)" means a protein encoded by a nucleotide sequence having at least about 80% sequence identity to SEQ ID NO:88, preferably, at least about 85% sequence identity, preferably at least about 90% sequence identity, preferably at least about 95% sequence identity, preferably at least about 98% sequence identity, preferably at least about 99% sequence identity to SEQ ID NO:88.

Preferably, reference to a "choline phosphotransferase (CPT1)" means a protein encoded by the nucleotide sequence of SEQ ID NO:88 and/or a protein comprising the amino acid sequence of SEQ ID NO:89.

Preferably, reference to "ethanolamine phosphotransferase (EPT1)" means a protein comprising an amino acid sequence having at least about 80% sequence identity to SEQ ID NO:91, preferably, at least about 85% sequence identity, preferably at least about 90% sequence identity, preferably at least about 95% sequence identity, preferably at least about 98% sequence identity, preferably at least about 99% sequence identity to SEQ ID NO:91.

Preferably, reference to "ethanolamine phosphotransferase (EPT1)" means a protein encoded by a nucleotide sequence having at least about 80% sequence identity to SEQ ID NO:90, preferably, at least about 85% sequence identity, preferably at least about 90% sequence identity, preferably at least about 95% sequence identity, preferably at least about 98% sequence identity, preferably at least about 99% sequence identity to SEQ ID NO:90.

Preferably, reference to a "ethanolamine phosphotransferase (EPT1)" means a protein encoded by the nucleotide sequence of SEQ ID NO:90 and/or a protein comprising the amino acid sequence of SEQ ID NO:91.

According to another aspect of the present invention, there is provided a cell of a non-human organism described herein. Preferably, the cell is a recombinant cell.

According to another aspect of the present invention, there is provided a seed for producing a plant as described herein.

According to another aspect of the present invention, there is provided a seed, fruit or a leaf obtained from a plant as described herein.

According to another aspect of the present invention, there is provided triacylglycerol produced from a non-human organism or a cell thereof as described herein.

Preferably, there is provided triacylglycerol produced from a plant, preferably a seed, fruit or a leaf of a plant as described herein.

Preferably, the triacylglycerol comprises more than about 30% of the C16:0 at the sn-2 position, preferably more than about 35%, preferably more than about 40%, preferably more than about 45%, preferably more than about 50%, preferably more than about 55%, preferably more than about 60%, preferably more than about 65%, most preferably more than about 70% of the C16:0 at the sn-2 position.

Preferably, the triacylglycerol comprises between about 30% and about 100% of the C16:0 at the sn-2 position, preferably between about 35% and about 100%, preferably between about 40% and about 100%, preferably between about 45% and about 100%, preferably between about 50% and about 100%, preferably between about 55% and about 100%, preferably between about 60% and about 100%, preferably between about 65% and about 100%, most preferably between about 70% and about 100% of the C16:0 at the sn-2 position.

Preferably the organism is a plant and the triacylglycerol is obtained from a seed, fruit and/or a leaf of the plant.

According to another aspect of the invention, there is provided a method for extracting triacylglycerol from an organism as described herein, preferably a plant as described herein, preferably wherein the method comprises mechanical extraction and/or solvent extraction.

According to another aspect of the invention, there is provided a method for making triacylglycerol from a yeast as described herein, the method comprising culturing said yeast and extracting triacylglycerol therefrom.

In another aspect of the present invention, there is provided a method for producing an infant formula, comprising obtaining triacylglycerol from a non-human organism or a cell thereof as described herein and using said triacylglycerol to produce an infant formula.

Preferably, the organism is a plant and the triacylglycerol is extracted from the plant.

Preferably, the triacylglycerol is extracted from a seed, fruit and/or a leaf of the plant.

According to another aspect of the present invention, there is provided infant formula comprising triacylglycerol as described herein and/or produced from a method as described herein.

According to another aspect of the present invention, there is provided a non-human organism comprising a C16:0 LPAT, wherein the organism is cultured in a media comprising a carbon source, wherein the carbon source comprises a mixture of (i) one or more sugars and (ii) one or more fatty acids and/or fatty acid esters.

Preferably, the carbon source comprises a mixture of (i) one or more sugars and (ii) one or more oils, preferably vegetable oils.

Preferably, the one or more sugars comprise one or more fermentable sugars.

Preferably, the one or more sugars is selected from one or more of xylose, lactose, cellulose, glucose, fructose, sucrose, or hydrolysed lignocellulosic materials.

Preferably, the one or more fatty acids and/or fatty acid esters comprises C16:0.

Preferably, the one or more fatty acids and/or fatty acid esters comprises a mixture of fatty acids and/or fatty acid esters wherein at least about 30% w/w of the fatty acids and/or fatty acid esters comprises C16:0 and/or at least about 30% w/w of the fatty acids and/or fatty acid esters comprises C18:1.

Preferably, the carbon source comprises palm oil in combination with glucose and/or glycerol.

Preferably, the organism is treated or genetically modified to express a C16:0 LPAT.

Preferably, the C16:0 LPAT is a heterologous C16:0 LPAT.

As will be appreciated, the triacylglycerol forms part of the infant formula as an ingredient therein.

Preferably, the infant formula comprises one or more additional ingredients. Preferably, the one or more additional ingredients include one or more of water, lactose, emulsifiers, pre-biotics, pro-biotics, vitamins and/or minerals.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

DETAILED DESCRIPTION

Figure 4:
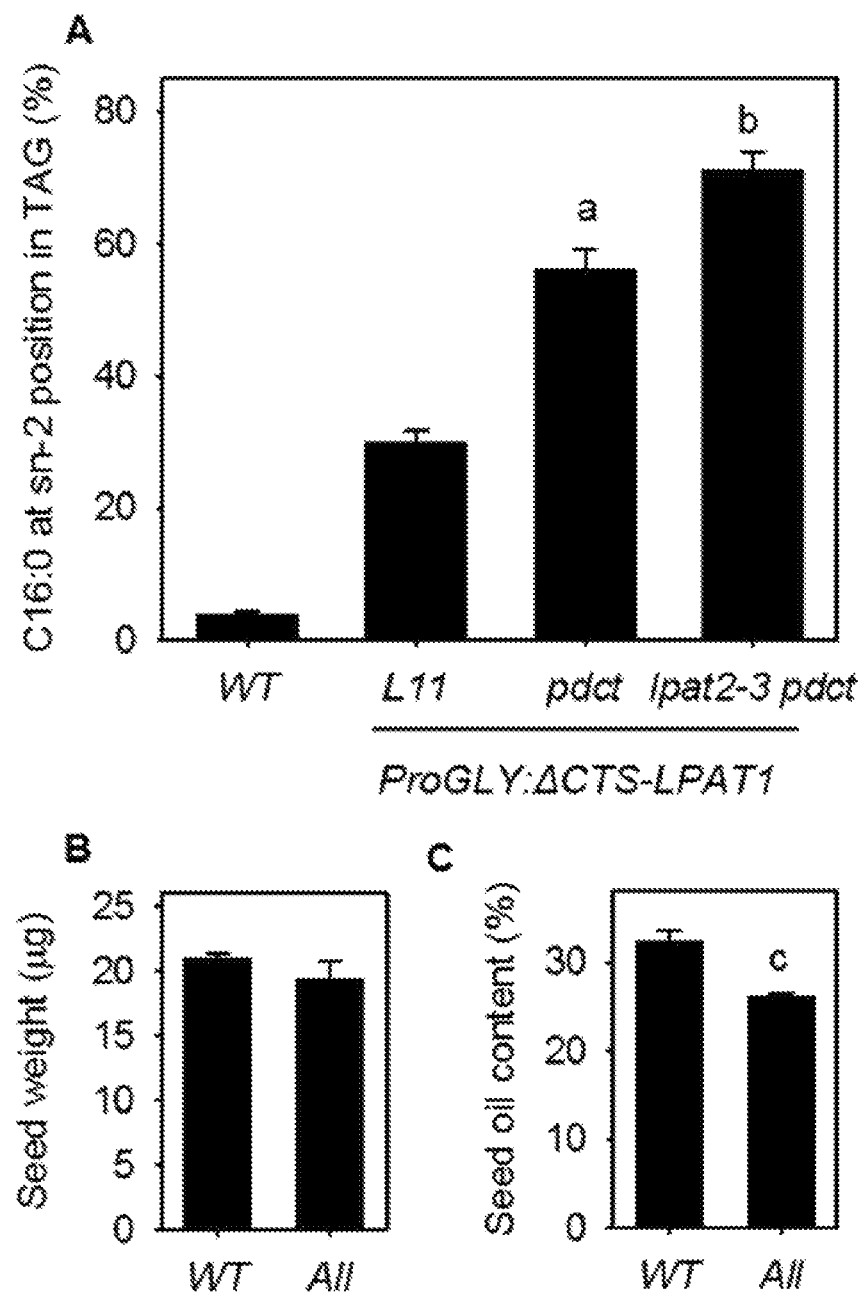
Figure 5:
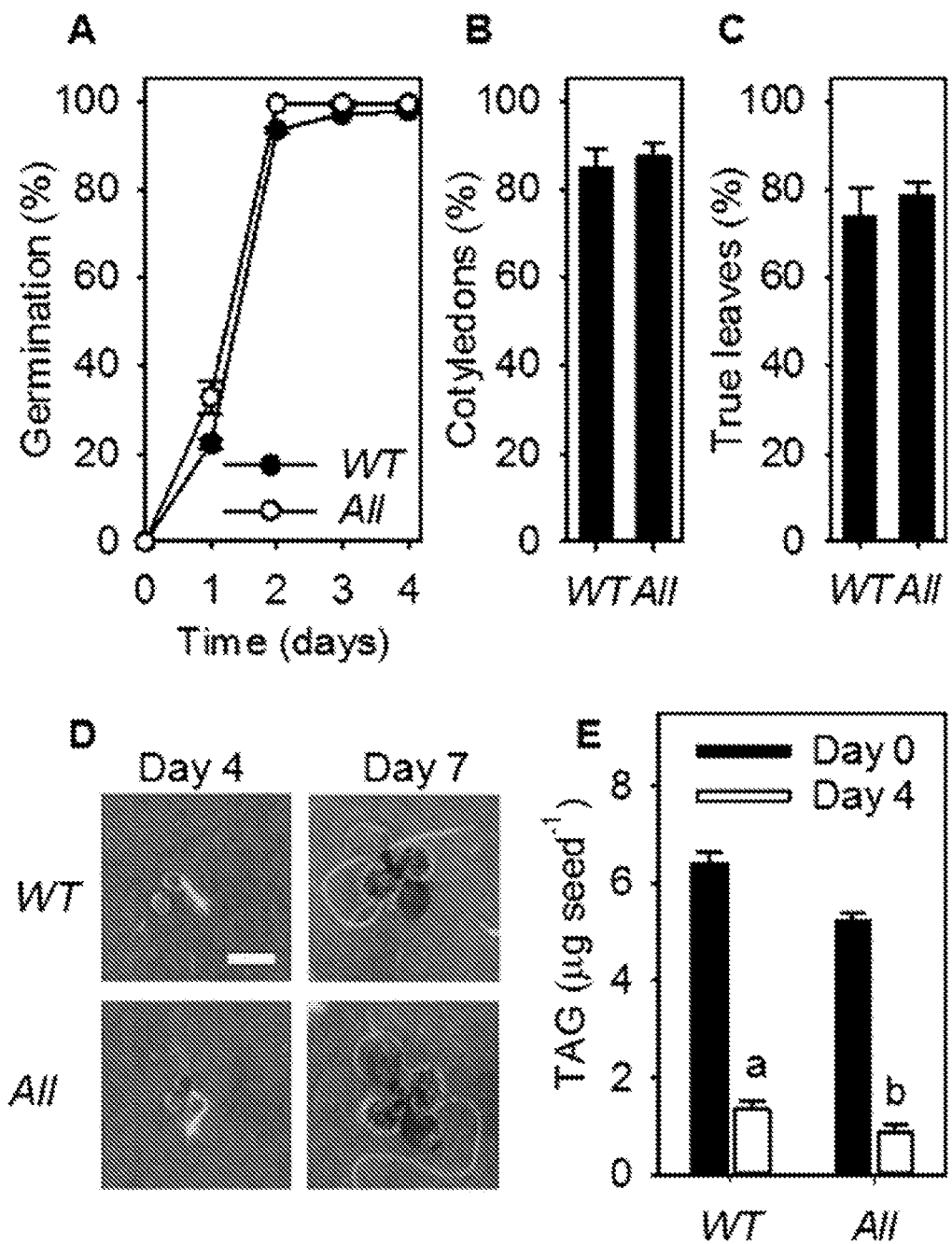
Figure 6:
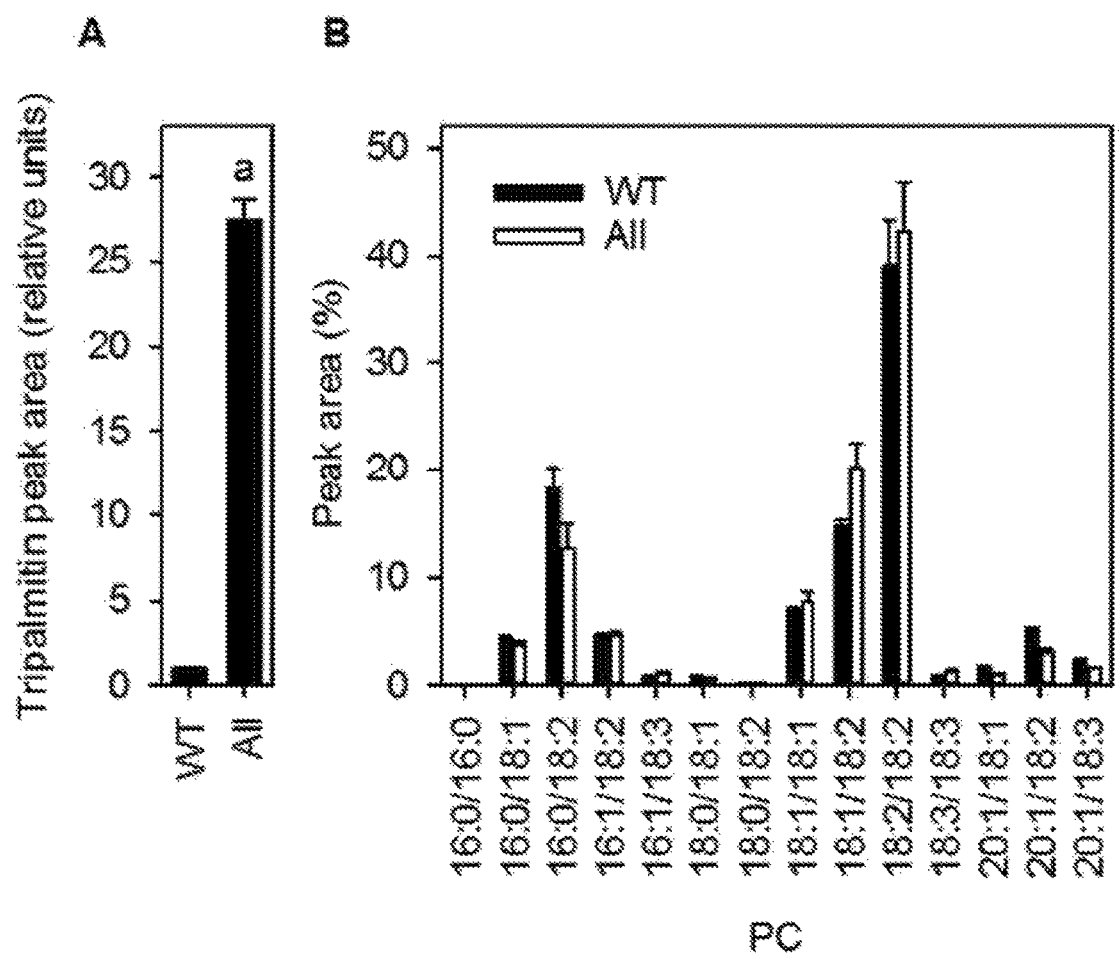
Figure 7:
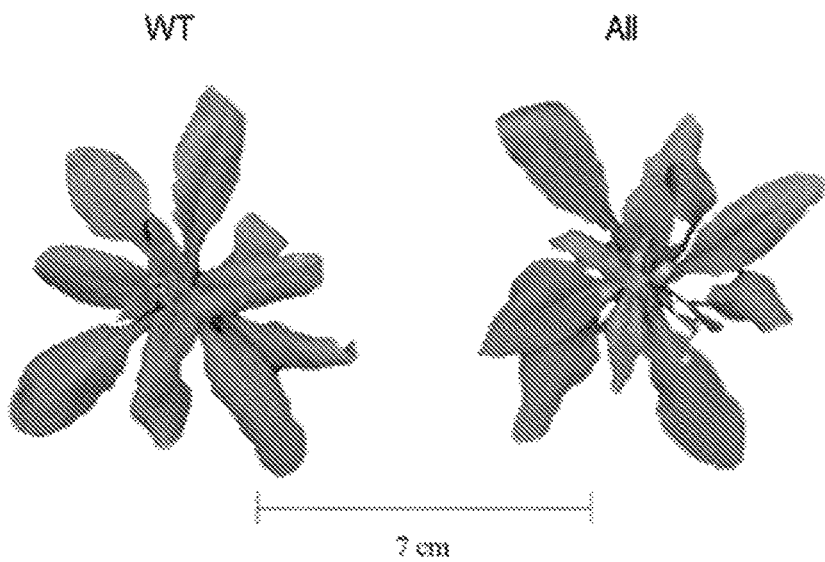
Figure 8:
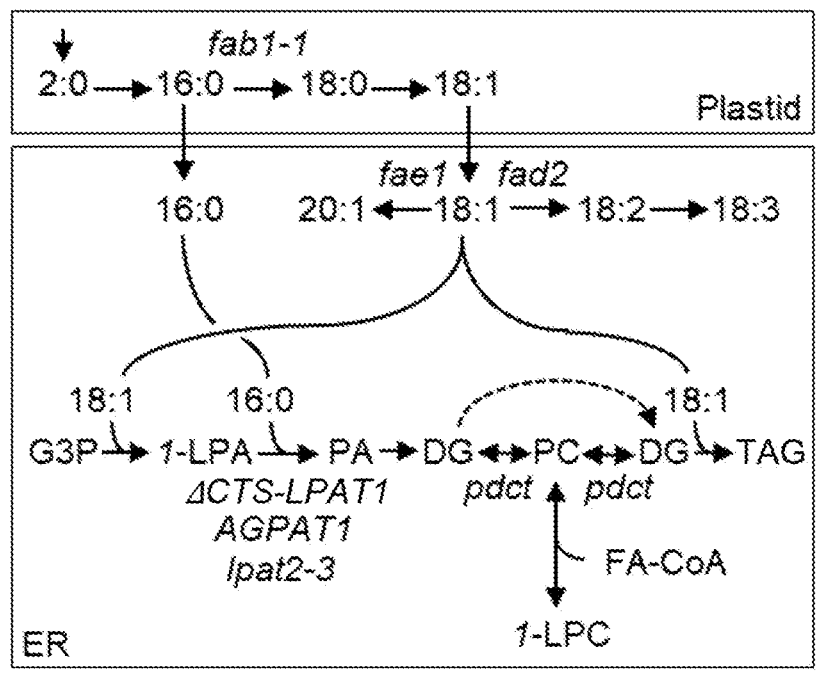
Figure 9:
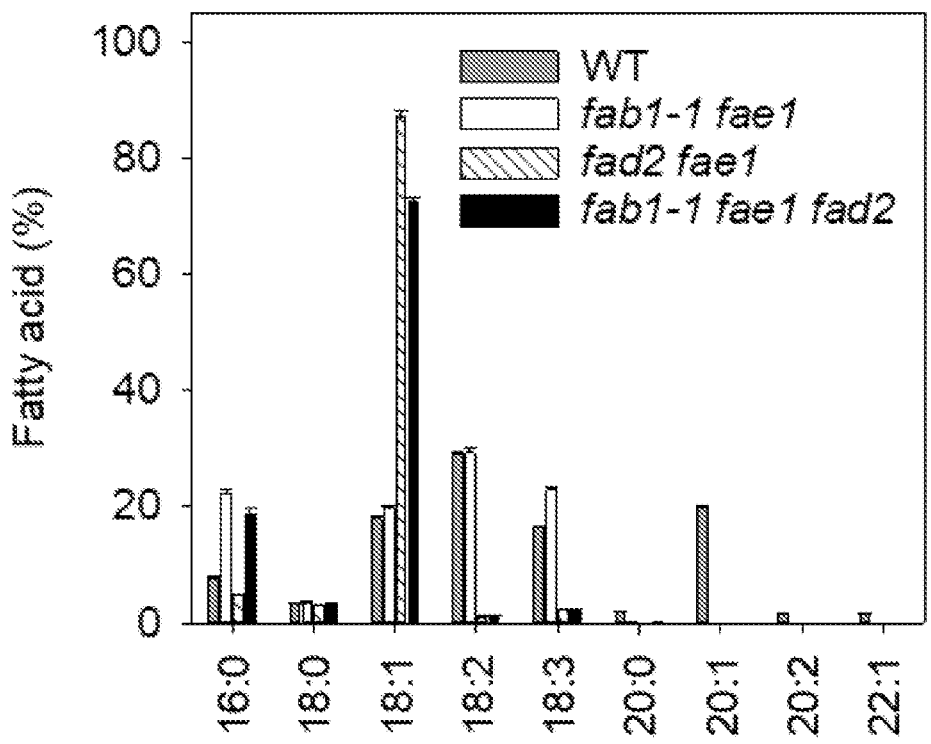
Figure 10:
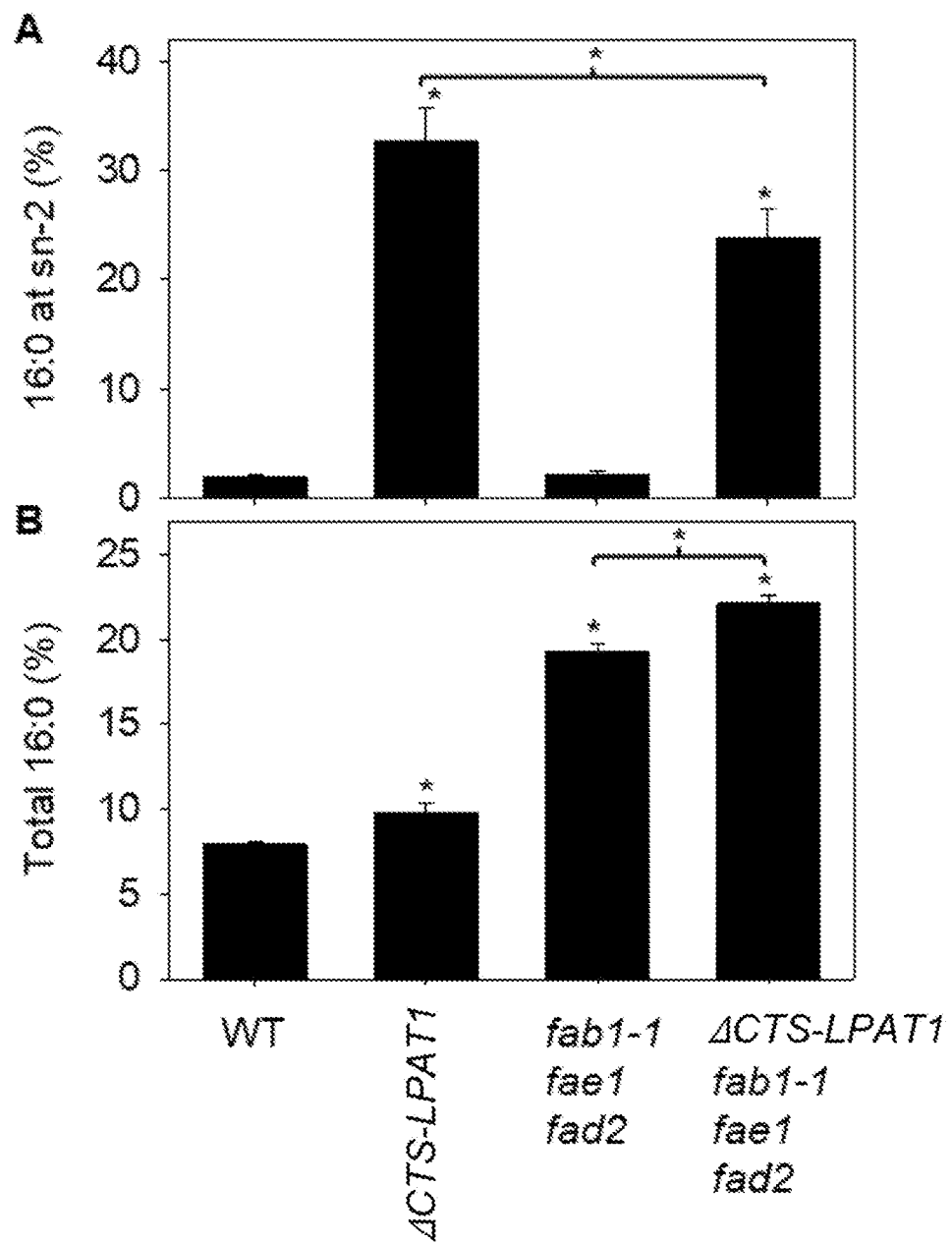
Figure 11:
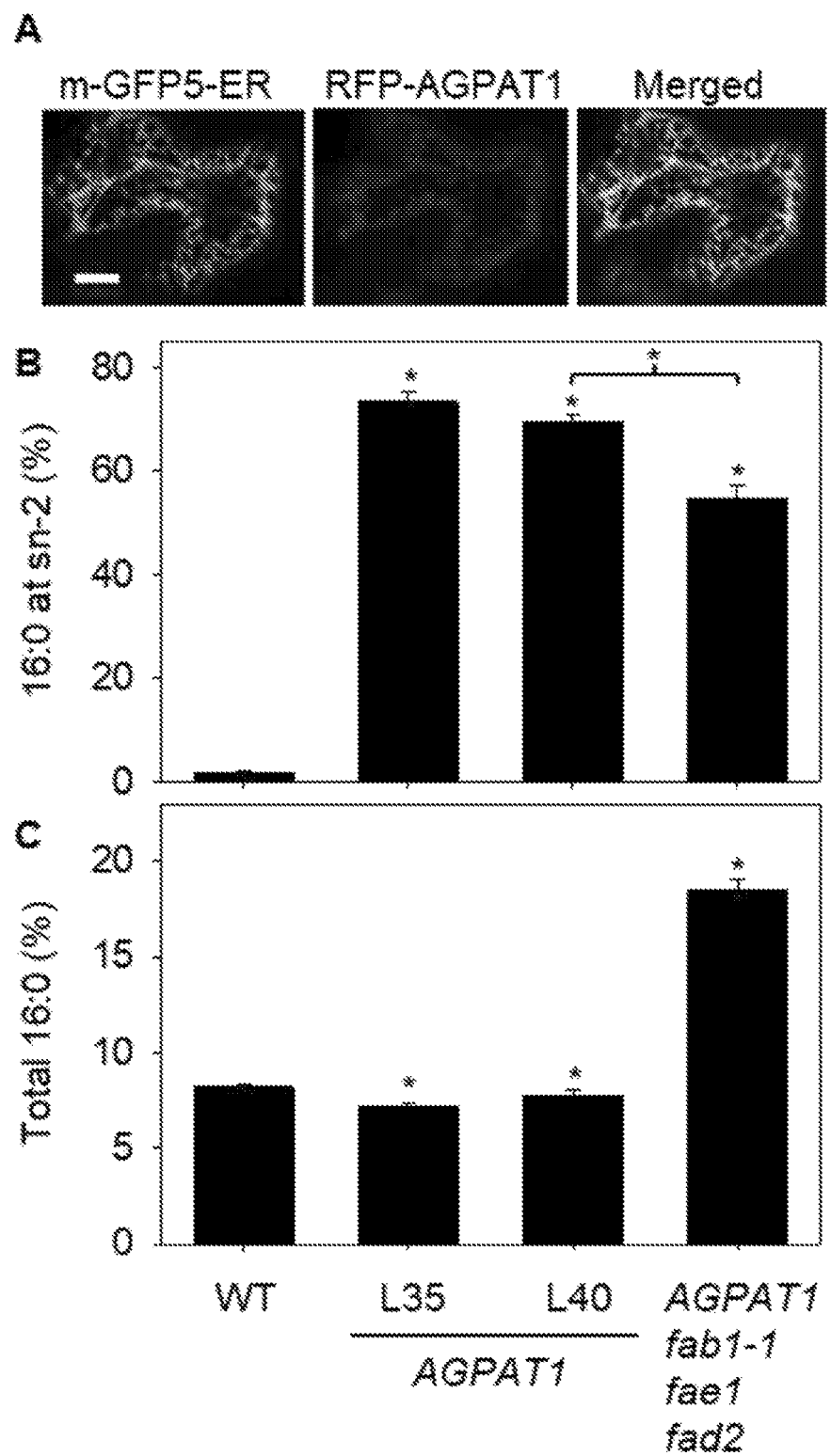

Example embodiments of the present invention will now be described with reference to the accompanying Figures, in which FIG. 1A shows a diagram illustrating the cytosolic and chloroplastic pathways for de novo glycerolipid biosynthesis in *Arabidopsis*. Three modifications enabled palmitoyl (C16:0) groups (white bars) to be incorporated into the sn-2 (or β) position of TAG in developing seeds. (1) Retargeting of LPAT1 to the ER, (2) knock down of LPAT2 and (3) knock out of PDCT. C18:x, long-chain mono- or polyunsaturated fatty acyl groups (black bars); CoA, Coenzyme A; ACP, acyl carrier protein; G3P, glycerol-3-phosphate; 1-LPA, sn-1 lysophosphatidic acid; PA, phosphatidic acid, DAG, diacylglycerol, TAG, triacylglycerol; PC, phosphatidylcholine; 1-LPC, sn-1 lysophosphatidylcholine; FFA, free fatty acid; LPAT, 1-LPA acyltransferase; PDCT, PC:DAG cholinephosphotransferase;

FIG. 1B shows the DNA sequence (SEQ ID NO:1) and the amino acid sequence (SEQ ID NO:2) of ΔCTS-LPAT1;

FIG. 2 shows that chloroplast LPAT1 can be retargeted to the cytosolic glycerolipid biosynthetic pathway to incorporate C16:0 into the sn-2 position of TAG. (A) Laser scanning confocal microscopy image of a *N. benthamiana* epidermal cell transiently expressing RFP-ΔCTS-LPAT1 and m-GFP5-ER marker. Scale bar=20 μm. (B) Effect of seed-specific ΔCTS-LPAT1 expression in *Arabidopsis* on the percentage of C16:0 esterified to the sn-2 position of TAG, verses sn-1+3. WT=wild type; L30, L6 and L11=three independent homozygous ProGLY:ΔCTS-LPAT1 lines. Values are the mean±SE of measurements made on separate seed batches from three plants of each genotype (n=3). a, b and c denote values significantly (P<0.05) different from WT (ANOVA+ Tukey HSD test);

FIG. 3 shows disruption of ER-resident LPAT2 increases C16:0 incorporation into the sn-2 position of TAG. (A) Diagram of LPAT2 locus showing positions of T-DNA insertions in mutant alleles. Effect of lpat2 mutant backgrounds on (B) the percentage of C16:0 esterified to the sn-2 position of TAG, verses sn-1+3, and (C) LPAT2 transcript abundance in seeds expressing ΔCTS-LPAT1. WT=wild type; L11=homozygous ProGLY:ΔCTS-LPAT1 line. Values are the mean±SE of measurements made on separate batches of dry seeds in B and developing siliques in C from three plants of each genotype (n=3). LPAT2 expression was normalised to the geometric mean of three reference genes and expressed relative to WT. a, b & c denote values significantly (P<0.05) different from L11 (ANOVA+Tukey HSD test);

FIG. 4 shows that bypassing flux through PC increases C16:0 incorporation into the sn-2 position of TAG. (A) Effect of pdct mutant background on percentage of C16:0 esterified to the sn-2 position of TAG in ProGLY:ΔCTS-LPAT1 and ProGLY:ΔCTS-LPAT1 lpat2-3 seeds. WT=wild type; L11=homozygous ProGLY:ΔCTS-LPAT1 line. (B) Seed weight and (C) percentage oil content of WT and ProGLY:ΔCTS-LPAT1 lpat2-3 pdct (All). Values are the mean±SE of measurements on separate seed batches from between three and six plants in A and five plants in B and C of each genotype (n=3 to 6). a and b denote values significantly (P<0.05) different from L11 and pdct, respectively (ANOVA+Tukey HSD test) and c from WT (two-tailed Student's t test);

FIG. 5 shows the effect of genetic modifications on seed vigour. Percentage (A) seed germination, (B) cotyledons expanded by day 4 and (C) true leaves developing by day 7. (D) Representative images of seedlings with expanded cotyledons and developing true leaves. (E) Seed/seedling TAG content at day 0 and 4. WT=wild type; All=ProGLY:ΔCTS-LPAT1 lpat2-3 pdct. Values are the mean±SE of measurements made on separate seed batches from three plants of each genotype (n=3). In D, scale bar=2 mm. a and b denote values significantly (P<0.05) different from WT (two-tailed Student's t tests);

FIG. 6 shows the effect of genetic modifications on seed lipid composition. (A) Tripalmitin content and (B) PC composition. WT=wild type; All=ProGLY:ΔCTS-LPAT1 lpat2-3 pdct. Values are the mean±SE of measurements made on separate seed batches from five plants of each genotype (n=5). a denotes a value significantly (P<0.05) different from WT (two-tailed Student's t tests);

FIG. 7 shows images of wild type (WT) and ProGLY:ΔCTS-LPAT1 lpat2-3 pdct (All) plants at onset of flowering;

FIG. 8 shows a simplified diagram illustrating the strategy used to produce OPO in *Arabidopsis* seeds. A combination of the hypomorphic fab1-1 and null fae1 and fad2 mutant alleles was used to produce high levels of 16:0 and 18:1 in seeds. Expression of an ER-localised LPAT with 16:0-CoA preference combined with a hypomorphic lpat2-3 and null pdct mutant allele was then used to enable 16:0 to be preferentially esterified to the sn-2 position of 1-LPA and the products channelled into TG. 16:0, palmitic acid; 18:1, oleic acid; CoA, Coenzyme A; G3P, glycerol-3-phosphate; 1-LPA, sn-1 lysophosphatidic acid; PA, phosphatidic acid, DG, diacylglycerol, TAG, triacylglycerol; PC, phosphatidylcholine; 1-LPC, sn-1 lysophosphatidylcholine; FA, fatty acid;

FIG. 9 shows fatty acid composition of TAG from HPHO seeds. Total fatty acid composition of TAG isolated from WT, fab1-1 fae1, fad2 fae1 and fab1-1 fae1 fad2 seeds. Values are the mean±SE of measurements on seeds from three plants of each genotype;

FIG. 10 shows 16:0 in TAG from WT and HPHO seeds expressing ΔCTS-LPAT1. Percentage of 16:0 esterified to the sn-2 position (A) and 16:0 as a percentage of total fatty acid content (B) measured in TAG isolated from WT, ProGLY:ΔCTS-LPAT1, fab1-1 fad2 fae1 and ProGLY:ΔCTS-LPAT1 fab1-1 fad2 fae1 seeds. Values are the mean±SE of measurements on seeds from three plants of each genotype. * denote values significantly (P<0.05) different either from WT or, where marked in parenthesis, from one another (ANOVA+Tukey HSD test);

FIG. 11 shows 16:0 in TAG from WT and HPHO seeds expressing AGPAT1. Laser scanning confocal microscopy image of a *N. benthamiana* epidermal cell transiently expressing RFP-AGPAT1 and m-GFP5-ER marker (A). Scale bar=20 μm. Percentage of 16:0 esterified to the sn-2 position (B) and 16:0 as a percentage of total fatty acid content (C) measured in TAG isolated from WT, ProGLY: AGPAT1, fab1-1 fad2 fae1 and ProGLY:AGPAT1 fab1-1 fad2 fae1 seeds. Values are the mean±SE of measurements on seeds from three plants of each genotype.

Figure 12:
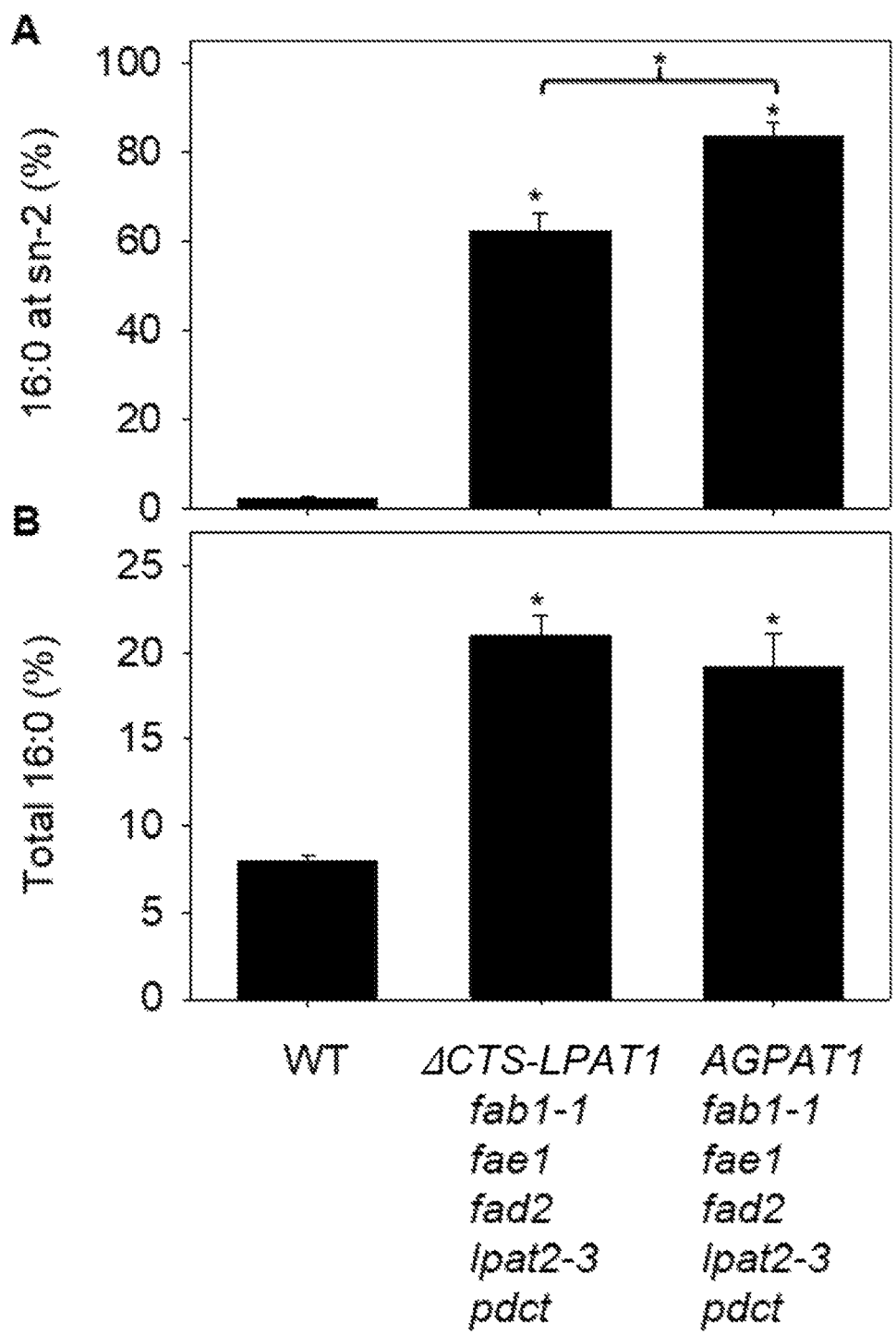
Figure 13:
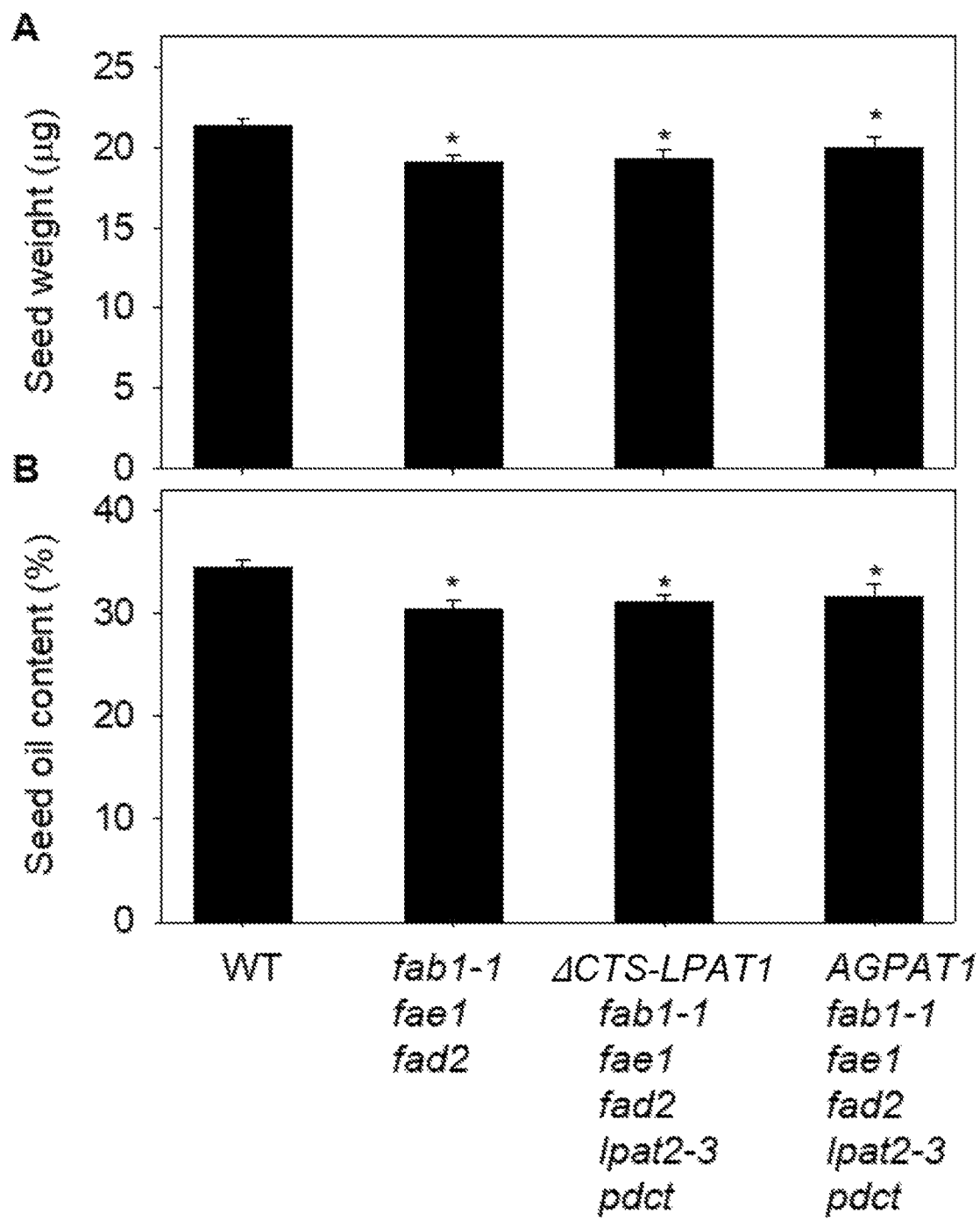
Figure 14:
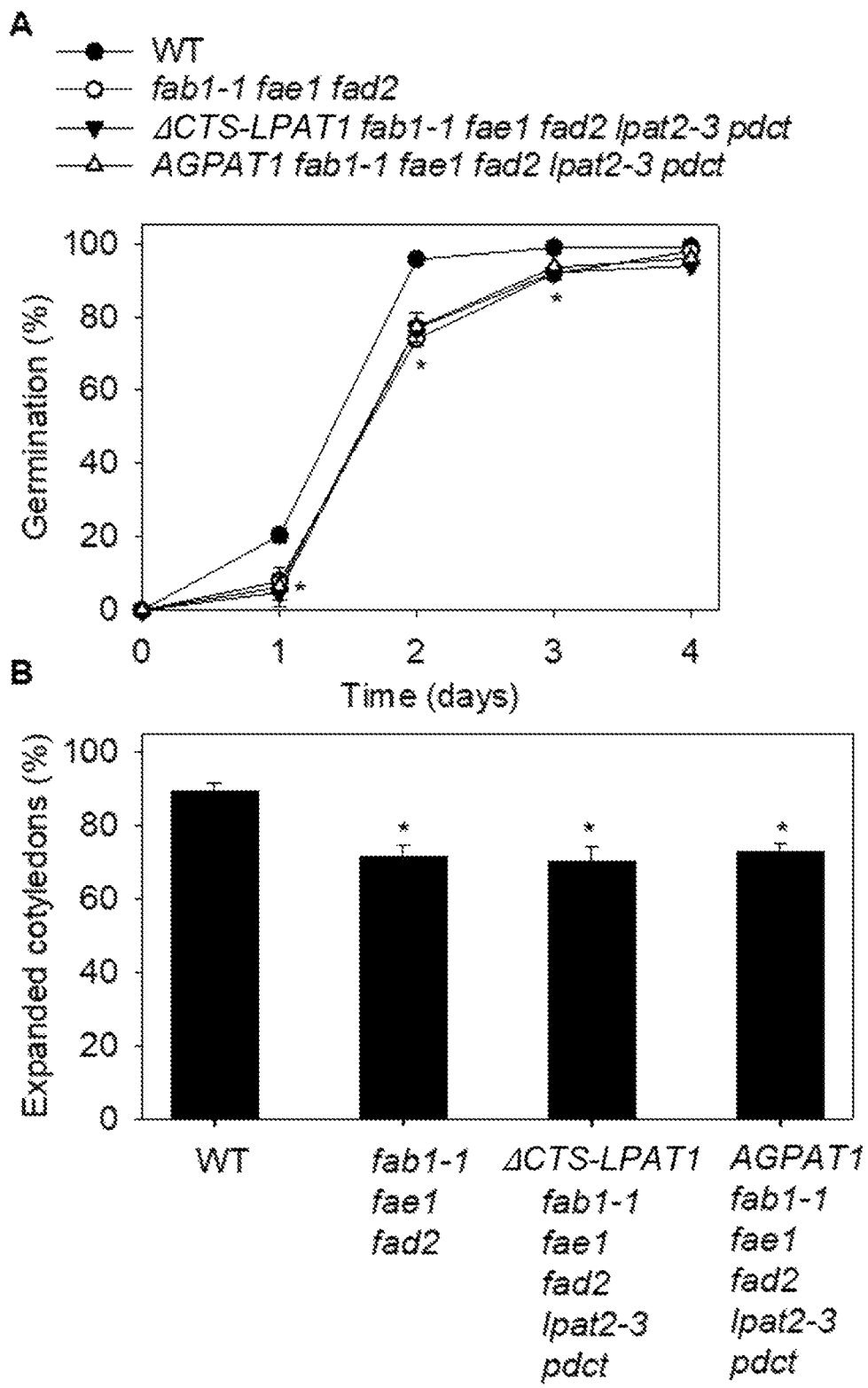

* denote values significantly (P<0.05) different either from WT or, where marked in parenthesis, from one another (ANOVA+Tukey HSD test);

FIG. 12 shows 16:0 in TAG from HPHO lpat2-3 pdct seeds expressing ΔCTS-LPAT1 or AGPAT1. Percentage of 16:0 esterified to the sn-2 position (A) and 16:0 as a percentage of total fatty acid content (B) measured in TAG isolated from WT, ProGLY:ΔCTS-LPAT1 fab1-1 fae1 fad2, lpat2-3 pdct and ProGLY:AGPAT1 fab1-1 fae1 fad2 lpat2-3 pdct seeds. Values are the mean±SE of measurements on seeds from three plants of each genotype. * denote values significantly (P<0.05) different either from WT or, where marked in parenthesis, from one another (ANOVA+Tukey HSD test);

FIG. 13 shows oil content of HPHO lpat2-3 pdct seeds expressing ΔCTS-LPAT1 or AGPAT1. Seed weight (A) and percentage oil content (B) of WT, fab1-1 fae1 fad2, ProGLY:ΔCTS-LPAT1 fab1-1 fae1 fad2, lpat2-3 pdct and ProGLY:AGPAT1 fab1-1 fae1 fad2 lpat2-3 pdct seeds. Values are the mean±SE of measurements on seeds from three plants of each genotype. * denote values significantly (P<0.05) different either from WT (ANOVA+Tukey HSD test); and FIG. 14 shows vigour of HPHO lpat2-3 pdct seeds expressing ΔCTS-LPAT1 or AGPAT1. Percentage seed germination (A) and cotyledons fully expanded by day 4 (B) of WT, fab1-1 fae1 fad2, ProGLY ΔCTS-LPAT1 fab1-1 fae1 fad2, lpat2-3 pdct and ProGLY:AGPAT1 fab1-1 fae1 fad2 lpat2-3 pdct seeds. Values are the mean±SE of measurements on seeds from three plants of each genotype. * denote values significantly (P<0.05) different either from WT (ANOVA+Tukey HSD test).

The present invention relates to a non-human organism for producing triacylglycerol in which the fatty acid stereoisomeric structure of human triacylglycerol is mimicked. In particular, the invention provides non-human organisms which produce triacylglycerol with a similar percentage of C16:0 at the sn-2 position of the glycerol backbone to that of human triacylglycerol.

The aim of the invention described herein was to explore whether the stereoisomeric structure of vegetable oil can be altered by iterative metabolic engineering, so that it mimics HMF. To our knowledge, no land plant (Embryophyta) produces TAG enriched in C16:0 at the sn-2 (verses sn-1/3 positions) and C16:0 is largely excluded from this position in virtually all cases (4,5,8). Even in palm oil that contains ~48% C16:0 in total, only 9% of this occupies the sn-2 position. Described herein is a method for modifying TAG biosynthesis, in the model oilseed *Arabidopsis thaliana*, that results in a stereoisomeric redistribution of acyl groups such that the amount of C16:0 at the sn-2 position increases more than 20-fold to over 70% of the total; a level of enrichment that is comparable to HMF. It is envisaged that applying this technology to oilseed crops will provide a cheaper and therefore more widely accessible source of HMFS for infant formula, given that it could abrogate the need for enzyme-based catalysis.

Within this specification, the term "about" means plus or minus 20%, more preferably plus or minus 10%, even more preferably plus or minus 5%, most preferably plus or minus 2%. Within this specification, the term "a lysophosphatidic acid acyltransferase specific for C16:0-Coenzyme A" means a lysophatidic acid acyltransferase which esterifies C16:0 to the sn-2 position on the glycerol backbone in preference to other fatty acyl-CoA substrates, preferably in preference to longer chain unsaturated fatty acyl-CoAs. Put another way, "a lysophosphatidic acid acyltransferase specific for C16:0-Coenzyme A" has greater activity using C16:0-Coenzyme A than other fatty acyl-CoAs, preferably than longer chain unsaturated fatty acyl-CoAs.

Preferably, the term "a lysophosphatidic acid acyltransferase specific for C16:0-Coenzyme A" means a lysophosphatidic acid acyltransferase which esterifies C16:0 to the sn-2 position on the glycerol backbone of sn-1 lysophosphatidic acid in preference to using fatty acyl-CoA substrates with acyl groups of more than 16 carbon atoms chain length and containing one or more double bonds.

Within this specification, the term "a lysophosphatidic acid acyltransferase which is not specific for C16:0-Coenzyme A" means a lysophosphatidic acid acyltransferase which does not esterify C16:0 to the sn-2 position on the glycerol backbone in preference to other fatty acyl-CoA substrates, preferably in preference to longer chain unsaturated fatty acyl-CoAs. Put another way, "a lysophosphatidic acid acyltransferase which is not specific for C16:0-Coenzyme A" has lower activity using C16:0-Coenzyme A than other fatty acyl-CoAs, preferably than longer chain unsaturated fatty acyl-CoAs.

Preferably, the term "a lysophosphatidic acid acyltransferase which is not specific for C16:0-Coenzyme A" means a lysophosphatidic acid acyltransferase which does not esterify C16:0 to the sn-2 position on the glycerol backbone of sn-1 lysophosphatidic acid in preference to using fatty acyl-CoA substrates with acyl groups of more than 16 carbon atoms and containing one or more double bonds.

Within this specification, "identity," as it is known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. Percentage identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SLAM J. Applied Math., 48: 1073 (1988), all of which are incorporated herein by reference in their entirety. Preferred methods to determine identity are designed to give the largest match between the sequences tested. Methods to determine identity are codified in publicly available computer programs. Preferred computer program methods to determine percentage identity between two sequences include, but are not limited to, the GCG program package (Devereux, J., et al., Nucleic Acids Research 12(1): 387 (1984), which is incorporated herein by reference in its entirety), BLASTP, BLASTN, and FASTA (Atschul, S. F. et al., J. Molec. Biol. 215: 403-410 (1990), which is incorporated herein by reference in its entirety). The BLAST X program is publicly available from NCBI and other sources (BLAST Manual, Altschul, S., et al, NCBI NLM NIH Bethesda, Md. 20894; Altschul, S., et al., J. Mol. Biol. 215: 403-410 (1990), which is incorporated herein by reference in its entirety). As an illustration, by a polynucleotide having a nucleotide sequence having at least, for example, 95% "identity" to a reference nucleotide sequence of "SEQ ID NO: A" it is intended that the nucleotide sequence of the polynucleotide is identical to the reference sequence except that the polynucleotide sequence may include up to five point mutations per each 100 nucleotides of the reference nucleotide sequence of "SEQ ID NO: A." In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of "SEQ ID NO:B" is intended that the amino acid sequence of the polypeptide is identical to the reference sequence except that the polypeptide sequence may include up to five amino acid alterations per each 100 amino acids of the reference amino acid of "SEQ ID NO: B." In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

With reference to the sequence identity described herein, it will be appreciated that many of the non-human organisms to which the present invention relates are polyploid. This means that they can have multiple copies of each gene with small variations in sequence identity. It will, therefore, be appreciated that reference to a particular gene or protein described herein also includes reference to one or more additional copies of that gene and associated encoded protein from the same organism.

Preferably, the non-human organism is polyploid and reference to a particular sequence referred to herein includes reference to a sequence having at least about 80% sequence identity to said sequence, preferably at least about 85% sequence identity, preferably at least about 90% sequence identity, preferably at least about 95% sequence identity, preferably at least about 98% sequence identity, preferably at least about 99% sequence identity to said sequence.

It will be appreciated that reference to "one or more" includes reference to "a plurality".

Within this specification, "genetically modified" means an organism in which the DNA of the organism has been

Example 1

Results and Discussion
LPAT1 can be Redirected to the ER by Removing its Chloroplast Targeting Signal In plant cells, triacylglycerol (TAG) is formed by a cytosolic glycerolipid biosynthetic pathway situated on the endoplasmic reticulum (ER) and the enzyme responsible for acylation of the sn-2 position is lysophosphatidic acid acyltransferase (LPAT) (FIG. 1A). ER-resident isoforms of LPAT can discriminate against C16:0-Coenzyme A (CoA) as a substrate and this might be why C16:0 is excluded from the sn-2 position. To overcome this limitation, we decided to express an LPAT with specificity for C16:0-CoA (FIG. 1A). Several candidate transgenes have been described from cyanobacteria, mammals and algae. However, plants already possess an LPAT with the appropriate selectivity, that resides in the chloroplast (FIG. 1A). This LPAT uses a C16:0-acyl carrier protein (ACP) substrate but will also accept C16:0-CoA in vitro. We therefore decided to test whether chloroplast LPAT could be relocated to the ER (FIG. 1A). Chloroplast LPAT is an integral membrane protein that is nuclear encoded and contains an N-terminal chloroplast targeting signal (CTS). Using transient expression in Nicotiana benthamiana leaves, we found that when 101 amino acid residues containing the CTS are deleted from Brassica napus LPAT1 (FIG. 1B) and replaced with a red fluorescent protein (RFP) marker the RFP-ΔCTS-LPAT1 fusion protein localises to the ER (FIG. 2A).

ΔCTS-LPAT1 Expression Drives C16:0 Incorporation into the Sn-2 Position of TAG

Truncated versions of LPAT1 that lack the CTS are known to be active when expressed in Escherichia coli. To determine whether ΔCTS-LPAT1 functions in plants and can enable C16:0 to be incorporated into the sn-2 position of TAG, we expressed this truncated protein under the control of the seed-specific soybean glycinin-1 promoter (ProGLY) in the model oilseed Arabidopsis thaliana. We selected more than forty primary transformants (T1) using a DsRed fluorescent marker system and analysed the total fatty acyl composition of T2 seed batches. We found that several lines exhibited an increase in total C16:0 content, which suggested that the transgene was promoting C16:0 incorporation into TAG (Table 1).

TABLE 1

Total fatty acid composition of seed batches from individual wild type (WT) and segregating T2 ProGLY:ΔCTS-LPAT1 lines (L1-42). Asterisk denotes single copy lines taken forward for further analysis.

| Line | 16:0 | 18:0 | 18:1 | 18:2 | 18:3 | 20:1 |
|---|---|---|---|---|---|---|
| WT 1 | 8.00 | 2.78 | 13.90 | 30.90 | 22.67 | 22.01 |
| WT 2 | 8.22 | 2.89 | 13.98 | 30.61 | 22.82 | 21.74 |
| WT 3 | 8.25 | 2.89 | 13.55 | 30.63 | 23.06 | 21.88 |
| WT 4 | 8.01 | 2.92 | 14.42 | 30.68 | 22.47 | 21.75 |
| WT 5 | 8.16 | 2.60 | 13.91 | 31.08 | 22.23 | 22.27 |
| L1 | 7.83 | 3.67 | 18.16 | 31.16 | 18.99 | 20.19 |
| L2 | 9.27 | 3.42 | 17.90 | 31.03 | 19.03 | 19.34 |
| L3 | 8.28 | 3.20 | 16.88 | 31.52 | 19.19 | 20.93 |
| L4 | 8.92 | 3.99 | 17.69 | 30.77 | 19.33 | 19.31 |
| L5 | 8.15 | 4.06 | 18.24 | 32.40 | 18.13 | 19.02 |
| L6* | 9.97 | 3.55 | 17.16 | 30.69 | 20.03 | 18.60 |
| L7 | 7.84 | 3.16 | 17.09 | 31.15 | 20.44 | 20.33 |
| L8 | 7.72 | 3.21 | 17.71 | 31.37 | 20.14 | 19.86 |
| L9 | 8.47 | 3.43 | 17.85 | 30.87 | 19.51 | 19.88 |
| L10 | 9.62 | 3.50 | 18.78 | 30.25 | 19.99 | 17.86 |
| L11* | 10.67 | 3.44 | 12.91 | 33.47 | 21.74 | 17.77 |
| L13 | 8.63 | 2.50 | 15.27 | 31.12 | 21.88 | 20.61 |
| L14 | 7.65 | 2.97 | 17.26 | 30.70 | 21.25 | 20.18 |
| L15 | 8.43 | 3.42 | 17.09 | 30.41 | 20.35 | 20.30 |
| L16 | 7.92 | 3.34 | 18.25 | 31.03 | 19.90 | 19.55 |
| L17 | 9.73 | 3.05 | 15.59 | 31.22 | 21.84 | 18.58 |
| L18 | 7.95 | 3.44 | 18.56 | 30.79 | 19.82 | 19.44 |
| L19 | 8.22 | 3.38 | 17.62 | 30.97 | 20.17 | 19.65 |
| L20 | 7.62 | 3.61 | 18.74 | 31.27 | 20.16 | 18.60 |
| L21 | 7.77 | 3.47 | 17.55 | 30.67 | 20.70 | 19.84 |
| L22 | 8.20 | 3.37 | 19.47 | 31.89 | 17.86 | 19.21 |
| L23 | 7.81 | 3.12 | 18.98 | 30.55 | 19.32 | 20.22 |
| L24 | 7.64 | 3.67 | 18.94 | 30.96 | 19.11 | 19.69 |
| L25 | 9.06 | 2.64 | 12.92 | 33.09 | 21.56 | 20.74 |
| L26 | 9.64 | 2.79 | 20.64 | 28.78 | 19.87 | 18.29 |
| L27 | 7.83 | 3.50 | 18.73 | 31.22 | 19.15 | 19.56 |
| L28 | 7.62 | 3.59 | 19.73 | 31.55 | 18.56 | 18.96 |
| L29 | 7.45 | 3.72 | 19.45 | 31.55 | 18.94 | 18.89 |
| L30* | 9.88 | 3.57 | 19.36 | 30.37 | 19.14 | 17.68 |
| L31 | 7.60 | 3.53 | 18.40 | 31.11 | 19.59 | 19.77 |
| L32 | 9.19 | 3.64 | 18.45 | 31.83 | 18.60 | 18.30 |
| L33 | 7.71 | 3.76 | 18.37 | 31.26 | 19.65 | 19.25 |
| L34 | 7.56 | 3.62 | 19.03 | 30.69 | 19.46 | 19.64 |
| L35 | 7.36 | 3.61 | 20.01 | 31.15 | 18.32 | 19.55 |
| L36 | 8.81 | 3.64 | 18.75 | 31.23 | 18.99 | 18.58 |
| L37 | 7.55 | 3.78 | 19.42 | 31.55 | 18.46 | 19.24 |
| L38 | 7.34 | 3.99 | 23.01 | 30.95 | 15.89 | 19.82 |
| L39 | 8.07 | 3.70 | 19.15 | 31.74 | 18.50 | 18.84 |
| L41 | 9.59 | 3.84 | 18.05 | 31.58 | 19.13 | 17.82 |
| L42 | 7.80 | 3.46 | 18.69 | 30.51 | 21.11 | 19.43 |

We selected three independent single copy T2 lines (L30, L6 and L11) with high C16:0 content and obtained homozygous T3 seed. When we purified TAG from these homozygous seed batches and determined its stereochemistry using lipase digestion, we found that the percentage of C16:0 at the sn-2 position (versus sn-1+3), had increased more than 16-fold, from only ~2% in wild type to values ranging between ~32 and ~39% in the three independent ProGLY: ΔCTS-LPAT1 lines (FIG. 2B; Table 2).

TABLE 2

Total and sn-2 fatty acyl composition of TAG from wild type (WT) and homozygous ProGLY:ΔCTS-LPAT1 seeds.

| Line | 16:0 | 18:0 | 18:1 | 18:2 | 18:3 | 20:0 | 20:1 | 20:2 | 22:1 |
|---|---|---|---|---|---|---|---|---|---|
| Total | | | | | | | | | |
| WT 1 | 8.23 | 4.17 | 17.56 | 28.10 | 15.87 | 1.97 | 21.02 | 1.63 | 1.36 |
| WT 2 | 8.14 | 4.05 | 18.19 | 28.06 | 16.31 | 2.01 | 20.21 | 1.62 | 1.42 |
| WT 3 | 8.31 | 3.99 | 16.46 | 28.77 | 16.48 | 2.10 | 20.53 | 1.83 | 1.53 |
| L30 1 | 9.39 | 3.08 | 17.75 | 29.03 | 16.15 | 1.90 | 19.49 | 1.56 | 1.64 |
| L30 2 | 10.26 | 3.27 | 19.08 | 28.37 | 15.43 | 1.95 | 18.89 | 1.37 | 1.38 |
| L30 3 | 8.53 | 3.24 | 18.90 | 28.24 | 15.23 | 1.94 | 20.80 | 1.48 | 1.64 |
| L6 1 | 8.55 | 3.08 | 17.70 | 28.49 | 16.28 | 1.85 | 20.74 | 1.64 | 1.67 |
| L6 2 | 9.58 | 3.26 | 17.94 | 28.43 | 16.32 | 1.95 | 19.54 | 1.53 | 1.53 |
| L6 3 | 8.04 | 2.77 | 17.50 | 29.24 | 16.26 | 1.70 | 20.94 | 1.74 | 1.74 |
| L11 1 | 7.15 | 3.15 | 16.97 | 27.94 | 18.17 | 2.43 | 20.75 | 1.93 | 1.50 |
| L11 2 | 7.68 | 3.29 | 16.20 | 26.98 | 15.14 | 2.14 | 24.81 | 2.19 | 1.30 |
| L11 3 | 7.57 | 3.27 | 15.79 | 26.20 | 18.70 | 2.13 | 21.95 | 2.46 | 1.93 |

TABLE 2-continued

Total and sn-2 fatty acyl composition of TAG from wild type
(WT) and homozygous ProGLY:ΔCTS-LPAT1 seeds.

| Line | \multicolumn{9}{c}{Fatty acid content (%)} | | | | | | | | |
|---|---|---|---|---|---|---|---|---|---|
| | 16:0 | 18:0 | 18:1 | 18:2 | 18:3 | 20:0 | 20:1 | 20:2 | 22:1 | sn-2

| Line | 16:0 | 18:0 | 18:1 | 18:2 | 18:3 | 20:0 | 20:1 | 20:2 | 22:1 |
|---|---|---|---|---|---|---|---|---|---|
| WT 1 | 0.53 | 0.25 | 18.07 | 53.05 | 28.10 | 0.00 | 0.00 | 0.00 | 0.00 |
| WT 2 | 0.33 | 0.24 | 18.49 | 52.52 | 28.43 | 0.00 | 0.00 | 0.00 | 0.00 |
| WT 3 | 0.60 | 0.53 | 16.70 | 54.30 | 27.87 | 0.00 | 0.00 | 0.00 | 0.00 |
| L30 1 | 9.22 | 0.30 | 16.65 | 49.81 | 24.03 | 0.00 | 0.00 | 0.00 | 0.00 |
| L30 2 | 7.50 | 0.64 | 19.15 | 49.70 | 23.01 | 0.00 | 0.00 | 0.00 | 0.00 |
| L30 3 | 10.01 | 0.64 | 17.79 | 48.73 | 22.83 | 0.00 | 0.00 | 0.00 | 0.00 |
| L6 1 | 10.17 | 0.68 | 15.88 | 49.23 | 24.04 | 0.00 | 0.00 | 0.00 | 0.00 |
| L6 2 | 9.21 | 0.26 | 17.24 | 48.90 | 24.40 | 0.00 | 0.00 | 0.00 | 0.00 |
| L6 3 | 8.59 | 0.75 | 15.53 | 50.71 | 24.42 | 0.00 | 0.00 | 0.00 | 0.00 |
| L11 1 | 8.49 | 0.37 | 14.99 | 48.02 | 28.13 | 0.00 | 0.00 | 0.00 | 0.00 |
| L11 2 | 9.77 | n.d. | 14.34 | 48.84 | 27.06 | 0.00 | 0.00 | 0.00 | 0.00 |
| L11 3 | 7.88 | 1.17 | 14.76 | 47.08 | 29.12 | 0.00 | 0.00 | 0.00 | 0.00 |

ΔCTS-LPAT1 expression was therefore sufficient to allow incorporation of C16:0 into the sn-2 position of TAG, but not to achieve positive enrichment at this position verses the sn-1/3 positions, which can already incorporate a low proportion of C16:0 (FIG. 1A).

Disruption of LPAT2 Enhances C16:0 Incorporation into the Sn-2 Position of TAG

Competition between heterologous and native acyltransferases might be a factor that can limit the incorporation of specific fatty acyl groups into TAG. We therefore investigated whether ΔCTS-LPAT1-dependent incorporation of C16:0 into the sn-2 position of TAG could be enhanced by disrupting the function of the native ER-resident LPAT; believed to be LPAT2 in Arabidopsis (FIG. 1A). The lpat2-1 null mutant is embryo lethal. However, T-DNA insertions in non-coding regions of essential genes can be used to produce viable hypomorphic alleles. We therefore isolated two T-DNA mutants (lpat2-2 and lpat2-3) with insertions 302 and 139 bp 5' of the LPAT2 translational start site (FIG. 3A). We then crossed ProGLY:ΔCTS-LPAT1 L11 into each of the new lpat2 alleles and recovered homozygous seed batches. When we purified TAG from these seed batches and performed positional analysis, we found that the percentage of C16:0 at the sn-2 position had increased from ~33% in the parental ProGLY:ΔCTS-LPAT1 line to ~51% in the lpat2-3 background, whereas the effect in the lpat2-2 background was not significant (P>0.05) (FIG. 3B; Table 3).

TABLE 3

Total and sn-2 fatty acyl composition of TAG from wild type (WT) and
homozygous ProGLY:ΔCTS-LPAT1 seeds containing lpat2 mutant alleles.

| Line | 16:0 | 18:0 | 18:1 | 18:2 | 18:3 | 20:0 | 20:1 | 20:2 | 22:1 |
|---|---|---|---|---|---|---|---|---|---|

Total

| Line | 16:0 | 18:0 | 18:1 | 18:2 | 18:3 | 20:0 | 20:1 | 20:2 | 22:1 |
|---|---|---|---|---|---|---|---|---|---|
| WT 1 | 7.39 | 3.51 | 18.41 | 29.26 | 16.08 | 2.00 | 20.41 | 1.70 | 1.25 |
| WT 2 | 7.53 | 3.44 | 17.51 | 29.13 | 16.69 | 2.02 | 20.32 | 1.80 | 1.56 |
| WT 3 | 7.96 | 3.41 | 17.68 | 29.31 | 16.91 | 1.92 | 19.64 | 1.72 | 1.46 |
| L11 1 | 8.58 | 3.45 | 13.18 | 26.68 | 19.35 | 2.73 | 22.10 | 2.11 | 1.82 |
| L11 2 | 9.03 | 2.79 | 15.48 | 27.50 | 20.67 | 1.90 | 19.16 | 1.84 | 1.63 |
| L11 3 | 8.49 | 2.87 | 15.33 | 27.07 | 20.89 | 1.96 | 20.00 | 1.89 | 1.50 |
| L11 lpat2-2 1 | 8.69 | 3.29 | 15.66 | 26.67 | 19.76 | 2.10 | 20.58 | 1.82 | 1.44 |
| L11 lpat2-2 2 | 9.28 | 3.31 | 15.51 | 27.53 | 19.74 | 1.94 | 19.49 | 1.80 | 1.40 |
| L11 lpat2-2 3 | 8.58 | 2.77 | 13.18 | 29.05 | 20.04 | 2.30 | 20.56 | 2.02 | 1.50 |
| L11 lpat2-3 1 | 9.04 | 3.17 | 18.75 | 27.28 | 15.90 | 1.64 | 21.58 | 1.28 | 1.36 |
| L11 lpat2-3 2 | 9.08 | 3.09 | 18.33 | 27.50 | 16.11 | 1.63 | 21.37 | 1.39 | 1.50 |
| L11 lpat2-3 3 | 8.20 | 3.09 | 18.04 | 27.90 | 15.18 | 1.72 | 22.84 | 1.51 | 1.53 | sn-2

| Line | 16:0 | 18:0 | 18:1 | 18:2 | 18:3 | 20:0 | 20:1 | 20:2 | 22:1 |
|---|---|---|---|---|---|---|---|---|---|
| WT 1 | 0.78 | 0.53 | 18.54 | 54.22 | 25.93 | 0.00 | 0.00 | 0.00 | 0.00 |
| WT 2 | 0.78 | 0.52 | 17.22 | 54.11 | 27.37 | 0.00 | 0.00 | 0.00 | 0.00 |
| WT 3 | 0.75 | 0.53 | 17.38 | 53.89 | 27.44 | 0.00 | 0.00 | 0.00 | 0.00 |
| L11 1 | 9.56 | 0.68 | 14.68 | 46.54 | 28.53 | 0.00 | 0.00 | 0.00 | 0.00 |
| L11 2 | 7.83 | 0.00 | 14.05 | 46.24 | 31.88 | 0.00 | 0.00 | 0.00 | 0.00 |
| L11 3 | 8.10 | 0.00 | 14.43 | 46.01 | 31.46 | 0.00 | 0.00 | 0.00 | 0.00 |
| L11 lpat2-2 1 | 9.56 | 0.37 | 15.63 | 45.83 | 28.61 | 0.00 | 0.00 | 0.00 | 0.00 |
| L11 lpat2-2 2 | 9.79 | 0.65 | 14.12 | 45.05 | 30.39 | 0.00 | 0.00 | 0.00 | 0.00 |
| L11 lpat2-2 3 | 9.29 | 0.35 | 13.62 | 49.00 | 27.74 | 0.00 | 0.00 | 0.00 | 0.00 |
| L11 lpat2-3 1 | 13.31 | 0.60 | 16.58 | 46.78 | 22.73 | 0.00 | 0.00 | 0.00 | 0.00 |
| L11 lpat2-3 2 | 13.88 | 0.95 | 15.53 | 46.81 | 22.82 | 0.00 | 0.00 | 0.00 | 0.00 |
| L11 lpat2-3 3 | 12.82 | 1.30 | 16.70 | 48.02 | 21.15 | 0.00 | 0.00 | 0.00 | 0.00 | qRT-PCR analysis showed that LPAT2 expression is reduced by ~83% in developing lpat2-3 siliques, but only by ~24% in lpat2-2. (FIG. 3B). These data support the hypothesis that LPAT2 contributes to TAG biosynthesis in Arabidopsis seeds and that it competes with ΔCTS-LPAT1. The level of C16:0 enrichment at sn-2 also appears to respond to the strength of LPAT2 repression and achieving a greater reduction than ~83% might therefore lead to even stronger enrichment.

Disruption of PDCT Also Enhances C16:0 Incorporation into the Sn-2 Position of TAG In developing Arabidopsis seeds >90% of the glycerol backbone in TAG is derived from the membrane lipid phosphatidylcholine (PC), owing to rapid diacylglycerol (DAG)-PC interconversion, catalysed mainly by the plant-specific head group exchange enzyme PC:DAG cholinephosphotransferase (PDCT) (FIG. 1A). Although LPAT is responsible for the initial acylation of glycerolipids at sn-2, once these acyl groups are in PC they might be removed and replaced by acyl editing activities (FIG. 1A). To determine whether bypassing glycerolipid flux through PC (FIG. 1A) might increase ΔCTS-LPAT1-dependent incorporation of C16:0 into the sn-2 position of TAG, we crossed ProGLY:ΔCTS-LPAT1 L11 into the pdct (reduced oleate desaturation1) mutant. When we purified TAG from ProGLY:ΔCTS-LPAT1 pdct seed batches and performed positional analysis, we found that the percentage of C16:0 at sn-2 had increased from ~30% in the parental ProGLY:ΔCTS-LPAT1 line to ~56% in the pdct background (FIG. 4A; Table 4).

TABLE 4

Total and sn-2 fatty acyl composition of TAG from
wild type (WT) and homozygous ProGLY:ΔCTS-LPAT1
seeds containing rod1 and lpat2-3 mutant alleles.

| Line | Fatty acid content (%) | | | | | | | | |
|---|---|---|---|---|---|---|---|---|---|
| | 16:0 | 18:0 | 18:1 | 18:2 | 18:3 | 20:0 | 20:1 | 20:2 | 22:1 |
| Total | | | | | | | | | |
| WT 1 | 7.84 | 3.38 | 17.20 | 28.95 | 16.89 | 2.02 | 20.2 | 1.82 | 1.69 |
| WT 2 | 7.89 | 3.43 | 17.97 | 29.09 | 16.58 | 1.90 | 19.8 | 1.69 | 1.63 |
| WT 3 | 7.65 | 3.77 | 15.95 | 28.91 | 17.43 | 2.31 | 20.5 | 1.85 | 1.59 |
| WT 4 | 7.67 | 3.80 | 17.03 | 28.57 | 16.88 | 2.18 | 20.5 | 1.74 | 1.54 |
| WT 5 | 8.14 | 3.60 | 17.39 | 28.98 | 16.12 | 2.00 | 20.4 | 1.74 | 1.61 |
| WT 6 | 7.96 | 3.35 | 15.79 | 29.27 | 17.67 | 1.89 | 20.5 | 1.73 | 1.75 |
| L11 1 | 9.06 | 3.48 | 15.98 | 28.47 | 18.30 | 0.00 | 21.4 | 1.74 | 1.51 |
| L11 2 | 6.47 | 3.08 | 15.13 | 27.52 | 19.77 | 2.18 | 22.4 | 1.52 | 1.57 |
| L11 3 | 10.16 | 3.37 | 19.48 | 27.91 | 15.94 | 1.88 | 18.6 | 1.26 | 1.33 |
| L11 4 | 7.66 | 3.15 | 38.93 | 13.00 | 13.24 | 1.72 | 20.5 | 0.39 | 1.37 |
| L11 5 | 8.35 | 3.03 | 36.89 | 14.26 | 14.30 | 1.64 | 19.7 | 0.42 | 1.41 |
| L11 6 | 10.34 | 3.27 | 18.30 | 27.89 | 16.78 | 1.85 | 18.8 | 1.37 | 1.35 |
| L11 pdct 1 | 9.63 | 3.06 | 33.88 | 13.74 | 15.46 | 1.73 | 19.3 | 1.29 | 1.82 |
| L11 pdct 2 | 8.80 | 3.15 | 34.60 | 12.20 | 14.33 | 1.86 | 20.5 | 1.64 | 2.85 |
| L11 pdct 3 | 8.75 | 2.91 | 34.46 | 14.41 | 14.33 | 1.73 | 21.1 | 0.55 | 1.70 |
| L11 lpat2-3 pdct 1 | 10.44 | 2.92 | 35.40 | 15.08 | 14.48 | 1.41 | 18.4 | 0.46 | 1.38 |
| L11 lpat2-3 pdct 2 | 10.88 | 2.84 | 35.97 | 15.31 | 13.77 | 1.27 | 18.2 | 0.53 | 1.19 |
| L11 lpat2-3 pdct 3 | 8.77 | 2.95 | 36.57 | 13.57 | 12.28 | 1.48 | 22.9 | 0.00 | 1.41 |
| L11 lpat2-3 pdct 4 | 9.36 | 2.86 | 35.16 | 13.55 | 13.69 | 1.55 | 21.5 | 0.62 | 1.60 |
| L11 lpat2-3 pdct 5 | 9.50 | 3.07 | 34.06 | 13.88 | 14.43 | 1.64 | 21.4 | 0.63 | 1.33 |
| sn-2 | | | | | | | | | |
| WT 1 | 0.67 | 0.41 | 17.41 | 53.86 | 27.65 | 0.00 | 0.00 | 0.00 | 0.00 |
| WT 2 | 0.70 | 0.52 | 17.67 | 54.01 | 27.11 | 0.00 | 0.00 | 0.00 | 0.00 |
| WT 3 | 1.48 | 1.20 | 15.30 | 52.76 | 29.26 | 0.00 | 0.00 | 0.00 | 0.00 |
| WT 4 | 0.85 | 0.85 | 16.42 | 53.22 | 28.67 | 0.00 | 0.00 | 0.00 | 0.00 |
| WT 5 | 0.80 | 0.81 | 16.33 | 54.37 | 29.78 | 0.00 | 0.00 | 0.00 | 0.00 |
| WT 6 | 0.91 | 0.86 | 14.79 | 53.66 | 28.43 | 0.00 | 0.00 | 0.00 | 0.00 |
| L11 1 | 8.54 | 0.56 | 14.09 | 48.35 | 28.46 | 0.00 | 0.00 | 0.00 | 0.00 |
| L11 2 | 6.88 | 0.33 | 12.68 | 48.70 | 31.41 | 0.00 | 0.00 | 0.00 | 0.00 |
| L11 3 | 7.90 | 0.88 | 18.17 | 48.31 | 24.74 | 0.00 | 0.00 | 0.00 | 0.00 |
| L11 4 | 6.79 | 0.39 | 47.28 | 23.74 | 21.80 | 0.00 | 0.00 | 0.00 | 0.00 |
| L11 5 | 8.00 | 0.00 | 43.04 | 25.61 | 23.36 | 0.00 | 0.00 | 0.00 | 0.00 |
| L11 6 | 8.03 | 0.79 | 17.28 | 48.36 | 25.53 | 0.00 | 0.00 | 0.00 | 0.00 |
| L11 pdct 1 | 16.16 | 0.00 | 36.12 | 23.39 | 24.32 | 0.00 | 0.00 | 0.00 | 0.00 |
| L11 pdct 2 | 16.24 | 0.59 | 38.52 | 21.43 | 23.23 | 0.00 | 0.00 | 0.00 | 0.00 |
| L11 pdct 3 | 13.35 | 0.00 | 38.81 | 25.71 | 22.14 | 0.00 | 0.00 | 0.00 | 0.00 |
| L11 lpat2-3 pdct 1 | 19.54 | 0.00 | 36.33 | 23.93 | 20.20 | 0.00 | 0.00 | 0.00 | 0.00 |
| L11 lpat2-3 pdct 2 | 22.57 | 0.38 | 35.99 | 23.04 | 18.02 | 0.00 | 0.00 | 0.00 | 0.00 |
| L11 lpat2-3 pdct 3 | 20.36 | 0.41 | 40.58 | 21.56 | 17.09 | 0.00 | 0.00 | 0.00 | 0.00 |
| L11 lpat2-3 pdct 4 | 21.18 | 0.00 | 37.97 | 21.86 | 18.99 | 0.00 | 0.00 | 0.00 | 0.00 |
| L11 lpat2-3 pdct 5 | 20.30 | 0.00 | 37.53 | 22.35 | 19.82 | 0.00 | 0.00 | 0.00 | 0.00 |

These data suggest that a more direct flux of newly made DAG into TAG (FIG. 1A) favours C16:0 incorporation and/or retention at the sn-2 position. In WT seeds it is conceivable that C16:0 entering the sn-2 position of PC might either be edited from it by the action of lysophosphatidylcholine acyltransferase (LPCAT) or a phospholipase A2. Interestingly, some groups have provided in vitro evidence that the reverse activities of *Arabidopsis* LPCAT1 and LPCAT2 can selectively remove certain fatty acyl groups from PC, but C16:0 was not tested.

Disruption of LPAT2 and PDCT has an Additive Effect on Incorporation of C16:0 at Sn-2

To determine whether the combination of reducing LPAT competition and bypassing flux through PC would have an additive effect on ΔCTS-LPAT1-dependent incorporation of C16:0 into the sn-2 position of TAG (FIG. 1A), we crossed ProGLY:ΔCTS-LPAT lpat2-3 with ProGLY:ΔCTS-LPAT1 pdct. When we purified TAG from homozygous seed batches and performed positional analysis, we found that the percentage of C16:0 at sn-2 had increased from ~56% in ProGLY:ΔCTS-LPAT pdct to ~71% in ProGLY:ΔCTS-LPAT lpat2-3 pdct (FIG. 4A; Table 4). The combination of just three modifications to the TAG biosynthetic pathway in *Arabidopsis* (i.e. ΔCTS-LPAT1 expression, plus LPAT2 and PDCT suppression) is therefore sufficient to replicate the level of C16:0 enrichment at the sn-2 position (versus sn-1+3) that is found in HMF. Analysis of TAG composition in ProGLY:ΔCTS-LPAT1 lpat2-3 pdct (All) seeds using high resolution/accurate mass (HR/AM) lipidomics also confirmed the presence of C16:0 groups at the sn-2 position, since tripalmitin was 27-fold more abundant than in WT (FIG. 6A). By contrast, no dipalmitoyl PC was detected in ProGLY:ΔCTS-LPAT1 lpat2-3 pdct seeds and molecular species of PC containing one C16:0 group were not increased (FIG. 6B). These data suggest that an asymmetrical distribution of saturated and unsaturated fatty acyl groups in PC is maintained in ProGLY:ΔCTS-LPAT1 lpat2-3 pdct seeds and this may be important to prevent membranes assuming the gel phase at physiological temperatures.

Redistribution of C16:0 Reduces Seed Oil Content, but not Germination or Establishment Many studies have shown that modifying fatty acyl composition can reduce TAG accumulation in oilseeds and in some cases can also impair seed germination and seedling establishment. Our primary objective in this study was not to alter fatty acyl composition per se, but to change the stereoisomeric structure of TAG. To examine the physiological impact of C16:0 enrichment at the sn-2 position of TAG, we compared seed batches from wild type and ProGLY: ΔCTS-LPAT1 lpat2-3 pdct plants that had been grown together under standard laboratory conditions. We found no significant difference (P>0.05) in seed weight between the two genotypes (FIG. 4B).

However, the fatty acid content of ProGLY:ΔCTS-LPAT1 lpat2-3 pdct seeds was significantly (P<0.05) lower than that of wild type, when expressed as a percentage of seed weight (FIG. 4C). These data suggest that the modifications leading to incorporation of C16:0 into the sn-2 position, reduce TAG biosynthetic flux. This finding is consistent with previous studies in which seed TAG composition has been modified either using genetic engineering or mutant breeding methods. Despite the reduction in fatty acid content, ProGLY: ΔCTS-LPAT1 lpat2-3 pdct seed germination, scored as radicle emergence (FIG. 5A) and seedling establishment, scored as cotyledon expansion (FIG. 5B) and true leaf development (FIG. 5C), did not appear to be significantly (P<0.05) impaired. TAG breakdown also was not impeded in ProGLY:ΔCTS-LPAT1 lpat2-3 pdct seeds following germination (FIG. 5D), and this contrasts with some studies where seeds have been modified to incorporate uncommon fatty acyl groups into TAG. Finally, although ProGLY:ΔCTS-LPAT lpat2-3 pdct carries a hypomorphic allele of the essential gene LPAT2, this does not appear to adversely affect growth and morphology at the rosette stage (FIG. 7).

Materials and Methods

Plant Material and Growth Conditions

*Arabidopsis thaliana* wild type (Col-0) and LPAT2 (At3g57650) T-DNA insertion lines SALK 108026 (lpat2-2) and SALK 004681 (lpat2-3) (1) were obtained from the European *Arabidopsis* Stock Centre (University of Nottingham, UK). The pdct (rod1) mutant has been described previously (2). Seeds were surface sterilized, stratified at 4° C. for two days and germinated on agar plates containing ½ strength MS medium (Sigma-Aldrich) pH 5.7. Seedlings were transplanted to 7 cm² pots containing Levington F2 compost and grown in a chamber set to a 16-h light (22° C.)/8-h dark (16° C.) cycle, with a light intensity of 250 µmol m$^{-2}$ s$^{-1}$. The plants were bagged individually at the onset of flowering and the seeds were harvested at maturity.

Cloning and Transformation

RNA was isolated from *Brassica napus* (cv. Kumily) seedlings and DNAse treated using the RNAeasy Plant Mini kit (Qiagen). RNA was reverse transcribed into cDNA with the SuperScript III Reverse Transcriptase kit (ThermoFisher Scientific). *B. napus* LPAT1 (GenBank: AF111161) lacking the chloroplast targeting sequence (CTS) was amplified by PCR with KOD DNA polymerase (Merck) using primer pair P1+P2 (Table 5).

TABLE 5

Primers used in study

| | |
|---|---|
| P1: | 5'-CACCATGTCGGATCTTTCAGGAGCTG-3' (SEQ ID NO: 3) |
| P2 | 5'-TCAACTCAAGAGATTCATAGATTCA-3' (SEQ ID NO: 4) |
| P3 | 5'-CGGAATTCATGTCGGATCTTTCAGGAGC-3' (SEQ ID NO: 5) |
| P4 | 5'-GCTCTAGATCAACTCAAGAGATTCATAGATTC-3' (SEQ ID NO: 6) |
| P5: | 5'-GTTGATTGAATCGAGGAAGGA-3' (SEQ ID NO: 7) |
| P6: | 5'-CTTTTTACCACATGCAAAGGG-3' (SEQ ID NO: 8) |
| P7: | 5'-CCATTTTGGTGGTCGTCTAT-3' (SEQ ID NO: 9) |
| P8: | 5'-CAGAAAAATTAACCGGGTGGT-3' (SEQ ID NO: 10) |
| P9: | 5'-CAGCTGAAACCGACGTCTCT-3' (SEQ ID NO: 11) |
| P10: | 5'-GGTCACGCGCTCTTTGAATC-3' (SEQ ID NO: 12) |
| P11: | 5'-GTAGCACCCAAGGCTTCCA-3' (SEQ ID NO: 13) |
| P12: | 5'-GCCAGTGATCATCAGGACG-3' (SEQ ID NO: 14) |
| P13: | 5'-GCGTGGACCGCTTGCTGCAACT-3' (SEQ ID NO: 15) |
| P14: | 5'-CTGGTGGGCTGGAGTTAAGA-3' (SEQ ID NO: 16) |
| P15: | 5'-AGAATCCATCCCACAAGCCA-3' (SEQ ID NO: 17) |
| P16: | 5'-TGTCATCGGTTGGGCTATGT-3' (SEQ ID NO: 18) |
| P17: | 5'-CATCAGCGTTATTGGCACCA-3' (SEQ ID NO: 19) |
| P18: | 5'-GACGCTTCATCTCGTCC-3' (SEQ ID NO: 20) |
| P19: | 5'-CCACAGGTTGCGTTAG-3' (SEQ ID NO: 21) |
| P20: | 5'-TCCAGCTAAGGGTGCC-3' (SEQ ID NO: 22) |
| P21: | 5'-GGTGGGTACTCGGAGA-3' (SEQ ID NO: 23) |

TABLE 5-continued

Primers used in study

P22: 5'-GAATTACCCGACGGACA-3' (SEQ ID NO: 24)

P23: 5'-ACGGTCTGCAATACCT-3' (SEQ ID NO: 25)

The resulting PCR product was purified with the QIAquick Gel Extraction Kit (Qiagen). For localisation studies, ΔCTS-LPAT1 was cloned behind Red Fluorescent Protein (RFP) in the pK7WGR2 vector (Vlaams Institute for Biotechnology). The PCR product was cloned in the pENTR™/D-TOPO™ vector (Thermo Fisher Scientific), sequenced (FIG. 1B) and recombined into the pK7WGR2 vector using the Gateway™ LR Clonase™ II Enzyme mix (Thermo Fisher Scientific). ΔCTS-LPAT1 was cloned in the pBinGlyRed3 vector in between the soybean glycinin-1 (GLY) promoter and terminator for seed specific expression (3). ΔCTS-LPAT1 was PCR-amplified from the pENTR-D-TOPO vector using KOD DNA polymerase and primer pair P3+P4. The PCR product was gel purified and digested with EcoRI and XbaI. The pBinGlyRed3 vector was also digested with EcoRI and XbaI, alkaline phosphatase treated (Promega), gel purified and ΔCTS-LPAT1 was ligated into the vector using T4 DNA ligase (NEB). Heat shock was used to transform the vectors into *Agrobacterium tumefaciens* strain GV3101 and *Arabidopsis* transformation was then carried out using the floral-dip method (4). T1 seeds expressing the selectable marker were identified under a Leica M205 FA microscope using the DsRed filter.

Transient Expression in *Nicotiana benthamiana* and Imaging

Transient expression in *Nicotiana benthamiana* leaves was carried out as described by Wood et al., (5) using *A. tumefaciens* cultures transformed with vectors harbouring Pro35S:RFP-ΔCTS-LPAT1, Pro35S:m-GFP5-ER or Pro35S:p19. Cultures were hand-infiltrated into leaves and the inoculated plants were left for 48 h. *N. benthamiana* leaves were then mounted in water on a Zeiss LSM 780 laser scanning confocal microscope under an Apochromat 63x/1.20 W Korr M27 objective. GFP was excited at a wavelength of 488 nm and RFP at 561 nm. Filters with an emission band at 473-551 nm were used for detection.

Genotyping

Genomic DNA was isolated using the DNeasy Plant Mini Kit (Qiagen). Homozygous T-DNA insertional mutants were identified by PCR (1) using the Promega PCR Master Mix (Promega). The following primer pairs were used for genotyping lpat2-2 (WT: P5+P6 or T-DNA: P5+P7) and lpat2-3 (WT: P8+P9 or T-DNA: P8+P7). PDCT was genotyped by sequencing PCR products amplified with primer pair P10+P11 spanning the site of the point mutation (2). ProGLY:ΔCTS-LPAT1 was genotyped by PCR using primer pair P12+P13 spanning ProGLY and ΔCTS-LPAT1.

Lipid Analysis

Total lipids were extracted from seeds and seedlings and TAG was purified as described previously (6). TAG stereochemical analysis was performed by lipase digestion following the method described previously (7), except that 2-monoacylglycerols were separated by thin layer chromatography (Silica gel 60, 20x20 cm; Sigma-Aldrich/Merck) using hexane:diethylether:acetic acid (35:70:1.5, v/v/v) (8). Fatty acyl groups present in whole seeds and purified lipid fractions were trans-methylated and quantified by gas chromatography (GC) coupled to flame ionization detection, as described previously (9), using a 7890A GC system fitted with DB-23 columns (30 m×0.25 mm i.d.×0.25 μm) (Agilent Technologies).

TAG and PC molecular species composition were analysed by high resolution/accurate mass (HR/AM) lipidomics (10-12) using a Vanquish—Q Exactive Plus UPLC-MS/MS system (Thermo Fisher Scientific). Work flow consisted of using total lipids purified at 3 μg/μl and diluted 1 in 100 in chloroform:methanol (1:1, v/v). Internal tripalmitin standard (0.857 μM) was added and 20 μl injected into the UPLC. Lipids were separated using a Accucore C18 (2.1×150 mm, 2.6 mm) column (Thermo Fisher Scientific) at 35° C. with autosampler tray temperature, 10° C. flow rate at 400 μl $min^{-1}$. Mobile phase: A=10 mM ammonium formate in 50% acetonitrile+0.1% formic acid, B=2 mM ammonium formate in acetonitrile:propan-2-ol:water (10:88:2 v/v)+0.02% formic acid. Elution gradient ran for 28 minutes from 35% B at start to 100% at 24 mins. Thermo Q Exactive HESI II probe conditions, sweep plate in use probe position in C. Conditions were adjusted for separate positive and negative runs, running samples in a single polarity resulted in more identifications. LC/MS at 140K resolution and data-independent HCD MS2 experiments (35K resolution) were performed in positive and negative ion modes. Full Scan @ 140,000 resolution m/z 150-1200 Top 15 most abundant MS/MS @ 35,000 resolution using an isolation window of 1 m/z, maximum integration time of 75 ms and dynamic exclusion window of 8 s. The stepped collision energy was 25, 30, 40 eV replacing 25 with 30 eV negative ion mode. Sheath gas set to 60, Aux gas 20, sweep gas 1 spray voltage 3.2 KV in positive ion mode with small adjustments in negative ion mode, capillary temperature 320 and aux gas heater set to 370° C. LipidSearch 4.2 experimental workflow (Thermo Fisher Scientific) was used for lipid characterization and potential lipid species were identified separately from positive or negative ion adducts. The data for each biological replicate were aligned within a chromatographic time window by combining the positive and negative ion annotations and merging these into a single lipid annotation.

qRT-PCR Analysis

DNAse-treated total RNA was isolated from developing siliques as described by Mendes et al., (13). The synthesis of single stranded cDNA was carried out using SuperScript™ II RNase H-reverse transcriptase from Invitrogen Ltd. (Paisley, UK). Quantitative (q)-PCR was performed as described previously (13), except that LPAT2 and ΔCTS-LPAT1 expression were normalized to the geometric mean of three reference genes (UBQ5, EF-1α and ACT8) that were selected owing to their stable expression over the course of seed development (14). Primer pairs P14+P15, P16+P17, P18+P19, P20+P21 and P22+P23, were used for LPAT2, ΔCTS-LPAT1, UBQ5, EF-1α and ACT8, respectively.

Seed Germination and Establishment Assays

Around 50 seeds from each plant were sown on a ½ MS agar plate, stratified at 4° C. for two days and transferred to a growth chamber set to 20° C., 16 h light/8 h dark, PPFD=150 μmol $m^{-2}$ $s^{-1}$. Germination (radicle emergence), expanded cotyledons and expanded true leaves were scored visually under a dissecting stereomicroscope every day for a week. Seeds and seedlings were also collected at zero and four days after stratification for lipid analysis.

Statistical Analysis

All experiments were carried out using between three and six biological replicates and the data are presented as the mean values ±standard error of the mean (SE). For statistical analysis we either used one-way analysis of variance (ANOVA) with post-hoc Tukey HSD (Honestly Significant Difference) tests, or two-tailed Student's t-tests.

CONCLUSIONS

As described herein it is shown that the TAG biosynthetic pathway in plants can be engineered so that the stereoisomeric structure of seed storage oil is altered to mimic that of HMF, with >70% of C16:0 concentrated at the middle (sn-2 or β) position on the glycerol backbone. There is mounting evidence that this configuration is beneficial for infant nutrition, but it has not been found to occur naturally in vegetable fats where C16:0 is virtually excluded from the sn-2 position. Many infant formulas contain HMFS that are made by restructuring vegetable fats using enzyme-based catalysis, but they are relatively costly to produce; particularly for the manufacture of true mimetics with >70% of C16:0 at the sn-2 position. Translation of our technology from the model species *Arabidopsis* to an oilseed crop might conceivably provide a cheaper and more sustainable source of HMFS for infant formula, since it would abrogate the need for enzyme-based catalysis. The infant formula market is currently estimated to use around 450,000 metric tons of vegetable-derived fat per year, of which about 38,000 metric tons is HMFS. Several oilseed crops may be considered as possible hosts for HMFS production, and it is noteworthy that conventional sunflower and genetically modified oilseed rape varieties have already been developed that have the appropriate fatty acyl composition. Even an oilseed crop with more modest C16:0 enrichment at the sn-2 position that we have achieved here may still be desirable since clinical trials have reported benefits with as little as 43% of C16:0 at the sn-2 position and product surveys have found that this level of enrichment is common in infant formulas that are supplemented with HMFS.

Further studies have been conducted as detailed below.

Example 2—Fab1-1 Fae1 Background

We crossed the ProGLY ΔCTS-LPAT1 lpat2-3 pdct line described in Example 1 into the fab1-1 fae1 mutant (15) to create ProGLY:ΔCTS-LPAT1 lpat2-3 pdct fab1-1 fae1. This *Arabidopsis thaliana* background has elevated levels of C16:0 in its seed TAG owing to a hypomorphic allele of the FAB1 gene encoding chloroplast 3-keto-acyl-ACP synthase II (KASII), and also reduced very long chain fatty acid levels due to a null FATTY ACID ELONGASE 1 (FAE1) allele (Nguyen et al., 2010). When we performed positional analysis, we found that the percentage of C16:0 at sn-2 was ~2% in fab1-1 fae1 and ~60% in ProGLY:ΔCTS-LPAT1 lpat2-3 pdct fab1-1 fae1 (Table 6). The data show that C16:0 enrichment at the sn-2 position in TAG can be produced in seeds with higher levels of total C16:0 than are present in WT seeds.

TABLE 6

Total and sn-2 C16:0 content of TAG from *A. thaliana* fab1-1 fae1 and ProGLY:ΔCTS-LPAT1 lpat2-3 pdct fab1-1 fae1 seeds. Values are measurements made on separate seed batches from two plants of each genotype.

| Genotype | Total C16:0 (%) | % of C16:0 at sn-2 |
|---|---|---|
| fab1-1 fae1 | 19.31 | 2.11 |
| fab1-1 fae1 | 18.60 | 3.03 |
| ProGLY:ΔCTS-LPAT1 lpat2-3 pdct fab-1 fae1 | 20.21 | 62.29 |
| ProGLY:ΔCTS-LPAT1 lpat2-3 pdct fab-1 fae1 | 19.06 | 57.80 |

Example 3—Human LPAT AGPAT1

We expressed a plant codon optimised version of the human LPAT AGPAT1 under the control of the glycinin promoter in wild type (WT) *A. thaliana* Col-0 and fab1-1 fae1 seeds following the procedures described in Example 1. When we performed positional analysis, we found that the percentage of C16:0 at sn-2 was up to ~73% in WT and up to ~55% in fab1-1 fae1 background (Table 7). The data show that C16:0 enrichment at the sn-2 position in TAG can be produced in seeds by expression of AGPAT1.

TABLE 7

Total and sn-2 C16:0 content of TAG from *A. thaliana* WT, fab1-1 fae1, ProGLY:AGPAT1 and ProGLY:AGPAT1 L3 fab1-1 fae1 seeds. Values are means ± SE of measurements made on separate seed batches from three plants of each genotype.

| Genotype | Total C16:0 (%) | % of C16:0 at sn-2 |
|---|---|---|
| WT | 8.22 ± 0.13 | 1.97 ± 0.31 |
| ProGLY:AGPAT1 L35 | 7.19 ± 0.16 | 73.35 ± 1.99 |
| ProGLY:AGPAT1 L40 | 7.77 ± 0.22 | 69.40 ± 1.46 |
| fab1-1 fae1 | 18.35 ± 0.31 | 2.69 ± 1.12 |
| ProGLY:AGPAT1 L3 fab1-1 fae1 | 15.49 ± 0.60 | 54.77 ± 1.22 |
| ProGLY:AGPAT1 L9 fab1-1 fae1 | 15.41 ± 2.11 | 43.55 ± 1.01 |

Codon Optimized AGPAT1 DNA Sequence (SEQ ID NO: 26)
ATGGATTTATGGCCTGGTGCTTGGATGTTATTATTATTATTATTCTTGT

TATTGCTCTTCCTCCTTCCTACTTTGTGGTTCTGTTCACCTTCTGCAAA

GTATTTCTTTAAGATGGCTTTCTACAACGGATGGATTCTTTTCTTGGCT

GTTTTGGCAATCCCAGTTTGTGCTGTGAGAGGTAGGAACGTTGAAAACA

TGAAGATTCTCAGACTCATGCTTTTGCATATCAAGTACCTTTACGGAAT

AAGAGTGGAAGTTAGGGGTGCTCATCACTTTCCTCCATCTCAACCTTAT

GTTGTGGTTTCAAACCACCAGTCTTCATTGGATCTCTTAGGAATGATGG

AAGTGCTCCCTGGTAGATGTGTTCCAATAGCAAAGAGGGAGCTTTTGTG

GGCTGGATCAGCAGGTCTTGCTTGCTGGTTGGCTGGAGTTATTTTTATC

GATAGAAAAGGACAGGTGATGCAATCTCAGTGATGAGTGAAGTTGCTC

AAACTCTCTTAACACAGGATGTGAGAGTTTGGGTGTTCCCTGAGGGAAC

CAGGAATCATAACGGTAGTATGTTACCATTTAAGAGAGGAGCTTTCCAC

CTCGCAGTTCAAGCTCAGGTTCCTATAGTGCCAATAGTTATGAGTTCTT

ACCAAGATTTCTACTGTAAGAAGGAAAGAAGGTTCACTAGTGGACAATG

-continued

```
CCAAGTTAGAGTGCTCCCTCCAGTTCCAACCGAGGGTTTAACTCCTGAT

GATGTGCCAGCTCTTGCAGATAGAGTTAGGCATTCTATGTTGACAGTGT

TCAGAGAGATTAGTACCGATGGAAGGGGAGGTGGAGATTATTTGAAGAA

GCCAGGTGGAGGAGGATGA
```

Example 4—*Camelina Sativa*

We expressed ΔCTS-LPAT1 in *Camelina sativa* while simultaneously suppressing endogenous ER LPAT. We constructed a multigene T-DNA vectors in the pBinGlyRed3 backbone (3) containing ΔCTS-LPAT1 and LPAT2-like gene specific artificial microRNAs (amiRNAs) under the control of the seed-specific oleosin and napin promoters, respectively. Three amiRNA sequences were selected to target *C. sativa* LPAT2-like genes (5'-TAAAGCGAGTTCCCTCGACAG-3' (SEQ ID NO:27), 5'-TTGTGCCCAGTGTACGGACTT-3' (SEQ ID NO:28) and 5'-TCAAAGGCACGATGATACCTG-3' (SEQ ID NO:29)) and used to replace the stem loops in the *Arabidopsis thaliana* MIR319a precursor (16). The constructs were transformed into *C. sativa* cv Suneson (WT) using *Agrobacterium tumefaciens* (17). Homozygous T3 seeds batches were obtained for multiple independent lines and lipid analysis was performed as described in Example 1. When we performed positional analysis, we found that the percentage of C16:0 at sn-2 was ~1% in WT and ~70% in ProOLE:ΔCTS-LPAT1 ProNAP:LPAT2amiRNA seeds (Table 8). The data show that C16:0 enrichment at the sn-2 position in TAG can be produced in *C. sativa* seeds.

TABLE 8

Total and sn-2 C16:0 content of TAG from *C. sativa* WT and ProOLE:ΔCTS-LPAT1 ProNAP:LPAT2amiRNA seeds. Values are from measurements made on single seed batches of each genotype.

| Genotype | Total (%) | C16:0 % of C16:0 at sn-2 |
| --- | --- | --- |
| WT (cv Suneson) | 4.39 | 0.77 |
| ProOLE:ΔCTS-LPAT1 ProNAP:LPAT2amiRNA L11 | 5.28 | 66.46 |
| ProOLE:ΔCTS-LPAT1 ProNAP:LPAT2amiRNA L12 | 5.62 | 76.57 |

Example 5—*Brassica Napus*

We expressed ΔCTS-LPAT1 or AGPAT1 in *Brassica napus* seeds while simultaneously suppressing endogenous ER LPAT and also expressing *Arabidopsis thaliana* FATE to increase total C16:0 content. We constructed multigene T-DNA vectors in the pBinGlyBar1 backbone (3) containing FATB, LPAT2-like gene specific amiRNAs and ΔCTS-LPAT1 or AGPAT1 under the control of the seed-specific gene promoters oleosin, napin and glycinin, respectively. We selected three amiRNA sequences to target *B. napus* LPAT2-like genes (5'-TCACTTGATGTGAAGATGCAC-3' (SEQ ID NO:30), 5-'TTAACAGCTGACACGAAGCCT-3' (SEQ ID NO:31) and 5'-TCACTTGATGTGAACACGCAC-3' (SEQ ID NO:32)) and used them to replace the stem loops in the *Arabidopsis thaliana* MIR319a precursor (16). The constructs were transformed into *Brassica napus* cv DH12075 (WT) using *Agrobacterium tumefaciens* (18). Homozygous T3 seeds batches were obtained for multiple independent lines and lipid analysis was performed as described in Example 1. When we performed positional analysis, we found that the percentage of C16:0 at sn-2 was ~2% in WT and up to 47% and 62% in ProOLE:FATB ProNAP:LPATamiRNA ProGLY ΔCTS-LPAT1 and ProOLE:FATB ProNAP:LPATamiRNA ProGLY:AGPAT seeds, respectively (Table 9). Total C16:0 content in seeds of the transgenic lines was also increased to between 24 and 30%. The data show that C16:0 enrichment at the sn-2 position in TAG can be produced in *B. napus* seeds that are also modified to have enhanced total C16:0 content.

FATB DNA Sequence (*Arabidopsis thaliana*)

(SEQ ID NO: 33)
```
ATGGTGGCCACCTCTGCTACGTCGTCATTCTTTCCTGTACCATCTTCTT

CACTTGATCCTAATGGAAAAGGCAATAAGATTGGGTCTACGAATCTTGC

TGGACTCAATTCTGCACCTAACTCTGGTAGGATGAAGGTTAAACCAAAC

GCTCAGGCTCCACCTAAGATTAATGGGAAAAAGGTTGGTTTGCCTGGTT

CTGTAGATATTGTAAGGACTGATACCGAGACCTCATCACACCCTGCGCC

GAGAACTTTCATCAACCAGTTACCTGACTGGAGCATGCTTCTTGCTGCT

ATAACTACGATTTTCTTAGCGGCTGAGAAACAGTGGATGATGCTTGATT

GGAAACCTAGGCGTTCTGACATGCTGGTGGATCCTTTTGGTATAGGGAG

AATTGTTCAGGATGGCCTTGTGTTCCGTCAGAATTTTTCTATTAGGTCA

TATGAAATAGGTGCTGATCGCTCTGCATCTATAGAAACCGTCATGAATC

ATCTGCAGGAAACGGCGCTTAATCATGTTAAGACTGCTGGATTGCTTGG

AGATGGGTTTGGCTCTACACCTGAGATGTTTAAGAAGAACTTGATATGG

GTTGTCACTCGTATGCAGGTTGTGGTTGATAAATATCCTACTTGGGGAG

ATGTTGTTGAAGTAGACACCTGGGTCAGTCAGTCTGGAAAGAATGGTAT

GCGTCGTGATTGGCTAGTTCGGGACTGTAATACTGGAGAAACCTTAACA

CGAGCATCAAGTGTGTGGGTGATGATGAATAAACTGACAAGGAGATTGT

CAAAGATTCCTGAAGAGGTTCGAGGGGAAATAGAGCCTTATTTTGTGAA

TTCTGATCCTGTCCTTGCCGAGGACAGCAGAAAGTTAACAAAAATTGAT

GACAAGACTGCTGACTATGTTCGATCTGGTCTCACTCCTCGATGGAGTG

ACCTAGATGTTAACCAGCATGTGAATAATGTAAAGTACATTGGGTGGAT

CCTGGAGAGTGCTCCAGTGGGAATAATGGAGAGGCAGAAGCTGAAAAGC

ATGACTCTGGAGTATCGGAGGGAATGCGGGAGAGACAGTGTGCTTCAGT

CCCTCACTGCAGTTACGGGTTGCGATATCGGTAACCTGGCAACAGCGGG

GGATGTGGAATGTCAGCATTTGCTCCGACTCCAGGATGGAGCGGAAGTG

GTGAGAGGAAGAACAGAGTGGAGTAGTAAAACACCAACAACAACTTGGG

GAACTGCACCGTAA
```

FATB Amino Acid Sequence (*Arabidopsis thaliana*)

(SEQ ID NO: 73)
```
MVATSATSSFFPVPSSSLDPNGKGNKIGSTNLAGLNSAPNSGRMKVKPN

AQAPPKINGKKVGLPGSVDIVRTDTETSSHPAPRTFINQLPDWSMLLAA

ITTIFLAAEKQWMMLDWKPRRSDMLVDPFGIGRIVQDGLVFRQNFSIRS

YEIGADRSASIETVMNHLQETALNHVKTAGLLGDGFGSTPEMFKKNLIW
```

-continued

VVTRMQVVVDKYPTWGDVVEVDTWVSQSGKNGMRRDWLVRDCNTGETLT

RASSVWVMMNKLTRRLSKIPEEVRGEIEPYFVNSDPVLAEDSRKLTKID

DKTADYVRSGLTPRWSDLDVNQHVNNVKYIGWILESAPVGIMERQKLKS

MTLEYRRECGRDSVLQSLTAVTGCDIGNLATAGDVECQHLLRLQDGAEV

VRGRTEWSSKTPTTTWGTAP

TABLE 9

Total and sn-2 C16:0 content of TAG from B. napus WT, ProOLE:FATB
ProNAP:LPATamiRNA ProGLY:ΔCTS-LPAT1
and ProOLE:FATB ProNAP:LPATamiRNA ProGLY:AGPAT1
seeds. Values are means ± SE of measurements made on separate seed
batches from three plants of each genotype.

| Genotype | Total C16:0 | % of C16:0 as sn-2 |
| --- | --- | --- |
| WT (DH12075) | 4.3 ± 0.1 | 2.3 ± 0.3 |
| ProOLE:FATB ProNAP:LPATamiRNA ProGLY:ΔCTS-LPAT1 L1 | 24.3 ± 0.9 | 47.2 ± 1.99 |
| ProOLE:FATB ProNAP:LPATamiRNA ProGLY:ΔCTS-LPAT1 L2 | 29.8 ± 2.2 | 44.9 ± 1.46 |
| ProOLE:FATB ProNAP:LPATamiRNA ProGLY:AGPAT1 L1 | 24.1 ± 0.8 | 61.8 ± 1.12 |
| ProOLE:FATB ProNAP:LPATamiRNA ProGLY:AGPAT1 L2 | 25.9 ± 1.4 | 59.77 ± 1.22 |

Example 6—Yarrowia Lipolytica

We overexpressed ΔCTS-LPAT1 (PLPAT, SEQ ID NO:38), AGPAT1 (SEQ ID NO:37) or a Chlamydomonas reinhardtii LPAT (CRELPAT, SEQ ID NO:36) in the oleaginous yeast Yarrowia lipolytica. When we performed TAG positional analysis, we found that the percentage of C16:0 at sn-2 was ~3% in WT and increased to up to ~63% in some mutant strains (Table 14). The data show that C16:0 enrichment at the sn-2 position in TAG can be produced in Y. lipolytica cells.

The E. coli and yeast strains used in this study are listed in Table 10 and Table 11, respectively, and their culture maintenance and growth conditions have been described by Sambrook and Russell (2001) (20) and Barth and Gaillardin (1996) (19), respectively. Y. lipolytica media, culture growth conditions and biomass harvesting for lipid extraction under nitrogen limitation were the same as reported previously (Bhutada et al., 2017) (23). For the growth of ura3Δ or leu2Δ auxotrophic strains media were supplemented with 0.1 g L$^{-1}$ uracil or leucine.

All PCR reactions for cloning and amplification of sequencing templates were performed using Herculase II Fusion DNA Polymerase (Agilent Technologies), and with GoTaq (Promega) for confirmation of chromosomal integration of the transformation cassettes. The restriction enzymes used in this study were obtained from Roche or New England Biolabs (NEB). The DNA fragments from PCR and restriction digestion were recovered from agarose gels using GeneJET kits (Thermo Scientific). For ligations, the Fast-Link DNA Ligation Kit (Epicenter) or Gibson assembly (Gibson et al., 2009 (21); Kulasekara, 2011 (22)) was used. For transformation into Y. lipolytica standard protocols for lithium acetate were used (Le Dall et al., 1994 (25)). All primers are listed in Table 12.

TABLE 10

Plasmids used in this study.

| Plasmid | Genotype | Reference |
| --- | --- | --- |
| pFA6aURA3-09 | Parent Plasmid (5'_MCS-loxP-PPURA3TT-loxP-MCS_3') | (Bhutada et al., 2017) |
| pGMKGSY12 | YlGSY1$^P$-loxP-PURA3T-loxP-YlGSY1$^T$ | (Bhutada et al., 2017) |
| YlAGPAT1 | pUC57-5'_AGPAT1-Syn$^T$_3' | This work/GenScript |
| YlCRELPAT | pUC57-5'_CRELPAT-Syn$^T$_3' | This work/GenScript |
| YlPLPAT | pUC57-5'_PLPAT-Syn$^T$_3' | This work/GenScript |
| pGSYTEF | YlGSY1$^P$-TEF1$^P$-loxP-PURA3T-loxP-YlGSY1$^T$ | This work |
| pTEFAGPAT1 | YlGSY1$^P$-TEF1$^P$-AGPAT1-Syn$^T$-loxP-PURA3T-loxP-YlGSY1$^T$ | This work |
| pTEFCRELPAT | YlGSY1$^P$-TEF1$^P$-CRELPAT-Syn$^T$-loxP-PURA3T-loxP-YlGSY1$^T$ | This work |
| pTEFPLPAT | YlGSY1$^P$-TEF1$^P$-PLPAT-Syn$^T$-loxP-PURA3T-loxP-YlGSY1$^T$ | This work |

TABLE 11

Strains used in this study.

| strains | Genotype | source |
| --- | --- | --- |
| Yarrowia lipolytica | | |
| WT (W29) | MATa wild type | (Barth and Gaillardin, 1996) |
| PO1d (JMY2101) | MATa ura3-302, xpr2-322, pURA3-SUC2 | (Barth and Gaillardin, 1996) |
| gsy1Δ | MATa ura3-302, xpr2-322, pURA3-SUC2, gsy1Δ::URA3 | This work |
| gsy1Δ-AGPAT1 | MATa ura3-302, xpr2-322, pURA3-SUC2, gsy1Δ::YlTEF1$^P$-AGPAT1-Syn$^T$-URA3 | This work |
| gsy1Δ-CreLPAT | MATa ura3-302, xpr2-322, pURA3-SUC2, gsy1Δ: YlTEF1$^P$-CreLPAT-Syn$^T$-URA3 | This work |
| gsy1Δ-PLPAT | MATa ura3-302, xpr2-322, pURA3-SUC2, gsy1Δ::YlTEF1$^P$-PLPAT-Syn$^T$-URA3 | This work |

TABLE 12

Primers used in this study

| Primer | Sequence 5' to 3' |
| --- | --- |
| TEF-GSY-F | CTCGCAACAACCGATTCCAACAAGAGACCGGGTTGGC GGCGCA (SEQ ID NO: 34) |
| TEF-GSY-R | ATAACTTCGTATAATGTATGCTATACGAAGTTATAAG CTTTGAATGATTCTTATACTCAGAAGGAAATGCTTAA (SEQ ID NO: 35) |

Construction of a Mutant with Lysophosphatidic Acyltransferase (LPAT) Expression To obtain a strain with LPAT expression, gene synthesis of codon optimized LPAT CDS sequence belonging to Human, Plant and Algal species together with Tsynt25 (Syn$^T$) synthetic terminator fragment (Curran et al., 2015) was done. The previously described plasmid pGMKGSY_12 (Bhutada et al., 2017) harbouring glycogen storage elimination cassette flanked by 1 kb recombination regions for the glycogen synthase, GSY1 locus was linearized with HindIII digest and for strong constitutive expression of LPAT genes assembled by Gibson assembly with the TEF1 promoter fragment, which was PCR amplified from W29 genomic DNA with the primers TEF-GSY-F/TEF-GSY-R resulting in plasmid pGSYTEF.

The gene synthesized pUC7 vectors harbouring LPAT CDS-SynT was digested with HindIII to excise the cloning inserts corresponding to AGPAT, CRELPAT and PLPAT. pGSYTEF was digested with the same enzyme to linearize the vector and it was re-ligated with the above gel purified inserts under the TEF1$^P$ promoter fragment, resulting in pTEFAGPAT1, pTEFCRELPAT and pTEFPLPAT. The correct assembly of the episomal YlGSY1$^P$-loxP-URA3-loxP-TEF$^P$AGPAT1 Syn$^T$-YlGSY1$^T$, YlGSY1$^P$-loxP-URA3-loxP-TEF$^P$CRELPAT Syn$^T$-YlGSY1$^T$, and YlGSY1$^P$-loxP-URA3-loxP-TEF$^P$PLPATSyn$^T$-YlGSY1$^T$ cassette was confirmed by sequencing. These cassettes were excised NotI digested, purified and used for transformation of strain PO1d (Table 11). Transformants with integration of the cassette at the GSY1 locus were identified by Lugol's iodine staining (1% KI, 0.5% 12) and confirmed by control primer PCR and sequencing.

Analytical Methods

Lipids were extracted and analysed as described in Example 1.

TABLE 13

Total and sn-2 fatty acyl composition of TAG of *Y. lipolytica* strains in nitrogen-limited media. Values are means ± SD of measurements made on three separate cultures for each genotype.

| Strain | Total fatty acid composition in TAG (%) | | | | |
|---|---|---|---|---|---|
| | 16:0 | 18:0 | 16:1 | 18:1 | 18:2 |
| WT | 21.28 ± 1.21 | 11.7 ± 0.45 | 6.49 ± 0.48 | 46.31 ± 2.4 | 14.22 ± 1.22 |
| PO1d | 21.07 | 9.4 | 6.91 | 42.9 | 19.73 |
| gsy1Δ | 9.68 ± 0.89 | 11.55 ± 0.78 | 4.68 ± 0.57 | 57.96 ± 2.16 | 16.13 ± 1.37 |
| gsy1Δ-AGPAT1 | 16.56 ± 0.6 | 11.28 ± 0.3 | 3.65 ± 0.31 | 52.8 ± 0.85 | 15.7 ± 0.54 |
| gsy1Δ-CreLPAT | 19.19 ± 1.31 | 12.64 ± 4.13 | 3.33 ± 0.21 | 50.26 ± 4.18 | 14.58 ± 1.78 |
| gsy1Δ-PLPAT | 8.98 ± 0.22 | 14.17 ± 0.12 | 3.67 ± 0.05 | 60.46 ± 0.47 | 12.72 ± 0.23 |

| Strain | Fatty acid species at sn-2 position (%) | | | | |
|---|---|---|---|---|---|
| | 16:0 | 18:0 | 16:1 | 18:1 | 18:2 |
| WT | 2.21 ± 1.29 | 1.9 ± 1.87 | 2.06 ± 0.25 | 73.15 ± 0.52 | 20.68 ± 2.39 |
| PO1d | 0.44 | 0.44 | 2.26 | 73.77 | 23.08 |
| gsy1Δ | 1.57 ± 0.48 | 0.57 ± 0.62 | 1.24 ± 0.52 | 75.6 ± 1.46 | 21.02 ± 1.74 |
| gsy1Δ-AGPAT1 | 28.7 ± 0.46 | 1.36 ± 0.23 | 3.24 ± 0.03 | 48.98 ± 0.41 | 17.72 ± 0.84 |
| gsy1Δ-CreLPAT | 35.9 ± 1.4 | 3.63 ± 3.79 | 3.33 ± 0.84 | 43.72 ± 1.68 | 13.43 ± 1.2 |
| gsy1Δ-PLPAT | 3.13 ± 0.55 | 1.57 ± 0.43 | 1.06 ± 0.09 | 77.2 ± 1.28 | 17.05 ± 0.32 |

TABLE 14

Total C16:0 enrichment at the sn-2 position in TAG of *Y. lipolytica* strains in nitrogen-limited media. Values are means ± SD of measurements made on three separate cultures for each geneotype.

| Strain | % of C16:0 at sn-2 position |
|---|---|
| WT | 3.53 ± 2.22 |
| PO1d | 0.64 |
| gsy1Δ | 5.5 ± 2.09 |
| gsy1Δ-AGPAT1 | 57.83 ± 2.76 |
| gsy1Δ-CreLPAT | 62.68 ± 6.17 |
| gsy1Δ-PLPAT | 11.6 ± 1.79 |

Optimized Gene sequence synthesis for expression in *Y. lipolytica*. With reference to the sequences below, the underlined parts show where the coding sequences have restriction sites added at each end and a 3'UTR/terminator.

CreLPAT—

(SEQ ID NO: 36)

AAGCTTATG

TCTGTCCTCACCAAGTGGCTGGGTCTCCCCTCTTTCCTGTTCTCCGTCTTCGTGTTCTACTGGTCTCTCCCCATC

TTCGCCATTCTGTACCGAATCCGATTCGCTTCCCTGGGAAAGCGAAACGACATGCTCGACTGGGCTCGAGCCCTG

GTCGCCTACTTCCGAGTGACCCTGCTCCAGGCTGGCGAGCACACCCTGTACAAGGGCGGTCCCTGCCTGTACCTC

TGTAACCACCGATCCTGGGCTGACTTCTTCATTGACGCTTACCTGACCGAGGGACGAGCTGCTCTCATGTCTCGA

TGGCTGGTCTACTTCGTGTTCCCCGTCTTCTGCACCTCCTGTATGATCCTCAAGGGTATTGTCCTGTTCAAGCGA

GGAACCATTGCCGACAAGGAAGCCTTCAACGCCTGGCTGGACCAGACCCTGGGATCCTCTCACGTCCCTGGACTG

CTGGTGTACCCCGAGGGACACCGATCTACCAAGCCTGCCTCCCTGCCTCTCAAGCGAGGTATGCTCCACTACGCT

CACTCTCGAAAGCTGCCCGTGCAGATTGTCGTGACCCGAGGCAAGGACGAGGTCCTGTCCGAGAAGTCTCAGTCC

GTGCACTTCGGACGAACCTGCGTCACCACCTTCTCTAAGGTGCTCAAGTCCGCTGACTACCCCAACTTCGAGGCC

TTCTTCACCGACCTGCAGGCTACCTGGGACTCTTGTTGGGCCGCTACCTACGGACTGGAGGACCTCAAGAACGTG

CCTCGATTCTCTATGCCCGGACCTCAGGCCTACTCCTACTCCTCTTCCATGTGGGTGCAGCAGCTCGCCATCACC

-continued

CTCGTGTCTATTCTGGTCTTCGCTGGAGTTTGTTACGGCTCCTGGCGAGGTCTGGCCGCTGCCCTGGCTGCTACC

GGTGCTGCCCAGCAGGTGGTTGCTCTGGTGCTGGCTGCTTGGGTGGGTTCTTCCGTGCTCCGATCCTTCCTG

<u>TAACGATCGTTTTTTTTTATATATATATATATATATATATAACTGTCTAGAAATAAAGAGTATCATCTTTCAAAA</u>

<u>AGCTT</u>

AGPAT1—

(SEQ ID NO: 37)
<u>AAGCTTATG</u>

GACCTGTGGCCCGGAGCTTGGATGCTGCTCCTGCTCCTGTTCCTCCTCCTGCTGTTCCTCCTGCCCACCCTGTGG

TTCTGCTCCCCCTCTGCTAAGTACTTCTTCAAGATGGCCTTCTACAACGGTTGGATTCTGTTCCTGGCCGTCCTG

GCTATTCCCGTCTGTGCTGTGCGAGGACGAAACGTGGAGAACATGAAGATCCTCCGACTGATGCTCCTGCACATC

AAGTACCTGTACGGAATTCGAGTTGAGGTCCGAGGCGCCCACCACTTCCCTCCCTCCCAGCCTTACGTCGTGGTC

TCTAACCACCAGTCCTCTCTGGACCTCCTGGGTATGATGGAGGTGCTCCCTGGACGATGTGTCCCTATCGCTAAG

CGAGAGCTGCTCTGGGCTGGTTCCGCTGGACTGGCTTGTTGGCTGGCTGGCGTCATCTTCATTGACCGAAAGCGA

ACCGGTGACGCTATTTCCGTGATGTCTGAGGTGGCTCAGACCCTCCTGACCCAGGACGTTCGAGTCTGGGTGTTC

CCTGAGGGAACCCGAAACCACAACGGTTCCATGCTGCCCTTCAAGCGAGGCGCCTTCCACCTCGCTGTCCAGGCT

CAGGTCCCTATTGTGCCCATTGTCATGTCCTCTTACCAGGACTTCTACTGCAAGAAGGAGCGACGATTCACCTCT

GGACAGTGTCAGGTCCGAGTGCTGCCTCCCGTGCCTACCGAGGGACTGACCCCCGACGACGTTCCTGCTCTGGCT

GACCGAGTCCGACACTCCATGCTGACCGTGTTCCGAGAGATTTCTACCGACGGTCGAGGCGGTGGAGACTACCTC

AAGAAGCCCGGCGGTGGAGGC

<u>TAACGATCGTTTTTTTTTATATATATATATATATATATATAACTGTCTAGAAATAAAGAGTATCATCTTTCAAAA</u>

<u>AGCTT</u>

PLPAT—

(SEQ ID NO: 38)
<u>AAGCTTATG</u>

TCCGACCTGTCTGGTGCTGCTACCCCCGAGTCCACCTACCCTGAGCCTGAGATCAAGCTGTCCTCTCGACTCCGA

GGAATTTGCTTCTGTCTCGTCGCCGGCGTGTCTGCTATCGTCCTGATTGTGCTCATGATCACCGGCCACCCCTTC

GTCCTGCTCTTCGACCGATACCGACGAAAGTTCCACCACTTCATCGCCAAGCTGTGGGCTTCCATCTCTATCTAC

CCCTTCTACAAGACCGACATTCAGGGTCTGGAGAACCTCCCCTCCTCTGACACCCCCTGCGTCTACGTGTCCAAC

CACCAGTCTTTCCTGGACATCTACACCCTGCTCTCCCTCGGACAGTCTTACAAGTTCATTTCCAAGACCGGCATC

TTCGTCATTCCCGTGATCGGCTGGGCCATGTCCATGATGGGTGTCGTGCCCCTGAAGCGAATGGACCCCCGATCT

CAGGTCGACTGCCTGAAGCGATGTATGGAGCTCGTCAAGAAGGGTGCCTCCGTCTTCTTCTTCCCCGAGGGAACC

CGATCTAAGGACGGACGACTGGGCCCCTTCAAGAAGGGCGCTTTCACCATTGCTGCTAAGACCGGTGTGCCTGTG

GTGCCCATTACCCTGATGGGCACCGGCAAGATCATGCCCACCGGTTCCGAGGGAATTCTCAACCACGGTGACGTC

CGAGTGATCATTCACAAGCCCATCTACGGATCTAAGGCTGACCTGCTCTGTGACGAGGCCCGAAACAAGATTGCT

GAGTCCATGAACCTGCTCTCT

<u>TAACGATCGTTTTTTTTTATATATATATATATATATATATAACTGTCTAGAAATAAAGAGTATCATCTTTCAAAA</u>

<u>AGCTT</u>

Example 7—Cultivation of *Yarrowia lipolytica* on Various Carbon Sources

In Example 6, TAG fatty acyl composition and % of C16:0 at the sn-2 position were evaluated in *Y. lipolytica* strains grown on nitrogen-limited media with 20 g $L^{-1}$ glycerol as the carbon source. In this example, we additionally evaluated use of sugar, vegetable oil and mixtures of these carbon sources to examine whether there is an effect on % C16:0 at the sn-2 position in TAG, total fatty acyl composition of TAG, total lipid content and biomass formation. The sugar, oil and mixed carbon sources used in this example are as follows:

20 g $L^{-1}$ glycerol (see Example 6)
20 g $L^{-1}$ glucose
20 g $L^{-1}$ palm oil
10 g $L^{-1}$ glucose and 10 g $L^{-1}$ palm oil
10 g $L^{-1}$ glycerol and 10 g $L^{-1}$ palm oil The culture media and growth conditions for *Y. lipolytica* strains were the same as described for Example 6, except that when cells were grown with palm oil, the media was supplemented to 0.1% Tween-80 per gram of oil used. Lipid extraction and analyses were performed as described in Example 1.

Cultivation on Glucose

The data presented in Table 15 and Table 19 show that when *Y. lipolytica* WT, gsy1Δ and gsy1Δ-CreLPAT strains are supplied glucose as a carbon source in nitrogen-limited media, the TAG fatty acyl profile and % of C16:0 at the sn-2 position (Table 19) are similar to those observed when the strains are cultured on glycerol (Example 6).

TABLE 15

Total and sn-2 fatty acyl composition of TAG of *Y lipolytica* strains in nitrogen-limited media with glucose as the carbon source. Values are means ± SD of measurements made on three separate cultures for each genotype. nd is not detected.

| | Total fatty acid composition in TAG (%) | | | | |
|---|---|---|---|---|---|
| Strain | 16:0 | 18:0 | 16:1 | 18:1 | 18:2 |
| WT | 22.5 ± 0.13 | 8.6 ± 0.05 | 6.5 ± 0.15 | 50.1 ± 0.15 | 12.2 ± 0.30 |
| gsy1Δ | 10.2 ± 0.29 | 8.8 ± 0.27 | 4.6 ± 0.18 | 64.6 ± 0.31 | 11.7 ± 0.16 |
| gsy1Δ-CreLPAT | 19.8 ± 0.28 | 8.3 ± 0.12 | 3.5 ± 0.12 | 58.3 ± 0.07 | 10.1 ± 0.20 |

| | Fatty acid species at sn-2 position (%) | | | | |
|---|---|---|---|---|---|
| Strain | 16:0 | 18:0 | 16:1 | 18:1 | 18:2 |
| WT | 0.7 ± 0.37 | 0.6 ± 0.36 | nd | 76.9 ± 0.92 | 20.5 ± 0.22 |
| gsy1Δ | 0.7 ± 0.23 | 0.4 ± 0.09 | nd | 81.3 ± 0.23 | 16.9 ± 0.15 |
| gsy1Δ-CreLPAT | 36.5 ± 0.34 | 0.4 ± 0.04 | 0.8 ± 0.04 | 49.0 ± 0.51 | 10.4 ± 0.16 |

Cultivation on Palm Oil

The data presented in Table 16 and Table 19 show that when *Y. lipolytica* WT and gsy1Δ-CreLPAT strains are supplied palm oil as a carbon source in nitrogen-limited media, the TAG fatty acyl profiles are altered relative to culture on glycerol or glucose. The total % of C16:0 in TAG is increased from ~20% to ~26% in gsy1Δ-CreLPAT and the total % of stearic acid (C18:0) is decreased from ~8% to ~1%. For gsy1Δ-CreLPAT, the % of C16:0 at the sn-2 position is similar when cultured on palm oil, glucose or glycerol. However, the % of total long chain saturated fatty acyl groups (C16:0+C18:0) at the sn-1/3 positions is decreased when gsy1Δ-CreLPAT is cultured on palm oil verses glucose or glycerol, because the total % of C18:0 in TAG is lowered and C18:0 is predominantly esterified at the sn-1/3 positions. In WT and gsy1Δ-CreLPAT, culture on palm oil also leads to a higher cell biomass, cell lipid content and lipid titre than culture on glucose or glycerol (Table 20).

TABLE 16

Total and sn-2 fatty acyl composition of TAG of *Y. lipolytica* strains in nitrogen-limited media with palm oil as the carbon source. Values are means ± SD of measurements made on three separate cultures for each genotype. nd is not detected.

| | Total fatty acid composition in TAG (%) | | | | |
|---|---|---|---|---|---|
| Strain | 16:0 | 18:0 | 16:1 | 18:1 | 18:2 |
| WT | 30.3 ± 0.53 | 2.2 ± 0.23 | 5.4 ± 1.14 | 39.2 ± 0.27 | 22.8 ± 0.44 |
| gsy1Δ-CreLPAT | 26.2 ± 0.96 | 1.1 ± 0.09 | 3.7 ± 0.10 | 42.2 ± 0.56 | 26.3 ± 0.67 |

| | Fatty acid species at sn-2 position (%) | | | | |
|---|---|---|---|---|---|
| Strain | 16:0 | 18:0 | 16:1 | 18:1 | 18:2 |
| WT | 0.40 ± 0.07 | 0.3 ± 0.04 | nd | 64.0 ± 0.31 | 35.3 ± 0.21 |
| gsy1Δ-CreLPAT | 48.8 ± 0.93 | 1.0 ± 0.77 | 0.7 ± 0.06 | 37.5 ± 1.04 | 11.7 ± 0.64 |

Cultivation on Glucose and Palm Oil

The data presented in Table 17 and Table 19 show that when *Y. lipolytica* WT and gsy1Δ-CreLPAT strains are supplied with a mixture of glucose and palm oil as carbon sources in nitrogen-limited media, the TAG fatty acyl profiles are altered relative to culture on glucose or palm oil alone. The total % of C16:0 in TAG is increased in gsy1Δ-CreLPAT (to ~24%) relative to culture on glucose or glycerol and the total % of C18:0 is also decreased. For gsy1Δ-CreLPAT, the % of C16:0 at the sn-2 position is higher on glucose+palm oil (~69%) than it is on glucose, palm oil or glycerol alone (~62%). The % of total long chain saturated fatty acids (C16:0+C18:0) at the sn-1/3 positions is lower on glucose+palm oil than it is on glucose, palm oil or glycerol alone. Human milk fat (HMF) usually has a total % C16:0 content of 20 to 25% with ~70% of C16:0 at the sn-2 position and a relatively low total C18:0 content of ~5%. The TAG fatty acyl composition of gsy1Δ-CreLPAT when cultured on glucose+palm oil is therefore a better substitute, providing an adequate total % of C16:0 while minimising the % of, not only C16:0 but also, total long chain saturated fatty acyl groups (C16:0+C18:0) present at sn-1/3. In WT and gsy1Δ-CreLPAT, culture on glucose+palm oil also leads to a higher cell biomass, cell lipid content and lipid titre than culture on glucose or glycerol (Table 20).

TABLE 17

Total and sn-2 fatty acyl composition of TAG of *Y. lipolytica* strains in nitrogen-limited media with a mixture of palm oil and glucose as the carbon sources. Values are means ± SD of measurements made on three separate cultures for each genotype. nd is not detected.

| | Total fatty acid composition in TAG (%) | | | | |
|---|---|---|---|---|---|
| Strain | 16:0 | 18:0 | 16:1 | 18:1 | 18:2 |
| WT | 24.5 ± 2.50 | 2.3 ± 0.14 | 3.0 ± 0.35 | 48.6 ± 1.91 | 21.7 ± 0.49 |
| gsy1Δ-CreLPAT | 23.9 ± 3.15 | 1.2 ± 0.09 | 3.2 ± 0.12 | 49.4 ± 2.69 | 21.7 ± 1.17 |

TABLE 17-continued

Total and sn-2 fatty acyl composition of
TAG of *Y. lipolytica* strains in
nitrogen-limited media with a mixture of palm oil and glucose as the
carbon sources. Values are means ± SD of measurements made on
three separate cultures for each genotype. nd is not detected.

| | Fatty acid species at sn-2 position (%) | | | | |
|---|---|---|---|---|---|
| Strain | 16:0 | 18:0 | 16:1 | 18:1 | 18:2 |
| WT | 0.60 ± 0.48 | 0.5 ± 0.35 | nd | 69.1 ± 1.02 | 29.8 ± 1.19 |
| gsy1Δ-CreLPAT | 49.4 ± 3.76 | 0.5 ± 0.15 | 0.7 ± 0.06 | 39.0 ± 3.94 | 9.80 ± 0.07 |

Cultivation on Glycerol and Palm Oil

The data presented in Table 18, Table 19 and Table 20 show that when *Y. lipolytica* gsy1Δ-CreLPAT is supplied with a mixture of glycerol and palm oil as carbon sources in nitrogen-limited media, the TAG fatty acyl profile, % of C16:0 at the sn-2 position (Table 19), cell biomass, lipid content and lipid titre are more similar to those observed when the strain is cultured on glucose+palm oil than on glucose or glycerol alone. No dipalmitoyl PC was detected in *Y. lipolytica* WT or gsy1Δ-CreLPAT cultured on carbon sources used in Example 6 & 7. Samples were analysed using the method described in Example 1. This suggests that *Y. lipolytica* cells expressing a C16:0 LPAT exclude C16:0 from the sn-2 position of PC; something that we have also observed in *Arabidopsis* seeds expressing C16:0 LPATs. Therefore C16:0 incorporation into the sn-2 position of TAG in *Y. lipolytica* expressing a C16:0 LPAT may also be restricted by enzyme activities responsible for DG/PC conversion, for example C16:0 incorporation into the sn-2 position of TAG could be enhanced by suppressing or preventing the activity of choline phosphotransferase (CPT1; EC 2.7.8.2) and/or ethanolamine phosphotransferase (EPT1; EC 2.7.8.1).

TABLE 18

Total and sn-2 fatty acyl composition of TAG of
*Y. lipolytica* strains in
nitrogen-limited media with a mixture of palm oil and glycerol
as carbon sources. Values are of measurements
made on a single culture for each genotype.

| | Total fatty acid composition in TAG (%) | | | | |
|---|---|---|---|---|---|
| Strain | 16:0 | 18:0 | 16:1 | 18:1 | 18:2 |
| gsy1Δ-CreLPAT | 23.0 | 2.7 | 4.3 | 44.2 | 25.7 |

| | Fatty acid species at sn-2 position (%) | | | | |
|---|---|---|---|---|---|
| Strain | 16:0 | 18:0 | 16:1 | 18:1 | 18:2 |
| gsy1Δ-CreLPAT | 48.3 | 0.4 | 1.6 | 37.1 | 12.2 |

TABLE 19

Total C16:0 enrichment at the sn-2 position in TAG of *Y. lipolytica*
strains in nitrogen-limited media with various carbon sources.
Values are means ± SD of measurements made on three
separate cultures for each genotype, except for gsy1Δ-CreLPAT
on Glycerol + Palm oil where the value is for a single culture.

| Strain | Substrate | % of C16:0 at sn-2 position |
|---|---|---|
| WT | Glucose | 1.10 ± 0.56 |
| gsy1Δ | | 2.10 ± 0.77 |

TABLE 19-continued

Total C16:0 enrichment at the sn-2 position in TAG of *Y. lipolytica*
strains in nitrogen-limited media with various carbon sources.
Values are means ± SD of measurements made on three
separate cultures for each genotype, except for gsy1Δ-CreLPAT
on Glycerol + Palm oil where the value is for a single culture.

| Strain | Substrate | % of C16:0 at sn-2 position |
|---|---|---|
| gsy1Δ-CreLPAT | | 61.6 ± 0.94 |
| WT | Palm oil | 0.50 ± 0.07 |
| gsy1Δ-CreLPAT | | 62.2 ± 3.15 |
| WT | Glucose + | 0.90 ± 0.66 |
| gsy1Δ-CreLPAT | Palm oil | 69.1 ± 3.98 |
| gsy1Δ-CreLPAT | Glycerol + Palm oil | 69.9 |

TABLE 20

*Y. lipolytica* strain biomass, lipid content and lipid titre in nitrogen-
limited media with various carbon sources. Values are means ±
SD of measurements made on three separate cultures
for each genotype, except for gsy1Δ-CreLPAT on Glycerol +
Palm oil where the value is for a single culture.

| Strain | Substrate | Biomass (g L$^{-1}$) | Lipid (mg g$^{-1}$ Biomass) | Lipid (g L$^{-1}$) |
|---|---|---|---|---|
| WT | Glucose | 4.0 ± 0.13 | 101.3 ± 17.84 | 0.4 ± 0.06 |
| gsy1Δ | | 3.6 ± 0.06 | 181.6 ± 3.44 | 0.7 ± 0.01 |
| gsy1Δ-CreLPAT | | 3.7 ± 0.05 | 170.5 ± 16.73 | 0.6 ± 0.06 |
| WT | Glycerol | 4.0 ± 0.13 | 115.2 ± 5.39 | 0.5 ± 0.04 |
| gsy1Δ-CreLPAT | | 3.3 ± 0.07 | 215.1 ± 9.11 | 0.7 ± 0.04 |
| WT | Palm oil | 6.3 ± 1.06 | 480.3 ± 65.06 | 3.1 ± 0.81 |
| gsy1Δ-CreLPAT | | 6.7 ± 1.29 | 465.7 ± 40.53 | 3.1 ± 0.48 |
| WT | Glucose + | 5.9 ± 0.23 | 424.5 ± 21.98 | 2.5 ± 0.09 |
| gsy1Δ-CreLPAT | Palm oil | 5.9 ± 1.27 | 468.1 ± 21.69 | 2.8 ± 0.50 |
| gsy1Δ-CreLPAT | Glycerol + Palm oil | 4.84 | 405 | 1.96 |

Example 8

Although the examples discussed above show that plant lipid metabolism can be engineered to preferentially esterify 16:0 to the sn-2 position in TAG, it would be desirable for the total fatty acid composition of the *Arabidopsis* seeds to more closely resemble that of human milk. 16:0 is ~3-fold less abundant in *Arabidopsis* seeds and they contain a high proportion of polyunsaturated and very-long-chain fatty acid species that are essentially absent from human milk. The most abundant fatty acid in human milk is 18:1 and, because of the unusual regiospecific distribution of the next most abundant fatty acid 16:0, the major molecular species of TAG is usually 1,3-olein-2-palmitin (OPO) accounting for ~14% of the total. We decided to investigate whether *Arabidopsis* seeds can be engineered to produce OPO, by combining 16:0 enrichment at the sn-2 position in TAG with a total fatty acid composition rich in the appropriate ratio of 16:0 and 18:1.

Results

Seed of fab1-1 fae1 fad2 are high in 16:0 and 18:1 (HPHO)

To obtain *Arabidopsis* seeds with 16:0 content equivalent to human milk the level must be increase ~3-fold to 20-25%. One approach to achieve this is to reduce fatty acid synthase catalysed 16:0 elongation by disrupting the β-ketoacyl-ACP synthase II gene FATTY ACID BIOSYNTHESIS 1 (FAB1) (FIG. 8). FAB1 is an essential gene in *Arabidopsis*, but a single hypomorphic fab1-1 allele has been characterised that contains ~17% 16:0 in is seeds. 16:0 can then be increased to ~24% in a fatty acid elongase 1 (fae1) mutant background, which is deficient in very-long-chain fatty acid synthesis (FIG. 8). However, fab1-1 fae1 seeds still contain a high proportion of polyunsaturated fatty acids, produced via FATTY ACID DESATURASE 2 (FAD2) (FIG. 8). To create a background high both 16:0 and 18:1 (HPHO) we therefore constructed a fab1-1 fae1 fad2 mutant by crossing. Analysis of homozygous fab1-1 fae1 fad2 seeds showed that the fatty acid composition of the TAG is high in 16:0 and 18:1, which account for ~20 and ~70% of total fatty acid, respectively (FIG. 9). Other fatty acid species that are normally abundant in wild type Arabidopsis Col-0 seed TAG, such as linoleic acid (18:2), linolenic acid (18:3) and eicosenoic acid (20:1), each account for <3% (FIG. 9). Comparison with the double mutants showed that 16:0 content in fab1-1 fae1 is reduced significantly (P>0.05) in the fad2 background (FIG. 9). Nevertheless, the HPHO composition of fab1-1 fae1 fad2 seeds suggests that this genetic background is appropriate to test whether OPO can be produced in seeds.

ΔCTS-LPAT1 Expression in HPHO Seed Drives 16:0 Incorporation into the Sn-2 Position of TAG As discussed above, we have shown that expression of an ER-retargeted version of the chloroplast LPAT (ΔCTS-LPAT1) in WT Arabidopsis seeds, under the soybean glycinin-1 promoter (ProGLY), leads to a substantial increase in esterification of 16:0 to the sn-2 position in TAG. To determine what effect ΔCTS-LPAT1 expression has in a HPHO background, we constructed a ProGLY:ΔCTS-LPAT1 fab1-1 fae1 fad2 line by crossing. When we purified TAG from the seeds and determined its regiochemistry, we found that the percentage of 16:0 at the sn-2 position (versus sn-1+3), had increased from ~3% in the fab1-1 fad2 fae1 background to ~24% in ProGLY:ΔCTS-LPAT1 fab1-1 fad2 fae1 (FIG. 10A). The total fatty acid composition of fab1-1 fad2 fae1 seeds was not altered greatly by ΔCTS-LPAT1 expression, except that there was a small but significant (P>0.05) increase in 16:0 abundance, from ~19 to ~22% (FIG. 10B). We previously observed a small increase in total 16:0 content when we expressed ΔCTS-LPAT1 in WT seeds. Our data show that ΔCTS-LPAT1 expression in HPHO seeds allows incorporation of 16:0 into the sn-2 position of TAG. However, the level of enrichment is significantly lower (P>0.05) than in WT seeds containing ProGLY:ΔCTS-LPAT1 (FIG. 10A).

AGPAT1 Expression Drives Stronger 16:0 Incorporation into the Sn-2 Position of TAG To investigate whether other ER-localised LPATs might enable Arabidopsis to incorporate more 16:0 into the sn-2 position of TAG than ΔCTS-LPAT1, we decided to test Homo sapiens AGPAT1. Human milk fat globules are secreted by lactocytes in the mammary gland epithelium. It is not known which LPAT is responsible for human milk fat biosynthesis. However, AGPAT1 is expressed in mammary epithelial cells and in vitro assays suggest that AGPAT1 can use 16:0-CoA as a substrate. To test whether AGPAT1 can incorporate 16:0 into the sn-2 position of TAG we first expressed the protein in Saccharomyces cerevisiae under the GAL1 promoter (28). When we purified TAG and determined its regiochemistry, we found that the percentage of 16:0 at the sn-2 position had increased from ~4% in cells harbouring an empty vector control to ~45% in cells containing ProGAL1:AGPAT1 (Table 21).

TABLE 21

16:0 in TAG from S. cerevisiae cells expressing AGPAT1.

| Vector | 16:0 at sn-2 (%) | Total 16:0 (%) |
|---|---|---|
| pYES2 (EVC) | 3.8 ± 0.7 | 11.8 ± 0.2 |
| pYES2 + AGPAT1 | 44.7 ± 3.9* | 14.6 ± 0.3* |

Values are the mean ± SE of measurements on lipid extracts from three separate cultures.
*denote values significantly (P < 0.05) different either from empty vector control (EVC) (two-tailed Student's t-tests).

Using transient expression in Nicotiana benthamiana leaves, we also confirmed that AGPAT1 can localise to the ER in plant cells when it is expressed as a red fluorescent protein (RFP)-AGPAT1 fusion protein under the cauliflower mosaic virus 35S promoter (FIG. 11A). Next we transformed WT Arabidopsis plants with a ProGLY:AGPAT1 construct in order drive strong seed-specific expression of the transgene. From >40 primary transformants we selected two independent single copy T2 lines (L35 & L40) for analysis and obtained homozygous T3 seed. When we purified TAG from the homozygous seed batches and determined its regiochemistry, we found that the percentage of 16:0 at the sn-2 position was ~66% for L40 and ~74% for L35 (FIG. 11B). To determine what effect AGPAT1 expression has in the HPHO background we constructed a ProGLY:AGPAT1 fab1-1 fae1 fad2 line by crossing. When we purified TAG from these seeds and determined its regiochemistry, we found that the percentage of 16:0 at the sn-2 position was ~54% (FIG. 11B). The total 16:0 content of ProGLY:AGPAT1 fab1-1 fae1 fad2 seeds was not significantly different (P>0.05) from fab1-1 fae1 fad2 (FIG. 11C). AGPAT1 expression therefore allows a higher incorporation of 16:0 into the sn-2 position of TAG in WT and HPHO seeds than ΔCTS-LPAT1.

Disruption of LPAT2 and PDCT Enhances ΔCTS-LPAT1 and AGPAT1-Dependent 16:0 Incorporation into the Sn-2 Position of TAG in HPHO Seeds In wild type (WT) Arabidopsis seeds we previously found that ΔCTS-LPAT1-dependent incorporation of 16:0 into the sn-2 position of TAG could be increased by disrupting the enzymes LPAT2 and PDCT. LPAT2 is the main ER-localized LPAT isoform expressed in Arabidopsis seeds and therefore disruption likely reduces competition with ΔCTS-LPAT1 (FIG. 8). PDCT catalyses rapid DG/PC interconversion in Arabidopsis seeds. Although LPAT initially acylates glycerolipids at sn-2, once these acyl groups are in PC they can be removed and replaced by a deacylation-reacylation (acyl editing) cycle. Disruption of PDCT forces a more direct flux of newly made DG into TAG (FIG. 8). To determine whether LPAT2 and PDCT disruption affect the percentage of 16:0 esterified to the sn-2 position in TAG in HPHO seeds expressing ΔCTS-LPAT1 or AGPAT1, we constructed ProGLY:ΔCTS-LPAT1 fab1-1 fae1 fad2 lpat2-2 pdct and ProGLY:AGPAT1 fab1-1 fae1 fad2 lpat2-2 pdct lines by crossing. When we purified TAG from these seeds and determined its regiochemistry, we found that the percentage of 16:0 at the sn-2 position, was ~62% and ~83%, respectively (FIG. 12A). The total 16:0 content in ProGLY:ΔCTS-LPAT1 fab1-1 fae1 fad2 lpat2-2 pdct and ProGLY:AGPAT1 fab1-1 fae1 fad2 lpat2-2 pdct seeds was ~21 and ~18%, respectively (FIG. 12B).

HPHO Seeds have Reduced Oil Content and Seed Vigour but this is not Compounded by Redistribution of 16:0 to the Sn-2 Position Modification of fatty acid composition can reduce TAG accumulation in oilseeds and can also impair seed germination and seedling establishment. As discussed above, we have found that ProGLY:ΔCTS-LPAT1 lpat2-3 pdct seeds, which have a low total 16:0 content but ~70% esterified to the sn-2 position, exhibit a reduction in TAG content as a percentage of seed weight. However, their germination and initial seedling growth were not significantly impaired. To examine the physiological impact of 16:0 enrichment at the sn-2 position of TAG in HPHO seeds, we compared seed batches from WT, fab1-1 fae1 fad2, ProGLY:ΔCTS-LPAT1 fab1-1 fae1 fad2 lpat2-2 pdct and ProGLY:AGPAT1 fab1-1 fae1 fad2 lpat2-2 pdct plants that had been grown together under standard laboratory conditions. We found that both seed weight and percentage oil content were significantly reduced (P>0.05) in fab1-1 fae1 fad2 relative to WT (FIG. 13). However, no significant difference was observed between fab1-1 fae1 fad2 and ProGLY:ΔCTS-LPAT1 fab1-1 fae1 fad2 lpat2-2 pdct or ProGLY:AGPAT1 fab1-1 fae1 fad2 lpat2-2 pdct seeds (FIG. 13). These data suggest that TAG biosynthetic flux is impaired in fab1-1 fae1 fad2 seeds, but that the further genetic modifications leading to incorporation of 16:0 into the sn-2 position of TAG are not detrimental in this background. These findings contrast with what we observed in WT seeds. In standard laboratory conditions (20° C., 16 h photoperiod), the speed of fab1-1 fae1 fad2 seed germination (scored as radicle emergence) and seedling establishment (scored as cotyledon expansion) was significantly slower (P>0.05) than WT (FIG. 14). However, no significant difference (P>0.05) was observed between fab1-1 fae1 fad2 and ProGLY:ΔCTS-LPAT fab1-1 fae1 fad2 lpat2-2 pdct or ProGLY:AGPAT1 fab1-1 fae1 fad2 lpat2-2 pdct seeds (FIG. 14).

Discussion

In this example we show that *Arabidopsis* seeds can be engineered to produce OPO, since the TAG contains ~20% 16:0 and ~70% 18:1, with >80% of the 16:0 esterified to the sn-2 position on the glycerol backbone, by combining fab1-1, fae1 and fad2 alleles. OPO is the main TAG species present in human milk, but it is virtually absent from vegetable oils, which typically contain very little 16:0 esterified to the sn-2 position. The high OPO content of human milk is believed to confer nutritional benefits and therefore the development of a vegetable oil that is rich in OPO could provide a useful new source of ingredient for infant formulas.

The expression of an ER-retargeted version of the chloroplast LPAT (ΔCTS-LPAT1) in WT *Arabidopsis* seeds allows ~30 to 40% of the 16:0 present in the TAG to occupy the sn-2 position. However, when we expressed ΔCTS-LPAT1 in the HPHO background, we found the incorporation of 16:0 into the sn-2 position was reduced to ~20%. Disruption of LPAT2 and PDCT then lead to an increase in the percentage of 16:0 at sn-2 to ~62%. This level of 16:0 enrichment at sn-2 is also lower than we were able to achieve in WT using the same approach. However, the total fatty acid composition of HPHO is far more appropriate for an infant formula ingredient and ~62% 16:0 at sn-2 still compares favourably with commercially available HMFS that are produced by in vitro enzyme-catalysis.

Generally, in human milk fat >70% of the 16:0 is esterified to the sn-2 position of TAG and this level of enrichment therefore remains the target for HMFS. The human LPAT AGPAT1 can use 16:0-CoA as a substrate and is expressed in lactocytes. When we expressed AGPAT1 in WT *Arabidopsis* seeds we found that 60 to 70% of the 16:0 present in the TAG occupied the sn-2 position.

When we expressed AGPAT1 in a HPHO background, incorporation of 16:0 into the sn-2 position was reduced to ~54%, but disruption of LPAT2 and PDCT then lead to an increase in the percentage of 16:0 at sn-2 to ~83%. This level of enrichment of 16:0 at sn-2 is greater than or equal to that reported in human milk fat.

Metabolic pathway engineering can often have detrimental effects on TAG accumulation in oilseeds and can impair seed vigour. In EXAMPLE 1 discussed above, we found that redirecting 16:0 to the sn-2 position of TAG in WT *Arabidopsis* seeds reduced oil accumulation. HPHO seeds also have a lower seed oil content than WT. However, engineering a similar shift in positional distribution of 16:0 did not lead to a further reduction. Given that WT seeds have a ~3-fold lower 16:0 content than HPHO seeds, it may be that 16:0 availability restricts the rate of TAG biosynthesis in seeds engineered to only possess 16:0-CoA LPAT activity. Conversely, the ~3-fold higher 16:0 content in HPHO seeds might conceivably restrict TAG biosynthesis because native LPATs (and other acyltransferase activities) have too little 16:0-CoA activity. HPHO seeds are also significantly impaired in seed germination and early seedling growth. However, redirecting 16:0 to the sn-2 position of TAG in HPHO seeds does not compound this effect. Poorer HPHO seed vigour may be caused by the reduction in long-chain fatty acid unsaturation, which raises the melting temperature of the oil. This property is not greatly influenced by the positional distribution of the fatty acid.

Materials and Methods

Plant Material and Growth Conditions

The *Arabidopsis thaliana* Colombia-0 mutants fab1-1, fae1, fad2, pdct and lpat2-3 have been described previously (26) (27) (2). For experiments performed on media, ~50 seeds from individual plants were surface sterilized, plated on agar plates containing one-half strength Murashige and Skoog salts (Sigma-Aldrich) pH 5.7 and imbibed in the dark for 4 d at 4° C. The plates were then placed in a growth chamber set to 16-h light (photosynthetic photon flux density=150 μmol m$^{-2}$ s$^{-1}$)/8-h dark cycle at a constant temperature of 20° C. Germination (radicle emergence) and cotyledon expansion was scored visually under a dissecting stereomicroscope as described previously herein. Individual seedlings were also transplanted to 7 cm$^2$ pots containing Levington F2 compost and grown in a chamber set to a 16-h light (22° C.)/8-h dark (16° C.) cycle, with a photosynthetic photon flux density of 250 μmol m$^{-2}$ s$^{-1}$. The plants were bagged individually at the onset of flowering and the seeds were harvested at maturity.

Genotyping

Genomic DNA was isolated from leaves using the DNeasy Plant Mini Kit (Qiagen). Homozygous lpat2-3 T-DNA insertional mutants were identified by PCR using Promega PCR Master Mix (Promega) and combinations of the gene specific and T-DNA left border primers pairs, as described previously herein. Homozygous fab1-1, fad2, fae1 and pdct mutants were identified by sequencing PCR products amplified with primer pair spanning the sites of the point mutations (26) (27) (2). The presence of ProGLY:ΔCTS-LPAT and ProGLY:AGPAT T-DNAs was determined by PCR using a primer pair spanning ProGLY and ΔCTS-LPAT1 or AGPAT1, as described previously herein.

Lipid Analysis

Total lipids were extracted from material and TAG was purified as described previously (6). TAG regiochemical analysis was performed by lipase digestion following the method described previously herein, except that 2-monoacylglycerols were separated by thin layer chromatography (Silica gel 60, 20×20 cm; Sigma-Aldrich/Merck) using hexane:diethylether:acetic acid (35:70:1.5, v/v/v) (8). Fatty acyl groups present in whole seeds and purified lipid fractions were trans-methylated and quantified by gas chromatography (GC) coupled to flame ionization detection, as described previously herein, using a 7890A GC system fitted with DB-23 columns (30 m×0.25 mm i.d.×0.25 μm) (Agilent Technologies). Seed oil and moisture contents of whole seeds were measured by low-resolution time domain NMR spectroscopy using a Minispec MQ20 device (Bruker) fitted with a robotic sample-handling system (Rohasys) as described previously herein and the percentage oil content was normalised to 9% moisture.

Cloning and Transformation

H. sapiens AGPAT1 (GenBank: NP 001358367, SEQ ID NO:40) was codon optimised for expression in Arabidopsis, synthesised by Genscript and supplied in pUC57. AGPAT1 was then amplified by PCR with KOD DNA polymerase (Merck) using primer pair 5'-CACCATGGATT-TATGGCCTGGTGC-3' (SEQ ID NO:74) & 5'-TCATCCTCCTCCACCTGG-3' (SEQ ID NO:75). The resulting PCR product was purified with the QIAquick Gel Extraction Kit (Qiagen). The PCR product was cloned in the pENTR/D-TOPO vector (Thermo Fisher Scientific), sequenced (SEQ ID NO:26) and recombined into pYES-DEST52 (Invitrogen) and pK7WGR2 (Vlaams Institute for Biotechnology) using the Gateway LR Clonase II Enzyme mix (Thermo Fisher Scientific). AGPAT was cloned in the pBinGlyRed3 vector in between the soybean glycinin-1 (GLY) promoter and terminator for seed specific expression (3). AGPAT1 was PCR-amplified from the pENTR-D-TOPO vector using KOD DNA polymerase and primer pair 5'-CG-GAATTCATGGATTTATGGCCTGGTGC-3' (SEQ ID NO:76) & 5'-GCTCTAGATCATCCTCCTCCACCTGG-3' (SEQ ID NO:77). The PCR product was gel purified and digested with EcoRI and XbaI. The pBinGlyRed3 vector was also digested with EcoRI and XbaI, alkaline phosphatase treated (Promega), gel purified and AGPAT1 was ligated into the vector using T4 DNA ligase (NEB). pYES-DEST52 was transformed into S. cerevisiae INVSc1 cells using the S. c. EasyComp kit (Invitrogen) and protein expression was induced as described by Kim et al., (2005) (28). Heat shock was used to transform the pK7WGR2 and pBinGlyRed3 vectors into Agrobacterium tumefaciens strain GV3101. Arabidopsis transformation was carried out using the floral-dip method (4). T1 seeds expressing the selectable marker were identified under a Leica M205 FA microscope using the DsRed filter.

Transient Expression in N. benthamiana and Imaging

Transient expression in N. benthamiana leaves was carried out as described by Wood et al., (2009) (5) using A. tumefaciens cultures transformed with vectors harbouring Pro35S:RFP-AGPAT1, Pro35S:m-GFP5-ER or Pro35S:p19. Cultures were hand-infiltrated into leaves and the inoculated plants were left for 48 h. N. benthamiana leaves were then mounted in water on a Zeiss LSM 780 laser scanning confocal microscope under an Apochromat 63x/1.20 W Korr M27 objective. GFP was excited at a wavelength of 488 nm and RFP at 561 nm. Filters with an emission band at 473-551 nm were used for detection.

Statistical Analyses

All experiments were carried out using three biological replicates and the data are presented as the mean values ±standard error of the mean (SE). For statistical analysis we either used one-way analysis of variance (ANOVA) with post-hoc Tukey HSD (Honestly Significant Difference) tests, or two-tailed Student's t-tests.

Accession Numbers

Sequence data described herein can be found in the GenBank/EMBL data libraries under, for example, accession numbers: NP 001358367 (AGPAT1), AF111161 (LPAT1), At1g74960 (FAB1), At3g12120 (FAD2), At4g34520 (FAE1), At3g57650 (LPAT2), At3g15820 (PDCT).

Appendix—Additional Sequence Information

```
>HsAGPAT1 cDNA sequence
                                                      (SEQ ID NO: 39)
ATGGATTTGTGGCCAGGGGCATGGATGCTGCTGCTGCTGCTCTTCCTGCTGCTGCTCTTCCTGCTGCCCA

CCCTGTGGTTCTGCAGCCCCAGTGCCAAGTACTTCTTCAAGATGGCCTTCTACAATGGCTGGATCCTCTT

CCTGGCTGTGCTCGCCATCCCTGTGTGTGCCGTGCGAGGACGCAACGTCGAGAACATGAAGATCTTGCGT

CTAATGCTGCTCCACATCAAATACCTGTACGGGATCCGAGTGGAGGTGCGAGGGGCTCACCACTTCCCTC

CCTCGCAGCCCTATGTTGTTGTCTCCAACCACCAGAGCTCTCTCGATCTGCTTGGGATGATGGAGGTACT

GCCAGGCCGCTGTGTGCCCATTGCCAAGCGCGAGCTACTGTGGGCTGGCTCTGCCGGGCTGGCCTGCTGG

CTGGCAGGAGTCATCTTCATCGACCGGAAGCGCACGGGGGATGCCATCAGTGTCATGTCTGAGGTCGCCC

AGACCCTGCTCACCCAGGACGTGAGGGTCTGGGTGTTTCCTGAGGGAACGAGAAACCACAATGGCTCCAT

GCTGCCCTTCAAACGTGGCGCCTTCCATCTTGCAGTGCAGGCCCAGGTTCCCATTGTCCCCATAGTCATG

TCCTCCTACCAAGACTTCTACTGCAAGAAGGAGCGTCGCTTCACCTCGGGACAATGTCAGGTGCGGGTGC

TGCCCCCAGTGCCCACGGAAGGGCTGACACCAGATGACGTCCCAGCTCTGGCTGACAGAGTCCGGCACTC

CATGCTCACTGTTTTCCGGGAAATCTCCACTGATGGCCGGGGTGGTGGTGACTATCTGAAGAAGCCTGGG

GGCGGTGGGTGA
```

>HsAGPAT1 amino acid sequence
(SEQ ID NO: 40)
MDLWPGAWMLLLLLFLLLLFLLPTLWFCSPSAKYFFKMAFYNGWILFLAVLAIPVCAVRGRNVENMKILRL

MLLHIKYLYGIRVEVRGAHHFPPSQPYVVVSNHQSSLDLLGMMEVLPGRCVPIAKRELLWAGSAGLACWLA

GVIFIDRKRTGDAISVMSEVAQTLLTQDVRVWVFPEGTRNHNGSMLPFKRGAFHLAVQAQVPIVPIVMSSY

QDFYCKKERRFTSGQCQVRVLPPVPTEGLTPDDVPALADRVRHSMLTVFREISTDGRGGGDYLKKPGGGG

>CreLPAT cDNA sequence (*Chlamydomonas reinhardtii* gene Cre17.g738350)
(SEQ ID NO: 41)
ATGTCCGTGCTCACAAAGTGGCTGGGCCTGCCCTCATTCTTGTTCTCCGTGTTTGTGTTCTACTGGAGTTT

GCCCATCTTTGCGATCCTATATCGTATCC

GCTTCGCCTCTCTGGGGAAGCGCAATGATATGCTCGACTGGGCCCGCGCGCTCGTCGCCTACTTCCGAGTA

ACGCTCCTGCAGGCGGGGGAGCACACGCT

GTACAAGGGAGGGCCATGCCTGTACCTGTGCAACCACCGCAGCTGGGCGGACTTCTTCATTGACGCCTACC

TCACTGAGGGCCGCGCGGCGCTCATGAGC

AGGTGGCTGGTGTATTTCGTGTTCCCAGTGTTCTGTACCTCGTGCATGATCCTCAAGGGGATAGTGCTGTT

CAAGCGCGGCACCATTGCGGATAAAGAGG

CCTTCAACGCCTGGCTTGACCAGACCCTGGGCAGCAGCCACGTGCCTGGGCTGCTGGTGTACCCCGAGGGC

CACCGCAGCACCAAGCCGGCCAGCCTGCC

GCTGAAGCGCGGCATGCTGCACTACGCGCACAGCCGCAAGCTGCCGGTGCAGATTGTCGTGACTCGCGGCA

AGGACGAGGTGCTGAGTGAGAAGTCGCAG

TCGGTGCACTTCGGCCGCACCTGCGTCACCACCTTCTCCAAGGTGCTCAAGTCGGCCGACTACCCCAACTT

TGAAGCCTTCTTCACGGACCTGCAGGCGA

CCTGGGACTCGTGCTGGGCAGCCACGTACGGCCTGGAGGATCTCAAAAACGTGCCGCGCTTCTCCATGCCG

GGGCCCCAGGCCTACAGCTACAGCTCCAG

CATGTGGGTCCAGCAGCTCGCCATCACGCTGGTCAGCATCCTAGTCTTTGCGGGCGTGTGCTACGGCTCCT

GGCGCGGCTTGGCGGCGGCGCTGGCGGCG

ACCGGCGCGGCGCAGCAGGTGGTGGCACTGGTGCTGGCGGCCTGGGTGGGCAGCTCCGTGCTTCGTAGCTT

CCTCTAG

>CreLPAT amino acid sequence
(SEQ ID NO: 42)
MSVLTKWLGLPSFLFSVFVFYWSLPIFAILYRIRFASLGKRNDMLDWARALVAYFRVTLLQAGEHTLYKGG

PCLYLCNHRSWADFFIDAYLTEGRAALMSRWLVYFVFPVFCTSCMILKGIVLFKRGTIADKEAFNAWLDQT

LGSSHVPGLLVYPEGHRSTKPASLPLKRGMLHYAHSRKLPVQIVVTRGKDEVLSEKSQSVHFGRTCVTTFS

KVLKSADYPNFEAFFTDLQATWDSCWAATYGLEDLKNVPRFSMPGPQAYSYSSSMWVQQLAITLVSILVFA

GVCYGSWRGLAAALAATGAAQQVVALVLAAWVGSSVLRSFL

>LC107611.1 *Nannochloropsis* sp. NIES-2145 LPAT2 mRNA for
lysophosphatidate acyltransferase 2, complete cds
(SEQ ID NO: 43)
ATGTCTGGTCCAGCCGATGCCAGGGGCCCTGCCCGAGTATCCGATACCATTATTGGTGCGCCCGACCGCC

ACCATGTCGGTCTGACCATCCTCGTCGCCCTTCTCCTGAGCGCCTTTTGCTTTTGCGAATTCTTCATGCT

GCCCGTGGCGATGGCGTTACTGCCCGTGCCAGGTACAACATCGAGGAAGTTGCTGCGGCGCTGGGAGGGC

TTGGTAGCCAAAACTTGGCTGTCCTTTGGAGGGTGGCTCCTGGAAAATGTGGGTGGGGTCAAGCTCATTC

TTACGGGCGACTCGATACTCCCCGGTGATCGTGTGCTGATTCTCAGCAATCATAGGACGAGAATTGATTG

GATGTTTCTATGGTGCTGGGCTGCACGTTTCGACCTGCTTTCCTCGTACCGAGTCATTCTCAAGTCGTCT

TTACGCACTTTCCCCTGGTGGGGCTGGGGGATGAGTTTATGTTTGTTTCCTTTCATCCACCGAGGAAGCA

-continued

```
ACAATCGCGACGCGGATTTGACCCGTATTGAACATATTTGTCAGTATTTAAGCGAGCTGGGTGTGCCAAA

CTCCCTCATTCTCTTCCCAGAAGGAACTGACCTTTCCCAATCTAACCAAAAACGCGATCGTGATTATGCT

CTAGCCAAAAACCTACCCATTTACCATAACGTGCTTCACCCACGTTCAGGCGCCTTTATTGCTAGCTTGA

CGGCCATGCGTCCTCATTTGGATGCTGTTGTGGATCTTACTATCGGCTATGTCGATTACACACCAGGGGA

AAGACCTTCCGAGCTCTCTCTTCTCAAGGGCCGGCTACCGCACGAGGTCCACATAAATATGAAACGATGG

GACATAAAGACGACTCCCTTACTTCGAGAGAACCCATCGGACCGGGCGGAACAATTTTTGCGCGAATCTT

TTGATCGGAAAGAGGCATTGCTGACAGCCTTCTACAGCAACAACACGGACACTTCAGGTGGTGGGCTCAA

GCAAACGTCATCATTGCTCGTATCCTCTTCCTCTTCACCTTTCTCCAATAGCAGTGCACCTTTAGGATTT

CCTTCCTTCTCCTCCCCCTCCACCTCCGTCGCCTCTTCTTACAACGAGCCAGTGTATGTACACAATGCTC

ACTGGACATACGGCAAAGGGCTTTTGGGGACGGGGATTGCCATGGCGTTGGTGCTGATGTTAGCGTGCTG

CTTGCCTGCTGTTGCGTTTTGCGGGTATAGTATCGTTGTCTTTTTGTTGTTCGTGACAGTGAATTCGGTG

TGGGAGGGCTTCGATACCTTGGAATTGAATTTGGCTGTGTGGTGGGCGGGCAGGCAGGGCAAACGAAGC

AAGAGTGA
```

>Nannochloropsis sp. NIES-2145 LPAT2 amino acid sequence
(SEQ ID NO: 44)

```
MSGPADARGPARVSDTIIGAPDRHHVGLTILVALLLSAFCFCEFFMLPVAMALLPVPGTT

SRKLLRRWEGLVAKTWLSFGGWLLENVGGVKLILTGDSILPGDRVLILSNHRTRIDWMFL

WCWAARFDLLSSYRVILKSSLRTFPWWGWGMSLCLFPFIHRGSNNRDADLTRIEHICQYL

SELGVPNSLILFPEGTDLSQSNQKRDRDYALAKNLPIYHNVLHPRSGAFIASLTAMRPHL

DAVVDLTIGYVDYTPGERPSELSLLKGRLPHEVHINMKRWDIKTTPLLRENPSDRAEQFL

RESFDRKEALLTAFYSNNTDTSGGGLKQTSSLLVSSSSSPFSNSSAPLGFPSFSSPSTSV

ASSYNEPVYVHNAHWTYGKGLLGTGIAMALVLMLACCLPAVAFCGYSIVVFLLFVTVNSV

WEGFDTLELNLAVWWGGQAGQTKQE
```

>LC107612.1 Nannochloropsis sp. NIES-2145 LPAT3 mRNA for lysophosphatidate acyltransferase 3, complete cds
(SEQ ID NO: 45)

```
ATGTGGGCTTATTATGGAAACACATGACCCTACGACTCCTCTTCGTCTCAGTCTGCTTGGTCACCTCCT

CCATCGGCGCCAACATGATGGCCCTCGCCCTCTTCCTCGTCATCCGACCCTTTTCCCGCTCGCTGTATCG

ACGGTTGGTGTCACAGTGTGTGGCATGCATGTGGATCGATGCACTGTCCTTGCTCCTACCGGGAACCAAC

ATCCACATTGCTGCTGACTCTGACATGCCCGACGGGATCACTGCCGGCATCGTGGTGGCCAATCACCAAT

ACGAAGGTGATTGGTGGTTCATGCTCATGGTCGCCCGCTTCCTGGGCCTGCATGGGAACGTGAAGATAAT

AGTCAGGGAGGGCCTTAAGAAGATCCCCCTCTTGGGGTGGCTGGTCCGGCTTGTCGAGTACCCATTCATC

TCCTCCTCCTGGTCGCTCTCCCGCACGAACCTCTTTGGGCTGCTGCGGAGTTTCAATGCGGACGACTTCC

CCGTCCTCCTCTTCCAGTTCCCCGAGGGCGATCGCATCGATGCCAAAGTCCGTCAGCAATCGCTTGCCTT

TGCGGCCAAGGAGCAACGCCCGCACCTCCTCCACGTCCTCCTCCCCCGTACTACCGGTTTCAACACCTGC

ATCGAAGCGCTTAGGACTTCCCATCCCCCCGTCTATGATATGACAATTGCCATCCCTGGCACCACGGGCC

AGCCTTCCTCCTCCTCCTCCTCCTCACCTTCTGCTGCAGCTGCTGCGGCGTCTCCATCTGCTGGTGC

GGCGGCGGCGGCGGCGGCGAGCAACACATCAACCAACCCTTCTTCCAACCCTCCCTCGAGCAGCAGC

ACCGATACTAGTCCAGCTGCTGCTGCTGCTGCTGCTGCTGATGCCGCTGCTGCCGAGAGTCATGACGCTT

CTCTCTTTCACACCTTCCTCCGTTTCTGCAACGGCGAGGGCCCACGGGACGTGCATATCAGACTCAAGCG

CTACTCCCTCAACGACGTCCTGGCCGACCCCACTGGCTCGACACCAAATGGGCCGAGAAAGACCGCGTC

TTGACCTACTTTTCCCGCCACGCCTGCTTTCCTGCTCCGCTCCCTCCCCACATGGCCAATGGTGGGGGCA

GCACTCAGACACACGGGGGAGGGGGGCCCCAGAGGGCCGGCGGGCTCTCATGCCGTGGTGGGAGCAGC
```

-continued

```
GGGTAACGCCCAGTATCTCCGGTCGTTCAATTCCCGGAAATTCAAAGCAGAAACGAGTTTTTTGGCGTTG

GCACGACTGTTACTCACGCCGTTGTGCCTTCCCTTGTTGTTGCTGATGGCCTGTCCGCTCATGACTCTGT

ATGTATGCGTGAGCACCGTCCGAAGGTGGTTGGGGGAGGAGATTGTGTTCTCGCCAGGAGGACGGGAGGG

AGGGAGGGAGGGCGACGCCGTTTACGAGTCCGTTAATTGGAGCGTTTGA
```

\>*Nannochloropsis* sp. NIES-2145 LPAT3 amino acid sequence (SEQ ID NO: 46)

```
MWGLLWKHMTLRLLFVSVCLVTSSIGANMMALALFLVIRPFSRSLYRRLVSQCVACMWID

ALSLLLPGTNIHIAADSDMPDGITAGIVVANHQYEGDWWFMLMVARFLGLHGNVKIIVRE

GLKKIPLLGWLVRLVEYPFISSSWSLSRTNLFGLLRSFNADDFPVLLFQFPEGDRIDAKV

RQQSLAFAAKEQRPHLLHVLLPRTTGFNTCIEALRTSHPPVYDMTIAIPGTTGQPSSSSS

SSSPSAAAAAASPSAGAAAAAAAASNTSTNPSSNPPSSSSTDTSPAAAAAAAADAAAAES

HDASLFHTFLRFCNGEGPRDVHIRLKRYSLNDVLADPHWLDTKWAEKDRVLTYFSRHACF

PAPLPPHMANGGGSTQTHGGRGGPRGPAGSHAVVGAAGNAQYLRSFNSRKFKAETSFLAL

ARLLLTPLCLPLLLLMACPLMTLYVCVSTVRRWLGEEIVFSPGGREGGREGDAVYESVNW

SV
```

\>LC107613.1 *Nannochloropsis* sp. NIES-2145 LPAT4 mRNA for lysophosphatidate acyltransferase 4, complete cds (SEQ ID NO: 47)

```
ATGCCGACCTATGCGGACCCTCCCAGGTCGCGCGCCTACCAGCACGAAAGCTCCTCCTACAGCATTGATA

ATCCGATCCGCAGCACCCACGCCTCCAGCCCACCCGACTATTTCAATCAAAACTCCCTCCGTGAGTCCCC

CTCCCTCCACTCCTCATCCTCAGAATCCGAGATGGACTCTCAGAGCAATGGCAATGGCAGGACCCCTCAA

CAGCGGCGAGGCGACATTCAAAGGCAGACAAACAACCCTTCCGCCTCCGGCACGAACGGCACCCCCCGAG

GAGCATTCAAGAGCACAATCTTCTCCATGGCCCACGCTGTCGTCCTCTGCTGGCTCGTGATGGCCATGTC

CTTCGGCATCAATATTTTGAATTTCCTCGTTTTTGTAACCGTCCGTCCTTGGTCCCGCCTGACGGCCCGA

AGGCTCATCGGTCACTGGTGGCAACGGATGTGGGTCTCAGTAATGAGCTACTTGCTCCCTAAGAGCGAGA

TGATTCTGACAGGGGACATCGTGCTTAACACTGTGGATTCCTCTCGCCCGGCCATCATCATCGCGAATCA

CCAGGTGGATGCGGATTTTTGGTATGTCTGGGAAGTGGCGCGGGCCTACGGAATGCATGGACGGTTGAAG

ATCATTTTGAAAGCCGATTTGGCTGTGGTCCCCATCGTGGGCTGGGGATGAAACAATTTGAATTTTGTT

TTTTGCAACGCAATTGGCAGAGGGACCGGAGGGCGTTCACGCGCTTGTTGTCGTCGTTTGTCGAGGACGG

GTATAAGTGTGCCTTGCTCCTCTTTCCAGAGGGCACGACCATCAACACTGAAGCTGTCACCAAGTCCCAC

CGCTTCGGCCGTGAGCAGAAGAGGCCTCACCTCGACCATTGCATCCTACCGCGTTCCACGGGCTTTGCGG

CTTTGGTCGAGACAATGTGCCAGTCCCCCCATGGCCATTCTCCTGTTATTTACGATCTGACCGTCGCCTA

TCACGGTTACTCAGGCGAAGTTCCCACCTATGAGATGGGCTACGACCGAGAACAAGACATGGACGTCCCG

AACGTGTTCAAAATGATACAGGGACGGGCATGTCCAAAGGTTCATGTCCACGTCAAGACGTACGAAGTCG

ATGAGGCCTTGGTTAATAATCCCGAGCAGTGGTTGGATGCTCGATGGTTGGAAAAAGACGCGCTGCTGGA

ACGGTTTATTCAGACGCAGAGTTTTAGGGGGGAGAAGGAGGGAGGGACACGGATCATTCATCCTCAGGGG

AGCTTGGCCTCGCTGCTTTTTTTGTTGATGTTGCCGCTGATTATCACCGTCCTCCTTCCTGCCCTGCTCT

TGATCACTTTGGTGGCCTGGCCTGTGATTCTTCTGGCGGCACGCTCAACTTTCTGAACTTTGTCTCGCG

TTCGGCCATGGGTGTGGTAGTCGGGAGCAGCAGCAGCCGTGGGTCTTTCTCCACGTCTTGGCATCAGTCC

TCCCAACACCGGCACCAGCACCAGCAACGGGTCAGTGGCAATAGCACCAGTAGCACCAGTACCAGCAACA

GTACCAGCAGTAGCATTGGTCGGAAGGAAGGGGCATTGAACTGCAGGCGAAGTTCTCGCCGAAGCCCCAG

CCGTGAGGGATGTGGCCACGCCAATGGAGAAGGACCGAGCTGTCCTCTCCTCTCTGTAAGCCTGCCGCCT

CTCCCTGCCGCAGCTGCTGCTGCCGCTCCTGCTGCTCCTGCTTCTTCGGCTCCATCTTCTCCGCTATTGG
```

-continued

GGAGCACGCCGTCGCCACGCCGGTCCCCACGGTGGAAGACTCCGGCGGGGATATCCCCTGTAGTGCAGAG

CTACGGGAACAGGAAGGGGAAGGAAGGAGGATGGGGTCTAATGGCTGCGGCGGCCGCAGCGGCAACGACG

GAAGAGGAGGATCGGTACTAG

>*Nannochloropsis* sp. NIES-2145 LPAT4 amino acid sequence
(SEQ ID NO: 48)

MPTYADPPRSRAYQHESSSYSIDNPIRSTHASSPPDYFNQNSLRESPSLHSSSSESEMDS

QSNGNGRTPQQRRGDIQRQTNNPSASGTNGTPRGAFKSTIFSMAHAVVLCWLVMAMSFGI

NILNFLVFVTVRPWSRLTARRLIGHWWQRMWVSVMSYLLPKSEMILTGDIVLNTVDSSRP

AIIIANHQVDADFWYVWEVARAYGMHGRLKIILKADLAVVPIVGWGMKQFEFCFLQRNWQ

RDRRAFTRLLSSFVEDGYKCALLLFPEGTTINTEAVTKSHRFGREQKRPHLDHCILPRST

GFAALVETMCQSPHGHSPVIYDLTVAYHGYSGEVPTYEMGYDREQDMDVPNVFKMIQGRA

CPKVHVHVKTYEVDEALVNNPEQWLDARWLEKDALLERFIQTQSFRGEKEGGTRIIHPQG

SLASLLFLLMLPLIITVLLPALLLITLVAWPVILLAGTLNFLNFVSRSAMGVVVGSSSSR

GSFSTSWHQSSQHRHQHQQRVSGNSTSSTSTSNSTSSSIGRKEGALNCRRSSRRSPSREG

CGHANGEGPSCPLLSVSLPPLPAAAAAAAPAAPASSAPSSPLLGSTPSPRRSPRWKTPAG

ISPVVQSYGNRKGKEGGWGLMAAAAAAATTEEEDRY

>BAA18602.1 sll1848 [*Synechocystis* sp. PCC 6803] mRNA sequence
(SEQ ID NO: 49)

GTGGATTCCGAGATTAATCATCGTGGTGGTTTGAGTGCTCCCCGCCCAAGGGAAACGTCA

CTTAATTTAGCTCTCTACCGGGGCTTGAAATGGGGGGTGGTGCGGCCACTGCTCCATGGA

TTGTTCCAGGCCCAGGTATATGGTCAGGAATTGGTGCCAACCCGGGGGCCGGCCTTGGTG

GTGAGCAACCATGCCAGTTATTTTGACCCCCCATTTTTGTCCTGTGCCATGGCCCGGCCG

GTGGCCTTTATGGCCAAGGAAGAGTTATTTAATGTGCCCCTGCTGGGTCCAGCCATTCGC

CTCTATGGGCCTATCCAGTCAAACGGGGCAGTGGCGATCGGGGAGCATTGCGGGCCGCC

TTGACGGCGCTGGGGGATGGTTGGTTAGTGGGGGTCTTTCTGGAGGGAACCAGAACAAAG

GATGGCCGCATTCACCAGCCAAAATTGGGGGCTGCCATGATTGCAGCTAAAGCCCAAGTG

CCCATTATTCCCGTCAGCCTAGGGGGAGTAGAGCAAATTTTTCAGCCCGGTTCCCCCTGG

CCCCATCCTGTGCCTTTAACTATTCGCATTGGTAAGGCGATCGCCCCTCCAGTAAAGAAT

AGGAAACCCGAATTGGAAGCGGTTACTAAAGCTTGCCAAGCCCAAATTCACGAGATGCTG

GATTTAGGCAGGGATTAG

>BAA18602.1 sll1848 [*Synechocystis* sp. PCC 6803] amino acid sequence
(SEQ ID NO: 50)

MDSEINHRGGLSAPRPRETSLNLALYRGLKWGVVRPLLHGLFQAQVYGQELVPTRGPALVVSNHASYFDP

PFLSCAMARPVAFMAKEELFNVPLLGPAIRLYGAYPVKRGSGDRGALRAALTALGDGWLVGVFLEGTRTK

DGRIHQPKLGAAMIAAKAQVPIIPVSLGGVEQIFQPGSPWPHPVPLTIRIGKAIAPPVKNRKPELEAVTK

ACQAQIHEMLDLGRD

Nucleotide sequence encoding ER LPAT2 of *Arabidopsis thaliana*:
>ENA|AEE79683|AEE79683.1 *Arabidopsis thaliana* (thale cress)
lysophosphatidyl acyltransferase 2
(SEQ ID NO: 51)

ATGGTGATTGCTGCAGCTGTCATCGTGCCTTTGGGCCTTCTCTTCTTCATATCTGGTCTC

GCTGTCAATCTCTTTCAGGCAGTTTGCTATGTACTCATTCGACCACTGTCTAAGAACACA

TACAGAAAAATTAACCGGGTGGTTGCAGAAACCTTGTGGTTGGAGCTTGTATGGATAGTT

GACTGGTGGGCTGGAGTTAAGATCCAAGTGTTTGCTGATAATGAGACCTTCAATCGAATG

GGCAAAGAACATGCTCTTGTCGTTTGTAATCACCGAAGTGATATTGATTGGCTTGTGGGA

-continued

```
TGGATTCTGGCTCAGCGGTCAGGTTGCCTGGGAAGCGCATTAGCTGTAATGAAGAAGTCT

TCCAAATTCCTTCCAGTCATAGGCTGGTCAATGTGGTTCTCGGAGTATCTCTTTCTGGAA

AGAAATTGGGCCAAGGATGAAAGCACTCTAAAGTCAGGTCTTCAGCGCTTGAGCGACTTC

CCTCGACCTTTCTGGTTAGCCCTTTTTGTGGAGGGAACTCGCTTTACAGAAGCCAAACTT

AAAGCCGCACAAGAGTATGCAGCCTCCTCTGAATTGCCTATCCCTCGAAATGTGTTGATT

CCTCGCACCAAAGGTTTCGTGTCAGCTGTTAGTAATATGCGTTCATTTGTCCCAGCAATT

TATGATATGACAGTGACTATTCCAAAAACCTCTCCACCACCCACGATGCTAAGACTATTC

AAAGGACAACCTTCAGTGGTGCATGTTCACATCAAGTGTCACTCGATGAAAGACTTACCT

GAATCAGATGACGCAATTGCACAGTGGTGCAGAGATCAGTTTGTGGCTAAGGATGCTCTG

TTAGACAAACACATAGCTGCAGACACTTTCCCCGGTCAACAAGAACAGAACATTGGCCGT

CCCATAAAGTCCCTTGCGGTGGTTCTATCATGGGCATGCGTACTAACTCTTGGAGCAATA

AAGTTCCTACACTGGGCACAACTCTTTTCTTCATGGAAAGGTATCACGATATCGGCGCTT

GGTCTAGGTATCATCACTCTCTGTATGCAGATCCTGATACGCTCGTCTCAGTCAGAGCGT

TCGACCCCAGCCAAAGTCGTCCCAGCCAAGCCAAAAGACAATCACCACCCAGAATCATCC

TCCCAAACAGAAACGGAGAAGGAGAAGTAA

Amino acid sequence for ER LPAT2 of Arabidopsis thaliana:
>sp|Q8LG50|LPAT2_ARATH 1-acyl-sn-glycerol-3-phosphate acyltransferase 2
OS = Arabidopsis thaliana OX = 3702 GN = LPAT2 PE = 1 SV = 2
                                                          (SEQ ID NO: 52)
MVIAAAVIVPLGLLFFISGLAVNLFQAVCYVLIRPLSKNTYRKINRVVAETLWLELVWIV

DWWAGVKIQVFADNETFNRMGKEHALVVCNHRSDIDWLVGWILAQRSGCLGSALAVMKKS

SKFLPVIGWSMWFSEYLFLERNWAKDESTLKSGLQRLSDFPRPFWLALFVEGTRFTEAKL

KAAQEYAASSELPIPRNVLIPRTKGFVSAVSNMRSFVPAIYDMTVTIPKTSPPPTMLRLF

KGQPSVVHVHIKCHSMKDLPESDDAIAQWCRDQFVAKDALLDKHIAADTFPGQQEQNIGR

PIKSLAVVLSWACVLTLGAIKFLHWAQLFSSWKGITISALGLGIITLCMQILIRSSQSER

STPAKVVPAKPKDNHHPESSSQTETEKEK

Nucleotide sequence encoding ER LPAT2 of Helianthus annuus:
>ENA|OTG36509|OTG36509.1 Helianthus annuus (common sunflower) putative
1-acyl-sn-glycerol-3-phosphate acyltransferase 2
                                                          (SEQ ID NO: 53)
ATGGCTATCGCAGCAGCAGCTGTTATCGTCCCTATTGGCGTCCTCTTCTTCGTCTCCGGC

CTCATCGTCAATCTCATTCAGGCGATTATATTTGTGACTGTACGACCGTTCTCGAAGAGC

TTGTTTAGGCGGATTAACAGACAGGTAGCTGAGTTGTTGTGGCTGGAGCTTGTGTGGATT

GTTGATTGGTGGGCTGGAGTTAAGGTTAACCTGTACACAGATGCCGAGACCCTGAAGATG

ATGGGTAAAGAACATGCTCTTGTGATAGCTAATCATAAAAGTGACATTGATTGGCTCATT

GGATGGGTGTTTGCTCAGAGATCAGGTTGTCTTGGTAGCACATTGGCTGTCATGAAGAAA

TCATCGAAGTTTCTTCCCGTCATTGGTTGGTCAATGTGGTTTTCTGAGTATCTTTTTCTT

GAGAGAAGTTGGGCTAAAGATGAAAGTACCTTGAAGTCAGGCCTCCGACGTCTAAAAGAT

TACCCTCAACCCTTTTGGTTGGCCCTTTTTGTTGAAGGGACTCGCTTTACTAAAGCAAAA

CTTTTAGCAGCTCAAGAATATGCATCTTCAATGGGATTACCTGTTCCCAGAAATGTCTTA

ATTCCAAGAACAAAGGGATTTGTTACTTCAGTGAGTGAAATGAGATCATTTGCTCCTGCA

ATTTACGATATGACGGTTGCGATTCCCAAAGATTCAACTCCGCCAACAATGCTGCGCCTC

TTTAAAGGGCAGTCGTCTGTGATTCACGTTAAAGTTAAGCGTCATTTAATGAAGGACCTG

CCAGAAACAGATGAAGGTGTTGCACAATGGTGTAAAGATATTTTTGTTGCCAAGGATGAT

ATATTAGATAAACATAAAGAATTAAACGCCTTTCCTGATTCAGAACTCCATGAAATTGGC
```

```
CGACCATTGAAGTCTCTTGTGGTGGTTGTATCTTGGGCATGTCTGCTTGTACTCGGGATC

TTCAAGTTCCTGCAATGGTCTAATCTTTTATCCTCATGGAAGGGGCTCACATTCACTGCA

ATTGGGTTGGGGATTGTTACCTTTTTAATGCAAATCTTGATTCAGTTTTCGCAATCTGAA

CGTTCTACACCTGCAAAAGTGGCCCCCACAAGGTCTAGCAATGGTAATGTACAAGAGAAA

CTGCACTGA
```

Amino acid sequence for LPAT2 of *Helianthus annuus*:
>tr|E6Y2I1|E6Y2I1_HELAN Putative 1-acyl-sn-glycerol-3-phosphate
acyltransferase 2 OS = *Helianthus annuus* OX = 4232 GN = LPAAT2 PE = 2 SV = 1
(SEQ ID NO: 54)

```
MAIAAAAVIVPIGVLFFVSGLIVNLIQAIIFVTVRPFSKSLFRRINRQVAELLWLELVWI

VDWWAGVKVNLYTDAETLKMMGKEHALVIANHKSDIDWLIGWVFAQRSGCLGSTLAVMKK

SSKFLPVIGWSMWFSEYLFLERSWAKDESTLKSGLRRLKDYPQPFWLALFVEGTRFTKAK

LLAAQEYASSMGLPVPRNVLIPRTKGFVTSVSEMRSFAPAIYDMTVAIPKDSTPPTMLRL

FKGQSSVIHVKVKRHLMKDLPETDEGVAQWCKDIFVAKDDILDKHKELNAFPDSELHEIG

RPLKSLVVVSWACLLVLGIFKFLQWSNLLSSWKGLTFTAIGLGIVTFLMQILIQFSQSE

RSTPAKVAPTRSSNGNVQEKLH
```

Nucleotide sequence encoding for ER LPAT2 of *Camelina sativa*:
>XM_010429345.2 PREDICTED: *Camelina sativa* 1-acyl-sn-glycerol-3-
phosphate acyltransferase 2 (LOC104712441), mRNA
(SEQ ID NO 55)

```
CTCCTTATAATTTCAATCGCTCCCATTTAATCGCAAAGTTATTTTTATTTTATTTTCTGGTTGGCTTAT

TTTTTATTTTATTTTATGTTTTAAATGTTCTGCAACTTGTCTTGAAATCTGGGGTAAAAAGAAAAAAGAA

AAAAAAAACTTCGCTATTGGTTTTTCTGGAAATCTCAGAAACGATTATTTTGGGTTTTCTATACTTCGCT

TCCTCACATTAGAGCTTCGGTGTTCTTTTTTTTCCTTTTCTTTTTCTTTTTATTTGGGTGTGAGGGACAT

TTTTCCATGGTGATTGCTGCAGCTGTCATCGTGCCTTTGGGCCTTCTCTTCTTCATATCTGGTCTCGTTG

TCAATCTCATTCAGGCACTTTGCTATGTCCTCATTCGGCCACTGTCTAAGAACACTTACCGGAAAATCAA

CCGGGTGGTTGCTGAAACCTTGTGGTTGGAGCTTGTTTGGATTGTTGATTGGTGGGCTGGAGTAAAGATC

CAAGTGTTTGCTGATAATGAGACCTTCAATCGAATGGGCAAAGAACACGCTCTTGTCGTTTGTAATCACC

GTAGTGATATTGATTGGCTTGTTGGATGGGTTCTGGCTCAGCGGTCAGGTTCCCTGGGAAGCGCTTTGGC

TGTAATGAAGAAGTCTTCCAAATTCCTTCCAGTCATAGGCTGGTCAATGTGGTTCTCAGAGTATCTGTTT

CTGGAAAGAAATTGGTCCAAGGATGAAAGCACTCTAAAGTCAGGTCTTCAGCGCTTGAGTGACTTTCCTC

GACCTTTCTGGCTAGCCCTTTTTGTGGAGGGAACTCGCTTTACAGAGGCTAAACTCAAAGCAGCACAAGA

GTATGCAGCCTCCTCTGACTTGCCTATCCCTCGAAATGTGTTGATTCCTCGCACCAAAGGTTTTGTGTCA

GCTGTTAGTAATATGCGTTCATTTGTCCCAGCCATTTATGATATGACAGTGACTATTCCAAAAACTTCTC

CACCGCCCACGATGCTAAGACTATTCAAAGGACAACCTTCTGTGGTACATGTTCACATCAAGTGTCACTC

CATGAAAGACTTGCCTGAATCAGATGACGCAATTGCACAGTGGTGCAGAGATCAGTTTGTGGCTAAGGAT

GCTTTGTTAGACAAACACATAGCTGCAGACACTTTCCCCGGTCAACAGGAACAGAACATTGGCCGTCCCA

TAAAGTCCCTTGCGGTGGTTCTATCATGGGCATGCGTATTAACTCTTGGAGCAATTAAGTTCCTACACTG

GGCACAACTCTTTTCGTCATGGAAAGGTATCGCGCTATCGGGGCTTGCTCTGGGTATCATCACTCTCGGT

ATGCAGATCCTGATACGCTCGTCTCAGTCAGAGCGTTCAACCCCAGCCAAAGTGGTTCCAGCAAAGCCAA

AGGACCATCACAACTCAGAATCATCCTCCCAAACAGAAGTGGAGAAGCAGAAGTAAAAAAGTGGATATC

AAAGATCAAACAACAAACAGAAGAAGAAAAGCGTATCAGTTTTGTTA
```

Amino acid sequence of ER LPAT2 of *Camelina sativa*:
>XP_010427647.1 PREDICTED: 1-acyl-sn-glycerol-3-phosphate
acyltransferase 2 [*Camelina sativa*]

(SEQ ID NO: 56)

MVIAAAVIVPLGLLFFISGLVVNLIQALCYVLIRPLSKNTYRKINRVVAETLWLELVWIVDWWAGVKIQV

FADNETFNRMGKEHALVVCNHRSDIDWLVGWVLAQRSGSLGSALAVMKKSSKFLPVIGWSMWFSEYLFLE

RNWSKDESTLKSGLQRLSDFPRPFWLALFVEGTRFTEAKLKAAQEYAASSDLPIPRNVLIPRTKGFVSAV

SNMRSFVPAIYDMTVTIPKTSPPPTMLRLFKGQPSVVHVHIKCHSMKDLPESDDAIAQWCRDQFVAKDAL

LDKHIAADTFPGQQEQNIGRPIKSLAVVLSWACVLTLGAIKFLHWAQLFSSWKGIALSGLALGIITLGMQ

ILIRSSQSERSTPAKVVPAKPKDHHNSESSSQTEVEKQK

Nucleotide sequence encoding for ER LPAT2 of *Brassica napus*:
>ENA|CAB09138|CAB09138.1 *Brassica napus* (rape) acyl-CoA: 1-acylglycerol-
3-phosphate acyltransferase (SEQ ID NO: 57)

ATGGCGATGGCAGCAGCAGTGATTGTGCCTTTGGGGATTCTCTTCTTCATTTCTGGCCTC

GTTGTCAATCTCCTCCAGGCAGTTTGCTATGTCCTCGTTCGACCTATGTCTAAGAACACA

TACAGAAAGATCAACCGGGTGGTTGCAGAAACCTTGTGGTTGGAGCTTGTCTGGATCGTT

GACTGGTGGGCTGGAGTCAAGATCCAAGTCTTTGCTGATGATGAGACCTTTAATCGAATG

GGCAAGAACATGCTCTTGTCGTTTGTAATCACCGAAGTGATATTGATTGGCTTGTTGGA

TGGATTCTCGCTCAGAGGTCAGGTTGCCTGGGAAGCGCATTAGCTGTAATGAAGAAGTCT

TCCAAATTTCTCCCAGTCATAGGCTGGTCAATGTGGTTCTCCGAGTATCTGTTTCTTGAA

AGAAATTGGGCAAAGGATGAAAGCACTTTACAGTCAGGTCTTCAACGCTTGAACGACTTC

CCACGGCCTTTCTGGCTAGCTCTTTTTGTGGAGGGAACCCGCTTCACAGAGGCAAAACTT

AAAGCAGCACAAGAGTACGCAGCCTCCTCTGAGTTGCCTGTCCCTCGAAATGTGTTGATT

CCTCGCACCAAAGGTTTTGTGTCAGCTGTTAGTAACATGCGTTCATTTGTGCCAGCCATA

TATGATATGACCGTGGCTATTCCAAAAACTTCTCCACCCCCAACGATGCTAAGACTATTC

AAAGGACAACCTTCTGTGGTGCATGTTCACATCAAGTGTCACTCGATGAAGGACTTGCCT

GAACCAGAAGACGAAATTGCACAGTGGTGCAGAGATCAGTTTGTGGCTAAGGATGCACTG

TTAGACAAACACATAGCTGCAGACACTTTCCCCGGTCAGAAAGAACAGAACATTGGCCGT

CCCATAAAGTCTCTTGCAGTGGTTGTATCATGGGCATGCCTACTAACTCTTGGAGCAATG

AAGTTCTTACACTGGTCAAACCTCTTTTCTTCGTGGAAAGGCATCGCATTATCAGCCTTT

GGTCTAGGCATCATCACTCTCTGTATGCAGATCCTGATCCGCTCCTCTCAGTCGGAGCGT

TCAACACCTGCCAAAGTCGCTCCAGCCAAGCCAAAGGACAATCACCAGTCAGGACCATCC

TCCCAAACAGAAGTGGAGGAGAAGCAGAAGTAA

Amino acid sequence of ER LPAT2 of *Brassica napus*:
>sp|Q9XFW4|LPAT2_RANA 1-acyl-sn-glycerol-3-phosphate acyltransferase 2
OS = *Brassica napus* OX = 3708 GN = LPAT2 PE = 2 SV = 1

(SEQ ID NO: 58)

MAMAAAVIVPLGILFFISGLVVNLLQAVCYVLVRPMSKNTYRKINRVVAETLWLELVWIV

DWWAGVKIQVFADDETFNRMGKEHALVVCNHRSDIDWLVGWILAQRSGCLGSALAVMKKS

SKFLPVIGWSMWFSEYLFLERNWAKDESTLQSGLQRLNDFPRPFWLALFVEGTRFTEAKL

KAAQEYAASSELPVPRNVLIPRTKGFVSAVSNMRSFVPAIYDMTVAIPKTSPPPTMLRLF

KGQPSVVHVHIKCHSMKDLPEPEDEIAQWCRDQFVAKDALLDKHIAADTFPGQKEQNIGR

PIKSLAVVVSWACLLTLGAMKFLHWSNLFSSWKGIALSAFGLGIITLCMQILIRSSQSER

STPAKVAPAKPKDNHQSGPSSQTEVEEKQK

-continued

Nucleotide sequence encoding ER LPAT2 of *Glycine max*:
>XM_003535809.4 *Glycine max* 1-acyl-sn-glycerol-3-phosphate
acyltransferase 2 (LOC100814107), mRNA (SEQ ID NO: 59)
ATGACTGCAGTTGTGGTCGTCCCATTGGGCCTTCTCTTCTTCGCTTCCGGCCTCATCGTTAACCTCATTCA

GGCAATATGCTACGTGGTTGTGCGGCCGTGTCGAAGAATCTGTACCGGCGGATGAACAGGGTGGTGGCGG

AGCTGCTCTGGCTGGAGCTCGTGTGGATTATTGATTGGTGGGCCGGTGTTAAGGTTCAAGTATTCACAGAT

CCTGAAACCTTTCGTTCAATGGGTAAAGAGCATGCTCTTGTTATCTCCAATCACAGAAGTGACATTGATTG

GCTTGTTGGATGGGTTTTAGCTCAGCGTTCAGGTTGCCTTGGCAGCACTCTTGCTGTGATGAAGAAATCAT

CGAAGTTTCTACCGGTCATTGGTTGGTCAATGTGGTTTTCTGAATATCTTTTCCTGGAGAGAAGTTGGGCC

AAGGATGAACGCACATTAAAGTCAGGCCTACAGCAACTGAGGGATTTCCCTCTTCCCTTTTGGTTGGCTCT

CTTTGTAGAAGGAACTCGCTTTACACAGGCCAAACTATTAGCTGCTCAGGAGTATGCAGCCTCAGCTGGAT

TGCCTGTTCCAAGAAATGTTTTGATTCCAAGAACTAAGGGTTTTGTTTCAGCAGTAAACCATATGCGCTCT

TTTGTTCCTGCCATTTATGATGTAACTGTGGCAATTCCCAAGAGTTCACCTGCTCCTACAATGCTAAGACT

CTTCAGAGGGAAATCTTCAGTGGTTCATGTGCATATTAAGCGGCATGCAATGAAGGATTTGCCAGAAGAAG

ATGAAGCTGTTGCTCAATGGTGTCGAGATATGTTTGTGGCTAAGGATACATTGTTAGACAAACATATAGCT

GAGGACACATTCAGTGATCAAGAGCTGCAGGATACCGGTCGACCCATAAAGTCTCTAGTGGTTGTCATATC

GTGGGCATGTGTCGTTGTTATGGGGGTCGTAAAGTTCCTCCAATGGTCATCACTACTATCCTCCTGGAAGG

GTGTTGCATTTTCAGCATTTGGTTTGGGAGTTGTTACTCTACTCATGCACATCTTGATCATGTTCTCACAA

TCTGAGCGTTCAACCCCTACCAAGGTTGCCCCTGCAAAGTCCAAGAATAGCGAACAACTGGAGGCTAGGGA

TAACAAACAAGACTAG

Amino acid sequence for LPAT2 of *Glycine max*:
>XP_003535857.1 1-acyl-sn-glycerol-3-phosphate acyltransferase 2
[*Glycine max*]

(SEQ ID NO: 60)
MTAVVVPLGLLFFASGLIVNLIQAICYVVVRPVSKNLYRRMNRVVAELLWLELVWIIDWWAGVKVQVFT

DPETFRSMGKEHALVISNHRSDIDWLVGWVLAQRSGCLGSTLAVMKKSSKFLPVIGWSMWFSEYLFLERS

WAKDERTLKSGLQQLRDFPLPFWLALFVEGTRFTQAKLLAAQEYAASAGLPVPRNVLIPRTKGFVSAVNH

MRSFVPAIYDVTVAIPKSSPAPTMLRLFRGKSSVVHVHIKRHAMKDLPEEDEAVAQWCRDMFVAKDTLLD

KHIAEDTFSDQELQDTGRPIKSLVVVISWACVVVMGVVKFLQWSSLLSSWKGVAFSAFGLGVVTLLMHIL

IMFSQSERSTPTKVAPAKSKNSEQLEARDNKQD

Nucleotide sequence encoding for ER LPAT of *Yarrowia lipolytica*:
>ENA|CAG79722|CAG79722.1 *Yarrowia lipolytica* CLIB122 YALI0E18964p:
Location: 1..849

(SEQ ID NO: 61)
ATGTCCGTTGCATCCAAGCTCGTCTTCTACGTCCGCGCCGCCATCGCCGTGGTCATCTTT

GCCGCCTGTGCCACCTACGGCGTGCTGGCGTCCACCATTCTCACCGCCATCGGCAAGCAG

GGCCTGGCCCAATGGACCGTTGCCAGAGCCTTCTACTACTCGGTGCGCATCTTCCTGGGT

ATCAGCATCAAGCTGCGTAGCCGGCAGGTGACCGGAACCGCCGGTCTGGATGCCTCCAAG

ATCCAGGTCGCCAACACCACCAAGCCCATTGACGACATCACCAAACACCTGCCCCGACCA

TGCATTCTGATTTCCAACCACCAGAACGAAATGGACATTCTGGTGCTCGGTCGCATCTTC

CCCCAGTACTGCTCCGTCACCGCCAAAAAGGCCCTCAAGTGGTACCCTCTGCTGGGCCAG

TTCATGGCGCTGTCCGGCACCATCTTCCTGGACCGAAAGGACCGAACCAAGTCCGTGCAG

ACCCTCGGCGGCGCCGTCAAGACCATCCAGAGCGGCAACGGAGGCAAGGGCCAGAGCGTC

TTCATGTTCCCCGAGGGAACCCGATCCTACTCCAAGGACGTCGGCATCATGCCCTTCAAG

AAGGGCTGTTTCCACCTGGCGGTCCAGTCGGGCGCTCCCATTGTCCCCGTGGTGGTCCAG

-continued

```
AACACCTCCCGAATGTTTTCTTTCGGCCGAGGCAAGCTGGACGCCGGAGAGATCCTTGTC

GACGTCCTGAGCCCCATTGAGACCAAGGGTCTGGACGCCAGCAACGTCGACGCTCTCATG

GCCACCACTTATAAGGCCATGTGCGAGACTGCCGACCAGATTGGCTACGCTGGCCAGAAG

ACTCAGTAG
```

Amino acid sequence for ER LPAT of *Yarrowia lipolytica*:
>tr|Q6C5D5|Q6C5D5_YARLI 1-acyl-sn-glycerol-3-phosphate acyltransferase
OS = *Yarrowia lipolytica* (strain CLIB 122/E 150) OX = 284591
GN = YALI0_E18964g PE = 3 SV = 1

(SEQ ID NO: 62)

```
MSVASKLVFYVRAAIAVVIFAACATYGVLASTILTAIGKQGLAQWTVARAFYYSVRIFLG

ISIKLRSRQVTGTAGLDASKIQVANTTKPIDDITKHLPRPCILISNHQNEMDILVLGRIF

PQYCSVTAKKALKWYPLLGQFMALSGTIFLDRKDRTKSVQTLGGAVKTIQSGNGGKGQSV

FMFPEGTRSYSKDVGIMPFKKGCFHLAVQSGAPIVPVVVQNTSRMFSFGRGKLDAGEILV

DVLSPIETKGLDASNVDALMATTYKAMCETADQIGYAGQKTQ
```

Nucleotide sequence encoding for PDCT of *Arabidopsis thaliana*:
>ENA|AEE75730|AEE75730.1 *Arabidopsis thaliana* (thale cress)
phosphatidic acid phosphatase-related/PAP2-like protein (SEQ ID NO: 63)

```
ATGTCAGCCGCCGCAGCTGAAACCGACGTCTCTCTCCGTCGCAGATCTAACTCTCTTAAC

GGAAACCACACTAACGGCGTCGCCATTGACGGAACCCTAGACAACAACAACCGTCGCGTC

GGAGATACAAACACTCACATGGATATATCTGCTAAGAAAACTGACAACGGCTACGCCAAT

GGTGTCGGAGGAGGAGGATGGAGAAGCAAAGCGTCGTTCACGACGTGGACGGCGCGTGAT

ATCGTCTACGTGGTGAGATACCATTGGATACCGTGCATGTTCGCTGCCGGACTTCTGTTC

TTCATGGGCGTGGAGTACACGCTTCAGATGATTCCCGCGAGATCTGAGCCGTTCGATCTT

GGGTTTGTGGTCACGCGCTCTTTGAATCGCGTATTAGCATCTTCACCGGATCTTAACACT

GTTTTAGCCGCACTAAACACGGTGTTCGTAGGGATGCAAACAACGTATATTGTATGGACA

TGGTTAGTGGAAGGACGAGCACGAGCCACCATCGCGGCTTTATTCATGTTCACTTGTCGC

GGCATTCTCGGCTACTCTACTCAGCTTCCTCTCCCTCAGGACTTTCTAGGATCAGGGGTT

GATTTTCCGGTGGGAAATGTCTCTTTCTTCCTCTTCTTCTCTGGCCATGTCGCCGGCTCG

ATGATCGCATCATTGGACATGAGAAGAATGCAGAGGTTGAGACTTGCAATGGTCTTTGAC

ATCCTCAATGTATTACAGTCGATCAGACTGCTCGGTACAAGAGGACATTACACAATCGAC

CTTGCGGTTGGAGTTGGCGCTGGGATTCTCTTCGACTCATTGGCCGGAAAGTACGAAGAG

ATGATGAGCAAGAGACATTTAGGCACTGGTTTTAGTTTGATTTCGAAAGACTCTCTAGTC

AATTAA
```

Amino acid sequence for PDCT of *Arabidopsis thaliana*:
>sp|Q9LVZ7|PDCT1_ARATH Phosphatidylcholine: diacylglycerol
cholinephosphotransferase 1 OS = *Arabidopsis thaliana* OX = 3702 GN = ROD1
PE = 1 SV = 1

(SEQ ID NO: 64)

```
MSAAAAETDVSLRRRSNSLNGNHTNGVAIDGTLDNNNRRVGDTNTHMDISAKKTDNGYAN

GVGGGGWRSKASFTTWTARDIVYVVRYHWIPCMFAAGLLFFMGVEYTLQMIPARSEPFDL

GFVVTRSLNRVLASSPDLNTVLAALNTVFVGMQTTYIVWTWLVEGRARATIAALFMFTCR

GILGYSTQLPLPQDFLGSGVDFPVGNVSFFLFFSGHVAGSMIASLDMRRMQRLRLAMVFD

ILNVLQSIRLLGTRGHYTIDLAVGVGAGILFDSLAGKYEEMMSKRHLGTGFSLISKDSLV

N
```

Nucleotide sequence encoding for PDCT of *Helianthus annuus*:
>ENA|ARQ87993|ARQ87993.1 *Helianthus annuus* (common sunflower)
phosphatidylcholine: Location: 1..840

(SEQ ID NO: 65)

ATGGGGACAATCACAATGAACGCCGATAAGATCCACCAACGTTCCATACCACAAACAACC

ACCCTCCTCAAAACATCAAACAACGTTTCCATTAACAATTTCAATCTCAAAAAGACCAAC

AATTCTACGACCACATGGGATCGCTAGCGGACGCGTCGTTTTTACAATGGACAACATCG

GATGTGTTCGGTTTGTTTAAGTACCACCCCGTCCCGTGTTTCTTTGCTGTTTCGTTACTG

TTTTTTATGGGTGTGGAGTATACGCTGCGGATGATACCGCCCTCGTCACCCCCGTTTGAT

ATTGGGTTCGTTGCCACTGCGTATTTGCATCGTGTCCTCGTCGCTAGTCCGACGCTAAAC

ACAGTTCTCGCAGGGCTTAATACGGTGTTTGTGGGGATGCAAACAACCTATATAATAGGG

ACGTGGGTCATTGAAGGGCGGCCAGAGAGCCACAGTCGCGGCGCTGTTCATGTTTACTTGC

AGAGGGATTTTGGGTTATTCGACACAGCTTCCTTTGCCTGAGGGATTCTTGGGTTCGGGA

GCAGACTTTCCGGTAGGCAATGTGTCCTTCTTCTTGTTTTATTCTGGTCATGTAGCAGGA

TCAGTAATTGCATCGTTTGATATGAAGAGAATGCATAGGTGGGAGTTGGCCTTTCTATTC

GACACCTTGAACCTTTTGCAGGTGGTGCGGTTACTAAGCACAAGGGGACACTACACCATT

GACTTAGCCGTCGGAGTAGGTGCCGGCATGTTGTTTGATTCCCTCGCCGGAAAATACATG

AAGAAGGCTATGGCTGAAGGAGGTGATGTCTTGTATACAAACCTACCTCACTTATCTTAA

Amino acid sequence for PDCT of *Helianthus annuus*:
>tr|A0A3S5FWJ3|A0A3S5FWJ3_HELAN Phosphatidylcholine OS = *Helianthus
annuus* OX = 4232 GN = PDCT PE = 2 SV = 1

(SEQ ID NO: 66)

MGTITMNADKIHQRSIPQTTTLLKTSNNVSINNFNLKKTNNSTTTWGSLADASFLQWTTS

DVFGLFKYHPVPCFFAVSLLFFMGVEYTLRMIPPSSPPFDIGFVATAYLHRVLVASPTLN

TVLAGLNTVFVGMQTTYIIGTWVIEGRPRATVAALFMFTCRGILGYSTQLPLPEGFLGSG

ADFPVGNVSFFLFYSGHVAGSVIASFDMKRMHRWELAFLFDTLNLLQVVRLLSTRGHYTI

DLAVGVGAGMLFDSLAGKYMKKAMAEGGDVLYTNLPHLS

Nucleotide sequence encoding for PDCT of *Camelina sativa*:
>XM_010467272.2 PREDICTED: *Camelina sativa*
phosphatidylcholine: diacylglycerol cholinephosphotransferase 1
(LOC104745897), mRNA (SEQ ID NO: 67)

CACCAAAGAGTTAGAGTGTATTTAACTAACAACCATAAATTAAAAATGTCCTTCTCAAAAATAACTATTC

ATCACTTTCATATGACAATTTTCTAACCCAAACAAGTCTCCTTTGAAATCTCCGCCCTCGTATCTCTTAT

ATAACACATCTCTCTTCAAACTCCCAAAAATGTCCCTCTCCGTTAACTCTAACGGCCATGTCAGTCGCCG

CAGCTAAACCCGCCGTCTCTCGCCGTCACGTATCTAACGGAAACAACACTAACAACGTCGCCATTGACGA

CGATCACAACCACCAACGCCGCATCGTCGGAGATAAAAACACTCGAATGGAGATCGCTGCTAAGAACAAC

GGCTACGCCAACGGTGTCATCGGAGGAGGAGGATGGAGGAGCAAGGCGTCGTTCATGACGTGGACGACGC

GTGACGTTGTCTACGTGGCGAGACACCATTGGATACCGTGCATGTTCGCTGCCGGGCTTTTGTTCTTCAT

GGGGGTCGAGTACACGCTCCAGATGATTCCCGCGAGATCTGAGCCGTTCGATCTTGGGTTCGTGGCCACG

CGCTCTTTGAATCGCGTCTTAGCATCTTCCCCGGATCTTAACACCGTTTTAGCCGCACTAAACACGGTGT

TCGTATTGATGCAAACAACGTATATTGTATGGACATGGTTAGTGGAAGGACGAGCACGAGCAACCATCTC

GGCTTTATTCATGTTCACGTGTCGGGCATTCTCGGCTACTCTACTCAGCTTCCTCTCCCTCAGGATTTT

TTAGGATCAGGAGTTGATTTTCCAGTGGGAAACGTCTCTTTCTTCCTCTTCTTCTCGGGCCACGTTGCCG

GCTCGATGATCGCATCACTGGACATGAGGAGAATGCAGAGGTTTAAGCTGGCGAGGGTTTTTGACATCCT

CAATGTATTACAATCGATCAGGCTGCTCGGTACAAGAGGACACTACACCATCGACCTTGCGGTTGGAGTT

GGCGCTGGGATTCTCTTTGACTCACTGGCCGGGAAGTACGAAGAGATGAGCAGAAGACACCACCTAGGAA

-continued

```
CTGGTTTTAGTTTGATATCGAAAGACTCTCTAGTCAATTAAATTTGTTTTCTATCAAATGTTTTTAGTTC

AACACATTTAGTTAAGTTGAATTTAGTCTAATGACTTATTTATTTCTTCTTTATAAATGCCTAAATGGTT

CATTGTATACCGTTTGTTGAACCTAATTATCGATCTAATGTTACTTAAAGGGTTGTAGCCTTGTAGTTGT

A
```

Amino acid sequence for PDCT of *Camelina sativa*:
>XP_010465574.1 PREDICTED: phosphatidylcholine: diacylglycerol
cholinephosphotransferase 1 [*Camelina sativa*]

(SEQ ID NO: 68)

```
MSVAAAKPAVSRRHVSNGNNTNNVAIDDDHNHQRRIVGDKNTRMEIAAKNNGYANGVIGGGGWRSKASFM

TWTTRDVVYVARHHWIPCMFAAGLLFFMGVEYTLQMIPARSEPFDLGFVATRSLNRVLASSPDLNTVLAA

LNTVFVLMQTTYIVWTWLVEGRARATISALFMFTCRGILGYSTQLPLPQDFLGSGVDFPVGNVSFFLFFS

GHVAGSMIASLDMRRMQRFKLARVFDILNVLQSIRLLGTRGHYTIDLAVGVGAGILFDSLAGKYEEMSRR

HHLGTGFSLISKDSLVN
```

Nucleotide sequence encoding for PDCT of *Brassica napus*:
>XM_013791764.2 PREDICTED: *Brassica napus*
phosphatidylcholine: diacylglycerol cholinephosphotransferase 1
(LOC106352083), mRNA (SEQ ID NO: 69)

```
ATGAACTTTTGTAGCCCAAACAACCTTCCTTTCCTTCCACAAGTTTCATAATATCTCTTATATAACCCAT

ATCTCCAAGCCTCTCGAAATGTTCTTCTCCGTTAAATCTAACGGTCATGTCAACTACAACAATCGTCCCT

CTCCGTCGCAGTTCTAACTCTCTCAATGAATACCACACTAACGCAGTCGCCTTTGACGGAATCGTCGGGT

CAACAAGTACTAGCCAAATGGAGGAGATTGTTACGCAAACCGACGACTGCTACGCCAATCACAACGGAGA

TGGAGGGAGAAGCAAGGCATCGTTTATGACGTGGAGGATGTGCAATCCTGTCCAGGTGGCGAGAGTCCAT

TGGATACCGTGTTTGCTAGCGGTAGGAGTTCTGTTCTTCACGGGCGTAGAGGAGTACATGCTCCAGATGA

TTCCGGCGAGTTCTGAGCCGTTCGATATTGGTTTTGTGGCGACGCGCTCTCTGTATCGACTCTTGGCTTC

TTCACCGGATCTTAATACCGTTTTAGCTGCTCTCAACACGGTGTTTGTAGGGATGCAAACGACGTATATT

TTATGGACATGGTTGGTGGAAGGACGACCACGAGCGACCATCTCGGCTTGCTTCATGTTTACTTGTCGTG

GCATTCTTGGTTACTCTACTCAGCTCCCTCTTCCTCAGGATTTTCTAGGATCAGGGGTAGATTTTCCGGT

AGGAAACGTCTCGTTCTTCCTCTTCTACTCAGGCCATGTCGCAGGGTCGACGATAGCATCCTTGGATATG

AGGAGAATGAAGAGGTTGAGACTTGCCTTGCTTTTTGACATCCTCAATGTATTACAATCGATCAGGCTTC

TCGGGACAGAGGACAATACACGATCGATCTCGCTGTCGGAGTTGGCGCTGGGGTTCTCTTTGACTCACT

GGCTGGAAAATACGAAGAGATGATGAGCAAGAGACGCAATGTAGGCAATGGTTTTAGTTTGATTTCGTCT

CGCTAGTTATTAATTTTTGTTTTTTTTTTTTATGTTTTTAGTCTGGACATATTTAATTTAGTTGAAATC

TAATGACTTAAATTTGCTTTCTTTCAAAATGCTCTAACTGACGGACCTAACTAAATGTGTACGTTATTGT

GTAGTTACCATAGAGGTTTCGTATTGTCTTGAGCCTGATATTTTGATTTTAGAGCTCGTTTATACGGTAG

CTAATAATAAAAAA
```

Amino acid sequence for PDCT of *Brassica napus*:
>XP_013647218.1 phosphatidylcholine: diacylglycerol
cholinephosphotransferase 1 [*Brassica napus*]

(SEQ ID NO: 70)

```
MSTTTIVPLRRSSNSLNEYHTNAVAFDGIVGSTSTSQMEEIVTQTDDCYANHNGDGGRSKASFMTWRMCN

PVQVARVHWIPCLLAVGVLFFTGVEEYMLQMIPASSEPFDIGFVATRSLYRLLASSPDLNTVLAALNTVF

VGMQTTYILWTWLVEGRPRATISACFMFTCRGILGYSTQLPLPQDFLGSGVDFPVGNVSFFLFYSGHVAG

STIASLDMRRMKRLRLALLFDILNVLQSIRLLGTRGQYTIDLAVGVGAGVLFDSLAGKYEEMMSKRRNVG

NGFSLISSR
```

-continued

Nucleotide sequence encoding for PDCT of *Glycine max*:
>XM_003531670.4 PREDICTED: *Glycine max*
phosphatidylcholine: diacylglycerol cholinephosphotransferase 1
(LOC100790665), mRNA (SEQ ID NO: 71)
ATGAATGGCGGCGCTGAGGCCTCCCTCAATCACAGGCGCAAACACCCAAACAGCTCCCGCCGACGGCGCTAA

AGGCGTTAAGGTAGCAAACGGAGCCATGGGGAAGCCGTCCTCTTCCAAGCACTCCTGCGGCGCGTCGTTCA

TGAAATGGACCGTGGCTGACGCTGTCCACGTGGTGACGCACCATTGGATGCCGTGCTTGTTCGCATTGGGG

CTTCTCTTCTTCATGGCCGTGGAGTACACGCTTCTCATGGTGCCGCCGTCGTCGCCGCCCTTCGACCTTGG

CTTCATCGCCACACGCTCCCTCCACGCGCTCCTCGAGTCGTCGCCGAATCTCAACACGCTCTTCGCCGGGC

TCAATACGGTGTTTGTGGGGATGCAAACGAGTTATATCTTATGGACGTGGCTGATTGAAGGACGCCCCAGA

GCCACAATTTCAGCATTGTTCATGTTCACATGCCGTGGGATTTTAGGCTACTCCACCCAGCTCCCATTGCC

TCAGGGGTTTTTGGGCTCGGGTGTGGACTTCCCTGTTGGGAACGTGTCTTTTTTCTTGTTTTTTTCTGGGC

ACGTTGCAGGGTCAGTGATTGCTTCATTGGACATGAGGAGGATGCAGAGGTGGGAACTGGCTTGGACTTTT

GATGTGCTCAATGTTTTGCAAGCTGTGAGGTTGCTGGGTACAAGAGGCCATTACACTATTGATTTGGCCGT

AGGGGTTGGTGCTGGAATTCTCTTTGATTCTTTAGCTGGCAAGTACGAAGATAGCAAAAGGAATGGTGCTC

TCAAACACAATTTGATTGCGTGA

Amino acid sequence for PDCT of *Glycine max*:
>XP_003531718.1 phosphatidylcholine: diacylglycerol
cholinephosphotransferase 1 [*Glycine max*]

(SEQ ID NO: 72)
MNGGAEASLNHRRKHQTAPADGAKGVKVANGAMGKPSSSKHSCGASFMKWTVADAVHVVTHHWMPCLFAL

GLLFFMAVEYTLLMVPPSSPPFDLGFIATRSLHALLESSPNLNTLFAGLNTVFVGMQTSYILWTWLIEGR

PRATISALFMFTCRGILGYSTQLPLPQGFLGSGVDFPVGNVSFFLFFSGHVAGSVIASLDMRRMQRWELA

WTFDVLNVLQAVRLLGTRGHYTIDLAVGVGAGILFDSLAGKYEDSKRNGALKHNLIA

*Arabidopsis thaliana* At1g74960 (FAB1) nucleotide sequence (SEQ ID NO: 78)
ATGGTGGGTGCGTCTTCCTCTTACGCATCTCCGTTATGTACCTGGTTTGTTGCTGCTTGCATGTCCGTCTC

TCACGGTGGAGGAGATAGCCGTCAGGCTGTTGCTCTTCAATCTGGTGGGCGGAGTCGGCGAAGGAGGCAGC

TTAGCAAATGCTCTGTCGCTTCTGGATCCGCTAGCATTCAGGCTCTCGTCACTTCTTGTTTGGATTTTGGT

CCTTGTACTCACTACAACAACAACAATGCATTGTCTTCTCTCTTTGGATCGAATAGTGTTTCTTTGAATCG

AAACCAGAGGAGATTGAATCGTGCTGCTAGCTCCGGTGGAGCCATGGCAGTGATGGAGATGGAAAAGGAAG

CTGCGGTTAACAAGAAACCACCTACGGAGCAGCGTCGAGTTGTAGTGACAGGCATGGGAGTTGAAACATCA

TTGGGTCATGACCCACATACCTTCTATGAGAATTTGCTACAAGGCAACAGTGGTATTAGCCAGATTGAAAA

TTTTGATTGTTCTGAATTTCCTACGCGAATTGCGGGAGAGATCAAAAGCTTCTCGACTGAAGGATGGGTTG

CTCCAAAACTTTCTAAAAGGATGGACAAATTCATGCTCTATCTTCTCACAGCTGGTAAGAAAGCTTTGGCT

GATGGTGGGGTTACTGATGAAGTAATGGCAGAGTTTGACAAAACCAAATGTGGAGTTTTGATTGGCTCGGC

AATGGGAGGAATGAAGGTCTTTTACGATGCTATTGAAGCTCTGAGAATCTCTTACAAGAAGATGAATCCTT

TTTGTGTACCTTTTGCGACAACAAACATGGGTTCTGCTATGCTTGCCATGGATCTGGGATGGATGGGGCCA

AACTATTCTATTTCAACTGCTTGTGCCACAAGCAACTTTTGCATTCTGAATTCAGCAAACCACATTATTAA

AGGTGAAGCTGATGTAATGCTCTGTGGTGGCTCAGATGCAGTTATTATTCCAATAGGGTTGGGAGGTTTTG

TTGCATGCCGGGCTCTTTCACAAAGGAATAATGATCCCACAAAAGCTTCACGTCCTTGGGATACCAATCGA

GATGGTTTCGTGATGGGAGAGGGAGCTGGAGTTCTACTTTTGGAAGAACTCGAGCATGCTAAGAAAAGAGG

TGCAACTATCTACGCAGAGTTCCTCGGTGGGAGTTTCACATGTGATGCCTATCACATGACCGAGCCTCACC

CTGATGGGGCTGGTGTTATTCTCTGTATTGAGAGAGCGTTAGCTAGTGCTGGGATTTCCAAGGAACAAATA

AATTACATAAATGCACATGCAACCTCAACGCATGCTGGAGATATTAAGGAATACCAAGCCCTTGCTCACTG

-continued

TTTTGGCCAAAATCCTGAGCTTAAGGTAAATTCCACAAAATCTATGATTGGACACTTGCTGGGAGCTGCTG

GGGCCGTGGAGGCTGTTGCAACTGTGCAGGCGATACGGACCGGATGGGTTCATCCAAATATCAACCTCGAG

AATCCAGACAGTGGAGTGGATACAAAGCTGCTGGTGGGTCCTAAGAAGGAGAGACTGGACATTAAAGCAGC

CTTGTCAAATTCATTCGGGTTTGGTGGTCATAACTCCAGCATCATTTTTGCTCCTTACAAGTGA

Arabidopsis thaliana At1g74960 (FAB1)amino acid sequence
(SEQ ID NO: 79)
MVGASSSYASPLCTWFVAACMSVSHGGGDSRQAVALQSGGRSRRRRQLSKCSVASGSASIQALVTSCLDFG

PCTHYNNNNALSSLFGSNSVSLNRNQRRLNRAASSGGAMAVMEMEKEAAVNKKPPTEQRRVVVTGMGVETS

LGHDPHTFYENLLQGNSGISQIENFDCSEFPTRIAGEIKSFSTEGWVAPKLSKRMDKFMLYLLTAGKKALA

DGGVTDEVMAEFDKTKCGVLIGSAMGGMKVFYDAIEALRISYKKMNPFCVPFATTNMGSAMLAMDLGWMGP

NYSISTACATSNFCILNSANHIIKGEADVMLCGGSDAVIIPIGLGGFVACRALSQRNNDPTKASRPWDTNR

DGFVMGEGAGVLLLEELEHAKKRGATIYAEFLGGSFTCDAYHMTEPHPDGAGVILCIERALASAGISKEQI

NYINAHATSTHAGDIKEYQALAHCFGQNPELKVNSTKSMIGHLLGAAGAVEAVATVQAIRTGWVHPNINLE

NPDSGVDTKLLVGPKKERLDIKAALSNSFGFGGHNSSIIFAPYK

Arabidopsis thaliana At3g12120 (FAD2) nucleotide sequence
(SEQ ID NO: 80)
ATGGGTGCAGGTGGAAGAATGCCGGTTCCTACTTCTTCCAAGAAATCGGAAACCGACACCACAAAGCGTGT

GCCGTGCGAGAAACCGCCTTTCTCGGTGGGAGATCTGAAGAAAGCAATCCCGCCGCATTGTTTCAAACGCT

CAATCCCTCGCTCTTTCTCCTACCTTATCAGTGACATCATTATAGCCTCATGCTTCTACTACGTCGCCACC

AATTACTTCTCTCTCCTCCCTCAGCCTCTCTCTTACTTGGCTTGGCCACTCTATTGGGCCTGTCAAGGCTG

TGTCCTAACTGGTATCTGGGTCATAGCCCACGAATGCGGTCACCACGCATTCAGCGACTACCAATGGCTGG

ATGACACAGTTGGTCTTATCTTCCATTCCTTCCTCCTCGTCCCTTACTTCTCCTGGAAGTATAGTCATCGC

CGTCACCATTCCAACACTGGATCCCTCGAAAGAGATGAAGTATTTGTCCCAAAGCAGAAATCAGCAATCAA

GTGGTACGGGAAATACCTCAACAACCCTCTTGGACGCATCATGATGTTAACCGTCCAGTTTGTCCTCGGGT

GGCCCTTGTACTTAGCCTTTAACGTCTCTGGCAGACCGTATGACGGGTTCGCTTGCCATTTCTTCCCCAAC

GCTCCCATCTACAATGACCGAGAACGCCTCCAGATATACCTCTCTGATGCGGGTATTCTAGCCGTCTGTTT

TGGTCTTTACCGTTACGCTGCTGCACAAGGGATGGCCTCGATGATCTGCCTCTACGGAGTACCGCTTCTGA

TAGTGAATGCGTTCCTCGTCTTGATCACTTACTTGCAGCACACTCATCCCTCGTTGCCTCACTACGATTCA

TCAGAGTGGGACTGGCTCAGGGGAGCTTTGGCTACCGTAGACAGAGACTACGGAATCTTGAACAAGGTGTT

CCACAACATTACAGACACACACGTGGCTCATCACCTGTTCTCGACAATGCCGCATTATAACGCAATGGAAG

CTACAAAGGCGATAAAGCCAATTCTGGGAGACTATTACCAGTTCGATGGAACACCGTGGTATGTAGCGATG

TATAGGGAGGCAAAGGAGTGTATCTATGTAGAACCGGACAGGGAAGGTGACAAGAAAGGTGTGTACTGGTA

CAACAATAAGTTATGA

Arabidopsis thaliana At3g12120 (FAD2) amino acid sequence
(SEQ ID NO: 81)
MGAGGRMPVPTSSKKSETDTTKRVPCEKPPFSVGDLKKAIPPHCFKRSIPRSFSYLISDIIIASCFYYVAT

NYFSLLPQPLSYLAWPLYWACQGCVLTGIWVIAHECGHHAFSDYQWLDDTVGLIFHSFLLVPYFSWKYSHR

RHHSNTGSLERDEVFVPKQKSAIKWYGKYLNNPLGRIMMLTVQFVLGWPLYLAFNVSGRPYDGFACHFFPN

APIYNDRERLQIYLSDAGILAVCFGLYRYAAAQGMASMICLYGVPLLIVNAFLVLITYLQHTHPSLPHYDS

SEWDWLRGALATVDRDYGILNKVFHNITDTHVAHHLFSTMPHYNAMEATKAIKPILGDYYQFDGTPWYVAM

YREAKECIYVEPDREGDKKGVYWYNNKL

*Arabidopsis thaliana* At4g34520 (FAE1) nucleotide sequence (SEQ ID NO: 82)

ATGACGTCCGTTAACGTTAAGCTCCTTTACCGTTACGTCTTAACCAACTTTTTCAACCTCTGTTTGTTCCC

GTTAACGGCGTTCCTCGCCGGAAAAGCCTCTCGGCTTACCATAAACGATCTCCACAACTTCCTTTCCTATC

TCCAACACAACCTTATAACAGTAACTTTACTCTTTGCTTTCACTGTTTTCGGTTTGGTTCTCTACATCGTA

ACCCGACCCAATCCGGTTTATCTCGTTGACTACTCGTGTTACCTTCCACCACCGCATCTCAAAGTTAGTGT

CTCTAAAGTCATGGATATTTTCTACCAAATAAGAAAAGCTGATACTTCTTCACGGAACGTGGCATGTGATG

ATCCGTCCTCGCTCGATTTCCTGAGGAAGATTCAAGAGCGTTCAGGTCTAGGTGATGAGACGTACAGTCCT

GAGGGACTCATTCACGTACCACCGCGGAAGACTTTTGCAGCGTCACGTGAAGAGACAGAGAAGGTTATCAT

CGGTGCGCTCGAAAATCTATTCGAGAACACCAAAGTTAACCCTAGAGAGATTGGTATACTTGTGGTGAACT

CAAGCATGTTTAATCCAACTCCTTCGCTATCCGCTATGGTCGTTAATACTTTCAAGCTCCGAAGCAACATC

AAAAGCTTTAATCTAGGAGGAATGGGTTGTAGTGCTGGTGTTATTGCCATTGATTTGGCTAAAGACTTGTT

GCATGTTCATAAAAACACTTATGCTCTTGTGGTGAGCACTGAGAACATCACACAAGGCATTTATGCTGGAG

AAAATAGATCAATGATGGTTAGCAATTGCTTGTTTCGTGTTGGTGGGCCGCGATTTTGCTCTCTAACAAG

TCGGGAGACCGGAGACGGTCCAAGTACAAGCTAGTTCACACGGTCCGAACGCATACTGGAGCTGATGACAA

GTCTTTTCGATGTGTGCAACAAGAAGACGATGAGAGCGGCAAAATCGGAGTTTGTCTGTCAAAGGACATAA

CCAATGTTGCGGGGACAACACTTACGAAAAATATAGCAACATTGGGTCCGTTGATTCTTCCTTTAAGCGAA

AAGTTTCTTTTTTTCGCTACCTTCGTCGCCAAGAAACTTCTAAAGGATAAAATCAAGCATTACTATGTTCC

GGATTTCAAGCTTGCTGTTGACCATTTCTGTATTCATGCCGGAGGCAGAGCCGTGATCGATGAGCTAGAGA

AGAACTTAGGACTATCGCCGATCGATGTGGAGGCATCTAGATCAACGTTACATAGATTTGGGAATACTTCA

TCTAGCTCAATTTGGTATGAATTAGCATACATAGAGGCAAAGGGAAGAATGAAGAAAGGGAATAAAGCTTG

GCAGATTGCTTTAGGATCAGGGTTTAAGTGTAATAGTGCGGTTTGGGTGGCTCTACGCAATGTCAAGGCAT

CGGCAAATAGTCCTTGGCAACATTGCATCGATAGATATCCGGTTAAAATTGATTCTGATTTGTCAAAGTCA

AAGACTCATGTCCAAAACGGTCGGTCCTAA

*Arabidopsis thaliana* At4g34520 (FAE1) amino acid sequence (SEQ ID NO: 83)

MTSVNVKLLYRYVLTNFFNLCLFPLTAFLAGKASRLTINDLHNFLSYLQHNLITVTLLFAFTVFGLVLYIV

TRPNPVYLVDYSCYLPPPHLKVSVSKVMDIFYQIRKADTSSRNVACDDPSSLDFLRKIQERSGLGDETYSP

EGLIHVPPRKTFAASREETEKVIIGALENLFENTKVNPREIGILVVNSSMFNPTPSLSAMVVNTFKLRSNI

KSFNLGGMGCSAGVIAIDLAKDLLHVHKNTYALVVSTENITQGIYAGENRSMMVSNCLFRVGGAAILLSNK

SGDRRRSKYKLVHTVRTHTGADDKSFRCVQQEDDESGKIGVCLSKDITNVAGTTLTKNIATLGPLILPLSE

KFLFFATFVAKKLLKDKIKHYYVPDFKLAVDHFCIHAGGRAVIDELEKNLGLSPIDVEASRSTLHRFGNTS

SSSIWYELAYIEAKGRMKKGNKAWQIALGSGFKCNSAVWVALRNVKASANSPWQHCIDRYPVKIDSDLSKS

KTHVQNGRS

*Yarrowia lipolytica* YALI0B10153g (FAD2) nucleotide sequence (SEQ ID NO: 84)

atggattcgaccacgcagaccaacaccggcaccggcaaggtggccgtgcagcccccacg gccttcattaagcccattgagaaggtgtccgagcccgtactcgacaccctttggcaacgag ttcactcctccagactactctatcaaggatattctggatgccattccccaggagtgctac aagcggtcctacgttaagtcctactcgtacgtggcccgagactgcttctttatcgccgtt tttgcctacatggcctacgcgtacctgcctcttattccctcggcttccggccgagctgtg gcctgggccatgtactccattgtccagggtctgtttggcaccggtctgtgggttcttgcc cacgagtgtggccactctgctttctccgactctaacaccgtcaacaacgtcaccggatgg -continued

```
gttctgcactcctccatgctggtcccttactacgcctggaagctgacccactccatgcac cacaagtccactggtcacctcacccgtgatatggtgtttgtgcccaaggaccgaaaggag tttatggagaaccgaggcgcccatgactggtctgagcttgctgaggacgctcccctcatg accctctacggcctcatcacccagcaggtgtttggatggcctctgtatctgctgtctaac gttaccggacagaagtaccccaagctcaacaaatgggctgtcaaccacttcaacccccaac gccccgctgtttgagaagaaggactggttcaacatctggatctctaacgtcggtattggt atcaccatgtccgtcatcgcatactccatcaaccgatggggcctggcttccgtcaccctc tactacctgatcccctacctgtgggtcaaccactggctcgtggccatcacctacctgcag cacaccgaccccactctgccccactaccacgccgaccagtggaacttcacccgaggagcc gccgccaccatcgaccgagagtttggcttcatcggctccttctgcttccatgacatcatc gagacccacgttctgcaccactacgtgtctcgaattcccttctacaacgcccgaatcgcc actgagaagatcaagaaggtcatgggcaagcactaccgacacgacgacaccaacttcatc aagtctctttacactgtcgcccgaacctgccagtttgttgaaggtaaggaaggcattcag atgtttagaaacgtcaatggagtcggagttgctcctgacggcctgccttctaaaaagtag
```

Yarrowia lipolytica YALI0B10153p (FAD2) amino acid sequence (SEQ ID NO: 85)

```
MDSTTQTNTGTGKVAVQPPTAFIKPIEKVSEPVYDTFGNEFTPPDYSIKDILDAIPQECY

KRSYVKSYSYVARDCFFIAVFAYMAYAYLPLIPSASGRAVAWAMYSIVQGLFGTGLWVLA

HECGHSAFSDSNTVNNVTGWVLHSSMLVPYYAWKLTHSMHHKSTGHLTRDMVFVPKDRKE

FMENRGAHDWSELAEDAPLMTYGLITQQVFGWPLYLLSNVTGQKYPKLNKWAVNHFNPN

APLFEKKDWFNIWISNVGIGITMSVIAYSINRWGLASVTLYYLIPYLWVNHWLVAITYLQ

HTDPTLPHYHADQWNFTRGAAATIDREFGFIGSFCFHDIIETHVLHHYVSRIPFYNARIA

TEKIKKVMGKHYRHDDTNFIKSLYTVARTCQFVEGKEGIQMFRNVNGVGVAPDGLPSKK
```

Yarrowia lipolytica YALI0B20196p (FAE1/ELO2) nucleotide sequence (SEQ ID NO: 86)

```
atgagcgccgtccctattgaattcaacgtcccctccgtggaccgaccctttggtatctac ctctgggccatctttgaccaggcctgggagaagcttttcggctggcccgcgtcctctttc attttcgtgcgaaatgaccccaacatcccctttcctctaccctcccgtgatcattgcc atcattgtgtactacattgtcatctttggcggccgagaggtgatgcgaaacctgtctccc atccgactcaactggctcttccagatccacaacatcttcctcacccttctgtccggtatg ctcctcctcctcctcgttgagcagctcttccccatcattgtccgacagggtatcctctac gccatctgcgactacggatcttggactcagcccattgtcttctgctactacctcaactac ctgaccaagtactttgagctgatcgacaccgttttccttgtgctgcgaaagaagaagctg actttcctccacacctaccaccatggtgccactgctcttctgtgctacacccagctcatt ggtaagacctcggtctcttgggtcccatcacccttaacctgtttgtccacgttgtcatg tacttctactacttcctggctgcgcgaggtatccgagtgtggtggaaggagtgggtcacc cggctccagatcatccagttcgttatcgatcttggatttgtctactttgcctcttacacc tacttcacctctacctactggccctggatgcccaacatgggctcttgtgccggcgaggag tttgctgctatttacggctgtggtctgctgacctcttacctcttcctcttcatcgccttc tacatcaactcttaccgaaagcccttcaagggaccttccaagcctgttgttgctgtc gatggccctgttggcggcgtcaacgcccagactggtgcttctcgaggccagaccactacc cgatctcgacgagcataa
```

Yarrowia lipolytica YALI0B20196p (FAE1/ELO2) amino acid sequence
(SEQ ID NO: 87)
MSAVPIEFNVPSVDRPFGIYLWAIFDQAWEKLFGWPASSFIFVRNDPNIPFSSTPPVIIA

IIVYYIVIFGGREVMRNLSPIRLNWLFQIHNIFLTLLSGMLLLLLVEQLFPIIVRQGILY

AICDYGSWTQPIVFCYYLNYLTKYFELIDTVFLVLRKKKLTFLHTYHHGATALLCYTQLI

GKTSVSWVPITLNLFVHVVMYFYYFLAARGIRVWWKEWVTRLQIIQFVIDLGFVYFASYT

YFTSTYWPWMPNMGSCAGEEFAAIYGCGLLTSYLFLFIAFYINSYRKPSSKGPSKPVVAV

DGPVGGVNAQTGASRGQTTTRSRRA

Yarrowia lipolytica YALI0C10989g (CPT1) nucleotide sequence
(SEQ ID NO: 88)
ATGGGCGTATTCATTAAACAGGAGCAGCTTCCGGCTCTCAAGAAGTACAAGTACTCCGCCGAGGATCACT

CGTTCATCTCCAACAACATTCTGCGCCCCTTCTGGCGACAGTTTGTCAAAATCTTCCCTCTGTGGATGGC

CCCCAACATGGTGACTCTGTTGGGCTTCTTCTTTGTCATTGTGAACTTCATCACCATGCTCATTGTTGAT

CCCACCCACGACCGCGAGCCTCCCAGATGGGTCTACCTCACCTACGCTCTGGGTCTGTTCCTTTACCAGA

CATTTGATGCCTGTGACGGATCCCATGCCCGACGAACTGGCCAGAGTGGACCCCTTGGAGAGCTGTTTGA

CCACTGTGTCGACGCCATGAATACCTCTCTGATTCTCACGGTGGTGGTGTCCACCACCCATATGGGATAT

AACATGAAGCTGCTGATTGTGCAGATTGCCGCTCTCGGAAACTTCTACCTGTCGACCTGGGAGACCTACC

ATACCGGAACTCTGTACCTTTCTGGCTTCTCTGGTCCTGTTGAAGGTATCTTGATTCTGGTGGCTCTTTT

CGTCCTCACCTTCTTCACTGGTCCCAACGTGTACGCTCTGACCGTCTACGAGGCTCTTCCCGAATCCATC

ACTTCGCTGCTGCCTGCCAGCTTCCTGGACGTCACCATCACCCAGATCTACATTGGATTCGGAGTGCTGG

GCATGGTGTTCAACATCTACGGCGCCTGCGGAAACGTGATCAAGTACTACAACAACAAGGGCAAGAGCGC

TCTCCCCGCCATTCTCGGAATCGCCCCCTTTGGCATCTTCTACGTCGGCGTCTTTGCCTGGGCCCATGTT

GCTCCTCTGCTTCTCTCCAAGTACGCCATCGTCTATCGTTTGCCATTGGGGCTGCCTTTGCCATGCAAG

TCGGCCAGATGATTCTTGCCCATCTCGTGCTTGCTCCCTTCCCCCACTGGAACGTGCTGCTCTTCTTCCC

CTTTGTGGGACTGGCAGTGCACTACATTGCACCCGTGTTTGGCTGGGACGCCGATATCGTGTCGGTTAAC

ACTCTCTTCACCTGTTTTGGCGCCACCCTCTCCATTTACGCCTTCTTTGTGCTTGAGATCATCGACGAGA

TCACCAACTACCTCGATATCTGGTGTCTGCGAATCAAGTACCCTCAGGAGAAGAAGACTGAGTAA

Yarrowia lipolytica YALI0C10989p (CPT1) amino acid sequence
(SEQ ID NO: 89)
MGVFIKQEQLPALKKYKYSAEDHSFISNNILRPFWRQFVKIFPLWMAPNMVTLLGFFFVIVNFITMLIVD

PTHDREPPRWVYLTYALGLFLYQTFDACDGSHARRTGQSGPLGELFDHCVDAMNTSLILTVVVSTTHMGY

NMKLLIVQIAALGNFYLSTWETYHTGTLYLSGFSGPVEGILILVALFVLTFFTGPNVYALTVYEALPESI

TSLLPASFLDVTITQIYIGFGVLGMVFNIYGACGNVIKYYNNKGKSALPAILGIAPFGIFYVGVFAWAHV

APLLLSKYAIVYLFAIGAAFAMQVGQMILAHLVLAPFPHWNVLLFFPFVGLAVHYIAPVFGWDADIVSVN

TLFTCFGATLSIYAFFVLEIIDEITNYLDIWCLRIKYPQEKKTE

Yarrowia lipolytica YALI0E26565g (EPT1) nucleotide sequence
(SEQ ID NO: 90)
ATGGGTAAAAGCCCCTCTATGATTGGGACTTGCGGTTGGGTTGGGCTGGGTACAAACACATGCTATGCTC

ATCAGCTCAGCCGTGCCATGGGCCATCAACCAACTTTTCTCCCGACCCTAATCCCCTCCACACTACTAAT

GCCAGGATTCCACCACATCAACCCCGACAGTCTAGTGCATCTAAAGTCGTACCAGTACAGAAGCGTCGAT

AAATCCTACCTGTCTAAGTACATCCTGAACCCATGGTGGACTTACGCAGCAACCTTCATGCCTGATTGGC

TGGCTCCCAACGCCATCACTCTCATCGGTGTCTCCGGCATGCTCCTGTCAATCTTCTTCACCGTCTGGTA

CACCCCCGAGCTCACCGGCGACGGTCCCTCCTGGATCTACTTCTTCTCTGCCTTTTCGCTCTTCTTCTAC

CAGACCATGGACAATATTGACGGCAAGCAGGCCCGTCGAACTGGCTCTTCCTCTCCTCTGGGAGAGCTGT

```
                                     -continued
TTGACCACGGAATCGACTCCCTCAACTGCACCTACGGCGGAATTGTCAACTGCGGTGCTGTGGCCCTTGG

TTCCACCTCCTACGGAGGCCTCATGGTTCTGTCCACCTGTATTGGTATGTACTTTTCTACCTGGGAGACT

TACTACACCCACACTCTTTACCTGGGAGTTGTTAACGGCCCCACCGAAGGGCTAGTGGTGGCCCTGTCTA

CCATGCTAATCTCCGGCTTCATGGGCACCGACATCTGGAAGGAGGATGCCGTTGAGGTGCTCCCCTTCCT

CTCCTTCATGGTTCCCGAGTACCTCAAGCTCAACGAGTTCTGGGTCTGGGTCGTCATGTTCACCCTCGTG

GTGCTGCACGTGCCTTTCTGCGTGTGGAACGTCTATTGGGCCTGCAAGGAGGACGATGTGCCTTTCTCCG

AGGCTCTGGTGGGCCTCCTGCCCTTTGGCGTGGCCGGAGGAGCTGCCTACGTGTGGCTGCAGAGTCCTTA

TTCCACTGTGCTGGTTGACAACCACCTTGTGCTATTTGGACTGACCGCCTCGTGGGTCTTTGGCCGGCTG

ACCACCGGTGTGATTCTCAACCACCTCACCAAGCTCGAGTTCCCTCTGTGGAACTCCACCCTGATTCCTC

TTCTGGGAGCCACCGTTCTGTTCTACCTGCTCCCTGCCCTGGGTCTACTGCCCCAGGACAATCCCCACTT

CGAGACTCTGTATCTGTGGGGCTTCTTTGTCTACGCTGCCGCGAACTTTTTGACCTGGGCTGTTAACACC

ATCAATGTCATCTGTTCCTACCTTGGCATCCGATGTCTGTCTCTGCGACCCGTGGACAACAAGACCAACT

AG

Yarrowia lipolytica YALI0E26565p (EPT1) amino acid sequence
                                                              (SEQ ID NO: 91)
MGKSPSMIGTCGWVGLGTNTCYAHQLSRAMGHQPTFLPTLIPSTLLMPGFHHINPDSLVHLKSYQYRSVD

KSYLSKYILNPWWTYAATFMPDWLAPNAITLIGVSGMLLSIFFTVWYTPELTGDGPSWIYFFSAFSLFFY

QTMDNIDGKQARRTGSSSPLGELFDHGIDSLNCTYGGIVNCGAVALGSTSYGGLMVLSTCIGMYFSTWET

YYTHTLYLGVVNGPTEGLVVALSTMLISGFMGTDIWKEDAVEVLPFLSFMVPEYLKLNEFWVWVVMFTLV

VLHVPFCVWNVYWACKEDDVPFSEALVGLLPFGVAGGAAYVWLQSPYSTVLVDNHLVLFGLTASWVFGRL

TTGVILNHLTKLEFPLWNSTLIPLLGATVLFYLLPALGLLPQDNPHFETLYLWGFFVYAAANFLTWAVNT

INVICSYLGIRCLSLRPVDNKTN
```

REFERENCES

1) Alonso J M et al., (2003) Genome-wide insertional mutagenesis of *Arabidopsis thaliana*. Science 301: 653-657.
2) Lu C, Xin Z, Ren Z, Miguel M, Browse J (2009) An enzyme regulating triacylglycerol composition is encoded by the ROD1 gene of *Arabidopsis*. Proc Natl Acad Sci USA 106: 18837-18842.
3) Zhang C et al., (2013) Genetic and biochemical basis for alternative routes of tocotrienol biosynthesis for enhanced vitamin E antioxidant production. Plant J 73: 628-639.
4) Clough S J, Bent A F (1998) Floral dip: a simplified method for *Agrobacterium*-mediated transformation of *Arabidopsis thaliana*. Plant J 16: 735-743.
5) Wood C C et al., (2009) A leaf-based assay using interchangeable design principles to rapidly assemble multistep recombinant pathways. Plant Biotech J 7: 914-924.
6) Kelly A A et al., (2013) The SUGAR-DEPENDENT1 lipase limits triacylglycerol accumulation in vegetative tissues of *Arabidopsis*. Plant Physiol. 162: 1282-1289.
7) van Erp H, Bates P D, Burgal J, Shockey J, Browse J (2011) Castor phospholipid: diacylglycerol acyltransferase facilitates efficient metabolism of hydroxy fatty acids in transgenic *Arabidopsis*. Plant Physiol. 155: 683-693.
8) Bates P D, Browse J (2011) The pathway of triacylglycerol synthesis through phosphatidylcholine in *Arabidopsis* produces a bottleneck for the accumulation of unusual fatty acids in transgenic seeds. Plant J. 68: 387-399.
9) van Erp H, Kelly A A, Menard G, Eastmond P J (2014) Multigene engineering of triacylglycerol metabolism boosts seed oil content in *Arabidopsis*. Plant Physiol. 165: 30-36.
10) Yamada T et al., (2013) Development of a lipid profiling system using reverse-phase liquid chromatography coupled to high-resolution mass spectrometry with rapid polarity switching and an automated lipid identification software. J Chrom. A 1292: 211-218.
11) Narvaez-Rivas M, Zhang G (2016) Comprehensive untargeted lipidomic analysis using core-shell C30 particle column and high field orbitrap mass spectrometer. J Chrom. A 1440: 123-134.
12) Turner N et al., (2018) A selective inhibitor of ceramide synthase 1 reveals a novel role in fat metabolism, Nature Comm. 9: 3165.
13) Mendes A et al., (2013) bZIP67 regulates the omega-3 fatty acid content of *Arabidopsis* seed oil by activating FATTY ACID DESATURASE 3. Plant Cell 25: 3104-3116.
14) Gutierrez L et al., (2008) The lack of a systematic validation of reference genes: a serious pitfall undervalued in reverse transcription-polymerase chain reaction (RT-PCR) analysis in plants. Plant Biotechnol J. 6: 609-618.
15) Nguyen H T, Mishra G, Whittle E, Pidkowich M S, Bevan S A, Merlo A O, Walsh T A, Shanklin J (2010) Metabolic engineering of seeds can achieve levels of omega-7 fatty acids comparable with the highest levels found in natural plant sources. Plant Physiol. 154: 1897-1904.

16) Ossowski S, Schwab R, Weigel D (2008) Gene silencing in plants using artificial microRNAs and other small RNAs. Plant J. 53: 674-690.
17) Nguyen H T, Park H, Koster K L, Cahoon R E, Nguyen H T, Shanklin J, Clemente T E, Cahoon E B (2015) Redirection of metabolic flux for high levels of omega-7 monounsaturated fatty acid accumulation in camelina seeds. Plant Biotechnol J. 13: 38-50.
18) Moloney, M. M. Walker, J. M. and Sharma, K. K. (1989) High efficiency, transformation of Brassica napus using agrobacterium vectors. Plant Cell Rep., 8, 238-242.
19) Barth G, Gaillardin C. 1996. Yarrowia lipolytica. In:. Nonconv. Yeasts Biotechnol.
SE—10. Springer Berlin Heidelberg, pp. 313-388.
20) Sambrook J, Russell D W. 2001. Molecular Cloning: A Laboratory Manual, 3rd edn. Cold Spring Harbour, NY, USA Cold Spring Harb. Lab. Press. 2001. Vol. 1-3.
21) Gibson D G, Young L, Chuang R-Y, Venter J C, Hutchison C A, Smith H O. 2009. Enzymatic assembly of DNA molecules up to several hundred kilobases. Nat. Methods 6:343-345.
22) Kulasekara H D. 2011. Gibson Assembly. Samuel Mill. Lab, UW, Seattle. http://miller-lab.net/MillerLab/protocols/molecular-biology-and-cloning/gibson-assembly/.
23) Bhutada G, Kavšček M, Ledesma-Amaro R, Thomas S, Rechberger G N, Nicaud J-M, Natter K. 2017. Sugar versus fat: Elimination of glycogen storage improves lipid accumulation in Yarrowia lipolytica. FEMS Yeast Res. 17.
24) Curran K A, Morse N J, Markham K A, Wagman A M, Gupta A, Alper H S. 2015. Short, Synthetic Terminators for Improved Heterologous Gene Expression in Yeast. ACS Synth. Biol.
25) Le Dall M T, Nicaud J M, Gaillardin C. 1994. Multiple-copy integration in the yeast Yarrowia lipolytica. Curr. Genet. 26:38-44.
26) Wu J, James D W Jr, Dooner H K, Browse J (1994) A Mutant of Arabidopsis Deficient in the Elongation of Palmitic Acid. Plant Physiol 106: 143-150
27) Smith M A, Moon H, Chowrira G, Kunst L (2003) Heterologous expression of a fatty acid hydroxylase gene in developing seeds of Arabidopsis thaliana. Planta 217: 507-516
28) Kim H U, Li Y, Huang A H (2005) Ubiquitous and endoplasmic reticulum-located lysophosphatidyl acyltransferase, LPAT2, is essential for female but not male gametophyte development in Arabidopsis. Plant Cell 17: 1073-1089

As described herein, in human milk fat, saturated fatty acids are esterified to the middle position on the glycerol backbone giving the triacylglycerol molecules an unusual stereochemistry that assists nutrient absorption in the infant gut. However, the fat used in most infant formulas is derived from plants, which esterify saturated fatty acids to the outer positions. Here we have engineered the metabolism of an oilseed plant so that it accumulates triacylglycerol with more than 70% of the saturated fatty acid palmitate in the middle position, thereby mimicking human milk fat stereoisomeric structure. Applying this technology to oilseed crops (or oleaginous microbes) could provide a new source of human milk fat substitute for infant nutrition.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The content of all references cited herein is incorporated herein by reference in its entirety.

The invention claimed is:

1. A plant or fungal organism for producing triacylglycerol
   (A) wherein the plant or fungal organism is genetically modified to express a lysophosphatidic acid acyltransferase specific for C16:0-Coenzyme A (C16:0 LPAT) and wherein, once expressed, the C16:0 LPAT is localised in the endoplasmic reticulum; or
   (B) in which:
   (a) a lysophosphatidic acid acyltransferase specific for C16:0-Coenzyme A (C16:0 LPAT) is localised in the endoplasmic reticulum; and (b) activity of native endoplasmic reticulum lysophosphatidic acid acyltransferase (ER LPAT) is suppressed or prevented.

2. The plant or fungal organism according to claim 1, wherein the activity of diacylglycerol conversion to and from phosphatidylcholine is suppressed or prevented.

3. The plant or fungal organism according to claim 1, wherein the activity of phosphatidylcholine: diacylglycerol cholinephosphotransferase (PDCT) is suppressed or prevented.

4. The plant or fungal organism according to claim 1, wherein the organism is an oilseed plant.

5. The plant or fungal organism according to claim 4, wherein the plant is selected from *Arabidopsis thaliana, Helianthus annuus, Glycine max, Camelina sativa* and *Brassica napus*.

6. The plant or fungal organism according to claim 1, wherein the organism is a yeast.

7. The plant or fungal organism according to claim 6, wherein the organism is *Yarrowia lipolytica*.

8. The plant or fungal organism according to claim 1, wherein the plant or fungal organism is cultured in a media comprising a carbon source, wherein the carbon source comprises (i) one or more sugars, and (ii) one or more fatty acids and/or fatty acid esters.

9. The plant or fungal organism m according to claim 8, wherein the carbon source comprises a mixture of fatty acids and/or fatty acid esters wherein at least about 30% w/w of the fatty acids and/or fatty acid esters comprises C16:0 and/or at least about 30% w/w of the fatty acids and/or fatty acid esters comprises C18:1.

10. The plant or fungal organism according to claim 8, wherein the media comprises glycerol.

11. The plant or fungal organism according to claim 1, wherein the organism is cultured in a media comprising a carbon source, wherein the carbon source comprises palm oil.

12. The plant or fungal organism according to claim 11, wherein the carbon source comprises palm oil in combination with glucose and/or glycerol.

13. The plant or fungal organism according to claim 1, wherein the C16:0 LPAT is selected from:
(i) a chloroplast LPAT which lacks a functional chloroplast targeting sequence;
(ii) AGPAT1 (Human 1-acylglycerol-3-phosphate O-acyltransferase isoform 1);
(iii) CreLPAT;
(iv) *Nannochloropsis* sp. LPAT2;
(v) *Nannochloropsis* sp. LPAT3;
(vi) *Nannochloropsis* sp. LPAT4; and
(vii) *Synechocystis* sp. LPAT.

14. The plant or fungal organism according to claim 1, wherein the plant or fungal organism expresses a FATB thioesterase.

15. The plant or fungal organism according to claim 1, wherein the plant or fungal organism expresses a FATB thioesterase and is treated or genetically modified to disrupt the fatty acid desaturase 2 gene (FAD2).

16. The plant or fungal organism according to claim 1, wherein the plant or fungal organism is treated or genetically modified to disrupt the KASII gene FAB1, fatty acid elongase gene (FAE1) and/or fatty acid desaturase 2 gene (FAD2).

17. The plant or fungal organism according to claim 1, wherein (i) the plant or fungal organism expresses a FATB thioesterase and is treated or genetically modified to disrupt the fatty acid desaturase 2 gene (FAD2), (ii) conversion of diacylglycerol to phosphatidylcholine is suppressed or prevented in the plant or fungal organism, and (iii) activity of native endoplasmic reticulum lysophosphatidic acid acyltransferase (ER LPAT) is suppressed or prevented in the plant or fungal organism.

18. The plant or fungal organism according to claim 1, wherein the plant or fungal organism is a plant.

19. A seed for producing a plant according to claim 18.

20. A seed, fruit or a leaf obtained from a plant according to claim 18.

21. A cell of the plant or fungal organism according to claim 1.

22. A method for extracting triacylglycerol from the plant or fungal organism according to claim 1.

23. A method for producing an infant formula, comprising obtaining triacylglycerol from a plant or fungal organism or a cell thereof according to claim 1 and using said triacylglycerol to produce an infant formula.

* * * * *

SEQUENCE LISTING

```
<160> NUMBER OF SEQ ID NOS: 91

<210> SEQ ID NO 1
<211> LENGTH: 777
<212> TYPE: DNA
<213> ORGANISM: Arabidopsis thaliana

<400> SEQUENCE: 1
atgtcggatc tttcaggagc tgcaacccct gaatctactt atccagaacc agagattaag      60
ttgagctcaa gactcagagg gatatgcttt tgtctcgttg ctggcgtttc cgccattgtt     120
ctcatcgtcc tgatgatcac tggccatcct ttcgtccttc tatttgatcg ttacaggagg     180
aagttccatc acttcattgc taagctctgg gcttccataa gcatctaccc gttttacaaa     240
accgacatcc aaggtttgga gaatctgcca tcatcagaca ctccttgtgt gtacgtttcg     300
aaccaccaga gttttctgga tatatacaca cttctcagcc ttggccaaag ctataagttc     360
atcagcaaga cagggatatt cgttattcct gtcatcggtt gggctatgtc catgatgggg     420
gttgttccct tgaagaggat ggacccaaga agccaagtgg attgcttaaa acgctgcatg     480
gaactagtga agaagggagc ttccgtcttt ttcttcccag agggaacgag gagtaaggat     540
ggtcggttag gtcctttcaa gaaagggggct tttacgatag cagctaagac aggagttcca     600
gtggtgccaa taacgctgat gggaacaggg aagatcatgc cgacgggtag tgaaggtata     660
ctgaatcatg gggatgtgag agtgatcatc cacaagccga tatatggaag caaagctgat     720
```
cttctttgcg atgaggctag aaacaagata gctgaatcta tgaatctctt gagttga      777

<210> SEQ ID NO 2
<211> LENGTH: 258
<212> TYPE: PRT
<213> ORGANISM: Arabidopsis thaliana

<400> SEQUENCE: 2

```
Met Ser Asp Leu Ser Gly Ala Ala Thr Pro Glu Ser Thr Tyr Pro Glu
1               5                   10                  15

Pro Glu Ile Lys Leu Ser Arg Leu Arg Gly Ile Cys Phe Cys Leu
            20                  25                  30

Val Ala Gly Val Ser Ala Ile Val Leu Ile Val Leu Met Ile Thr Gly
        35                  40                  45

His Pro Phe Val Leu Leu Phe Asp Arg Tyr Arg Arg Lys Phe His His
    50                  55                  60

Phe Ile Ala Lys Leu Trp Ala Ser Ile Ser Ile Tyr Pro Phe Tyr Lys
65                  70                  75                  80

Thr Asp Ile Gln Gly Leu Glu Asn Leu Pro Ser Ser Asp Thr Pro Cys
                85                  90                  95

Val Tyr Val Ser Asn His Gln Ser Phe Leu Asp Ile Tyr Thr Leu Leu
            100                 105                 110

Ser Leu Gly Gln Ser Tyr Lys Phe Ile Ser Lys Thr Gly Ile Phe Val
        115                 120                 125

Ile Pro Val Ile Gly Trp Ala Met Ser Met Met Gly Val Val Pro Leu
    130                 135                 140

Lys Arg Met Asp Pro Arg Ser Gln Val Asp Cys Leu Lys Arg Cys Met
145                 150                 155                 160

Glu Leu Val Lys Lys Gly Ala Ser Val Phe Phe Pro Glu Gly Thr
                165                 170                 175

Arg Ser Lys Asp Gly Arg Leu Gly Pro Phe Lys Lys Gly Ala Phe Thr
            180                 185                 190

Ile Ala Ala Lys Thr Gly Val Pro Val Val Pro Ile Thr Leu Met Gly
        195                 200                 205

Thr Gly Lys Ile Met Pro Thr Gly Ser Glu Gly Ile Leu Asn His Gly
    210                 215                 220

Asp Val Arg Val Ile Ile His Lys Pro Ile Tyr Gly Ser Lys Ala Asp
225                 230                 235                 240

Leu Leu Cys Asp Glu Ala Arg Asn Lys Ile Ala Glu Ser Met Asn Leu
                245                 250                 255

Leu Ser
```

<210> SEQ ID NO 3
<211> LENGTH: 26
<212> TYPE: DNA
<213> ORGANISM: Artificial Sequence
<220> FEATURE:
<223> OTHER INFORMATION: Primer P1

<400> SEQUENCE: 3
caccatgtcg gatctttcag gagctg      26

<210> SEQ ID NO 4
<211> LENGTH: 25
<212> TYPE: DNA
<213> ORGANISM: Artificial Sequence
<220> FEATURE:
<223> OTHER INFORMATION: Primer P2

```
<400> SEQUENCE: 4
tcaactcaag agattcatag attca                                          25

<210> SEQ ID NO 5
<211> LENGTH: 28
<212> TYPE: DNA
<213> ORGANISM: Artificial Sequence
<220> FEATURE:
<223> OTHER INFORMATION: Primer P3

<400> SEQUENCE: 5
cggaattcat gtcggatctt tcaggagc                                       28

<210> SEQ ID NO 6
<211> LENGTH: 32
<212> TYPE: DNA
<213> ORGANISM: Artificial Sequence
<220> FEATURE:
<223> OTHER INFORMATION: Primer P4

<400> SEQUENCE: 6
gctctagatc aactcaagag attcatagat tc                                  32

<210> SEQ ID NO 7
<211> LENGTH: 21
<212> TYPE: DNA
<213> ORGANISM: Artificial Sequence
<220> FEATURE:
<223> OTHER INFORMATION: Primer P5

<400> SEQUENCE: 7
gttgattgaa tcgaggaagg a                                              21

<210> SEQ ID NO 8
<211> LENGTH: 21
<212> TYPE: DNA
<213> ORGANISM: Artificial Sequence
<220> FEATURE:
<223> OTHER INFORMATION: Primer P6

<400> SEQUENCE: 8 cttttacca catgcaaagg g                                               21

<210> SEQ ID NO 9
<211> LENGTH: 20
<212> TYPE: DNA
<213> ORGANISM: Artificial Sequence
<220> FEATURE:
<223> OTHER INFORMATION: Primer P7

<400> SEQUENCE: 9
ccattttggt ggtcgtctat                                                20

<210> SEQ ID NO 10
<211> LENGTH: 21
<212> TYPE: DNA
<213> ORGANISM: Artificial Sequence
<220> FEATURE:
<223> OTHER INFORMATION: Primer P8

<400> SEQUENCE: 10
cagaaaaatt aaccgggtgg t                                              21

<210> SEQ ID NO 11
```

```
<211> LENGTH: 20
<212> TYPE: DNA
<213> ORGANISM: Artificial Sequence
<220> FEATURE:
<223> OTHER INFORMATION: Primer P9

<400> SEQUENCE: 11
cagctgaaac cgacgtctct                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer P10

<400> SEQUENCE: 12
ggtcacgcgc tctttgaatc                                                    20

<210> SEQ ID NO 13
<211> LENGTH: 19
<212> TYPE: DNA
<213> ORGANISM: Artificial Sequence
<220> FEATURE:
<223> OTHER INFORMATION: Primer P11

<400> SEQUENCE: 13
gtagcaccca aggcttcca                                                     19

<210> SEQ ID NO 14
<211> LENGTH: 19
<212> TYPE: DNA
<213> ORGANISM: Artificial Sequence
<220> FEATURE:
<223> OTHER INFORMATION: Primer P12

<400> SEQUENCE: 14
gccagtgatc atcaggacg                                                     19

<210> SEQ ID NO 15
<211> LENGTH: 22
<212> TYPE: DNA
<213> ORGANISM: Artificial Sequence
<220> FEATURE:
<223> OTHER INFORMATION: Primer P13

<400> SEQUENCE: 15
gcgtggaccg cttgctgcaa ct                                                 22

<210> SEQ ID NO 16
<211> LENGTH: 20
<212> TYPE: DNA
<213> ORGANISM: Artificial Sequence
<220> FEATURE:
<223> OTHER INFORMATION: Primer P14

<400> SEQUENCE: 16
ctggtgggct ggagttaaga                                                    20

<210> SEQ ID NO 17
<211> LENGTH: 20
<212> TYPE: DNA
<213> ORGANISM: Artificial Sequence
<220> FEATURE:
<223> OTHER INFORMATION: Primer P15

<400> SEQUENCE: 17
```
agaatccatc ccacaagcca                                                    20

<210> SEQ ID NO 18
<211> LENGTH: 20
<212> TYPE: DNA
<213> ORGANISM: Artificial Sequence
<220> FEATURE:
<223> OTHER INFORMATION: Primer P16

<400> SEQUENCE: 18
tgtcatcggt tgggctatgt                                                    20

<210> SEQ ID NO 19
<211> LENGTH: 20
<212> TYPE: DNA
<213> ORGANISM: Artificial Sequence
<220> FEATURE:
<223> OTHER INFORMATION: Primer P17

<400> SEQUENCE: 19
catcagcgtt attggcacca                                                    20

<210> SEQ ID NO 20
<211> LENGTH: 17
<212> TYPE: DNA
<213> ORGANISM: Artificial Sequence
<220> FEATURE:
<223> OTHER INFORMATION: Primer P18

<400> SEQUENCE: 20
gacgcttcat ctcgtcc                                                       17

<210> SEQ ID NO 21
<211> LENGTH: 16
<212> TYPE: DNA
<213> ORGANISM: Artificial Sequence
<220> FEATURE:
<223> OTHER INFORMATION: Primer P19

<400> SEQUENCE: 21
ccacaggttg cgttag                                                        16

<210> SEQ ID NO 22
<211> LENGTH: 16
<212> TYPE: DNA
<213> ORGANISM: Artificial Sequence
<220> FEATURE:
<223> OTHER INFORMATION: Primer P20

<400> SEQUENCE: 22
tccagctaag ggtgcc                                                        16

<210> SEQ ID NO 23
<211> LENGTH: 16
<212> TYPE: DNA
<213> ORGANISM: Artificial Sequence
<220> FEATURE:
<223> OTHER INFORMATION: Primer P21

<400> SEQUENCE: 23
ggtgggtact cggaga                                                        16

<210> SEQ ID NO 24
<211> LENGTH: 17
<212> TYPE: DNA

```
<213> ORGANISM: Artificial Sequence
<220> FEATURE:
<223> OTHER INFORMATION: Primer P22

<400> SEQUENCE: 24
gaattacccg acggaca                                                      17

<210> SEQ ID NO 25
<211> LENGTH: 16
<212> TYPE: DNA
<213> ORGANISM: Artificial Sequence
<220> FEATURE:
<223> OTHER INFORMATION: Primer P23

<400> SEQUENCE: 25
acggtctgca atacct                                                       16

<210> SEQ ID NO 26
<211> LENGTH: 852
<212> TYPE: DNA
<213> ORGANISM: Homo sapiens

<400> SEQUENCE: 26
atggatttat ggcctggtgc ttggatgtta ttattattat tattcttgtt attgctcttc        60
ctccttccta ctttgtggtt ctgttcacct tctgcaaagt atttctttaa gatggctttc      120
tacaacggat ggattctttt cttggctgtt ttggcaatcc cagtttgtgc tgtgagaggt      180
aggaacgttg aaaacatgaa gattctcaga ctcatgcttt tgcatatcaa gtacctttac      240
ggaataagag tggaagttag gggtgctcat cactttcctc catctcaacc ttatgttgtg      300
gtttcaaacc accagtcttc attggatctc ttaggaatga tggaagtgct ccctggtaga      360
tgtgttccaa tagcaaagag ggagcttttg tgggctggat cagcaggtct tgcttgctgg      420
ttggctggag ttatttttat cgatagaaaa aggacaggtg atgcaatctc agtgatgagt      480
gaagttgctc aaactctctt aacacaggat gtgagagttt gggtgttccc tgagggaacc      540
aggaatcata acggtagtat gttaccattt aagagaggag ctttccacct cgcagttcaa      600
gctcaggttc ctatagtgcc aatagttatg agttcttacc aagatttcta ctgtaagaag      660
gaaagaaggt tcactagtgg acaatgccaa gttagagtgc tccctccagt tccaaccgag      720
ggtttaactc ctgatgatgt gccagctctt gcagatagag ttaggcattc tatgttgaca      780
gtgttcagag agattagtac cgatggaagg ggaggtggag attatttgaa gaagccaggt      840
ggaggaggat ga                                                          852

<210> SEQ ID NO 27
<211> LENGTH: 21
<212> TYPE: DNA
<213> ORGANISM: Artificial Sequence
<220> FEATURE:
<223> OTHER INFORMATION: amiRNA sequence 1

<400> SEQUENCE: 27
taaagcgagt tccctcgaca g                                                 21

<210> SEQ ID NO 28
<211> LENGTH: 21
<212> TYPE: DNA
<213> ORGANISM: Artificial Sequence
<220> FEATURE:
<223> OTHER INFORMATION: amiRNA sequence 2

<400> SEQUENCE: 28
```
ttgtgcccag tgtacggact t                                              21

<210> SEQ ID NO 29
<211> LENGTH: 21
<212> TYPE: DNA
<213> ORGANISM: Artificial Sequence
<220> FEATURE:
<223> OTHER INFORMATION: amiRNA sequence 3

<400> SEQUENCE: 29
tcaaaggcac gatgatacct g                                              21

<210> SEQ ID NO 30
<211> LENGTH: 21
<212> TYPE: DNA
<213> ORGANISM: Artificial Sequence
<220> FEATURE:
<223> OTHER INFORMATION: amiRNA sequence 4

<400> SEQUENCE: 30
tcacttgatg tgaagatgca c                                              21

<210> SEQ ID NO 31
<211> LENGTH: 21
<212> TYPE: DNA
<213> ORGANISM: Artificial Sequence
<220> FEATURE:
<223> OTHER INFORMATION: amiRNA sequence 5

<400> SEQUENCE: 31
ttaacagctg acacgaagcc t                                              21

<210> SEQ ID NO 32
<211> LENGTH: 21
<212> TYPE: DNA
<213> ORGANISM: Artificial Sequence
<220> FEATURE:
<223> OTHER INFORMATION: amiRNA sequence 6

<400> SEQUENCE: 32
tcacttgatg tgaacacgca c                                              21

<210> SEQ ID NO 33
<211> LENGTH: 1239
<212> TYPE: DNA
<213> ORGANISM: Arabidopsis thaliana

<400> SEQUENCE: 33
atggtggcca cctctgctac gtcgtcattc tttcctgtac catcttcttc acttgatcct     60
aatggaaaag gcaataagat tgggtctacg aatcttgctg gactcaattc tgcacctaac    120
tctggtagga tgaaggttaa accaaacgct caggctccac ctaagattaa tgggaaaaag    180
gttggtttgc ctggttctgt agatattgta aggactgata ccgagacctc atcacaccct    240
gcgccgagaa ctttcatcaa ccagttacct gactggagca tgcttcttgc tgctataact    300
acgattttct tagcggctga gaaacagtgg atgatgcttg attggaaacc taggcgttct    360
gacatgctgg tggatccttt tggtataggg agaattgttc aggatggcct tgtgttccgt    420
cagaattttt ctattaggtc atatgaaata ggtgctgatc gctctgcatc tatagaaacc    480
gtcatgaatc atctgcagga aacggcgctt aatcatgtta agactgctgg attgcttgga    540
gatgggtttg gctctacacc tgagatgttt aagaagaact tgatatgggt tgtcactcgt    600

```
atgcaggttg tggttgataa atatcctact tggggagatg ttgttgaagt agacacctgg    660
gtcagtcagt ctggaaagaa tggtatgcgt cgtgattggc tagttcggga ctgtaatact    720
ggagaaacct taacacgagc atcaagtgtg tgggtgatga tgaataaact gacaaggaga    780
ttgtcaaaga ttcctgaaga ggttcgaggg gaaatagagc cttatttttgt gaattctgat   840 cctgtccttg ccgaggacag cagaaagtta acaaaaattg atgacaagac tgctgactat    900
gttcgatctg gtctcactcc tcgatggagt gacctagatg ttaaccagca tgtgaataat    960
gtaaagtaca ttgggtggat cctggagagt gctccagtgg aataatggga gaggcagaag   1020
ctgaaaagca tgactctgga gtatcggagg gaatgcggga gagacagtgt gcttcagtcc   1080
ctcactgcag ttacggggttg cgatatcggt aacctggcaa cagcggggga tgtggaatgt  1140
cagcatttgc tccgactcca ggatggagcg gaagtggtga gaggaagaac agagtggagt   1200
agtaaaacac caacaacaac ttggggaact gcaccgtaa                          1239

<210> SEQ ID NO 34
<211> LENGTH: 43
<212> TYPE: DNA
<213> ORGANISM: Artificial Sequence
<220> FEATURE:
<223> OTHER INFORMATION: Primer TEF-GSY-F

<400> SEQUENCE: 34
ctcgcaacaa ccgattccaa caagagaccg ggttggcggc gca                      43

<210> SEQ ID NO 35
<211> LENGTH: 74
<212> TYPE: DNA
<213> ORGANISM: Artificial Sequence
<220> FEATURE:
<223> OTHER INFORMATION: Primer TEF-GSY-R

<400> SEQUENCE: 35
ataacttcgt ataatgtatg ctatacgaag ttataagctt tgaatgattc ttatactcag    60
aaggaaatgc ttaa                                                      74

<210> SEQ ID NO 36
<211> LENGTH: 1061
<212> TYPE: DNA
<213> ORGANISM: Chlamydomonas reinhardtii

<400> SEQUENCE: 36
aagcttatgt ctgtcctcac caagtggctg ggtctcccct ctttcctgtt ctccgtcttc    60
gtgttctact ggtctctccc catcttcgcc attctgtacc gaatccgatt cgcttccctg   120
ggaaagcgaa acgacatgct cgactgggct cgagccctgg tcgcctactt ccgagtgacc   180
ctgctccagg ctggcgagca caccctgtac aagggcggtc cctgcctgta cctctgtaac   240
caccgatcct gggctgactt cttcattgac gcttacctga ccgagggacg agctgctctc   300
atgtctcgat ggctggtcta cttcgtgttc cccgtcttct gcacctcctg tatgatcctc   360
aagggtattg tcctgttcaa gcgaggaacc attgccgaca aggaagcctt caacgcctgg   420
ctggaccaga ccctgggatc ctctcacgtc cctggactgc tggtgtaccc cgagggacac   480
cgatctacca agcctgcctc cctgcctctc aagcgaggta tgctccacta cgctcactct   540
cgaaagctgc ccgtgcagat tgtcgtgacc cgaggcaagg acgaggtcct gtccgagaag   600
tctcagtccg tgcacttcgg acgaacctgc gtcaccacct tctctaaggt gctcaagtcc   660
gctgactacc ccaacttcga ggccttcttc accgacctgc aggctacctg ggactcttgt   720
```

```
tgggccgcta cctacggact ggaggacctc aagaacgtgc ctcgattctc tatgcccgga    780
cctcaggcct actcctactc ctcttccatg tgggtgcagc agctcgccat caccctcgtg    840
tctattctgg tcttcgctgg agtttgttac ggctcctggc gaggtctggc cgctgccctg    900
gctgctaccg tgctgccca gcaggtggtt gctctggtgc tggctgcttg ggtgggttct    960
tccgtgctcc gatccttcct gtaacgatcg ttttttttta tatatatata tatatatata   1020
taactgtcta gaaataaaga gtatcatctt tcaaaaagct t                       1061
```

<210> SEQ ID NO 37
<211> LENGTH: 935
<212> TYPE: DNA
<213> ORGANISM: Homo sapiens

<400> SEQUENCE: 37

```
aagcttatgg acctgtggcc cggagcttgg atgctgctcc tgctcctgtt cctcctcctg     60
ctgttcctcc tgcccaccct gtggttctgc tccccctctg ctaagtactt cttcaagatg    120
gccttctaca acggttggat tctgttcctg gccgtcctgg ctattcccgt ctgtgctgtg    180
cgaggacgaa acgtggagaa catgaagatc ctccgactga tgctcctgca catcaagtac    240
ctgtacggaa ttcgagttga ggtccgaggc gcccaccact tccctccctc ccagccttac    300
gtcgtggtct ctaaccacca gtcctctctg gacctcctgg gtatgatgga ggtgctccct    360
ggacgatgtg tccctatcgc taagcgagag ctgctctggg ctggttccgc tggactggct    420
tgttggctgg ctggcgtcat cttcattgac cgaaagcgaa ccggtgacgc tatttccgtg    480
atgtctgagg tggctcagac cctcctgacc caggacgttc gagtctgggt gttccctgag    540
ggaacccgaa accacaacgg ttccatgctg cccttcaagc gaggcgcctt ccacctcgct    600
gtccaggctc aggtccctat tgtgcccatt gtcatgtcct cttaccagga cttctactgc    660
aagaaggagc gacgattcac ctctggacag tgtcaggtcc gagtgctgcc tcccgtgcct    720
accgagggac tgaccccga cgacgttcct gctctggctg accgagtccg acactccatg    780
ctgaccgtgt tccgagagat ttctaccgac ggtcgaggcg gtggagacta cctcaagaag    840
cccggcggtg gaggctaacg atcgtttttt tttatatata tatatatata tatataactg    900
tctagaaata aagagtatca tctttcaaaa agctt                               935
```

<210> SEQ ID NO 38
<211> LENGTH: 860
<212> TYPE: DNA
<213> ORGANISM: Arabidopsis thaliana

<400> SEQUENCE: 38

```
aagcttatgt ccgacctgtc tggtgctgct accccgagt ccacctaccc tgagcctgag     60
atcaagctgt cctctcgact ccgaggaatt tgcttctgtc tcgtcgccgg cgtgtctgct    120
atcgtcctga ttgtgctcat gatcaccggc caccccttcg tcctgctctt cgaccgatac    180
cgacgaaagt tccaccactt catcgccaag ctgtgggctt ccatctctat ctacccttc    240
tacaagaccg acattcaggg tctggagaac ctccctcct ctgacacccc ctgcgtctac    300
gtgtccaacc accagtcttt tctggacatc tacaccctgc tctccctcgg acagtcttac    360
aagttcattt ccaagaccgg catcttcgtc attcccgtga tcggctgggc catgtccatg    420
atgggtgtcg tgcccctgaa gcgaatggac ccccgatctc aggtcgactg cctgaagcga    480
tgtatggagc tcgtcaagaa gggtgcctcc gtcttcttct tccccgaggg aaccctgatct    540
```

```
aaggacggac gactgggccc cttcaagaag ggcgctttca ccattgctgc taagaccggt    600
gtgcctgtgg tgcccattac cctgatgggc accggcaaga tcatgcccac cggttccgag    660
ggaattctca accacggtga cgtccgagtg atcattcaca agcccatcta cggatctaag    720
gctgacctgc tctgtgacga ggcccgaaac aagattgctg agtccatgaa cctgctctct    780
taacgatcgt ttttttttat atatatatat atatatatat aactgtctag aaataaagag    840
tatcatcttt caaaaagctt                                                860
```

<210> SEQ ID NO 39
<211> LENGTH: 852
<212> TYPE: DNA
<213> ORGANISM: Homo sapiens

<400> SEQUENCE: 39

```
atggatttgt ggccaggggc atggatgctg ctgctgctgc tcttcctgct gctgctcttc     60
ctgctgccca ccctgtggtt ctgcagcccc agtgccaagt acttcttcaa gatggccttc    120
tacaatggct ggatcctctt cctggctgtg ctcgccatcc ctgtgtgtgc cgtgcgagga    180
cgcaacgtcg agaacatgaa gatcttgcgt ctaatgctgc tccacatcaa atacctgtac    240
gggatccgag tggaggtgcg aggggctcac cacttccctc cctcgcagcc ctatgttgtt    300
gtctccaacc accagagctc tctcgatctg cttgggatga tggaggtact gccaggccgc    360
tgtgtgccca ttgccaagcg cgagctactg tgggctggct ctgccgggct ggcctgctgg    420
ctggcaggag tcatcttcat cgaccggaag cgcacggggg atgccatcag tgtcatgtct    480
gaggtcgccc agaccctgct cacccaggac gtgagggtct gggtgtttcc tgagggaacg    540
agaaaccaca atggctccat gctgcccttc aaacgtggcg ccttccatct gcagtgcagg    600
gcccaggttc ccattgtccc catagtcatg tcctcctacc aagacttcta ctgcaagaag    660
gagcgtcgct tcacctcggg acaatgtcag gtgcgggtgc tgccccagt gcccacggaa    720 gggctgacac cagatgacgt cccagctctg gctgacagag tccggcactc catgctcact    780
gttttccggg aaatctccac tgatggccgg ggtggtggtg actatctgaa gaagcctggg    840
ggcggtgggt ga                                                        852
```

<210> SEQ ID NO 40
<211> LENGTH: 283
<212> TYPE: PRT
<213> ORGANISM: Homo sapiens

<400> SEQUENCE: 40

```
Met Asp Leu Trp Pro Gly Ala Trp Met Leu Leu Leu Leu Leu Phe Leu
1               5                   10                  15

Leu Leu Leu Phe Leu Leu Pro Thr Leu Trp Phe Cys Ser Pro Ser Ala
            20                  25                  30

Lys Tyr Phe Phe Lys Met Ala Phe Tyr Asn Gly Trp Ile Leu Phe Leu
        35                  40                  45

Ala Val Leu Ala Ile Pro Val Cys Ala Val Arg Gly Arg Asn Val Glu
    50                  55                  60

Asn Met Lys Ile Leu Arg Leu Met Leu Leu His Ile Lys Tyr Leu Tyr
65                  70                  75                  80

Gly Ile Arg Val Glu Val Arg Gly Ala His His Phe Pro Pro Ser Gln
                85                  90                  95

Pro Tyr Val Val Val Ser Asn His Gln Ser Ser Leu Asp Leu Leu Gly
            100                 105                 110
```

```
Met Met Glu Val Leu Pro Gly Arg Cys Val Pro Ile Ala Lys Arg Glu
            115                 120                 125

Leu Leu Trp Ala Gly Ser Ala Gly Leu Ala Cys Trp Leu Ala Gly Val
        130                 135                 140

Ile Phe Ile Asp Arg Lys Arg Thr Gly Asp Ala Ile Ser Val Met Ser
145                 150                 155                 160

Glu Val Ala Gln Thr Leu Leu Thr Gln Asp Val Arg Val Trp Val Phe
                165                 170                 175

Pro Glu Gly Thr Arg Asn His Asn Gly Ser Met Leu Pro Phe Lys Arg
            180                 185                 190

Gly Ala Phe His Leu Ala Val Gln Ala Gln Val Pro Ile Val Pro Ile
        195                 200                 205

Val Met Ser Ser Tyr Gln Asp Phe Tyr Cys Lys Lys Glu Arg Arg Phe
210                 215                 220

Thr Ser Gly Gln Cys Gln Val Arg Val Leu Pro Pro Val Pro Thr Glu
225                 230                 235                 240

Gly Leu Thr Pro Asp Asp Val Pro Ala Leu Ala Asp Arg Val Arg His
            245                 250                 255

Ser Met Leu Thr Val Phe Arg Glu Ile Ser Thr Asp Gly Arg Gly Gly
        260                 265                 270

Gly Asp Tyr Leu Lys Lys Pro Gly Gly Gly Gly
        275                 280

<210> SEQ ID NO 41
<211> LENGTH: 978
<212> TYPE: DNA
<213> ORGANISM: Chlamydomonas reinhardtii

<400> SEQUENCE: 41
atgtccgtgc tcacaaagtg gctgggcctg ccctcattct tgttctccgt gtttgtgttc      60
tactggagtt tgcccatctt tgcgatccta tatcgtatcc gcttcgcctc tctggggaag     120
cgcaatgata tgctcgactg ggcccgcgcg ctcgtcgcct acttccgagt aacgctcctg     180
caggcggggg agcacacgct gtacaaggga gggccatgcc tgtacctgtg caaccaccgc     240
agctgggcgg acttcttcat tgacgcctac ctcactgagg ccgcgcggc gctcatgagc     300 aggtggctgg tgtatttcgt gttcccagtg ttctgtacct cgtgcatgat cctcaagggg     360
atagtgctgt tcaagcgcgg caccattgcg gataaagagg ccttcaacgc ctggcttgac     420
cagaccctgg gcagcagcca cgtgcctggg ctgctggtgt accccgaggg ccaccgcagc     480
accaagccgg ccagcctgcc gctgaagcgc ggcatgctgc actacgcgca cagccgcaag     540
ctgccggtgc agattgtcgt gactcgcggc aaggacgagg tgctgagtga agtcgcag      600 tcggtgcact tcgccgcac ctgcgtcacc accttctcca aggtgctcaa gtcggccgac     660
taccccaact tgaagccctt cttcacggac ctgcaggcga cctgggactc gtgctgggca     720
gccacgtacg gcctggagga tctcaaaaac gtgccgcgct ctccatgcc ggggccccag     780 gcctacagct acagctccag catgtgggtc cagcagctcg ccatcacgct ggtcagcatc     840
ctagtctttg cgggcgtgtg ctacggctcc tggcgcggct tggcggcggc gctggcggcg     900
accggcgcgc gcagcaggt ggtggcactg gtgctggcgg cctgggtggg cagctccgtg     960
cttcgtagct tcctctag                                                   978

<210> SEQ ID NO 42
<211> LENGTH: 325
<212> TYPE: PRT
```

<213> ORGANISM: Chlamydomonas reinhardtii

<400> SEQUENCE: 42

```
Met Ser Val Leu Thr Lys Trp Leu Gly Leu Pro Ser Phe Leu Phe Ser
1               5                   10                  15
Val Phe Val Phe Tyr Trp Ser Leu Pro Ile Phe Ala Ile Leu Tyr Arg
            20                  25                  30
Ile Arg Phe Ala Ser Leu Gly Lys Arg Asn Asp Met Leu Asp Trp Ala
        35                  40                  45
Arg Ala Leu Val Ala Tyr Phe Arg Val Thr Leu Leu Gln Ala Gly Glu
50                  55                  60
His Thr Leu Tyr Lys Gly Gly Pro Cys Leu Tyr Leu Cys Asn His Arg
65                  70                  75                  80
Ser Trp Ala Asp Phe Phe Ile Asp Ala Tyr Leu Thr Glu Gly Arg Ala
                85                  90                  95
Ala Leu Met Ser Arg Trp Leu Val Tyr Phe Val Phe Pro Val Phe Cys
            100                 105                 110
Thr Ser Cys Met Ile Leu Lys Gly Ile Val Leu Phe Lys Arg Gly Thr
        115                 120                 125
Ile Ala Asp Lys Glu Ala Phe Asn Ala Trp Leu Asp Gln Thr Leu Gly
130                 135                 140
Ser Ser His Val Pro Gly Leu Leu Val Tyr Pro Glu Gly His Arg Ser
145                 150                 155                 160
Thr Lys Pro Ala Ser Leu Pro Leu Lys Arg Gly Met Leu His Tyr Ala
                165                 170                 175
His Ser Arg Lys Leu Pro Val Gln Ile Val Val Thr Arg Gly Lys Asp
            180                 185                 190
Glu Val Leu Ser Glu Lys Ser Gln Ser Val His Phe Gly Arg Thr Cys
        195                 200                 205
Val Thr Thr Phe Ser Lys Val Leu Lys Ser Ala Asp Tyr Pro Asn Phe
210                 215                 220
Glu Ala Phe Phe Thr Asp Leu Gln Ala Thr Trp Asp Ser Cys Trp Ala
225                 230                 235                 240
Ala Thr Tyr Gly Leu Glu Asp Leu Lys Asn Val Pro Arg Phe Ser Met
                245                 250                 255
Pro Gly Pro Gln Ala Tyr Ser Tyr Ser Ser Met Trp Val Gln Gln
            260                 265                 270
Leu Ala Ile Thr Leu Val Ser Ile Leu Val Phe Ala Gly Val Cys Tyr
        275                 280                 285
Gly Ser Trp Arg Gly Leu Ala Ala Leu Ala Thr Gly Ala Ala
290                 295                 300
Gln Gln Val Val Ala Leu Val Leu Ala Ala Trp Val Gly Ser Ser Val
305                 310                 315                 320
Leu Arg Ser Phe Leu
            325
```

<210> SEQ ID NO 43
<211> LENGTH: 1338
<212> TYPE: DNA
<213> ORGANISM: Nannochloropsis

<400> SEQUENCE: 43

```
atgtctggtc cagccgatgc caggggccct gcccgagtat ccgataccat tattggtgcg    60
cccgaccgcc accatgtcgg tctgaccatc ctcgtcgccc ttctcctgag cgccttttgc   120
```

```
ttttgcgaat tcttcatgct gcccgtggcg atggcgttac tgcccgtgcc aggtacaaca    180
tcgaggaagt gctgcggcg ctgggagggc ttggtagcca aaacttggct gtcctttgga     240
gggtggctcc tggaaaatgt gggtggggtc aagctcattc ttacgggcga ctcgatactc    300
cccggtgatc gtgtgctgat tctcagcaat cataggacga gaattgattg gatgtttcta    360
tggtgctggg ctgcacgttt cgacctgctt cctcgtacc gagtcattct caagtcgtct     420
ttacgcactt tcccctggtg gggctggggg atgagtttat gtttgtttcc tttcatccac    480
cgaggaagca acaatcgcga cgcggatttg acccgtattg aacatatttg tcagtattta    540
agcgagctgg gtgtgccaaa ctccctcatt ctcttcccag aaggaactga cctttcccaa    600
tctaaccaaa aacgcgatcg tgattatgct ctagccaaaa acctacccat ttaccataac    660
gtgcttcacc cacgttcagg cgcctttatt gctagcttga cggccatgcg tcctcatttg    720
gatgctgttg tggatcttac tatcggctat gtcgattaca caccagggga aagaccttcc    780
gagctctctc ttctcaaggg ccggctaccg cacgaggtcc acataaatat gaaacgatgg    840
gacataaaga cgactccctt acttcgagag aacccatcgg accgggcgga acaattttg     900
cgcgaatctt ttgatcggaa agaggcattg ctgacagcct tctacagcaa caacacggac    960
acttcaggtg gtgggctcaa gcaaacgtca tcattgctcg tatcctcttc ctcttcacct   1020
ttctccaata gcagtgcacc tttaggattt ccttccttct cctcccctc cacctccgtc    1080
gcctcttctt acaacgagcc agtgtatgta cacaatgctc actggacata cggcaaaggg   1140
cttttgggga cggggattgc catggcgttg gtgctgatgt tagcgtgctg cttgcctgct   1200
gttgcgtttt gcgggtatag tatcgttgtc tttttgttgt tcgtgacagt gaattcggtg   1260
tgggagggct tcgatacctt ggaattgaat ttggctgtgt ggtggggcgg gcaggcaggg   1320
caaacgaagc aagagtga                                                 1338
```

<210> SEQ ID NO 44
<211> LENGTH: 445
<212> TYPE: PRT
<213> ORGANISM: Nannochloropsis

<400> SEQUENCE: 44

```
Met Ser Gly Pro Ala Asp Ala Arg Gly Pro Ala Arg Val Ser Asp Thr
1               5                   10                  15

Ile Ile Gly Ala Pro Asp Arg His His Val Gly Leu Thr Ile Leu Val
                20                  25                  30

Ala Leu Leu Leu Ser Ala Phe Cys Phe Cys Glu Phe Phe Met Leu Pro
            35                  40                  45

Val Ala Met Ala Leu Leu Pro Val Pro Gly Thr Thr Ser Arg Lys Leu
        50                  55                  60

Leu Arg Arg Trp Glu Gly Leu Val Ala Lys Thr Trp Leu Ser Phe Gly
65                  70                  75                  80

Gly Trp Leu Leu Glu Asn Val Gly Val Lys Leu Ile Leu Thr Gly
                85                  90                  95

Asp Ser Ile Leu Pro Gly Asp Arg Val Leu Ile Leu Ser Asn His Arg
                100                 105                 110

Thr Arg Ile Asp Trp Met Phe Leu Trp Cys Trp Ala Ala Arg Phe Asp
            115                 120                 125

Leu Leu Ser Ser Tyr Arg Val Ile Leu Lys Ser Ser Leu Arg Thr Phe
        130                 135                 140

Pro Trp Trp Gly Trp Gly Met Ser Leu Cys Leu Phe Pro Phe Ile His
145                 150                 155                 160
```

```
Arg Gly Ser Asn Asn Arg Asp Ala Asp Leu Thr Arg Ile Glu His Ile
            165                 170                 175

Cys Gln Tyr Leu Ser Glu Leu Gly Val Pro Asn Ser Leu Ile Leu Phe
        180                 185                 190

Pro Glu Gly Thr Asp Leu Ser Gln Ser Asn Gln Lys Arg Asp Arg Asp
    195                 200                 205

Tyr Ala Leu Ala Lys Asn Leu Pro Ile Tyr His Asn Val Leu His Pro
210                 215                 220

Arg Ser Gly Ala Phe Ile Ala Ser Leu Thr Ala Met Arg Pro His Leu
225                 230                 235                 240

Asp Ala Val Val Asp Leu Thr Ile Gly Tyr Val Asp Tyr Thr Pro Gly
                245                 250                 255

Glu Arg Pro Ser Glu Leu Ser Leu Leu Lys Gly Arg Leu Pro His Glu
            260                 265                 270

Val His Ile Asn Met Lys Arg Trp Asp Ile Lys Thr Thr Pro Leu Leu
        275                 280                 285

Arg Glu Asn Pro Ser Asp Arg Ala Glu Gln Phe Leu Arg Glu Ser Phe
    290                 295                 300

Asp Arg Lys Glu Ala Leu Leu Thr Ala Phe Tyr Ser Asn Asn Thr Asp
305                 310                 315                 320

Thr Ser Gly Gly Gly Leu Lys Gln Thr Ser Ser Leu Leu Val Ser Ser
                325                 330                 335

Ser Ser Ser Pro Phe Ser Asn Ser Ser Ala Pro Leu Gly Phe Pro Ser
            340                 345                 350

Phe Ser Ser Pro Ser Thr Ser Val Ala Ser Ser Tyr Asn Glu Pro Val
        355                 360                 365

Tyr Val His Asn Ala His Trp Thr Tyr Gly Lys Gly Leu Leu Gly Thr
    370                 375                 380

Gly Ile Ala Met Ala Leu Val Leu Met Leu Ala Cys Cys Leu Pro Ala
385                 390                 395                 400

Val Ala Phe Cys Gly Tyr Ser Ile Val Val Phe Leu Leu Phe Val Thr
                405                 410                 415

Val Asn Ser Val Trp Glu Gly Phe Asp Thr Leu Glu Leu Asn Leu Ala
            420                 425                 430

Val Trp Trp Gly Gly Gln Ala Gly Gln Thr Lys Gln Glu
        435                 440                 445

<210> SEQ ID NO 45
<211> LENGTH: 1449
<212> TYPE: DNA
<213> ORGANISM: Nannochloropsis

<400> SEQUENCE: 45
atgtggggct tattatggaa acacatgacc ctacgactcc tcttcgtctc agtctgcttg      60
gtcacctcct ccatcggcgc caacatgatg gccctcgccc tcttcctcgt catccgaccc     120
ttttcccgct cgctgtatcg acggttggtg tcacagtgtg tggcatgcat gtggatcgat     180
gcactgtcct tgctcctacc gggaaccaac atccacattg ctgctgactc tgacatgccc     240
gacgggatca ctgccggcat cgtggtggcc aatcaccaat acgaaggtga ttggtggttc     300
atgctcatgg tcgcccgctt cctgggcctg catgggaacg tgaagataat agtcagggag     360
ggccttaaga agatccccct cttggggtgg ctggtccggc ttgtcgagta cccattcatc     420
tcctcctcct ggtcgctctc ccgcacgaac ctctttgggc tgctgcggag tttcaatgcg     480
```

-continued

```
gacgacttcc ccgtcctcct cttccagttc cccgagggcg atcgcatcga tgccaaagtc    540
cgtcagcaat cgcttgcctt tgcggccaag gagcaacgcc cgcacctcct ccacgtcctc    600
ctcccccgta ctaccggttt caacacctgc atcgaagcgc ttaggacttc ccatcccccc    660
gtctatgata tgacaattgc catccctggc accacgggcc agccttcctc ctcctcctcc    720
tcctcctcac cttctgctgc agctgctgcg gcgtctccat ctgctggtgc ggcggcggcg    780
gcggcggcgg cgagcaacac atcaaccaac ccttcttcca accctccctc gagcagcagc    840
accgatacta gtccagctgc tgctgctgct gctgctgctg atgccgctgc tgccgagagt    900
catgacgctt ctctctttca caccttcctc cgtttctgca acggcgaggg cccacgggac    960
gtgcatatca gactcaagcg ctactccctc aacgacgtcc tggccgaccc ccactggctc   1020
gacaccaaat gggccgagaa agaccgcgtc ttgacctact tttcccgcca cgcctgcttt   1080
cctgctccgc tccctccca catggccaat ggtggggca gcactcagac acacgggggg    1140
agggggggcc ccagagggcc ggcgggctct catgccgtgg tgggagcagc gggtaacgcc   1200
cagtatctcc ggtcgttcaa ttcccggaaa ttcaaagcag aaacgagttt tttggcgttg   1260
gcacgactgt tactcacgcc gttgtgcctt cccttgttgt tgctgatggc ctgtccgctc   1320
atgactctgt atgtatgcgt gagcaccgtc cgaaggtggt tggggagga gattgtgttc   1380
tcgccaggag gacgggaggg agggagggag ggcgacgccg tttacgagtc cgttaattgg   1440
agcgtttga                                                           1449
```

<210> SEQ ID NO 46
<211> LENGTH: 482
<212> TYPE: PRT
<213> ORGANISM: Nannochloropsis

<400> SEQUENCE: 46

```
Met Trp Gly Leu Leu Trp Lys His Met Thr Leu Arg Leu Leu Phe Val
1               5                   10                  15

Ser Val Cys Leu Val Thr Ser Ser Ile Gly Ala Asn Met Met Ala Leu
            20                  25                  30

Ala Leu Phe Leu Val Ile Arg Pro Phe Ser Arg Ser Leu Tyr Arg Arg
        35                  40                  45

Leu Val Ser Gln Cys Val Ala Cys Met Trp Ile Asp Ala Leu Ser Leu
    50                  55                  60

Leu Leu Pro Gly Thr Asn Ile His Ile Ala Ala Asp Ser Asp Met Pro
65                  70                  75                  80

Asp Gly Ile Thr Ala Gly Ile Val Val Ala Asn His Gln Tyr Glu Gly
                85                  90                  95

Asp Trp Trp Phe Met Leu Met Val Ala Arg Phe Leu Gly Leu His Gly
            100                 105                 110

Asn Val Lys Ile Ile Val Arg Glu Gly Leu Lys Lys Ile Pro Leu Leu
        115                 120                 125

Gly Trp Leu Val Arg Leu Val Glu Tyr Pro Phe Ile Ser Ser Ser Trp
    130                 135                 140

Ser Leu Ser Arg Thr Asn Leu Phe Gly Leu Leu Arg Ser Phe Asn Ala
145                 150                 155                 160

Asp Asp Phe Pro Val Leu Leu Phe Gln Phe Pro Glu Gly Asp Arg Ile
                165                 170                 175

Asp Ala Lys Val Arg Gln Gln Ser Leu Ala Phe Ala Ala Lys Glu Gln
            180                 185                 190

Arg Pro His Leu Leu His Val Leu Leu Pro Arg Thr Thr Gly Phe Asn
```

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |

Thr Cys Ile Glu Ala Leu Arg Thr Ser His Pro Pro Val Tyr Asp Met
    210                          215                          220

Thr Ile Ala Ile Pro Gly Thr Thr Gly Gln Pro Ser Ser Ser Ser Ser
225                        230                        235                      240

Ser Ser Ser Pro Ser Ala Ala Ala Ala Ala Ser Pro Ser Ala Gly
                  245                        250                      255

Ala Ala Ala Ala Ala Ala Ala Ala Ser Asn Thr Ser Thr Asn Pro Ser
    260                          265                          270

Ser Asn Pro Pro Ser Ser Ser Ser Thr Asp Thr Ser Pro Ala Ala Ala
        275                      280                        285

Ala Ala Ala Ala Asp Ala Ala Ala Glu Ser His Asp Ala Ser
    290                          295                        300

Leu Phe His Thr Phe Leu Arg Phe Cys Asn Gly Glu Gly Pro Arg Asp
305                        310                        315                      320

Val His Ile Arg Leu Lys Arg Tyr Ser Leu Asn Asp Val Leu Ala Asp
                  325                        330                      335

Pro His Trp Leu Asp Thr Lys Trp Ala Glu Lys Asp Arg Val Leu Thr
            340                      345                        350

Tyr Phe Ser Arg His Ala Cys Phe Pro Ala Pro Leu Pro Pro His Met
                  355                        360                  365

Ala Asn Gly Gly Gly Ser Thr Gln Thr His Gly Gly Arg Gly Gly Pro
370                        375                        380

Arg Gly Pro Ala Gly Ser His Ala Val Val Gly Ala Ala Gly Asn Ala
385                        390                        395                      400

Gln Tyr Leu Arg Ser Phe Asn Ser Arg Lys Phe Lys Ala Glu Thr Ser
                  405                        410                      415

Phe Leu Ala Leu Ala Arg Leu Leu Leu Thr Pro Leu Cys Leu Pro Leu
            420                      425                        430

Leu Leu Leu Met Ala Cys Pro Leu Met Thr Leu Tyr Val Cys Val Ser
                  435                        440                  445

Thr Val Arg Arg Trp Leu Gly Glu Glu Ile Val Phe Ser Pro Gly Gly
    450                        455                        460

Arg Glu Gly Gly Arg Glu Gly Asp Ala Val Tyr Glu Ser Val Asn Trp
465                        470                        475                      480

Ser Val

<210> SEQ ID NO 47
<211> LENGTH: 1911
<212> TYPE: DNA
<213> ORGANISM: Nannochloropsis

<400> SEQUENCE: 47

| | | | | | |
|---|---|---|---|---|---|
| atgccgacct | atgcggaccc | tcccaggtcg | cgcgcctacc | agcacgaaag | ctcctcctac | 60 |
| agcattgata | atccgatccg | cagcacccac | gcctccagcc | cacccgacta | tttcaatcaa | 120 |
| aactccctcc | gtgagtcccc | ctccctccac | tcctcatcct | cagaatccga | gatggactct | 180 |
| cagagcaatg | gcaatggcag | gacccctcaa | cagcggcgag | gcgacattca | aaggcagaca | 240 |
| aacaaccctt | ccgcctccgg | cacgaacggc | acccccgag | gagcattcaa | gagcacaatc | 300 |
| ttctccatgg | cccacgctgt | cgtcctctgc | tggctcgtga | tggccatgtc | cttcggcatc | 360 |
| aatattttga | atttcctcgt | ttttgtaacc | gtcgtccttt | ggtccgcgct | gacgcccga | 420 |
| aggctcatcg | gtcactggtg | gcaacggatg | tgggtctcag | taatgagcta | cttgctccct | 480 |

```
aagagcgaga tgattctgac aggggacatc gtgcttaaca ctgtggattc ctctcgcccg   540
gccatcatca tcgcgaatca ccaggtggat gcggattttt ggtatgtctg ggaagtggcg   600
cgggcctacg gaatgcatgg acggttgaag atcattttga aagccgattt ggctgtggtc   660
cccatcgtgg gctgggggat gaaacaattt gaattttgtt ttttgcaacg caattggcag   720
agggaccgga gggcgttcac gcgcttgttg tcgtcgtttg tcgaggacgg gtataagtgt   780
gccttgctcc tctttccaga gggcacgacc atcaacactg aagctgtcac caagtcccac   840
cgcttcggcc gtgagcagaa gaggcctcac ctcgaccatt gcatcctacc gcgttccacg   900
ggctttgcgg ctttggtcga acaatgtgc cagtccccc atggccattc tcctgttatt   960
tacgatctga ccgtcgccta tcacggttac tcaggcgaag ttcccaccta tgagatgggc  1020
tacgaccgag aacaagacat ggacgtcccg aacgtgttca aaatgataca gggacgggca  1080
tgtccaaagg ttcatgtcca cgtcaagacg tacgaagtcg atgaggcctt ggttaataat  1140
cccgagcagt ggttggatgc tcgatggttg gaaaaagacg cgctgctgga acggtttatt  1200
cagacgcaga gttttagggg ggagaaggag ggagggacac ggatcattca tcctcagggg  1260
agcttggcct cgctgctttt tttgttgatg ttgccgctga ttatcaccgt cctccttcct  1320
gccctgctct tgatcacttt ggtggcctgg cctgtgattc ttctggcggg cacgctcaac  1380
tttctgaact tgtctcgcg ttcggccatg ggtgtggtag tcgggagcag cagcagccgt  1440
gggtctttct ccacgtcttg gcatcagtcc tcccaacacc ggcaccagca ccagcaacgg  1500
gtcagtggca atagcaccag tagcaccagt accagcaaca gtaccagcag tagcattggt  1560
cggaaggaag gggcattgaa ctgcaggcga agttctcgcc gaagcccag ccgtgaggga  1620
tgtggccacg ccaatggaga aggaccgagc tgtcctctcc tctctgtaag cctgccgcct  1680
ctccctgccg cagctgctgc tgccgctcct gctgctcctg cttcttcggc tccatcttct  1740
ccgctattgg ggagcacgcc gtcgccacgc cggtccccac ggtggaagac tccggcgggg  1800
atatcccctg tagtgcagag ctacgggaac aggaagggga aggaaggagg atggggtcta  1860
atggctgcgg cggccgcagc ggcaacgacg gaagaggagg atcggtacta g          1911
```

<210> SEQ ID NO 48
<211> LENGTH: 636
<212> TYPE: PRT
<213> ORGANISM: Nannochloropsis

<400> SEQUENCE: 48

```
Met Pro Thr Tyr Ala Asp Pro Pro Arg Ser Arg Ala Tyr Gln His Glu
1               5                   10                  15

Ser Ser Ser Tyr Ser Ile Asp Asn Pro Ile Arg Ser Thr His Ala Ser
            20                  25                  30

Ser Pro Pro Asp Tyr Phe Asn Gln Asn Ser Leu Arg Glu Ser Pro Ser
        35                  40                  45

Leu His Ser Ser Ser Glu Ser Glu Met Asp Ser Gln Ser Asn Gly
    50                  55                  60

Asn Gly Arg Thr Pro Gln Gln Arg Arg Gly Asp Ile Gln Arg Gln Thr
65                  70                  75                  80

Asn Asn Pro Ser Ala Ser Gly Thr Asn Gly Thr Pro Arg Gly Ala Phe
                85                  90                  95

Lys Ser Thr Ile Phe Ser Met Ala His Ala Val Val Leu Cys Trp Leu
            100                 105                 110

Val Met Ala Met Ser Phe Gly Ile Asn Ile Leu Asn Phe Leu Val Phe
        115                 120                 125
```

```
Val Thr Val Arg Pro Trp Ser Arg Leu Thr Ala Arg Arg Leu Ile Gly
    130                 135                 140

His Trp Trp Gln Arg Met Trp Val Ser Val Met Ser Tyr Leu Leu Pro
145                 150                 155                 160

Lys Ser Glu Met Ile Leu Thr Gly Asp Ile Val Leu Asn Thr Val Asp
                165                 170                 175

Ser Ser Arg Pro Ala Ile Ile Ala Asn His Gln Val Asp Ala Asp
            180                 185                 190

Phe Trp Tyr Val Trp Glu Val Ala Arg Ala Tyr Gly Met His Gly Arg
        195                 200                 205

Leu Lys Ile Ile Leu Lys Ala Asp Leu Ala Val Val Pro Ile Val Gly
    210                 215                 220

Trp Gly Met Lys Gln Phe Glu Phe Cys Phe Leu Gln Arg Asn Trp Gln
225                 230                 235                 240

Arg Asp Arg Arg Ala Phe Thr Arg Leu Leu Ser Ser Phe Val Glu Asp
                245                 250                 255

Gly Tyr Lys Cys Ala Leu Leu Leu Phe Pro Glu Gly Thr Thr Ile Asn
            260                 265                 270

Thr Glu Ala Val Thr Lys Ser His Arg Phe Gly Arg Glu Gln Lys Arg
        275                 280                 285

Pro His Leu Asp His Cys Ile Leu Pro Arg Ser Thr Gly Phe Ala Ala
    290                 295                 300

Leu Val Glu Thr Met Cys Gln Ser Pro His Gly His Ser Pro Val Ile
305                 310                 315                 320

Tyr Asp Leu Thr Val Ala Tyr His Gly Tyr Ser Gly Glu Val Pro Thr
                325                 330                 335

Tyr Glu Met Gly Tyr Asp Arg Glu Gln Asp Met Asp Val Pro Asn Val
            340                 345                 350

Phe Lys Met Ile Gln Gly Arg Ala Cys Pro Lys Val His Val His Val
        355                 360                 365

Lys Thr Tyr Glu Val Asp Glu Ala Leu Val Asn Asn Pro Glu Gln Trp
    370                 375                 380

Leu Asp Ala Arg Trp Leu Glu Lys Asp Ala Leu Leu Glu Arg Phe Ile
385                 390                 395                 400

Gln Thr Gln Ser Phe Arg Gly Glu Lys Glu Gly Gly Thr Arg Ile Ile
                405                 410                 415

His Pro Gln Gly Ser Leu Ala Ser Leu Leu Phe Leu Leu Met Leu Pro
            420                 425                 430

Leu Ile Ile Thr Val Leu Leu Pro Ala Leu Leu Leu Ile Thr Leu Val
        435                 440                 445

Ala Trp Pro Val Ile Leu Leu Ala Gly Thr Leu Asn Phe Leu Asn Phe
    450                 455                 460

Val Ser Arg Ser Ala Met Gly Val Val Gly Ser Ser Ser Arg
465                 470                 475                 480

Gly Ser Phe Ser Thr Ser Trp His Gln Ser Gln His Arg His Gln
            485                 490                 495

His Gln Gln Arg Val Ser Gly Asn Ser Thr Ser Thr Ser Thr Ser
        500                 505                 510

Asn Ser Thr Ser Ser Ser Ile Gly Arg Lys Glu Gly Ala Leu Asn Cys
    515                 520                 525

Arg Arg Ser Ser Arg Arg Ser Pro Ser Arg Glu Gly Cys Gly His Ala
530                 535                 540
```

| | | | | | | | | | | | |
|---|---|---|---|---|---|---|---|---|---|---|---|
|Asn|Gly|Glu|Gly|Pro|Ser|Cys|Pro|Leu|Leu|Ser|Val Ser Leu Pro Pro|
|545| | | |550| | | |555| | |560|

Leu Pro Ala Ala Ala Ala Ala Ala Pro Ala Pro Ala Ser Ser
              565                  570                  575

Ala Pro Ser Ser Pro Leu Leu Gly Ser Thr Pro Ser Pro Arg Arg Ser
          580                  585                  590

Pro Arg Trp Lys Thr Pro Ala Gly Ile Ser Pro Val Val Gln Ser Tyr
      595                  600                  605

Gly Asn Arg Lys Gly Lys Glu Gly Gly Trp Gly Leu Met Ala Ala Ala
    610                  615                  620

Ala Ala Ala Ala Thr Thr Glu Glu Glu Asp Arg Tyr
625                    630                635

<210> SEQ ID NO 49
<211> LENGTH: 678
<212> TYPE: DNA
<213> ORGANISM: Synechocystis PCC6803

<400> SEQUENCE: 49

```
gtggattccg agattaatca tcgtggtggt ttgagtgctc cccgcccaag ggaaacgtca    60
cttaatttag ctctctaccg gggcttgaaa tggggggtgg tgcggccact gctccatgga   120
ttgttccagg cccaggtata tggtcaggaa ttggtgccaa cccgggggcc ggccttggtg   180
gtgagcaacc atgccagtta ttttgacccc ccatttttgt cctgtgccat ggcccggccg   240
gtggccttta tggccaagga agagttattt aatgtgcccc tgctgggtcc agccattcgc   300
ctctatgggg cctatccagt caaacggggc agtggcgatc ggggagcatt gcgggccgcc   360
ttgacggcgc tggggatgg ttggttagtg ggggtctttc tggagggaac cagaacaaag   420
gatggccgca ttcaccagcc aaaattgggg gctgccatga ttgcagctaa gcccaagtg   480
cccattattc ccgtcagcct aggggagta gagcaaattt ttcagcccgg ttccccctgg   540
ccccatcctg tgcctttaac tattcgcatt ggtaaggcga tcgccccctcc agtaaagaat   600
aggaaacccg aattggaagc ggttactaaa gcttgccaag cccaaattca cgagatgctg   660
gatttaggca gggattag                                                 678
```

<210> SEQ ID NO 50
<211> LENGTH: 225
<212> TYPE: PRT
<213> ORGANISM: Synechocystis PCC6803

<400> SEQUENCE: 50

Met Asp Ser Glu Ile Asn His Arg Gly Gly Leu Ser Ala Pro Arg Pro
1               5                  10               15

Arg Glu Thr Ser Leu Asn Leu Ala Leu Tyr Arg Gly Leu Lys Trp Gly
          20                  25                  30

Val Val Arg Pro Leu Leu His Gly Leu Phe Gln Ala Gln Val Tyr Gly
        35                  40                  45

Gln Glu Leu Val Pro Thr Arg Gly Pro Ala Leu Val Val Ser Asn His
    50                  55                  60

Ala Ser Tyr Phe Asp Pro Pro Phe Leu Ser Cys Ala Met Ala Arg Pro
65                70                  75               80

Val Ala Phe Met Ala Lys Glu Glu Leu Phe Asn Val Pro Leu Leu Gly
             85                  90               95

Pro Ala Ile Arg Leu Tyr Gly Ala Tyr Pro Val Lys Arg Gly Ser Gly
          100                 105              110

Asp Arg Gly Ala Leu Arg Ala Ala Leu Thr Ala Leu Gly Asp Gly Trp
            115                 120                 125

Leu Val Gly Val Phe Leu Glu Gly Thr Arg Thr Lys Asp Gly Arg Ile
        130                 135                 140

His Gln Pro Lys Leu Gly Ala Ala Met Ile Ala Ala Lys Ala Gln Val
145                 150                 155                 160

Pro Ile Ile Pro Val Ser Leu Gly Gly Val Glu Gln Ile Phe Gln Pro
                165                 170                 175

Gly Ser Pro Trp Pro His Pro Val Pro Leu Thr Ile Arg Ile Gly Lys
            180                 185                 190

Ala Ile Ala Pro Pro Val Lys Asn Arg Lys Pro Glu Leu Glu Ala Val
        195                 200                 205

Thr Lys Ala Cys Gln Ala Gln Ile His Glu Met Leu Asp Leu Gly Arg
    210                 215                 220

Asp
225

<210> SEQ ID NO 51
<211> LENGTH: 1170
<212> TYPE: DNA
<213> ORGANISM: Arabidopsis thaliana

<400> SEQUENCE: 51
atggtgattg ctgcagctgt catcgtgcct ttgggccttc tcttcttcat atctggtctc      60
gctgtcaatc tctttcaggc agtttgctat gtactcattc gaccactgtc taagaacaca     120
tacagaaaaa ttaaccgggt ggttgcagaa accttgtggt tggagcttgt atggatagtt     180
gactggtggg ctggagttaa gatccaagtg tttgctgata atgagacctt caatcgaatg     240
ggcaaagaac atgctcttgt cgtttgtaat caccgaagtg atattgattg gcttgtggga     300
tggattctgg ctcagcggtc aggttgcctg ggaagcgcat tagctgtaat gaagaagtct     360
tccaaattcc ttccagtcat aggctggtca atgtggttct cggagtatct ctttctggaa     420 agaaatttggg ccaaggatga agcactcta aagtcaggtc ttcagcgctt gagcgacttc     480 cctcgaccctt tctggttagc ccttttttgtg gagggaactc gctttacaga agccaaactt     540
aaagccgcac aagagtatgc agcctcctct gaattgccta tccctcgaaa tgtgttgatt     600
cctcgcacca aaggtttcgt gtcagctgtt agtaatatgc gttcatttgt cccagcaatt     660
tatgatatga cagtgactat tccaaaaacc tctccaccac ccacgatgct aagactattc     720
aaaggacaac cttcagtggt gcatgttcac atcaagtgtc actcgatgaa agacttacct     780
gaatcagatg acgcaattgc acagtggtgc agagatcagt ttgtggctaa ggatgctctg     840
ttagacaaac acatagctgc agacactttc cccggtcaac aagaacagaa cattggccgt     900
cccataaagt cccttgcggt ggttctatca tgggcatgcg tactaactct tggagcaata     960
aagttcctac actgggcaca actcttttct tcatggaaag gtatcacgat atcggcgctt    1020
ggtctaggta tcatcactct ctgtatgcag atcctgatac gctcgtctca gtcagagcgt    1080
tcgaccccag ccaaagtcgt cccagccaag ccaaaagaca atcaccaccc agaatcatcc    1140
tcccaaacag aaacggagaa ggagaagtaa                                     1170

<210> SEQ ID NO 52
<211> LENGTH: 389
<212> TYPE: PRT
<213> ORGANISM: Arabidopsis thaliana

<400> SEQUENCE: 52

```
Met Val Ile Ala Ala Val Ile Val Pro Leu Gly Leu Leu Phe Phe
1               5                   10                  15

Ile Ser Gly Leu Ala Val Asn Leu Phe Gln Ala Val Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
                100                 105                 110

Ala Leu Ala Val Met Lys Lys Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
                180                 185                 190

Pro Ile Pro Arg Asn Val Leu Ile Pro Arg Thr Lys Gly Phe Val Ser
            195                 200                 205

Ala Val Ser Asn Met Arg Ser Phe Val Pro Ala Ile Tyr Asp Met Thr
210                 215                 220

Val Thr Ile Pro Lys Thr Ser Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
    275                 280                 285

Thr Phe Pro Gly Gln Gln Glu Gln Asn Ile Gly Arg Pro Ile Lys Ser
    290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
370                 375                 380

Thr Glu Lys Glu Lys
385

<210> SEQ ID NO 53
<211> LENGTH: 1149
```

<212> TYPE: DNA
<213> ORGANISM: Helianthus annuus

<400> SEQUENCE: 53

```
atggctatcg cagcagcagc tgttatcgtc cctattggcg tcctcttctt cgtctccggc      60
ctcatcgtca atctcattca ggcgattata tttgtgactg tacgaccgtt ctcgaagagc     120
ttgtttaggc ggattaacag acaggtagct gagttgttgt ggctggagct tgtgtggatt     180
gttgattggt gggctggagt taaggttaac ctgtacacag atgccgagac ctgaagatg      240
atgggtaaag aacatgctct tgtgatagct aatcataaaa gtgacattga ttggctcatt     300
ggatgggtgt tgctcagag atcaggttgt cttggtagca cattggctgt catgaagaaa      360
tcatcgaagt ttcttcccgt cattggttgg tcaatgtggt tttctgagta tctttttctt     420
gagagaagtt gggctaaaga tgaaagtacc ttgaagtcag gcctccgacg tctaaaagat     480
taccctcaac cctttggtt ggcccttttt gttgaaggga ctcgctttac taaagcaaaa      540
cttttagcag ctcaagaata tgcatcttca atgggattac ctgttcccag aaatgtctta     600
attccaagaa caaagggatt tgttacttca gtgagtgaaa tgagatcatt tgctcctgca     660
atttacgata tgacggttgc gattcccaaa gattcaactc cgccaacaat gctgcgcctc     720
tttaagggc agtcgtctgt gattcacgtt aaagttaagc gtcatttaat gaaggacctg      780
ccagaaacag atgaaggtgt tgcacaatgg tgtaaagata tttttgttgc caaggatgat     840
atattagata acataaaga attaaacgcc tttcctgatt cagaactcca tgaaattggc      900
cgaccattga agtctcttgt ggtggttgta tcttgggcat gtctgcttgt actcgggatc     960
ttcaagttcc tgcaatggtc taatctttta tcctcatgga aggggctcac attcactgca    1020
attgggttgg ggattgttac ctttttaatg caaatcttga ttcagttttc gcaatctgaa    1080
cgttctacac ctgcaaaagt ggcccccaca aggtctagca tggtaatgt acaagagaaa     1140
ctgcactga                                                            1149
```

<210> SEQ ID NO 54
<211> LENGTH: 382
<212> TYPE: PRT
<213> ORGANISM: Helianthus annuus

<400> SEQUENCE: 54

```
Met Ala Ile Ala Ala Ala Val Ile Val Pro Ile Gly Val Leu Phe
1               5                   10                  15

Phe Val Ser Gly Leu Ile Val Asn Leu Ile Gln Ala Ile Ile Phe Val
            20                  25                  30

Thr Val Arg Pro Phe Ser Lys Ser Leu Phe Arg Arg Ile Asn Arg Gln
        35                  40                  45

Val Ala Glu Leu Leu Trp Leu Glu Leu Val Trp Ile Val Asp Trp Trp
    50                  55                  60

Ala Gly Val Lys Val Asn Leu Tyr Thr Asp Ala Glu Thr Leu Lys Met
65                  70                  75                  80

Met Gly Lys Glu His Ala Leu Val Ile Ala Asn His Lys Ser Asp Ile
                85                  90                  95

Asp Trp Leu Ile Gly Trp Val Phe Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ser Glu Tyr Leu Phe Leu Glu Arg Ser Trp
    130                 135                 140
```

```
Ala Lys Asp Glu Ser Thr Leu Lys Ser Gly Leu Arg Arg Leu Lys Asp
145                 150                 155                 160

Tyr Pro Gln Pro Phe Trp Leu Ala Leu Phe Val Glu Gly Thr Arg Phe
                165                 170                 175

Thr Lys Ala Lys Leu Leu Ala Ala Gln Glu Tyr Ala Ser Ser Met Gly
            180                 185                 190

Leu Pro Val Pro Arg Asn Val Leu Ile Pro Arg Thr Lys Gly Phe Val
        195                 200                 205

Thr Ser Val Ser Glu Met Arg Ser Phe Ala Pro Ala Ile Tyr Asp Met
    210                 215                 220

Thr Val Ala Ile Pro Lys Asp Ser Thr Pro Pro Thr Met Leu Arg Leu
225                 230                 235                 240

Phe Lys Gly Gln Ser Ser Val Ile His Val Lys Val Lys Arg His Leu
                245                 250                 255

Met Lys Asp Leu Pro Glu Thr Asp Glu Gly Val Ala Gln Trp Cys Lys
            260                 265                 270

Asp Ile Phe Val Ala Lys Asp Ile Leu Asp Lys His Lys Glu Leu
        275                 280                 285

Asn Ala Phe Pro Asp Ser Glu Leu His Glu Ile Gly Arg Pro Leu Lys
    290                 295                 300

Ser Leu Val Val Val Ser Trp Ala Cys Leu Leu Val Leu Gly Ile
305                 310                 315                 320

Phe Lys Phe Leu Gln Trp Ser Asn Leu Leu Ser Ser Trp Lys Gly Leu
                325                 330                 335

Thr Phe Thr Ala Ile Gly Leu Gly Ile Val Thr Phe Leu Met Gln Ile
            340                 345                 350

Leu Ile Gln Phe Ser Gln Ser Glu Arg Ser Thr Pro Ala Lys Val Ala
        355                 360                 365

Pro Thr Arg Ser Ser Asn Gly Asn Val Gln Glu Lys Leu His
    370                 375                 380

<210> SEQ ID NO 55
<211> LENGTH: 1517
<212> TYPE: DNA
<213> ORGANISM: Camelina Sativa

<400> SEQUENCE: 55
ctccttataa tttcaatcgc tcccatttaa tcgcaaagtt attttatttt tatttttctg    60
gttggcttat ttttattttt attttatgtt ttaaatgttc tgcaacttgt cttgaaatct   120
ggggtaaaaa gaaaaaagaa aaaaaaaact tcgctattgg ttttctggaa aatctcagaa   180
acgattattt tgggttttct atacttcgct tcctcacatt agagcttcgg tgttcttttt   240
tttccttttc tttttctttt tatttgggtg tgagggacat ttttccatgg tgattgctgc   300
agctgtcatc gtgcctttgg ccttctctt cttcatatct ggtctcgttg tcaatctcat   360
tcaggcactt tgctatgtcc tcattcggcc actgtctaag aacacttacc ggaaaatcaa   420
ccgggtggtt gctgaaacct tgtggttgga gcttgtttgg attgttgatt ggtgggctgg   480
agtaaagatc caagtgtttg ctgataatga accttcaat cgaatgggca agaacacgc    540 tcttgtcgtt tgtaatcacc gtagtgatat tgattggctt gttggatggg ttctggctca   600
gcggtcaggt tccctgggaa gcgctttggc tgtaatgaag aagtcttcca aattccttcc   660
agtcataggc tggtcaatgt ggttctcaga gtatctgttt ctggaaagaa attggtccaa   720
ggatgaaagc actctaaagt caggtcttca gcgcttgagt gactttcctc gacctttctg   780
```

```
gctagccctt tttgtggagg gaactcgctt tacagaggct aaactcaaag cagcacaaga    840
gtatgcagcc tcctctgact tgcctatccc tcgaaatgtg ttgattcctc gcaccaaagg    900
ttttgtgtca gctgttagta atatgcgttc atttgtccca gccatttatg atatgacagt    960
gactattcca aaaacttctc caccgcccac gatgctaaga ctattcaaag acaaccttc    1020
tgtggtacat gttcacatca agtgtcactc catgaaagac ttgcctgaat cagatgacgc   1080
aattgcacag tggtgcagag atcagtttgt ggctaaggat gctttgttag acaaacacat   1140
agctgcagac actttccccg gtcaacagga acagaacatt ggccgtccca taaagtccct   1200
tgcggtggtt ctatcatggg catgcgtatt aactcttgga gcaattaagt tcctacactg   1260
ggcacaactc ttttcgtcat ggaaaggtat cgcgctatcg gggcttgctc tgggtatcat   1320
cactctcggt atgcagatcc tgatacgctc gtctcagtca gagcgttcaa ccccagccaa   1380
agtggttcca gcaaagccaa aggaccatca caactcagaa tcatcctccc aaacagaagt   1440
ggagaagcag aagtaaaaaa agtggatatc aaagatcaaa caacaaacag aagaagaaaa   1500
gcgtatcagt tttgtta                                                  1517

<210> SEQ ID NO 56
<211> LENGTH: 389
<212> TYPE: PRT
<213> ORGANISM: Camelina Sativa

<400> SEQUENCE: 56

Met Val Ile Ala Ala Val Ile Val Pro Leu Gly Leu Leu Phe Phe
1               5                  10                  15

Ile Ser Gly Leu Val Val Asn Leu Ile Gln Ala Leu Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Val Leu Ala Gln Arg Ser Gly Ser Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ser
    130                 135                 140

Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Asp Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Thr Ile Pro Lys Thr Ser Pro Pro Thr Met Leu Arg Leu Phe
225                 230                 235                 240
```

```
Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
                260                 265                 270

Gln Phe Val Ala Lys Asp Ala Leu Leu Asp Lys His Ile Ala Ala Asp
            275                 280                 285

Thr Phe Pro Gly Gln Gln Glu Gln Asn Ile Gly Arg Pro Ile Lys Ser
        290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Ala
                325                 330                 335

Leu Ser Gly Leu Ala Leu Gly Ile Ile Thr Leu Gly Met Gln Ile Leu
                340                 345                 350

Ile Arg Ser Ser Gln Ser Glu Arg Ser Thr Pro Ala Lys Val Val Pro
                355                 360                 365

Ala Lys Pro Lys Asp His His Asn Ser Glu Ser Ser Ser Gln Thr Glu
        370                 375                 380

Val Glu Lys Gln Lys
385

<210> SEQ ID NO 57
<211> LENGTH: 1173
<212> TYPE: DNA
<213> ORGANISM: Brassica napus

<400> SEQUENCE: 57
atggcgatgg cagcagcagt gattgtgcct ttgggattc tcttcttcat ttctggcctc        60
gttgtcaatc tcctccaggc agtttgctat gtcctcgttc gacctatgtc taagaacaca       120
tacagaaaga tcaaccgggt ggttgcagaa accttgtggt ggagcttgt ctggatcgtt        180 gactggtggg ctggagtcaa gatccaagtc tttgctgatg atgagacctt taatcgaatg       240
ggcaaagaac atgctcttgt cgtttgtaat caccgaagtg atattgattg cttgttgga        300 tggattctcg ctcagaggtc aggttgcctg ggaagcgcat tagctgtaat gaagaagtct      360
tccaaatttc tcccagtcat aggctggtca atgtggttct ccgagtatct gtttcttgaa      420
agaaattggg caaggatga agcacttta cagtcaggtc ttcaacgctt gaacgacttc        480
ccacggcctt tctggctagc tcttttgtg gagggaaccc gcttcacaga ggcaaaactt       540
aaagcagcac aagagtacgc agcctcctct gagttgcctg tccctcgaaa tgtgttgatt      600
cctcgcacca aaggttttgt gtcagctgtt agtaacatgc gttcatttgt gccagccata      660
tatgatatga ccgtggctat tccaaaaact tctccacccc caacgatgct aagactattc      720
aaaggacaac cttctgtggt gcatgttcac atcaagtgtc actcgatgaa ggacttgcct      780
gaaccagaag acgaaattgc acagtggtgc agagatcagt ttgtggctaa ggatgcactg      840
ttagacaaac acatagctgc agacactttc cccggtcaga agaacagaa cattggccgt       900 cccataaagt ctcttgcagt ggttgtatca tgggcatgcc tactaactct tggagcaatg      960
aagttcttac actggtcaaa cctctttct tcgtggaaag gcatcgcatt atcagccttt      1020
ggtctaggca tcatcactct ctgtatgcag atcctgatcc gctcctctca gtcggagcgt      1080
tcaacacctg ccaaagtcgc tccagccaag ccaaaggaca atcaccagtc aggaccatcc     1140
tcccaaacag aagtggagga gaagcagaag taa                                   1173
```

<210> SEQ ID NO 58
<211> LENGTH: 390
<212> TYPE: PRT
<213> ORGANISM: Brassica napus

<400> SEQUENCE: 58

```
Met Ala Met Ala Ala Val Ile Val Pro Leu Gly Ile Leu Phe Phe
 1               5                  10                  15

Ile Ser Gly Leu Val Val Asn Leu Leu Gln Ala Val Cys Tyr Val Leu
                20                  25                  30

Val Arg Pro Met Ser Lys Asn Thr Tyr Arg Lys Ile Asn Arg Val Val
            35                  40                  45

Ala Glu Thr Leu Trp Leu Glu Leu Val Trp Ile Val Asp Trp Trp Ala
 50                  55                  60

Gly Val Lys Ile Gln Val Phe Ala Asp Asp Glu Thr Phe Asn Arg Met
 65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Lys Phe Leu Pro Val Ile Gly
            115                 120                 125

Trp Ser Met Trp Phe Ser Glu Tyr Leu Phe Leu Glu Arg Asn Trp Ala
130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
            195                 200                 205

Ala Val Ser Asn Met Arg Ser Phe Val Pro Ala Ile Tyr Asp Met Thr
210                 215                 220

Val Ala Ile Pro Lys Thr Ser Pro Pro Thr Met Leu Arg Leu Phe
225                 230                 235                 240

Lys Gly Gln Pro Ser Val His Val His Ile Lys Cys His Ser Met
                245                 250                 255

Lys Asp Leu Pro Glu Pro Glu Asp Glu Ile Ala Gln Trp Cys Arg Asp
            260                 265                 270

Gln Phe Val Ala Lys Asp Ala Leu Leu Asp Lys His Ile Ala Ala Asp
            275                 280                 285

Thr Phe Pro Gly Gln Lys Glu Gln Asn Ile Gly Arg Pro Ile Lys Ser
290                 295                 300

Leu Ala Val Val Ser Trp Ala Cys Leu Leu Thr Leu Gly Ala Met
305                 310                 315                 320

Lys Phe Leu His Trp Ser Asn Leu Phe Ser Ser Trp Lys Gly Ile Ala
                325                 330                 335

Leu Ser Ala Phe Gly Leu Gly Ile Ile Thr Leu Cys Met Gln Ile Leu
            340                 345                 350

Ile Arg Ser Ser Gln Ser Glu Arg Ser Thr Pro Ala Lys Val Ala Pro
            355                 360                 365

Ala Lys Pro Lys Asp Asn His Gln Ser Gly Pro Ser Ser Gln Thr Glu
370                 375                 380
```

Val Glu Glu Lys Gln Lys
385             390

<210> SEQ ID NO 59
<211> LENGTH: 1152
<212> TYPE: DNA
<213> ORGANISM: Glycine max

<400> SEQUENCE: 59

| | | |
|---|---|---|
| atgactgcag ttgtggtcgt cccattgggc cttctcttct tcgcttccgg cctcatcgtt | 60 |
| aacctcattc aggcaatatg ctacgtggtt gtgcggccgg tgtcgaagaa tctgtaccgg | 120 |
| cggatgaaca gggtggtggc ggagctgctc tggctggagc tcgtgtggat tattgattgg | 180 |
| tgggccggtg ttaaggttca agtattcaca gatcctgaaa cctttcgttc aatgggtaaa | 240 |
| gagcatgctc ttgttatctc caatcacaga agtgacattg attggcttgt tggatgggtt | 300 |
| ttagctcagc gttcaggttg ccttggcagc actcttgctg tgatgaagaa atcatcgaag | 360 |
| tttctaccgg tcattggttg gtcaatgtgg ttttctgaat atcttttcct ggagagaagt | 420 |
| tgggccaagg atgaacgcac attaaagtca ggcctacagc aactgaggga tttccctctt | 480 |
| cccttttggt tggctctctt tgtagaagga actcgcttta cacaggccaa actattagct | 540 |
| gctcaggagt atgcagcctc agctggattg cctgttccaa gaaatgtttt gattccaaga | 600 |
| actaagggtt ttgtttcagc agtaaaccat atgcgctctt tgttcctgc catttatgat | 660 |
| gtaactgtgg caattcccaa gagttcacct gctcctacaa tgctaagact cttcagaggg | 720 |
| aaatcttcag tggttcatgt gcatattaag cggcatgcaa tgaaggattt gccagaagaa | 780 |
| gatgaagctg ttgctcaatg gtgtcgagat atgtttgtgg ctaaggatac attgttagac | 840 |
| aaacatatag ctgaggacac attcagtgat caagagctgc aggataccgg tcgacccata | 900 |
| aagtctctag tggttgtcat atcgtgggca tgtgtcgttg ttatgggggt cgtaaagttc | 960 |
| ctccaatggt catcactact atcctcctgg aagggtgttg cattttcagc atttggtttg | 1020 |
| ggagttgtta ctctactcat gcacatcttg atcatgttct cacaatctga gcgttcaacc | 1080 |
| cctaccaagg ttgcccctgc aaagtccaag aatagcgaac aactggaggc tagggataac | 1140 |
| aaacaagact ag | 1152 |

<210> SEQ ID NO 60
<211> LENGTH: 383
<212> TYPE: PRT
<213> ORGANISM: Glycine max

<400> SEQUENCE: 60

Met Thr Ala Val Val Val Pro Leu Gly Leu Leu Phe Phe Ala Ser
1               5                   10                  15

Gly Leu Ile Val Asn Leu Ile Gln Ala Ile Cys Tyr Val Val Arg
            20                  25                  30

Pro Val Ser Lys Asn Leu Tyr Arg Arg Met Asn Arg Val Val Ala Glu
        35                  40                  45

Leu Leu Trp Leu Glu Leu Val Trp Ile Ile Asp Trp Trp Ala Gly Val
    50                  55                  60

Lys Val Gln Val Phe Thr Asp Pro Glu Thr Phe Arg Ser Met Gly Lys
65                  70                  75                  80

Glu His Ala Leu Val Ile Ser Asn His Arg Ser Asp Ile Asp Trp Leu
                85                  90                  95

Val Gly Trp Val Leu Ala Gln Arg Ser Gly Cys Leu Gly Ser Thr Leu

|     |     |     |     |     | 100 |     |     |     | 105 |     |     |     |     | 110 |     |
| --- | --- | --- | --- | --- | --- | --- | --- | --- | --- | --- | --- | --- | --- | --- | --- |
Ala Val Met Lys Lys Ser Ser Lys Phe Leu Pro Val Ile Gly Trp Ser
            115                 120                 125

Met Trp Phe Ser Glu Tyr Leu Phe Leu Glu Arg Ser Trp Ala Lys Asp
    130                 135                 140

Glu Arg Thr Leu Lys Ser Gly Leu Gln Gln Leu Arg Asp Phe Pro Leu
145                 150                 155                 160

Pro Phe Trp Leu Ala Leu Phe Val Glu Gly Thr Arg Phe Thr Gln Ala
                165                 170                 175

Lys Leu Leu Ala Ala Gln Glu Tyr Ala Ala Ser Ala Gly Leu Pro Val
            180                 185                 190

Pro Arg Asn Val Leu Ile Pro Arg Thr Lys Gly Phe Val Ser Ala Val
        195                 200                 205

Asn His Met Arg Ser Phe Val Pro Ala Ile Tyr Asp Val Thr Val Ala
    210                 215                 220

Ile Pro Lys Ser Ser Pro Ala Pro Thr Met Leu Arg Leu Phe Arg Gly
225                 230                 235                 240

Lys Ser Ser Val Val His Val His Ile Lys Arg His Ala Met Lys Asp
                245                 250                 255

Leu Pro Glu Glu Asp Glu Ala Val Ala Gln Trp Cys Arg Asp Met Phe
            260                 265                 270

Val Ala Lys Asp Thr Leu Leu Asp Lys His Ile Ala Glu Asp Thr Phe
        275                 280                 285

Ser Asp Gln Glu Leu Gln Asp Thr Gly Arg Pro Ile Lys Ser Leu Val
    290                 295                 300

Val Val Ile Ser Trp Ala Cys Val Val Met Gly Val Val Lys Phe
305                 310                 315                 320

Leu Gln Trp Ser Ser Leu Leu Ser Ser Trp Lys Gly Val Ala Phe Ser
                325                 330                 335

Ala Phe Gly Leu Gly Val Val Thr Leu Leu Met His Ile Leu Ile Met
            340                 345                 350

Phe Ser Gln Ser Glu Arg Ser Thr Pro Thr Lys Val Ala Pro Ala Lys
        355                 360                 365

Ser Lys Asn Ser Glu Gln Leu Glu Ala Arg Asp Asn Lys Gln Asp
    370                 375                 380

<210> SEQ ID NO 61
<211> LENGTH: 849
<212> TYPE: DNA
<213> ORGANISM: Yarrowia lipolytica

<400> SEQUENCE: 61

| | |
|---|---|
| atgtccgttg catccaagct cgtcttctac gtccgcgccg ccatcgccgt ggtcatcttt | 60 |
| gccgcctgtg ccacctacgg cgtgctggcg tccaccattc tcaccgccat cggcaagcag | 120 |
| ggcctggccc aatggaccgt tgccagagcc ttctactact cggtgcgcat cttcctgggt | 180 |
| atcagcatca agctgcgtag ccggcaggtg accggaaccg ccggtctgga tgcctccaag | 240 |
| atccaggtcg ccaacaccac caagcccatt gacgacatca ccaaacacct gccccgacca | 300 |
| tgcattctga tttccaacca ccagaacgaa atggacattc tggtgctcgg tcgcatcttc | 360 |
| ccccagtact gctccgtcac cgccaaaaag gccctcaagt ggtaccctct gctgggccag | 420 |
| ttcatggcgc tgtccggcac catcttcctg gaccgaaagg accgaaccaa gtccgtgcag | 480 |
| accctcggcg gcgccgtcaa gaccatccag agcggcaacg gaggcaaggg ccagagcgtc | 540 |

```
ttcatgttcc ccgagggaac ccgatcctac tccaaggacg tcggcatcat gcccttcaag    600
aagggctgtt tccacctggc ggtccagtcg ggcgctccca ttgtcccgt ggtggtccag     660 aacacctccc gaatgttttc tttcggccga ggcaagctgg acgccggaga gatccttgtc    720
gacgtcctga gccccattga gaccaagggt ctggacgcca gcaacgtcga cgctctcatg    780
gccaccactt ataaggccat gtgcgagact gccgaccaga ttggctacgc tggccagaag    840
actcagtag                                                             849
```

<210> SEQ ID NO 62
<211> LENGTH: 282
<212> TYPE: PRT
<213> ORGANISM: Yarrowia lipolytica

<400> SEQUENCE: 62

```
Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280
```

<210> SEQ ID NO 63
<211> LENGTH: 906
<212> TYPE: DNA
<213> ORGANISM: Arabidopsis thaliana

<400> SEQUENCE: 63

```
atgtcagccg ccgcagctga aaccgacgtc tctctccgtc gcagatctaa ctctcttaac    60
ggaaaccaca ctaacggcgt cgccattgac ggaaccctag acaacaacaa ccgtcgcgtc   120
ggagatacaa acactcacat ggatatatct gctaagaaaa ctgacaacgg ctacgccaat   180
ggtgtcggag gaggaggatg gagaagcaaa gcgtcgttca cgacgtggac ggcgcgtgat   240
atcgtctacg tggtgagata ccattggata ccgtgcatgt tcgctgccgg acttctgttc   300
ttcatgggcg tggagtacac gcttcagatg attcccgcga gatctgagcc gttcgatctt   360
gggtttgtgg tcacgcgctc tttgaatcgc gtattagcat cttcaccgga tcttaacact   420
gttttagccg cactaaacac ggtgttcgta gggatgcaaa caacgtatat tgtatggaca   480
tggttagtgg aaggacgagc acgagccacc atcgcggctt tattcatgtt cacttgtcgc   540
ggcattctcg gctactctac tcagcttcct ctccctcagg actttctagg atcagggagtt   600
gatttccgg tggaaatgt ctctttcttc tcttcttct ctggccatgt cgccggctcg   660
atgatcgcat cattggacat gaagaatg cagaggttga acttgcaat ggtctttgac   720
atcctcaatg tattacagtc gatcagactc tcggtacaa gaggacatta cacaatcgac   780
cttgcggttg gagttggcgc tgggattctc ttcgactcat tggccggaaa gtacgaagag   840
atgatgagca agagacattt aggcactggt tttagtttga tttcgaaaga ctctctagtc   900
aattaa                                                               906
```

<210> SEQ ID NO 64
<211> LENGTH: 301
<212> TYPE: PRT
<213> ORGANISM: Arabidopsis thaliana

<400> SEQUENCE: 64

```
Met Ser Ala Ala Ala Glu Thr Asp Val Ser Leu Arg Arg Ser
1               5                   10                  15

Asn Ser Leu Asn Gly Asn His Thr Asn Gly Val Ala Ile Asp Gly Thr
                20                  25                  30

Leu Asp Asn Asn Asn Arg Arg Val Gly Asp Thr Asn Thr His Met Asp
            35                  40                  45

Ile Ser Ala Lys Lys Thr Asp Asn Gly Tyr Ala Asn Gly Val Gly Gly
        50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
            100                 105                 110

Ala Arg Ser Glu Pro Phe Asp Leu Gly Phe Val Val Thr Arg Ser Leu
        115                 120                 125

Asn Arg Val Leu Ala Ser Ser Pro Asp Leu Asn Thr Val Leu Ala Ala
    130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190
```

```
Gln Asp Phe Leu Gly Ser Gly Val Asp Phe Pro Val Gly Asn Val Ser
            195                 200                 205

Phe Phe Leu Phe Phe Ser Gly His Val Ala Gly Ser Met Ile Ala Ser
        210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
                    260                 265                 270

Ser Leu Ala Gly Lys Tyr Glu Glu Met Met Ser Lys Arg His Leu Gly
            275                 280                 285

Thr Gly Phe Ser Leu Ile Ser Lys Asp Ser Leu Val Asn
            290                 295                 300

<210> SEQ ID NO 65
<211> LENGTH: 840
<212> TYPE: DNA
<213> ORGANISM: Helianthus annuus

<400> SEQUENCE: 65
atggggacaa tcacaatgaa cgccgataag atccaccaac gttccatacc acaaacaacc      60
accctcctca aaacatcaaa caacgtttcc attaacaatt tcaatctcaa aaagaccaac     120
aattctacga ccacatgggg atcgctagcg gacgcgtcgt ttttacaatg gacaacatcg     180
gatgtgttcg gtttgtttaa gtaccacccc gtcccgtgtt tctttgctgt ttcgttactg     240
ttttttatgg gtgtggagta tacgctgcgg atgataccgc cctcgtcacc cccgtttgat     300
attgggttcg ttgccactgc gtatttgcat cgtgtcctcg tcgctagtcc gacgctaaac     360
acagttctcg cagggcttaa tacggtgttt gtggggatgc aaacaaccta tataataggg     420
acgtgggtca ttgaagggcg gccgagagcc acagtcgcgg cgctgttcat gtttacttgc     480
agagggattt tgggttattc gacacagctt cctttgcctg agggattctt gggttcggga     540
gcagactttc cggtaggcaa tgtgtccttc ttcttgtttt attctggtca tgtagcagga     600
tcagtaattg catcgtttga tatgaagaga atgcataggt gggagttggc ctttctattc     660
gacaccttga acctttttgca ggtggtgcgg ttactaagca aaggggacac tacaccatt     720 gacttagccg tcggagtagg tgccggcatg ttgtttgatt ccctcgccgg aaaatacatg     780
aagaaggcta tggctgaagg aggtgatgtc ttgtatacaa acctacctca cttatcttaa    840

<210> SEQ ID NO 66
<211> LENGTH: 279
<212> TYPE: PRT
<213> ORGANISM: Helianthus annuus

<400> SEQUENCE: 66

Met Gly Thr Ile Thr Met Asn Ala Asp Lys Ile His Gln Arg Ser Ile
1               5                   10                  15

Pro Gln Thr Thr Thr Leu Leu Lys Thr Ser Asn Asn Val Ser Ile Asn
            20                  25                  30

Asn Phe Asn Leu Lys Lys Thr Asn Asn Ser Thr Thr Thr Trp Gly Ser
        35                  40                  45

Leu Ala Asp Ala Ser Phe Leu Gln Trp Thr Thr Ser Asp Val Phe Gly
    50                  55                  60

Leu Phe Lys Tyr His Pro Val Pro Cys Phe Phe Ala Val Ser Leu Leu
65                  70                  75                  80
```

```
Phe Phe Met Gly Val Glu Tyr Thr Leu Arg Met Ile Pro Ser Ser
                85                  90                  95

Pro Pro Phe Asp Ile Gly Phe Val Ala Thr Ala Tyr Leu His Arg Val
            100                 105                 110

Leu Val Ala Ser Pro Thr Leu Asn Thr Val Leu Ala Gly Leu Asn Thr
        115                 120                 125

Val Phe Val Gly Met Gln Thr Thr Tyr Ile Ile Gly Thr Trp Val Ile
    130                 135                 140

Glu Gly Arg Pro Arg Ala Thr Val Ala Ala Leu Phe Met Phe Thr Cys
145                 150                 155                 160

Arg Gly Ile Leu Gly Tyr Ser Thr Gln Leu Pro Leu Pro Glu Gly Phe
                165                 170                 175

Leu Gly Ser Gly Ala Asp Phe Pro Val Gly Asn Val Ser Phe Phe Leu
            180                 185                 190

Phe Tyr Ser Gly His Val Ala Gly Ser Val Ile Ala Ser Phe Asp Met
        195                 200                 205

Lys Arg Met His Arg Trp Glu Leu Ala Phe Leu Phe Asp Thr Leu Asn
    210                 215                 220

Leu Leu Gln Val Val Arg Leu Leu Ser Thr Arg Gly His Tyr Thr Ile
225                 230                 235                 240

Asp Leu Ala Val Gly Val Gly Ala Gly Met Leu Phe Asp Ser Leu Ala
                245                 250                 255

Gly Lys Tyr Met Lys Lys Ala Met Ala Glu Gly Gly Asp Val Leu Tyr
            260                 265                 270

Thr Asn Leu Pro His Leu Ser
        275

<210> SEQ ID NO 67
<211> LENGTH: 1261
<212> TYPE: DNA
<213> ORGANISM: Camelina Sativa

<400> SEQUENCE: 67
caccaaagag ttagagtgta tttaactaac aaccataaat taaaaatgtc cttctcaaaa      60
ataactattc atcactttca tatgacaatt ttctaaccca acaagtctc ctttgaaatc     120 tccgccctcg tatctcttat ataacacatc tctcttcaaa ctcccaaaaa tgtccctctc     180
cgttaactct aacggccatg tcagtcgccg cagctaaacc cgccgtctct cgccgtcacg     240
tatctaacgg aaacaacact aacaacgtcg ccattgacga cgatcacaac caccaacgcc     300
gcatcgtcgg agataaaaac actcgaatgg agatcgctgc taagaacaac ggctacgcca     360
acggtgtcat cggaggagga ggatggagga gcaaggcgtc gttcatgacg tggacgacgc     420
gtgacgttgt ctacgtggcg agacaccatt ggataccgtg catgttcgct gccgggcttt     480
tgttcttcat gggggtcgag tacacgctcc agatgattcc cgcgagatct gagccgttcg     540
atcttgggtt cgtggccacg cgctctttga atcgcgtctt agcatcttcc ccggatctta     600
acaccgtttt agccgcacta aacacggtgt tcgtattgat gcaaacaacg tatattgtat     660
ggacatggtt agtggaagga cgagcacgag caaccatctc ggctttattc atgttcacgt     720 gtcgggcat tctcggctac tctactcagc ttcctctccc tcaggatttt ttaggatcag     780
gagttgattt tccagtggga aacgtctctt tcttcctctt cttctcgggc acgttgccg     840 gctcgatgat cgcatcactg acatgaggga gaatgcagag gtttaagctg gcgagggttt     900
ttgacatcct caatgtatta caatcgatca ggctgctcgg tacaagagga cactacacca     960
```

```
tcgaccttgc ggttggagtt ggcgctggga ttctctttga ctcactggcc gggaagtacg    1020
aagagatgag cagaagacac cacctaggaa ctggttttag tttgatatcg aaagactctc    1080
tagtcaatta aatttgtttt ctatcaaatg tttttagttc aacacattta gttaagttga    1140
atttagtcta atgacttatt tatttcttct ttataaatgc ctaaatggtt cattgtatac    1200
cgtttgttga acctaattat cgatctaatg ttacttaaag ggttgtagcc ttgtagttgt    1260
a                                                                   1261
```

<210> SEQ ID NO 68
<211> LENGTH: 297
<212> TYPE: PRT
<213> ORGANISM: Camelina Sativa

<400> SEQUENCE: 68

```
Met Ser Val Ala Ala Lys Pro Ala Val Ser Arg Arg His Val Ser
1               5                   10                  15

Asn Gly Asn Asn Thr Asn Asn Val Ala Ile Asp Asp His Asn His
                20                  25                  30

Gln Arg Arg Ile Val Gly Asp Lys Asn Thr Arg Met Glu Ile Ala Ala
        35                  40                  45

Lys Asn Asn Gly Tyr Ala Asn Gly Val Ile Gly Gly Gly Trp Arg
50                  55                  60

Ser Lys Ala Ser Phe Met Thr Trp Thr Arg Asp Val Val Tyr Val
65                  70                  75                  80

Ala Arg His His Trp Ile Pro Cys Met Phe Ala Ala Gly Leu Leu Phe
                85                  90                  95

Phe Met Gly Val Glu Tyr Thr Leu Gln Met Ile Pro Ala Arg Ser Glu
        100                 105                 110

Pro Phe Asp Leu Gly Phe Val Ala Thr Arg Ser Leu Asn Arg Val Leu
        115                 120                 125

Ala Ser Ser Pro Asp Leu Asn Thr Val Leu Ala Ala Leu Asn Thr Val
        130                 135                 140

Phe Val Leu Met Gln Thr Thr Tyr Ile Val Trp Thr Trp Leu Val Glu
145                 150                 155                 160

Gly Arg Ala Arg Ala Thr Ile Ser Ala Leu Phe Met Phe Thr Cys Arg
                165                 170                 175

Gly Ile Leu Gly Tyr Ser Thr Gln Leu Pro Leu Pro Gln Asp Phe Leu
        180                 185                 190

Gly Ser Gly Val Asp Phe Pro Val Gly Asn Val Ser Phe Phe Leu Phe
        195                 200                 205

Phe Ser Gly His Val Ala Gly Ser Met Ile Ala Ser Leu Asp Met Arg
210                 215                 220

Arg Met Gln Arg Phe Lys Leu Ala Arg Val Phe Asp Ile Leu Asn Val
225                 230                 235                 240

Leu Gln Ser Ile Arg Leu Leu Gly Thr Arg Gly His Tyr Thr Ile Asp
                245                 250                 255

Leu Ala Val Gly Val Gly Ala Gly Ile Leu Phe Asp Ser Leu Ala Gly
        260                 265                 270

Lys Tyr Glu Glu Met Ser Arg Arg His His Leu Gly Thr Gly Phe Ser
        275                 280                 285

Leu Ile Ser Lys Asp Ser Leu Val Asn
290                 295
```

<210> SEQ ID NO 69
<211> LENGTH: 1204
<212> TYPE: DNA
<213> ORGANISM: Brassica napus

<400> SEQUENCE: 69

```
atgaactttt gtagcccaaa caaccttcct ttccttccac aagtttcata atatctctta      60
tataacccat atctccaagc ctctcgaaat gttcttctcc gttaaatcta acggtcatgt     120
caactacaac aatcgtccct ctccgtcgca gttctaactc tctcaatgaa taccacacta     180
acgcagtcgc ctttgacgga atcgtcgggt caacaagtac tagccaaatg gaggagattg     240
ttacgcaaac cgacgactgc tacgccaatc acaacggaga tggagggaga agcaaggcat     300
cgtttatgac gtggaggatg tgcaatcctg tccaggtggc gagagtccat tggataccgt     360
gtttgctagc ggtaggagtt ctgttcttca cgggcgtaga ggagtacatg ctccagatga     420
ttccggcgag ttctgagccg ttcgatattg gttttgtggc gacgcgctct ctgtatcgac     480
tcttggcttc ttcaccggat cttaataccg ttttagctgc tctcaacacg gtgtttgtag     540
ggatgcaaac gacgtatatt ttatggacat ggttggtgga aggacgacca cgagcgacca     600
tctcggcttg cttcatgttt acttgtcgtg gcattcttgg ttactctact cagctccctc     660
ttcctcagga ttttctagga tcaggggtag attttccggt aggaaacgtc tcgttcttcc     720
tcttctactc aggccatgtc gcagggtcga cgatagcatc cttggatatg aggagaatga     780
agaggttgag acttgccttg cttttgaca tcctcaatgt attacaatcg atcaggcttc     840
tcgggacgag aggacaatac acgatcgatc tcgctgtcgg agttggcgct ggggttctct     900
ttgactcact ggctggaaaa tacgaagaga tgatgagcaa gagacgcaat gtaggcaatg     960
gttttagttt gatttcgtct cgctagttat taattttgt ttttttttt ttatgttttt    1020
agtctggaca tatttaattt agttgaaatc taatgactta aatttgcttt cttcaaaat    1080
gctctaactg acggacctaa ctaaatgtgt acgttattgt gtagttacca tagaggtttc    1140
gtattgtctt gagcctgata ttttgatttt agagctcgtt tatacggtag ctaataataa    1200
aaaa                                                                1204
```

<210> SEQ ID NO 70
<211> LENGTH: 289
<212> TYPE: PRT
<213> ORGANISM: Brassica napus

<400> SEQUENCE: 70

```
Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn His Asn Gly Asp Gly Gly Arg Ser Lys Ala Ser Phe Met
    50                  55                  60

Thr Trp Arg Met Cys Asn Pro Val Gln Val Ala Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
```

|     |     | 115 |     |     |     | 120 |     |     |     | 125 |     |
| --- | --- | --- | --- | --- | --- | --- | --- | --- | --- | --- | --- |

Leu Asn Thr Val Leu Ala Ala Leu Asn Thr Val Phe Val Gly Met Gln
            130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
            195                 200                 205

Ala Gly Ser Thr Ile Ala Ser Leu Asp Met Arg Arg Met Lys Arg Leu
            210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
            275                 280                 285

Arg

<210> SEQ ID NO 71
<211> LENGTH: 804
<212> TYPE: DNA
<213> ORGANISM: Glycine max

<400> SEQUENCE: 71

```
atgaatggcg gcgctgaggc ctcccctcaat cacaggcgca acaccaaac agctcccgcc    60
gacggcgcta aaggcgttaa ggtagcaaac ggagccatgg ggaagccgtc ctcttccaag   120
cactcctgcg gcgcgtcgtt catgaaatgg accgtggctg acgctgtcca cgtggtgacg   180
caccattgga tgccgtgctt gttcgcattg gggcttctct tcttcatggc cgtggagtac   240
acgcttctca tggtgccgcc gtcgtcgccg cccttcgacc ttggcttcat cgccacacgc   300
tccctccacg cgctcctcga gtcgtcgccg aatctcaaca cgctcttcgc cgggctcaat   360
acggtgtttg tggggatgca aacgagttat atcttatgga cgtggctgat tgaaggacgc   420
cccagagcca caatttcagc attgttcatg ttcacatgcc gtgggatttt aggctactcc   480
acccagctcc cattgcctca ggggtttttg ggctcgggtg tggacttccc tgttgggaac   540
gtgtctttt tcttgttttt ttctgggcac gttgcagggt cagtgattgc ttcattggac   600
atgaggagga tgcagaggtg ggaactggct tggacttttg atgtgctcaa tgttttgcaa   660
gctgtgaggt tgctgggtac aagaggccat tacactattg atttggccgt aggggttggt   720
gctggaattc tctttgattc tttagctggc aagtacgaag atagcaaaag gaatggtgct   780
ctcaaacaca atttgattgc gtga                                          804
```

<210> SEQ ID NO 72
<211> LENGTH: 267
<212> TYPE: PRT
<213> ORGANISM: Glycine max

<400> SEQUENCE: 72

Met Asn Gly Gly Ala Glu Ala Ser Leu Asn His Arg Arg Lys His Gln

-continued

```
1               5                   10                  15
Thr Ala Pro Ala Asp Gly Ala Lys Gly Val Lys Val Ala Asn Gly Ala
                20                  25                  30
Met Gly Lys Pro Ser Ser Lys His Ser Cys Gly Ala Ser Phe Met
                35                  40                  45
Lys Trp Thr Val Ala Asp Ala Val His Val Val Thr His His Trp Met
        50                  55                  60
Pro Cys Leu Phe Ala Leu Gly Leu Leu Phe Phe Met Ala Val Glu Tyr
65                  70                  75                  80
Thr Leu Leu Met Val Pro Pro Ser Ser Pro Pro Phe Asp Leu Gly Phe
                85                  90                  95
Ile Ala Thr Arg Ser Leu His Ala Leu Leu Glu Ser Ser Pro Asn Leu
                100                 105                 110
Asn Thr Leu Phe Ala Gly Leu Asn Thr Val Phe Val Gly Met Gln Thr
                115                 120                 125
Ser Tyr Ile Leu Trp Thr Trp Leu Ile Glu Gly Arg Pro Arg Ala Thr
        130                 135                 140
Ile Ser Ala Leu Phe Met Phe Thr Cys Arg Gly Ile Leu Gly Tyr Ser
145                 150                 155                 160
Thr Gln Leu Pro Leu Pro Gln Gly Phe Leu Gly Ser Gly Val Asp Phe
                165                 170                 175
Pro Val Gly Asn Val Ser Phe Phe Leu Phe Phe Ser Gly His Val Ala
                180                 185                 190
Gly Ser Val Ile Ala Ser Leu Asp Met Arg Arg Met Gln Arg Trp Glu
        195                 200                 205
Leu Ala Trp Thr Phe Asp Val Leu Asn Val Leu Gln Ala Val Arg Leu
        210                 215                 220
Leu Gly Thr Arg Gly His Tyr Thr Ile Asp Leu Ala Val Gly Val Gly
225                 230                 235                 240
Ala Gly Ile Leu Phe Asp Ser Leu Ala Gly Lys Tyr Glu Asp Ser Lys
                245                 250                 255
Arg Asn Gly Ala Leu Lys His Asn Leu Ile Ala
                260                 265

<210> SEQ ID NO 73
<211> LENGTH: 412
<212> TYPE: PRT
<213> ORGANISM: Arabidopsis thaliana

<400> SEQUENCE: 73

Met Val Ala Thr Ser Ala Thr Ser Ser Phe Phe Pro Val Pro Ser Ser
1               5                   10                  15
Ser Leu Asp Pro Asn Gly Lys Gly Asn Lys Ile Gly Thr Asn Leu
                20                  25                  30
Ala Gly Leu Asn Ser Ala Pro Asn Ser Gly Arg Met Lys Val Lys Pro
                35                  40                  45
Asn Ala Gln Ala Pro Pro Lys Ile Asn Gly Lys Lys Val Gly Leu Pro
        50                  55                  60
Gly Ser Val Asp Ile Val Arg Thr Asp Thr Glu Thr Ser Ser His Pro
65                  70                  75                  80
Ala Pro Arg Thr Phe Ile Asn Gln Leu Pro Asp Trp Ser Met Leu Leu
                85                  90                  95
Ala Ala Ile Thr Thr Ile Phe Leu Ala Ala Glu Lys Gln Trp Met Met
                100                 105                 110
```

-continued

```
Leu Asp Trp Lys Pro Arg Arg Ser Asp Met Leu Val Asp Pro Phe Gly
            115                 120                 125

Ile Gly Arg Ile Val Gln Asp Gly Leu Val Phe Arg Gln Asn Phe Ser
130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                165                 170                 175

Gly Leu Leu Gly Asp Gly Phe Gly Ser Thr Pro Glu Met Phe Lys Lys
            180                 185                 190

Asn Leu Ile Trp Val Val Thr Arg Met Gln Val Val Asp Lys Tyr
        195                 200                 205

Pro Thr Trp Gly Asp Val Val Glu Val Asp Thr Trp Val Ser Gln Ser
        210                 215                 220

Gly Lys Asn Gly Met Arg Arg Asp Trp Leu Val Arg Asp Cys Asn Thr
225                 230                 235                 240

Gly Glu Thr Leu Thr Arg Ala Ser Ser Val Trp Val Met Met Asn Lys
                245                 250                 255

Leu Thr Arg Arg Leu Ser Lys Ile Pro Glu Glu Val Arg Gly Glu Ile
            260                 265                 270

Glu Pro Tyr Phe Val Asn Ser Asp Pro Val Leu Ala Glu Asp Ser Arg
        275                 280                 285

Lys Leu Thr Lys Ile Asp Asp Lys Thr Ala Asp Tyr Val Arg Ser Gly
        290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Ile Met
                325                 330                 335

Glu Arg Gln Lys Leu Lys Ser Met Thr Leu Glu Tyr Arg Arg Glu Cys
            340                 345                 350

Gly Arg Asp Ser Val Leu Gln Ser Leu Thr Ala Val Thr Gly Cys Asp
        355                 360                 365

Ile Gly Asn Leu Ala Thr Ala Gly Asp Val Glu Cys Gln His Leu Leu
        370                 375                 380

Arg Leu Gln Asp Gly Ala Glu Val Val Arg Gly Arg Thr Glu Trp Ser
385                 390                 395                 400

Ser Lys Thr Pro Thr Thr Thr Trp Gly Thr Ala Pro
                405                 410
```

<210> SEQ ID NO 74
<211> LENGTH: 24
<212> TYPE: DNA
<213> ORGANISM: Artificial Sequence
<220> FEATURE:
<223> OTHER INFORMATION: AGPAT1 Primer 1

<400> SEQUENCE: 74
caccatggat ttatggcctg gtgc    24

<210> SEQ ID NO 75
<211> LENGTH: 18
<212> TYPE: DNA
<213> ORGANISM: Artificial Sequence
<220> FEATURE:
<223> OTHER INFORMATION: AGPAT1 Primer 2

<400> SEQUENCE: 75
tcatcctcct ccacctgg                                               18

<210> SEQ ID NO 76
<211> LENGTH: 28
<212> TYPE: DNA
<213> ORGANISM: Artificial Sequence
<220> FEATURE:
<223> OTHER INFORMATION: AGPAT1 Primer 3

<400> SEQUENCE: 76
cggaattcat ggatttatgg cctggtgc                                    28

<210> SEQ ID NO 77
<211> LENGTH: 26
<212> TYPE: DNA
<213> ORGANISM: Artificial Sequence
<220> FEATURE:
<223> OTHER INFORMATION: AGPAT1 Primer 4

<400> SEQUENCE: 77
gctctagatc atcctcctcc acctgg                                      26

<210> SEQ ID NO 78
<211> LENGTH: 1626
<212> TYPE: DNA
<213> ORGANISM: Arabidopsis thaliana

<400> SEQUENCE: 78
atggtgggtg cgtcttcctc ttacgcatct ccgttatgta cctggtttgt tgctgcttgc     60
atgtccgtct ctcacggtgg aggagatagc cgtcaggctg ttgctcttca atctggtggg    120
cggagtcggc gaaggaggca gcttagcaaa tgctctgtcg cttctggatc cgctagcatt    180
caggctctcg tcacttcttg tttggatttt ggtccttgta ctcactacaa caacaacaat    240
gcattgtctt ctctctttgg atcgaatagt gtttctttga atcgaaacca gaggagattg    300
aatcgtgctg ctagctccgg tggagccatg gcagtgatgg agatggaaaa ggaagctgcg    360
gttaacaaga aaccacctac ggagcagcgt cgagttgtag tgacaggcat gggagttgaa    420
acatcattgg gtcatgaccc cataccttc tatgagaatt gctacaagg caacagtggt    480 attagccaga ttgaaaattt tgattgttct gaatttccta cgcgaattgc gggagagatc    540
aaaagcttct cgactgaagg atgggttgct ccaaaacttt ctaaaaggat ggacaaattc    600
atgctctatc ttctcacagc tggtaagaaa gctttggctg atggtggggt tactgatgaa    660
gtaatggcag agtttgacaa aaccaaatgt ggagttttga ttggctcggc aatgggagga    720
atgaaggtct tttacgatgc tattgaagct ctgagaatct cttacaagaa gatgaatcct    780
ttttgtgtac cttttgcgac aacaaacatg ggttctgcta tgcttgccat ggatctggga    840 tggatgggc caaactattc tatttcaact gcttgtgcca caagcaactt ttgcattctg    900
aattcagcaa accacattat taaaggtgaa gctgatgtaa tgctctgtgg tggctcagat    960
gcagttatta ttccaatagg gttgggaggt tttgttgcat gccgggctct ttcacaaagg   1020
aataatgatc ccacaaaagc ttcacgtcct tgggatacca atcgagatgg tttcgtgatg   1080
ggagagggag ctggagttct actttttgga gaactcgagc atgctaagaa aagaggtgca   1140
actatctacg cagagttcct cggtgggagt ttcacatgtg atgcctatca catgaccgag   1200
cctcaccctg atggggctgg tgttattctc tgtattgaga gagcgttagc tagtgctggg   1260
atttccaagg aacaaataaa ttacataaat gcacatgcaa cctcaacgca tgctggagat   1320
attaaggaat accaagccct tgctcactgt tttggccaaa atcctgagct taaggtaaat   1380

```
tccacaaaat ctatgattgg acacttgctg ggagctgctg gggccgtgga ggctgttgca   1440
actgtgcagg cgatacggac cggatgggtt catccaaata tcaacctcga gaatccagac   1500
agtggagtgg atacaaagct gctggtgggt cctaagaagg agagactgga cattaaagca   1560
gccttgtcaa attcattcgg gtttggtggt cataactcca gcatcatttt tgctccttac   1620
aagtga                                                              1626
```

```
<210> SEQ ID NO 79
<211> LENGTH: 541
<212> TYPE: PRT
<213> ORGANISM: Arabidopsis thaliana

<400> SEQUENCE: 79
```

| | | | | | | | | | | | | | | |
|---|---|---|---|---|---|---|---|---|---|---|---|---|---|---|
| Met | Val | Gly | Ala | Ser | Ser | Tyr | Ala | Ser | Pro | Leu | Cys | Thr | Trp | Phe |
| 1 | | | | 5 | | | | | 10 | | | | | 15 |

Val Ala Ala Cys Met Ser Val Ser His Gly Gly Asp Ser Arg Gln
            20                  25                  30

Ala Val Ala Leu Gln Ser Gly Arg Ser Arg Arg Arg Gln Leu
        35                  40                  45

Ser Lys Cys Ser Val Ala Ser Gly Ser Ala Ser Ile Gln Ala Leu Val
 50                  55                  60

Thr Ser Cys Leu Asp Phe Gly Pro Cys Thr His Tyr Asn Asn Asn Asn
 65                  70                  75                  80

Ala Leu Ser Ser Leu Phe Gly Ser Asn Ser Val Ser Leu Asn Arg Asn
                85                  90                  95

Gln Arg Arg Leu Asn Arg Ala Ala Ser Ser Gly Gly Ala Met Ala Val
            100                 105                 110

Met Glu Met Glu Lys Glu Ala Ala Val Asn Lys Lys Pro Pro Thr Glu
        115                 120                 125

Gln Arg Arg Val Val Val Thr Gly Met Gly Val Glu Thr Ser Leu Gly
130                 135                 140

His Asp Pro His Thr Phe Tyr Glu Asn Leu Leu Gln Gly Asn Ser Gly
145                 150                 155                 160

Ile Ser Gln Ile Glu Asn Phe Asp Cys Ser Glu Phe Pro Thr Arg Ile
                165                 170                 175

Ala Gly Glu Ile Lys Ser Phe Ser Thr Glu Gly Trp Val Ala Pro Lys
            180                 185                 190

Leu Ser Lys Arg Met Asp Lys Phe Met Leu Tyr Leu Thr Ala Gly
        195                 200                 205

Lys Lys Ala Leu Ala Asp Gly Gly Val Thr Asp Glu Val Met Ala Glu
210                 215                 220

Phe Asp Lys Thr Lys Cys Gly Val Leu Ile Gly Ser Ala Met Gly Gly
225                 230                 235                 240

Met Lys Val Phe Tyr Asp Ala Ile Glu Ala Leu Arg Ile Ser Tyr Lys
                245                 250                 255

Lys Met Asn Pro Phe Cys Val Pro Phe Ala Thr Thr Asn Met Gly Ser
            260                 265                 270

Ala Met Leu Ala Met Asp Leu Gly Trp Met Gly Pro Asn Tyr Ser Ile
        275                 280                 285

Ser Thr Ala Cys Ala Thr Ser Asn Phe Cys Ile Leu Asn Ser Ala Asn
    290                 295                 300

His Ile Ile Lys Gly Glu Ala Asp Val Met Leu Cys Gly Gly Ser Asp
305                 310                 315                 320

Ala Val Ile Ile Pro Ile Gly Leu Gly Gly Phe Val Cys Arg Ala
        325                 330                 335

Leu Ser Gln Arg Asn Asn Asp Pro Thr Lys Ala Ser Arg Pro Trp Asp
    340                 345                 350

Thr Asn Arg Asp Gly Phe Val Met Gly Glu Gly Ala Gly Val Leu Leu
    355                 360                 365

Leu Glu Glu Leu Glu His Ala Lys Lys Arg Gly Ala Thr Ile Tyr Ala
    370                 375                 380

Glu Phe Leu Gly Gly Ser Phe Thr Cys Asp Ala Tyr His Met Thr Glu
385                 390                 395                 400

Pro His Pro Asp Gly Ala Gly Val Ile Leu Cys Ile Glu Arg Ala Leu
                405                 410                 415

Ala Ser Ala Gly Ile Ser Lys Glu Gln Ile Asn Tyr Ile Asn Ala His
                420                 425                 430

Ala Thr Ser Thr His Ala Gly Asp Ile Lys Glu Tyr Gln Ala Leu Ala
            435                 440                 445

His Cys Phe Gly Gln Asn Pro Glu Leu Lys Val Asn Ser Thr Lys Ser
        450                 455                 460

Met Ile Gly His Leu Leu Gly Ala Ala Gly Ala Val Glu Ala Val Ala
465                 470                 475                 480

Thr Val Gln Ala Ile Arg Thr Gly Trp Val His Pro Asn Ile Asn Leu
                485                 490                 495

Glu Asn Pro Asp Ser Gly Val Asp Thr Lys Leu Leu Val Gly Pro Lys
                500                 505                 510

Lys Glu Arg Leu Asp Ile Lys Ala Ala Leu Ser Asn Ser Phe Gly Phe
            515                 520                 525

Gly Gly His Asn Ser Ser Ile Ile Phe Ala Pro Tyr Lys
        530                 535                 540

<210> SEQ ID NO 80
<211> LENGTH: 1152
<212> TYPE: DNA
<213> ORGANISM: Arabidopsis thaliana

<400> SEQUENCE: 80
atgggtgcag gtggaagaat gccggttcct acttcttcca agaaatcgga aaccgacacc      60
acaaagcgtg tgccgtgcga gaaaccgcct ttctcggtgg agatctgaa gaaagcaatc      120 ccgccgcatt gtttcaaacg ctcaatccct cgctctttct cctaccttat cagtgacatc      180
attatagcct catgcttcta ctacgtcgcc accaattact tctctctcct ccctcagcct      240
ctctcttact tggcttggcc actctattgg gcctgtcaag gctgtgtcct aactggtatc      300
tgggtcatag cccacgaatg cggtcaccac gcattcagcg actaccaatg ctggatgac       360 acagttggtc ttatcttcca ttccttcctc ctcgtccctt acttctcctg gagtatagt       420 catcgccgtc accattccaa cactggatcc ctcgaaagag atgaagtatt tgtcccaaag      480
cagaaatcag caatcaagtg gtacgggaaa taccctcaaca accctcttgg acgcatcatg      540
atgttaaccg tccagtttgt cctcgggtgg cccttgtact tagcctttaa cgtctctggc      600
agaccgtatg acgggttcgc ttgccatttc ttccccaacg ctcccatcta caatgaccga      660
gaacgcctcc agatatacct ctctgatgcg ggtattctag ccgtctgttt tggtctttac      720
cgttacgctg ctgcacaagg gatggcctcg atgatctgcc tctacggagt accgcttctg      780
atagtgaatg cgttcctcgt cttgatcact tacttgcagc acactcatcc ctcgttgcct      840
cactacgatt catcagagtg ggactggctc agggagcttt tggctaccgt agacagagac      900

```
tacggaatct tgaacaaggt gttccacaac attacagaca cacacgtggc tcatcacctg    960
ttctcgacaa tgccgcatta taacgcaatg gaagctacaa aggcgataaa gccaattctg   1020
ggagactatt accagttcga tggaacaccg tggtatgtag cgatgtatag ggaggcaaag   1080
gagtgtatct atgtagaacc ggacagggaa ggtgacaaga aggtgtgta ctggtacaac    1140 aataagttat ga                                                       1152
```

<210> SEQ ID NO 81
<211> LENGTH: 383
<212> TYPE: PRT
<213> ORGANISM: Arabidopsis thaliana

<400> SEQUENCE: 81

```
Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser
        35                  40                  45

Ile Pro Arg Ser Phe Ser Tyr Leu Ile Ser Asp Ile Ile Ala Ser
50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320
```

```
Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380

<210> SEQ ID NO 82
<211> LENGTH: 1521
<212> TYPE: DNA
<213> ORGANISM: Arabidopsis thaliana

<400> SEQUENCE: 82
atgacgtccg ttaacgttaa gctcctttac cgttacgtct taaccaactt tttcaacctc      60
tgtttgttcc cgttaacggc gttcctcgcc ggaaaagcct ctcggcttac cataaacgat     120
ctccacaact tcctttccta tctccaacac aaccttataa cagtaacttt actctttgct     180
ttcactgttt tcggtttggt tctctacatc gtaacccgac ccaatccggt ttatctcgtt     240
gactactcgt gttaccttcc accaccgcat ctcaaagtta gtgtctctaa agtcatggat     300
attttctacc aaataagaaa agctgatact tcttcacgga acgtggcatg tgatgatccg     360
tcctcgctcg atttcctgag gaagattcaa gagcgttcag gtctaggtga tgagacgtac     420
agtcctgagg gactcattca cgtaccaccg cggaagactt ttgcagcgtc acgtgaagag     480
acagagaagg ttatcatcgg tgcgctcgaa aatctattcg agaacaccaa agttaaccct     540
agagagattg gtatacttgt ggtgaactca agcatgttta atccaactcc ttcgctatcc     600
gctatggtcg ttaatacttt caagctccga agcaacatca aaagctttaa tctaggagga     660
atgggttgta gtgctggtgt tattgccatt gatttggcta agacttgtt gcatgttcat     720 aaaaacactt atgctcttgt ggtgagcact gagaacatca cacaaggcat ttatgctgga     780
gaaaatagat caatgatggt tagcaattgc ttgtttcgtg ttggtggggc cgcgattttg     840
ctctctaaca agtcgggaga ccggagacgg tccaagtaca agctagttca cacggtccga     900
acgcatactg gagctgatga caagtctttt cgatgtgtgc aacaagaaga cgatgagagc     960
ggcaaaatcg gagtttgtct gtcaaaggac ataaccaatg ttgcggggac aacacttacg    1020
aaaaatatag caacattggg tccgttgatt cttcctttaa gcgaaaagtt tctttttttc    1080
gctaccttcg tcgccaagaa acttctaaag gataaaatca agcattacta tgttccggat    1140
ttcaagcttg ctgttgacca tttctgtatt catgccggag gcagagccgt gatcgatgag    1200
ctagagaaga acttaggact atcgccgatc gatgtggagg catctagatc aacgttacat    1260
agatttggga atacttcatc tagctcaatt tggtatgaat tagcatacat agaggcaaag    1320
ggaagaatga agaaagggaa taaagcttgg cagattgctt taggatcagg gtttaagtgt    1380
aatagtgcgg tttgggtggc tctacgcaat gtcaaggcat cggcaaatag tccttggcaa    1440
cattgcatcg atagatatcc ggttaaaatt gattctgatt tgtcaaagtc aaagactcat    1500
gtccaaaacg gtcggtccta a                                              1521

<210> SEQ ID NO 83
<211> LENGTH: 506
<212> TYPE: PRT
<213> ORGANISM: Arabidopsis thaliana

<400> SEQUENCE: 83
```

```
Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
            165                 170                 175

Lys Val Asn Pro Arg Glu Ile Gly Ile Leu Val Val Asn Ser Ser Met
        180                 185                 190

Phe Asn Pro Thr Pro Ser Leu Ser Ala Met Val Val Asn Thr Phe Lys
    195                 200                 205

Leu Arg Ser Asn Ile Lys Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
            245                 250                 255

Ile Tyr Ala Gly Glu Asn Arg Ser Met Met Val Ser Asn Cys Leu Phe
        260                 265                 270

Arg Val Gly Gly Ala Ala Ile Leu Leu Ser Asn Lys Ser Gly Asp Arg
    275                 280                 285

Arg Arg Ser Lys Tyr Lys Leu Val His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
            325                 330                 335

Thr Thr Leu Thr Lys Asn Ile Ala Thr Leu Gly Pro Leu Ile Leu Pro
        340                 345                 350

Leu Ser Glu Lys Phe Leu Phe Phe Ala Thr Phe Val Ala Lys Lys Leu
    355                 360                 365

Leu Lys Asp Lys Ile Lys His Tyr Tyr Val Pro Asp Phe Lys Leu Ala
    370                 375                 380

Val Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
            405                 410                 415
```

```
Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
            435                 440                 445

Ala Trp Gln Ile Ala Leu Gly Ser Gly Phe Lys Cys Asn Ser Ala Val
450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
            485                 490                 495

Ser Lys Thr His Val Gln Asn Gly Arg Ser
            500                 505

<210> SEQ ID NO 84
<211> LENGTH: 1260
<212> TYPE: DNA
<213> ORGANISM: Yarrowia lipolytica

<400> SEQUENCE: 84
atggattcga ccacgcagac caacaccggc accggcaagg tggccgtgca gccccccacg     60
gccttcatta agcccattga aaggtgtcc gagcccgtct acgacacctt ggcaacgag     120
ttcactcctc cagactactc tatcaaggat attctggatg ccattcccca ggagtgctac    180
aagcggtcct acgttaagtc ctactcgtac gtggcccgag actgcttctt tatcgccgtt    240
tttgcctaca tggcctacgc gtacctgcct cttattccct cggcttccgg ccgagctgtg    300
gcctgggcca tgtactccat tgtccagggt ctgtttggca ccggtctgtg ggttcttgcc    360
cacgagtgtg gccactctgc tttctccgac tctaacaccg tcaacaacgt caccggatgg    420
gttctgcact cctccatgct ggtcccttac tacgcctgga agctgaccca ctccatgcac    480
cacaagtcca ctggtcacct caccgtgat atggtgtttg tgcccaagga ccgaaaggag    540
tttatggaga accgaggcgc ccatgactgg tctgagcttg ctgaggacgc tcccctcatg    600
accctctacg gcctcatcac ccagcaggtg tttggatggc ctctgtatct gctgtctaac    660
gttaccggac agaagtaccc caagctcaac aaatgggctg tcaaccactt caaccccaac    720
gccccgctgt tgagaagaa ggactggttc aacatctgga tctctaacgt cggtattggt    780
atcaccatgt ccgtcatcgc atactccatc aaccgatggg gctggcttc cgtcaccctc    840
tactacctga tccctacct gtgggtcaac cactggctcg tggccatcac ctacctgcag    900
cacaccgacc ccactctgcc ccactaccac gccgaccagt ggaacttcac ccgaggagcc    960
gccgccacca tcgaccgaga gtttggcttc atcggctcct tctgcttcca tgacatcatc   1020
gagacccacg ttctgcacca ctacgtgtct cgaattccct tctacaacgc ccgaatcgcc   1080
actgagaaga tcaagaaggt catgggcaag cactaccgac acgacgacac caacttcatc   1140
aagtctcttt acactgtcgc ccgaacctgc cagtttgttg aaggtaagga aggcattcag   1200
atgtttagaa acgtcaatgg agtcggagtt gctcctgacg gcctgccttc taaaaagtag   1260

<210> SEQ ID NO 85
<211> LENGTH: 419
<212> TYPE: PRT
<213> ORGANISM: Yarrowia lipolytica

<400> SEQUENCE: 85

Met Asp Ser Thr Thr Gln Thr Asn Thr Gly Thr Gly Lys Val Ala Val
1               5                   10                  15
```

```
Gln Pro Pro Thr Ala Phe Ile Lys Pro Ile Glu Lys Val Ser Glu Pro
                20                  25                  30
Val Tyr Asp Thr Phe Gly Asn Glu Phe Thr Pro Pro Tyr Ser Ile
         35                  40                  45
Lys Asp Ile Leu Asp Ala Ile Pro Gln Glu Cys Tyr Lys Arg Ser Tyr
     50                  55                  60
Val Lys Ser Tyr Ser Tyr Val Ala Arg Asp Cys Phe Phe Ile Ala Val
 65                  70                  75                  80
Phe Ala Tyr Met Ala Tyr Ala Tyr Leu Pro Leu Ile Pro Ser Ala Ser
                 85                  90                  95
Gly Arg Ala Val Ala Trp Ala Met Tyr Ser Ile Val Gln Gly Leu Phe
             100                 105                 110
Gly Thr Gly Leu Trp Val Leu Ala His Glu Cys Gly His Ser Ala Phe
         115                 120                 125
Ser Asp Ser Asn Thr Val Asn Asn Val Thr Gly Trp Val Leu His Ser
     130                 135                 140
Ser Met Leu Val Pro Tyr Tyr Ala Trp Lys Leu Thr His Ser Met His
145                 150                 155                 160
His Lys Ser Thr Gly His Leu Thr Arg Asp Met Val Phe Val Pro Lys
                 165                 170                 175
Asp Arg Lys Glu Phe Met Glu Asn Arg Gly Ala His Asp Trp Ser Glu
             180                 185                 190
Leu Ala Glu Asp Ala Pro Leu Met Thr Leu Tyr Gly Leu Ile Thr Gln
         195                 200                 205
Gln Val Phe Gly Trp Pro Leu Tyr Leu Leu Ser Asn Val Thr Gly Gln
     210                 215                 220
Lys Tyr Pro Lys Leu Asn Lys Trp Ala Val Asn His Phe Asn Pro Asn
225                 230                 235                 240
Ala Pro Leu Phe Glu Lys Lys Asp Trp Phe Asn Ile Trp Ile Ser Asn
                 245                 250                 255
Val Gly Ile Gly Ile Thr Met Ser Val Ile Ala Tyr Ser Ile Asn Arg
             260                 265                 270
Trp Gly Leu Ala Ser Val Thr Leu Tyr Tyr Leu Ile Pro Tyr Leu Trp
         275                 280                 285
Val Asn His Trp Leu Val Ala Ile Thr Tyr Leu Gln His Thr Asp Pro
     290                 295                 300
Thr Leu Pro His Tyr His Ala Asp Gln Trp Asn Phe Thr Arg Gly Ala
305                 310                 315                 320
Ala Ala Thr Ile Asp Arg Glu Phe Gly Phe Ile Gly Ser Phe Cys Phe
                 325                 330                 335
His Asp Ile Ile Glu Thr His Val Leu His His Tyr Val Ser Arg Ile
             340                 345                 350
Pro Phe Tyr Asn Ala Arg Ile Ala Thr Glu Lys Ile Lys Lys Val Met
         355                 360                 365
Gly Lys His Tyr Arg His Asp Asp Thr Asn Phe Ile Lys Ser Leu Tyr
     370                 375                 380
Thr Val Ala Arg Thr Cys Gln Phe Val Glu Gly Lys Glu Gly Ile Gln
385                 390                 395                 400
Met Phe Arg Asn Val Asn Gly Val Gly Val Ala Pro Asp Gly Leu Pro
                 405                 410                 415
Ser Lys Lys

<210> SEQ ID NO 86
```

-continued

```
<211> LENGTH: 978
<212> TYPE: DNA
<213> ORGANISM: Yarrowia lipolytica

<400> SEQUENCE: 86
atgagcgccg tccctattga attcaacgtc ccctccgtgg accgacccctt tggtatctac      60
ctctgggcca tctttgacca ggcctgggag aagcttttcg gctggcccgc gtcctctttc     120
attttcgtgc gaaatgaccc caacatcccc ttttcctcta cccctcccgt gatcattgcc     180
atcattgtgt actacattgt catctttggc ggccgagagg tgatgcgaaa cctgtctccc     240
atccgactca actggctctt ccagatccac aacatcttcc tcacccttct gtccggtatg     300
ctcctcctcc tcctcgttga gcagctcttc cccatcattg tccgacaggg tatcctctac     360
gccatctgcg actacggatc ttggactcag cccattgtct ctgctacta cctcaactac     420
ctgaccaagt actttgagct gatcgacacc gttttccttg tgctgcgaaa gaagaagctg     480
actttcctcc acacctacca ccatggtgcc actgctcttc tgtgctacac ccagctcatt     540
ggtaagacct cggtctcttg ggtccccatc acccttaacc tgtttgtcca cgttgtcatg     600
tacttctact acttcctggc tgcgcgaggt atccgagtgt ggtggaagga gtgggtcacc     660
cggctccaga tcatccagtt cgttatcgat cttggatttg tctactttgc ctcttacacc     720
tacttcaccct ctacctactg gccctggatg cccaacatgg gctcttgtgc cggcgaggag     780
tttgctgcta tttacggctg tggtctgctg acctcttacc tcttcctctt catcgccttc     840
tacatcaact cttaccgaaa gccctcttcc aagggacctt ccaagcctgt tgttgctgtc     900
gatggccctg ttggcggcgt caacgcccag actggtgctt ctcgaggcca gaccactacc     960
cgatctcgac gagcataa                                                    978

<210> SEQ ID NO 87
<211> LENGTH: 325
<212> TYPE: PRT
<213> ORGANISM: Yarrowia lipolytica

<400> SEQUENCE: 87

Met Ser Ala Val Pro Ile Glu Phe Asn Val Pro Ser Val Asp Arg Pro
1               5                   10                  15

Phe Gly Ile Tyr Leu Trp Ala Ile Phe Asp Gln Ala Trp Glu Lys Leu
            20                  25                  30

Phe Gly Trp Pro Ala Ser Ser Phe Ile Phe Val Arg Asn Asp Pro Asn
        35                  40                  45

Ile Pro Phe Ser Ser Thr Pro Val Ile Ile Ala Ile Ile Val Tyr Tyr
    50                  55                  60

Tyr Ile Val Ile Phe Gly Gly Arg Glu Val Met Arg Asn Leu Ser Pro
65                  70                  75                  80

Ile Arg Leu Asn Trp Leu Phe Gln Ile His Asn Ile Phe Leu Thr Leu
                85                  90                  95

Leu Ser Gly Met Leu Leu Leu Leu Leu Val Glu Gln Leu Phe Pro Ile
            100                 105                 110

Ile Val Arg Gln Gly Ile Leu Tyr Ala Ile Cys Asp Tyr Gly Ser Trp
        115                 120                 125

Thr Gln Pro Ile Val Phe Cys Tyr Tyr Leu Asn Tyr Leu Thr Lys Tyr
    130                 135                 140

Phe Glu Leu Ile Asp Thr Val Phe Leu Val Leu Arg Lys Lys Lys Leu
145                 150                 155                 160

Thr Phe Leu His Thr Tyr His His Gly Ala Thr Ala Leu Leu Cys Tyr
```

|     | 165 | | | 170 | | | 175 | | |
|---|---|---|---|---|---|---|---|---|---|

Thr Gln Leu Ile Gly Lys Thr Ser Val Ser Trp Val Pro Ile Thr Leu
            180                 185                 190

Asn Leu Phe Val His Val Val Met Tyr Phe Tyr Tyr Phe Leu Ala Ala
        195                 200                 205

Arg Gly Ile Arg Val Trp Trp Lys Glu Trp Val Thr Arg Leu Gln Ile
    210                 215                 220

Ile Gln Phe Val Ile Asp Leu Gly Phe Val Tyr Phe Ala Ser Tyr Thr
225                 230                 235                 240

Tyr Phe Thr Ser Thr Tyr Trp Pro Trp Met Pro Asn Met Gly Ser Cys
            245                 250                 255

Ala Gly Glu Glu Phe Ala Ala Ile Tyr Gly Cys Gly Leu Leu Thr Ser
        260                 265                 270

Tyr Leu Phe Leu Phe Ile Ala Phe Tyr Ile Asn Ser Tyr Arg Lys Pro
    275                 280                 285

Ser Ser Lys Gly Pro Ser Lys Pro Val Val Ala Val Asp Gly Pro Val
        290                 295                 300

Gly Gly Val Asn Ala Gln Thr Gly Ala Ser Arg Gly Gln Thr Thr Thr
305                 310                 315                 320

Arg Ser Arg Arg Ala
            325

<210> SEQ ID NO 88
<211> LENGTH: 1185
<212> TYPE: DNA
<213> ORGANISM: Yarrowia lipolytica

<400> SEQUENCE: 88

| | |
|---|---|
| atgggcgtat tcattaaaca ggagcagctt ccggctctca agaagtacaa gtactccgcc | 60 |
| gaggatcact cgttcatctc caacaacatt ctgcgcccct ctggcgaca gtttgtcaaa | 120 |
| atcttccctc tgtggatggc ccccaacatg gtgactctgt gggcttctt ctttgtcatt | 180 |
| gtgaacttca tcaccatgct cattgttgat cccacccacg accgcgagcc tcccagatgg | 240 |
| gtctacctca cctacgctct gggtctgttc ctttaccaga catttgatgc ctgtgacgga | 300 |
| tcccatgccc gacgaactgg ccagagtgga ccccttggag agctgtttga ccactgtgtc | 360 |
| gacgccatga atacctctct gattctcacg gtggtggtgt ccaccaccca tatgggatat | 420 |
| aacatgaagc tgctgattgt gcagattgcc gctctcggaa acttctacct gtcgacctgg | 480 |
| gagacctacc ataccggaac tctgtaccgt tctggcttct ctggtcctgt tgaaggtatc | 540 |
| ttgattctgg tggctctttt cgtcctcacc ttcttcactg gtcccaacgt gtacgctctg | 600 |
| accgtctacg aggctcttcc cgaatccatc acttcgctgc tgcctgccag cttcctggac | 660 |
| gtcaccatca cccagatcta cattggattc ggagtgctgg gcatggtgtt caacatctac | 720 |
| ggcgcctgcg aaacgtgat caagtactac aacaacaagg gcaagagcgc tctccccgcc | 780 |
| attctcggaa tcgcccccttt tggcatcttc tacgtcggcg tctttgcctg ggcccatgtt | 840 |
| gctcctctgc ttctctccaa gtacgccatc gtctatctgt tgccattggg gctgcctttt | 900 |
| gccatgcaag tcggccagat gattcttgcc catctcgtgc ttgctccctt cccccactgg | 960 |
| aacgtgctgc tcttcttccc ctttgtggga ctggcagtgc actacattgc accgtgtttt | 1020 |
| ggctgggacg ccgatatcgt gtcggttaac actctcttca cctgttttgg cgccaccctc | 1080 |
| tccatttacg ccttctttgt gcttgagatc atcgacgaga tcaccaacta cctcgatatc | 1140 |
| tggtgtctgc gaatcaagta ccctcaggag aagaagactg agtaa | 1185 |

<210> SEQ ID NO 89
<211> LENGTH: 394
<212> TYPE: PRT
<213> ORGANISM: Yarrowia lipolytica

<400> SEQUENCE: 89

```
Met Gly Val Phe Ile Lys Gln Glu Gln Leu Pro Ala Leu Lys Lys Tyr
1               5                   10                  15

Lys Tyr Ser Ala Glu Asp His Ser Phe Ile Ser Asn Asn Ile Leu Arg
            20                  25                  30

Pro Phe Trp Arg Gln Phe Val Lys Ile Phe Pro Leu Trp Met Ala Pro
        35                  40                  45

Asn Met Val Thr Leu Leu Gly Phe Phe Val Ile Val Asn Phe Ile
    50                  55                  60

Thr Met Leu Ile Val Asp Pro Thr His Asp Arg Glu Pro Pro Arg Trp
65                  70                  75                  80

Val Tyr Leu Thr Tyr Ala Leu Gly Leu Phe Leu Tyr Gln Thr Phe Asp
                85                  90                  95

Ala Cys Asp Gly Ser His Ala Arg Arg Thr Gly Gln Ser Gly Pro Leu
            100                 105                 110

Gly Glu Leu Phe Asp His Cys Val Asp Ala Met Asn Thr Ser Leu Ile
        115                 120                 125

Leu Thr Val Val Ser Thr Thr His Met Gly Tyr Asn Met Lys Leu
    130                 135                 140

Leu Ile Val Gln Ile Ala Ala Leu Gly Asn Phe Tyr Leu Ser Thr Trp
145                 150                 155                 160

Glu Thr Tyr His Thr Gly Thr Leu Tyr Leu Ser Gly Phe Ser Gly Pro
                165                 170                 175

Val Glu Gly Ile Leu Ile Leu Val Ala Leu Phe Val Leu Thr Phe Phe
            180                 185                 190

Thr Gly Pro Asn Val Tyr Ala Leu Thr Val Tyr Glu Ala Leu Pro Glu
        195                 200                 205

Ser Ile Thr Ser Leu Leu Pro Ala Ser Phe Leu Asp Val Thr Ile Thr
210                 215                 220

Gln Ile Tyr Ile Gly Phe Gly Val Leu Gly Met Val Phe Asn Ile Tyr
225                 230                 235                 240

Gly Ala Cys Gly Asn Val Ile Lys Tyr Tyr Asn Asn Lys Gly Lys Ser
                245                 250                 255

Ala Leu Pro Ala Ile Leu Gly Ile Ala Pro Phe Gly Ile Phe Tyr Val
            260                 265                 270

Gly Val Phe Ala Trp Ala His Val Ala Pro Leu Leu Leu Ser Lys Tyr
        275                 280                 285

Ala Ile Val Tyr Leu Phe Ala Ile Gly Ala Ala Phe Ala Met Gln Val
    290                 295                 300

Gly Gln Met Ile Leu Ala His Leu Val Leu Ala Pro Phe Pro His Trp
305                 310                 315                 320

Asn Val Leu Leu Phe Phe Pro Phe Val Gly Leu Ala Val His Tyr Ile
                325                 330                 335

Ala Pro Val Phe Gly Trp Asp Ala Asp Ile Val Ser Val Asn Thr Leu
            340                 345                 350

Phe Thr Cys Phe Gly Ala Thr Leu Ser Ile Tyr Ala Phe Phe Val Leu
        355                 360                 365

Glu Ile Ile Asp Glu Ile Thr Asn Tyr Leu Asp Ile Trp Cys Leu Arg
```

```
              370                 375                 380
Ile Lys Tyr Pro Gln Glu Lys Lys Thr Glu
385                 390

<210> SEQ ID NO 90
<211> LENGTH: 1332
<212> TYPE: DNA
<213> ORGANISM: Yarrowia lipolytica

<400> SEQUENCE: 90
atgggtaaaa gcccctctat gattgggact tgcggttggg ttgggctggg tacaaacaca      60
tgctatgctc atcagctcag ccgtgccatg ggccatcaac caacttttct cccgacccta     120
atcccctcca cactactaat gccaggattc caccacatca ccccgacag tctagtgcat      180
ctaaagtcgt accagtacag aagcgtcgat aaatcctacc tgtctaagta catcctgaac     240
ccatggtgga cttacgcagc aaccttcatg cctgattggc tggctcccaa cgccatcact     300
ctcatcggtg tctccggcat gctcctgtca atcttcttca ccgtctggta caccccgag      360
ctcaccggcg acggtccctc ctggatctac ttcttctctg ccttttcgct cttcttctac     420
cagaccatgg acaatattga cggcaagcag gcccgtcgaa ctggctcttc ctctcctctg     480
ggagagctgt ttgaccacgg aatcgactcc ctcaactgca cctacggcgg aattgtcaac     540
tgcggtgctg tggcccttgg ttccacctcc tacggaggcc tcatggttct gtccacctgt     600
attggtatgt acttttctac ctgggagact tactacaccc acactcttta cctgggagtt     660
gttaacggcc ccaccgaagg ctagtggtg cccctgtcta ccatgctaat ctccggcttc      720
atgggcaccg acatctggaa ggaggatgcc gttgaggtgc tccccttcct ctccttcatg     780
gttcccgagt acctcaagct caacgagttc tgggtctggg tcgtcatgtt cacccctcgtg    840
gtgctgcacg tgcctttctg cgtgtggaac gtctattggg cctgcaagga ggacgatgtg     900
cctttctccg aggctctggt gggcctcctg cccttttggcg tggccggagg agctgcctac    960
gtgtggctgc agagtcctta ttccactgtg ctggttgaca ccaccttgt gctatttgga     1020
ctgaccgcct cgtgggtctt tggccggctg accaccggtg tgattctcaa ccacctcacc    1080
aagctcgagt ccctctgtg gaactccacc ctgattcctc ttctgggagc caccgttctg     1140
ttctacctgc tccctgccct gggtctactg ccccaggaca atcccactt cgagactctg      1200
tatctgtggg gcttctttgt ctacgctgcc gcgaactttt tgacctgggc tgttaacacc    1260
atcaatgtca tctgttccta ccttggcatc cgatgtctgt ctctgcgacc cgtggacaac    1320
aagaccaact ag                                                        1332

<210> SEQ ID NO 91
<211> LENGTH: 443
<212> TYPE: PRT
<213> ORGANISM: Yarrowia lipolytica

<400> SEQUENCE: 91

Met Gly Lys Ser Pro Ser Met Ile Gly Thr Cys Gly Trp Val Gly Leu
1               5                   10                  15

Gly Thr Asn Thr Cys Tyr Ala His Gln Leu Ser Arg Ala Met Gly His
            20                  25                  30

Gln Pro Thr Phe Leu Pro Thr Leu Ile Pro Ser Thr Leu Leu Met Pro
        35                  40                  45

Gly Phe His His Ile Asn Pro Asp Ser Leu Val His Leu Lys Ser Tyr
    50                  55                  60
```

-continued

```
Gln Tyr Arg Ser Val Asp Lys Ser Tyr Leu Ser Lys Tyr Ile Leu Asn
 65                  70                  75                  80

Pro Trp Trp Thr Tyr Ala Ala Thr Phe Met Pro Asp Trp Leu Ala Pro
                 85                  90                  95

Asn Ala Ile Thr Leu Ile Gly Val Ser Gly Met Leu Leu Ser Ile Phe
            100                 105                 110

Phe Thr Val Trp Tyr Thr Pro Glu Leu Thr Gly Asp Gly Pro Ser Trp
        115                 120                 125

Ile Tyr Phe Phe Ser Ala Phe Ser Leu Phe Phe Tyr Gln Thr Met Asp
    130                 135                 140

Asn Ile Asp Gly Lys Gln Ala Arg Arg Thr Gly Ser Ser Ser Pro Leu
145                 150                 155                 160

Gly Glu Leu Phe Asp His Gly Ile Asp Ser Leu Asn Cys Thr Tyr Gly
                165                 170                 175

Gly Ile Val Asn Cys Gly Ala Val Ala Leu Gly Ser Thr Ser Tyr Gly
            180                 185                 190

Gly Leu Met Val Leu Ser Thr Cys Ile Gly Met Tyr Phe Ser Thr Trp
        195                 200                 205

Glu Thr Tyr Tyr Thr His Thr Leu Tyr Leu Gly Val Val Asn Gly Pro
    210                 215                 220

Thr Glu Gly Leu Val Val Ala Leu Ser Thr Met Leu Ile Ser Gly Phe
225                 230                 235                 240

Met Gly Thr Asp Ile Trp Lys Glu Asp Ala Val Glu Val Leu Pro Phe
                245                 250                 255

Leu Ser Phe Met Val Pro Glu Tyr Leu Lys Leu Asn Glu Phe Trp Val
            260                 265                 270

Trp Val Val Met Phe Thr Leu Val Val Leu His Val Pro Phe Cys Val
        275                 280                 285

Trp Asn Val Tyr Trp Ala Cys Lys Glu Asp Asp Val Pro Phe Ser Glu
    290                 295                 300

Ala Leu Val Gly Leu Leu Pro Phe Gly Val Ala Gly Gly Ala Ala Tyr
305                 310                 315                 320

Val Trp Leu Gln Ser Pro Tyr Ser Thr Val Leu Val Asp Asn His Leu
                325                 330                 335

Val Leu Phe Gly Leu Thr Ala Ser Trp Val Phe Gly Arg Leu Thr Thr
            340                 345                 350

Gly Val Ile Leu Asn His Leu Thr Lys Leu Glu Phe Pro Leu Trp Asn
        355                 360                 365

Ser Thr Leu Ile Pro Leu Leu Gly Ala Thr Val Leu Phe Tyr Leu Leu
    370                 375                 380

Pro Ala Leu Gly Leu Leu Pro Gln Asp Asn Pro His Phe Glu Thr Leu
385                 390                 395                 400

Tyr Leu Trp Gly Phe Phe Val Tyr Ala Ala Ala Asn Phe Leu Thr Trp
                405                 410                 415

Ala Val Asn Thr Ile Asn Val Ile Cys Ser Tyr Leu Gly Ile Arg Cys
            420                 425                 430

Leu Ser Leu Arg Pro Val Asp Asn Lys Thr Asn
        435                 440
```